US012735463B2

(12) United States Patent
Fischer et al.

(10) Patent No.: US 12,735,463 B2
(45) Date of Patent: Sep. 15, 2026

(54) PEPTIDE TAGS FOR LIGAND INDUCED DEGRADATION OF FUSION PROTEINS

(71) Applicants: DANA-FARBER CANCER INSTITUTE, INC., Boston, MA (US); THE GENERAL HOSPITAL CORPORATION, Boston, MA (US)

(72) Inventors: Eric Fischer, Newton, MA (US); Benjamin L. Ebert, Brookline, MA (US); Max Jan, Somerville, MA (US); Radoslaw Nowak, Boston, MA (US)

(73) Assignees: DANA-FARBER CANCER INSTITUTE, INC., Boston, MA (US); THE GENERAL HOSPITAL CORPORATION, Boston, MA (US)

( * ) Notice: Subject to any disclaimer, the term of this patent is extended or adjusted under 35 U.S.C. 154(b) by 1404 days.

(21) Appl. No.: 17/413,859

(22) PCT Filed: Dec. 18, 2019

(86) PCT No.: PCT/US2019/067130

§ 371 (c)(1),
(2) Date: Jun. 14, 2021

(87) PCT Pub. No.: WO2020/132039

PCT Pub. Date: Jun. 25, 2020

(65) Prior Publication Data

US 2022/0098251 A1 Mar. 31, 2022

Related U.S. Application Data

(60) Provisional application No. 62/781,034, filed on Dec. 18, 2018.

(51) Int. Cl.

| | |
|---|---|
| ***C07K 14/47*** | (2006.01) |
| ***A61K 31/4439*** | (2006.01) |
| ***A61K 35/17*** | (2025.01) |
| ***A61K 38/08*** | (2019.01) |
| ***A61K 38/10*** | (2006.01) |
| ***A61K 38/17*** | (2006.01) |
| ***A61K 39/00*** | (2006.01) |
| ***A61K 39/395*** | (2006.01) |
| ***A61K 48/00*** | (2006.01) |
| ***C07K 7/06*** | (2006.01) |
| ***C07K 7/08*** | (2006.01) |
| ***C07K 16/28*** | (2006.01) |

(52) U.S. Cl.

CPC .......... *C07K 14/47* (2013.01); *A61K 31/4439* (2013.01); *A61K 35/17* (2013.01); *A61K 38/08* (2013.01); *A61K 38/10* (2013.01); *A61K 38/1709* (2013.01); *A61K 39/001112* (2018.08); *A61K 39/3955* (2013.01); *C07K 7/06* (2013.01); *C07K 7/08* (2013.01); *C07K 16/2803* (2013.01); *A61K 2039/5156* (2013.01); *A61K 2039/5158* (2013.01); *A61K 48/00* (2013.01); *C07K 2319/02* (2013.01); *C07K 2319/03* (2013.01); *C07K 2319/30* (2013.01); *C07K 2319/33* (2013.01); *C07K 2319/95* (2013.01)

(58) Field of Classification Search

None

See application file for complete search history.

(56) References Cited

U.S. PATENT DOCUMENTS

| | | | |
|---|---|---|---|
| 12,110,292 | B2 | 10/2024 | Gray et al. |
| 2013/0065814 | A1 | 3/2013 | Guoliang et al. |

FOREIGN PATENT DOCUMENTS

| | | | |
|---|---|---|---|
| WO | 2003016571 | A1 | 2/2003 |
| WO | 2016057897 | A1 | 4/2016 |
| WO | 2017/044801 | A2 | 3/2017 |
| WO | 2019079569 | A1 | 4/2019 |
| WO | 2019089592 | A1 | 5/2019 |

OTHER PUBLICATIONS

Kronke et al. (Science. Jan. 17, 2014; 343(6168): 301-305) (Year: 2014).*

Sanchez-Tapia et al. (GenBank: AAR84585.1, Aug. 1, 2004) (Year: 2004).*

Koduri, V., et al., "Peptidic degron for MID-induced degradation of heterologous proteins," Proceedings of the National Academy of Sciences of the U.S.A, 2019, 116(7):2539-2544.

Kronke, J., et al., "Lenalidomide Causes Selective Degradation of IKZF1 and IKZF3 in Multiple Myeloma Cells," Science, 2014, 343(6168):301-305.

Sievers, Q.L., et al., "Defining the human C2H2 zinc finger degrome targeted by thalidomide analogs through CRBN," Science, 2018, 362(6414):1-35.

Petzold, G. et al., "Structural basis of lenalidomide-induced CK1α degradation by the CRL4(CRBN) ubiquitin ligase," Nature, vol. 532, 16 pps. (Apr. 7, 2016).

* cited by examiner

*Primary Examiner* — Sergio Coffa

(74) *Attorney, Agent, or Firm* — ArentFox Schiff LLP; Daniel W. Clarke; Shawn P. Foley

(57) ABSTRACT

Described herein are compositions and methods for modulating protein abundance in a target-specific manner via degron tags.

24 Claims, 38 Drawing Sheets

Specification includes a Sequence Listing.

FIG. 10

| | | | | | |
|---|---|---|---|---|---|
| 1 | ikzf1_orun_51.prepack_004383 | 100.0% | 100.0% | RKRPFTCDSCGAAFDRAEELNNHLNAHTG | SEQ ID NO: 90 |
| 2 | ikzf1_orun_134.prepack_000457 | 100.0% | 93.1% | RKRPFQCDRCGAAFDRAEELNNHLNAHTG | SEQ ID NO: 91 |
| 3 | ikzf1_orun_07.prepack_000064 | 100.0% | 86.2% | RERPFQCDACGAAYDRAEELNNHLNAHTG | SEQ ID NO: 92 |
| 4 | ikzf1_orun_21.prepack_001272 | 100.0% | 82.8% | RERPYQCDACGAAFDRAEELNNHLNAHSG | SEQ ID NO: 93 |
| 5 | ikzf1_orun_16.prepack_000734 | 100.0% | 93.1% | RERPFQCDSCGAAFDRAEELNNHLNAHTG | SEQ ID NO: 94 |
| 6 | ikzf1_orun_139.prepack_000511 | 100.0% | 82.8% | RKRPFQCDACGAAFDRSKELNDHLNAHTG | SEQ ID NO: 95 |
| 7 | ikzf1_orun_254.prepack_001756 | 100.0% | 82.8% | RKRPFQCDSCGAAFNRSKELNDHLNAHTG | SEQ ID NO: 96 |
| 8 | ikzf1_orun_251.prepack_001727 | 100.0% | 72.4% | RERPFMCDACGAAFNRSKELNDHLNAHSG | SEQ ID NO: 97 |
| 9 | ikzf1_orun_415.prepack_003474 | 100.0% | 82.8% | RERPFQCDACGAAFDRAEELNDHLNKHTG | SEQ ID NO: 98 |
| 10 | ikzf1_orun_440.prepack_003748 | 100.0% | 89.7% | RERPFVCTSCGAAFDRAEELNNHLNAHTG | SEQ ID NO: 99 |

FIG. 10 (continued)

| | | | | |
|---|---|---|---|---|
| 11 | ikzf1_orun_113.prepack_000235 | 100.0% | 86.2% | RERPFTCTACGAAFNRAEELNNHLNAHTG<br>SEQ ID NO: 100 |
| 12 | ikzf1_orun_384.prepack_003144 | 100.0% | 86.2% | RERPFVCEMCGAAFDRAEELNNHLNAHTG<br>SEQ ID NO: 101 |
| 13 | ikzf1_orun_278.prepack_002006 | 100.0% | 82.8% | RELPYVCDMCGAAFDRAEELNNHLNAHTG<br>SEQ ID NO: 102 |
| 14 | ikzf1_orun_124.prepack_000350 | 100.0% | 89.7% | RERPFQCESCGAAFDRAEELNNHLNAHTG<br>SEQ ID NO: 103 |
| 15 | ikzf1_orun_444.prepack_003785 | 100.0% | 82.8% | REMPYQCESCGAAFDRAEELNNHLNAHTG<br>SEQ ID NO: 104 |
| 16 | ikzf1_orun_260.prepack_001823 | 100.0% | 82.8% | RERPFQCEYCGAAFDRAEELNNHLNALTG<br>SEQ ID NO: 105 |
| 17 | ikzf1_orun_332.prepack_002585 | 100.0% | 79.3% | RERPFQCQYCGAAFDRAEELNNHLKNHTG<br>SEQ ID NO: 106 |
| 18 | ikzf1_orun_25.prepack_001707 | 100.0% | 75.9% | REAPFQCESCGARFNRAEELNNHLNRHTG<br>SEQ ID NO: 107 |
| 19 | ikzf1_orun_446.prepack_003799 | 100.0% | 75.9% | REAPFQCESCGARFNRAEELNNHLNNHTG<br>SEQ ID NO: 108 |

FIG. 10 (continued)

| | | | | |
|---|---|---|---|---|
| 20 | ikzf1_orun_55.prepack_004430 | 100.0% | 72.4% | RELPFQCESCGARFERAEELNYHLNVHTG<br>SEQ ID NO: 109 |
| 21 | ikzf1_orun_84.prepack_004701 | 100.0% | 79.3% | REMPFQCESCGARFNRAEELNNHLNAHTG<br>SEQ ID NO: 110 |
| 22 | ikzf1_orun_33.prepack_002557 | 100.0% | 79.3% | REMPFQCESCGARFNRAEELNNHLNAHTG<br>SEQ ID NO: 111 |
| 23 | ikzf1_orun_420.prepack_003524 | 100.0% | 79.3% | REMPFQCDSCGARFNRAEELNTHLNAHTG<br>SEQ ID NO: 112 |
| 24 | ikzf1_orun_451.prepack_003862 | 100.0% | 72.4% | RKAPFQCDVCGARFNRAEELNYHLNTLTG<br>SEQ ID NO: 113 |
| 25 | ikzf1_orun_217.prepack_001351 | 100.0% | 69.0% | REAPFQCDVCGARFNRAEELNYHLNLLTG<br>SEQ ID NO: 114 |
| 26 | ikzf1_orun_483.prepack_004197 | 100.0% | 69.0% | RKTPFQCEVCGARFNRAEELNYHLNLLTG<br>SEQ ID NO: 115 |
| 27 | ikzf1_orun_305.prepack_002296 | 100.0% | 69.0% | RKAPFQCEVCGARFNRAEELNTHLNILTG<br>SEQ ID NO: 116 |
| 28 | ikzf1_orun_59.prepack_004462 | 100.0% | 65.5% | RKAPFQCEVCGARFNRAEELNTHLNILKG<br>SEQ ID NO: 117 |

FIG. 10 (continued)

| | | | | | |
|---|---|---|---|---|---|
| 29 | ikzf1_orun_308.prepack_002325 | 100.0% | 72.4% | RKTPFQCDICGARFNRAEELNTHLNILTG | SEQ ID NO: 118 |
| 30 | ikzf1_orun_99.prepack_004847 | 100.0% | 72.4% | RKIPFQCDVCGARFNRAEELNTHLNILTG | SEQ ID NO: 119 |
| 31 | ikzf1_orun_134.prepack_000458 | 100.0% | 75.9% | RKAPFQCDVCGARFNRAEELNTHLNALTG | SEQ ID NO: 120 |
| 32 | ikzf1_orun_489.prepack_004257 | 100.0% | 75.9% | RKAPFQCDVCGARFNRAEELNNHLNRLTG | SEQ ID NO: 121 |
| 33 | ikzf1_orun_322.prepack_002484 | 100.0% | 79.3% | RKRPFQCEVCGARFNRAEELNNHLNALTG | SEQ ID NO: 122 |
| 34 | ikzf1_orun_334.prepack_002606 | 100.0% | 72.4% | RKAPFQCEVCGARFNRAEELNNHLNALLG | SEQ ID NO: 123 |
| 35 | ikzf1_orun_93.prepack_004790 | 100.0% | 75.9% | RERPFQCEVCGARFNRAEELNNHLNALTG | SEQ ID NO: 124 |
| 36 | ikzf1_orun_427.prepack_003597 | 100.0% | 75.9% | RERPFQCEVCGARFNRAEELNNHLNALTG | SEQ ID NO: 125 |
| 37 | ikzf1_orun_349.prepack_002766 | 100.0% | 72.4% | REAPFQCEVCGARFNRAEELNNHLNALTG | SEQ ID NO: 126 |
| 38 | ikzf1_orun_460.prepack_003961 | 100.0% | 72.4% | RKAPFQCESCGARFNRWEELATHLNAHTG | SEQ ID NO: 127 |

FIG. 10 (continued)

| | | | | |
|---|---|---|---|---|
| 39 | ikzf1_orun_50.prepack_004380 | 100.0% | 65.5% | REAPFQCEMCGARFNRWEELASHLNAHTG<br>SEQ ID NO: 128 |
| 40 | ikzf1_orun_295.prepack_002187 | 100.0% | 69.0% | RKMPFQCEVCGARFNRWEELANHLNALTG<br>SEQ ID NO: 129 |
| 41 | ikzf1_orun_191.prepack_001073 | 100.0% | 65.5% | RKAPFQCDVCGARFNRKEELDDHLNKLTG<br>SEQ ID NO: 130 |
| 42 | ikzf1_orun_133.prepack_000451 | 100.0% | 58.6% | REAPFQCDVCGARFNRKEELDTHLTKLTG<br>SEQ ID NO: 131 |
| 43 | ikzf1_orun_60.prepack_004473 | 100.0% | 62.1% | REAPFQCEVCGARFNRKEELDNHLNNLTG<br>SEQ ID NO: 132 |
| 44 | ikzf1_orun_131.prepack_000434 | 100.0% | 72.4% | REAPFQCDACGARFNRKEELDNHLNAHTG<br>SEQ ID NO: 133 |
| 45 | ikzf1_orun_176.prepack_000914 | 100.0% | 82.8% | REAPFQCDSCGARFNRAEELNNHLNAHTG<br>SEQ ID NO: 134 |
| 46 | ikzf1_orun_249.prepack_001699 | 100.0% | 82.8% | REAPFQCDSCGARFNRAEELNNHLNAHTG<br>SEQ ID NO: 135 |

FIG. 10 (continued)

| | | | | |
|---|---|---|---|---|
| 47 | ikzf1_orun_451.prepack_003866 | 100.0% | 82.8% | REAPFQCDSCGARFNRAEELNNHLNAHTG<br>SEQ ID NO: 136 |
| 48 | ikzf1_orun_327.prepack_002533 | 100.0% | 79.3% | REAPFQCDACGARFNRAEELNNHLNAHTG<br>SEQ ID NO: 137 |
| 49 | ikzf1_orun_333.prepack_002603 | 100.0% | 79.3% | REAPFQCDACGARFNRAEELNNHLNAHTG<br>SEQ ID NO: 138 |
| 50 | ikzf1_orun_479.prepack_004154 | 100.0% | 75.9% | REAPFQCEACGARFNRAEELNNHLNAHTG<br>SEQ ID NO: 139 |

FIG. 11

| | | | | | |
|---|---|---|---|---|---|
| 1 | IKZF2\|140-162 | 100.0% | 100.0% | FHCNQCGASFTQKGNLLRH-IK-LH | SEQ ID NO: 34 |
| 2 | GZF1\|348-371 | 100.0% | 33.3% | YRCDTCGQTFANRCNLKSH-QRHVH | SEQ ID NO: 35 |
| 3 | GZF1\|377-400 | 100.0% | 37.5% | FPCELCGKKFKRKKDVKRH-VLQVH | SEQ ID NO: 36 |
| 4 | GZF1\|407-429 | 100.0% | 34.8% | HRCGQCGKGLSSKTALRLH-ER-TH | SEQ ID NO: 37 |
| 5 | GZF1\|435-457 | 100.0% | 39.1% | YGCTECGARFSQPSALKTH-MR-IH | SEQ ID NO: 38 |
| 6 | GZF1\|463-485 | 100.0% | 47.8% | FVCDECGARFTQNHMLIYH-KR-CH | SEQ ID NO: 39 |
| 7 | GZF1\|491-513 | 100.0% | 43.5% | FMCETCGKSFASKEYLKHH-NR-IH | SEQ ID NO: 40 |
| 8 | GZF1\|547-569 | 100.0% | 47.8% | YCCDQCGKQFTQLNALQRH-RR-IH | SEQ ID NO: 41 |
| 9 | GZF1\|575-597 | 100.0% | 52.2% | FMCNACGRTFTDKSTLRRH-TS-IH | SEQ ID NO: 42 |
| 10 | IKZF3\|146-168 | 100.0% | 95.7% | FQCNQCGASFTQKGNLLRH-IK-LH | SEQ ID NO: 43 |
| 11 | IKZF3\|118-140 | 100.0% | 30.4% | MNCDVCGLSCISFNVLMVH-KR-SH | SEQ ID NO: 44 |
| 12 | IKZF3\|202-224 | 100.0% | 30.4% | YKCEFCGRSYKQRSSLEEH-KE-RC | SEQ ID NO: 45 |
| 13 | IKZF1\|145-167 | 100.0% | 95.7% | FQCNQCGASFTQKGNLLRH-IK-LH | SEQ ID NO: 46 |
| 14 | IKZF1\|117-139 | 100.0% | 26.1% | LKCDICGIICIGPNVLMVH-KR-SH | SEQ ID NO: 47 |
| 15 | IKZF1\|201-224 | 100.0% | 33.3% | HKCGYCGRSYKQRSSLEEH-KERCH | SEQ ID NO: 48 |
| 16 | SALL4\|410-432 | 100.0% | 52.2% | FVCSVCGHRFTTKGNLKVH-FH-RH | SEQ ID NO: 49 |
| 17 | SALL4\|594-616 | 100.0% | 47.8% | FQCKICGRAFSTKGNLKTH-LG-VH | SEQ ID NO: 50 |
| 18 | SALL4\|870-892 | 100.0% | 30.4% | HGCTRCGKNFSSASALQIH-ER-TH | SEQ ID NO: 51 |
| 19 | SALL4\|898-920 | 100.0% | 56.5% | FVCNICGRAFTTKGNLKVH-YM-TH | SEQ ID NO: 52 |
| 20 | ZNF653\|528-550 | 100.0% | 43.5% | FTCETCGKSFKRKNHLEVH-RR-TH | SEQ ID NO: 53 |

FIG. 11 (continued)

| | | | | | |
|---|---|---|---|---|---|
| 21 | ZNF653\|556-578 | 100.0% | 34.8% | LQCEICGYQCRQRASLNWH-MK-KH | SEQ ID NO: 54 |
| 22 | ZNF653\|586-609 | 100.0% | 33.3% | FTCDRCGKRFEKLDSVKFHTLK-SH | SEQ ID NO: 55 |
| 23 | ZFP91\|400-422 | 100.0% | 39.1% | LQCEICGFTCRQKASLNWH-MK-KH | SEQ ID NO: 56 |
| 24 | ZFP91\|430-453 | 100.0% | 37.5% | FSCNICGKKFEKKDSVVAH-KAKSH | SEQ ID NO: 57 |
| 25 | ZNF692\|417-439 | 100.0% | 34.8% | LQCEICGFTCRQKASLNWH-QR-KH | SEQ ID NO: 58 |
| 26 | ZNF692\|448-471 | 100.0% | 29.2% | FPCEFCGKRFEKPDSVAAH-RSKSH | SEQ ID NO: 59 |
| 27 | ZNF827\|374-396 | 100.0% | 34.8% | FQCPICGLVIKRKSYWKRH-MV-IH | SEQ ID NO: 60 |
| 28 | ZNF827\|817-839 | 100.0% | 43.5% | FPCDVCGKVFGRQQTLSRH-LS-LH | SEQ ID NO: 61 |
| 29 | ZNF827\|897-919 | 100.0% | 26.1% | YSCHVCGFETELNVQFVSH-MS-LH | SEQ ID NO: 62 |
| 30 | ZBTB39\|605-627 | 100.0% | 26.1% | YSCKVCGKRFAHTSEFNYH-RR-IH | SEQ ID NO: 63 |
| 31 | ZBTB39\|661-683 | 100.0% | 21.7% | YRCTVCGHYSSTLNLMSKH-VG-VH | SEQ ID NO: 64 |
| 32 | WIZ\|769-791 | 100.0% | 34.8% | MRCDFCGAGFDTRAGLSSH-AR-AH | SEQ ID NO: 65 |
| 33 | WIZ\|304-326 | 100.0% | 34.8% | LACGECGWAFADPTALEQH-RQ-LH | SEQ ID NO: 66 |
| 34 | WIZ\|870-892 | 100.0% | 34.8% | TTCEVCGACFETRKGLSSH-AR-SH | SEQ ID NO: 67 |
| 35 | ZNF98\|210-232 | 100.0% | 30.4% | YKCKECGKAYNEASNLSTH-KR-IH | SEQ ID NO: 68 |
| 36 | ZNF98\|238-260 | 100.0% | 30.4% | YKCEECGKAFNRLSHLTTH-KI-IH | SEQ ID NO: 69 |
| 37 | ZNF98\|266-288 | 100.0% | 39.1% | YKCEECGKAFNQSANLTTH-KR-IH | SEQ ID NO: 70 |
| 38 | ZNF98\|322-344 | 100.0% | 34.8% | YKCEECGKAFSQSSTLTTH-KI-IH | SEQ ID NO: 71 |

FIG. 11 (continued)

| | | | | | |
|---|---|---|---|---|---|
| 39 | ZNF98\|350-372 | 100.0% | 30.4% | YKCEECGKAFSRLSHLTTH-KR-IH | SEQ ID NO: 72 |
| 40 | ZNF98\|378-400 | 100.0% | 34.8% | YKCEECGKAFKQSSTLTTH-KR-IH | SEQ ID NO: 73 |
| 41 | ZNF98\|434-456 | 100.0% | 30.4% | YKCEECGKAFNLSSQLTTH-KI-IH | SEQ ID NO: 74 |
| 42 | ZNF98\|462-484 | 100.0% | 34.8% | YKCEECGKAFNQSSTLSKH-KV-IH | SEQ ID NO: 75 |
| 43 | ZNF98\|490-512 | 100.0% | 34.8% | YKCEECGKAFNQSSHLTTH-KM-IH | SEQ ID NO: 76 |
| 44 | ZNF98\|518-540 | 100.0% | 34.8% | YKCEECGKAFNNSSILNRH-KM-IH | SEQ ID NO: 77 |

FIG. 15B

| ZFID | FQCNQCGASFTQKGNLLRHIKLH | #ΔIKZF3 | |
|---|---|---|---|
| IKZF3-IKZF3 | ----------------------- | 0 | SEQ ID NO: 151 |
| ZFP91-IKZF3 | M--EI--FTCR------------ | 7 | SEQ ID NO: 152 |
| SD01 | ---QV---R-SRWEE-YN-LLK- | 13 | SEQ ID NO: 153 |
| SD02 | ---EM---A-DRWEE-YN-KNA- | 13 | SEQ ID NO: 154 |
| SD03 | ---EI---R-KRWEE-YN-L-K- | 12 | SEQ ID NO: 155 |
| SD04 | ---EI---A-SRWEE-YN-L-R- | 12 | SEQ ID NO: 156 |
| SD05 | ---EI---R-FRWEE-YN-LAK- | 13 | SEQ ID NO: 157 |
| SD06 | ---SI---T-SRWEE-YN-LLK- | 13 | SEQ ID NO: 158 |
| SD07 | ---EI---R-SRWEE-YN-LNK- | 13 | SEQ ID NO: 159 |
| SD08 | ---EI---K-ENWED-YN-LLK- | 13 | SEQ ID NO: 160 |
| SD09 | ---K----V-SRWEE-YN-LTN- | 12 | SEQ ID NO: 161 |
| SD10 | ---K----V-SRWEE-YN-L-N- | 11 | SEQ ID NO: 162 |
| SD11 | ---K----V-KRWEE-YN-LLA- | 12 | SEQ ID NO: 163 |
| SD12 | ---EI---R-SRWEE-YN-LLK- | 13 | SEQ ID NO: 164 |
| SD13 | ---QV---R-SRWEE-YN-LSK- | 13 | SEQ ID NO: 165 |
| SD14 | ---QY---R-NRWEE-YD-LNK- | 13 | SEQ ID NO: 166 |
| SD15 | ---QM---A-DRWEE-YN-LLA- | 13 | SEQ ID NO: 167 |
| SD16 | ---V----R-NRWEE-YD-LNK- | 12 | SEQ ID NO: 168 |
| SD17 | ---KY---V-SRWEE-YN-LLA- | 13 | SEQ ID NO: 169 |
| SD18 | ---EI---R-SRWEE-YN-L-N- | 12 | SEQ ID NO: 170 |
| SD19 | -----------RWEE-YN-LLR- | 9 | SEQ ID NO: 171 |
| SD20 | ---QY---V--RWEE-YN-LLR- | 12 | SEQ ID NO: 172 |
| SD21 | ---S----A-NRWEE-YN-LLR- | 12 | SEQ ID NO: 173 |
| SD22 | ---DK---K-DRWEE-YN-NNA- | 13 | SEQ ID NO: 174 |
| SD23 | ---EI---R-ENWED-YN-LLK- | 13 | SEQ ID NO: 175 |
| SD24 | -T-TA---T--RAEE-NT-LSK- | 13 | SEQ ID NO: 176 |

FIG. 22
0
RERPFQCNQCGASFTQKGNLLRHIKLH
1 2 3 4 5 6 7 8 9 10 11 12 13 14 15 16 17 18 19 20 21 22 23 24 25 26 27
C

(SEQ ID NO: 144)

PEPTIDE TAGS FOR LIGAND INDUCED DEGRADATION OF FUSION PROTEINS

RELATED APPLICATIONS

This application is a national stage application, filed under 35 U.S.C. § 371, of International Application No. PCT/US2019/067130, filed Dec. 18, 2019, which claims the benefit of priority under 35 U.S.C. § 119(e) to U.S. Provisional Application No. 62/781,034, filed on Dec. 18, 2018, each of which is incorporated herein by reference in its entirety.

GOVERNMENT LICENSE RIGHTS

This invention was made with government support under grant number R01 CA214608 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 4, 2019, is named "52095-571001WO-SEQ-LIST_ST25" and is 19.3 KB in size.

BACKGROUND OF THE INVENTION

One of the fundamental challenges of chemical biology remains the ability to disrupt the function of any protein using a small molecule. It is estimated that about 80% of the proteome is "undruggable" by current methods. (Russ et al., Drug Discov. Today 10:1607-1610 (2005)). Moreover, typical small molecule therapeutics, such as enzyme inhibitors and receptor antagonists, target specific protein activities, while leaving other activities intact, such as scaffolding functions or other enzymatic functions in multidomain proteins. Thus, while progress has been made towards developing individual ligands to specific proteins, only about 300 molecular targets have been identified and characterized for FDA approved drugs. (Overington et al., Nat. Rev. Drug Discov. 5:993-996 (2006)).

In order to address these limitations, methods have been developed to control the expression of proteins at the transcriptional level. Protein expression can be regulated on a genetic level via techniques such as RNA interference and antisense deoxyoligonucleotides, and by small molecule-mediated transcriptional switches such as drug-responsive promoters. (Ryding et al., J. Endocrinol. 171:1-14 (2001)). However, controlling protein expression through repression of transcription is slow in onset because previously transcribed mRNAs continue to produce proteins. Also, genetic techniques can exhibit both sequence-independent and sequence-dependent off-target effects. Further, mRNA and protein abundance are not always correlated due to translational regulation of specific mRNAs. (Sigoillot et al., ACS Chem. Biol. 6:47-60 (2011); Battle et al., Science 347:664-667 (2015)).

Accordingly, methods have been developed to modulate protein abundance at the post-translational level. A number of these methods use small molecules to induce targeted protein degradation. Exemplary techniques include selective stabilization of a target protein via the Shield system, the auxin-inducible degron system (AID), small-molecule-assisted shutoff system (SMASh), induced displacement of cryptic degrons, degradation of HaloTag fusion proteins via hydrophobic tagging or Halo proteolysis targeting chimeric molecules (PROTACs), and degradation of degradation tag (dTag) fusion proteins via PROTACs.

In the Shield system, fusion proteins are engineered with mutants of the human FKBP12 protein that are rapidly and constitutively degraded when expressed in mammalian cells, and this instability is conferred to the proteins of interest (POIs) fused to these destabilizing domains. Addition of a synthetic ligand, Shield-1, that binds the destabilizing domains shields them from degradation, allowing fused proteins to perform their cellular functions. (Banaszynski et al., Cell 126:995-1004 (2006)).

In the AID system, the plant hormone, auxin (indole-3-acetic acid), is administered to dimerize a plant E3 ubiquitin ligase (TIR1) with a domain from the AUX/IAA transcriptional repressor (Aid1), which when fused to a protein of interest (POI) is ubiquitinated by proximity to TIR1. This method requires fusing the POI to Aid1, along with an introduction of the plant E3 ligase TIR1 into cells. (Nishimura et al., Nat. Methods 6:917-22 (2009)).

In the SMASh system, POIs are fused to a degron that removes itself in the absence of drug, leaving untagged protein. Clinically tested HCV protease inhibitors are used to block degron removal, which induces rapid degradation of subsequently synthesized protein copies. (Chung et al., Nat. Chem. Biol. 11:713-20 (2015)).

In the induced displacement of cryptic degrons system, a POI is fused to a Ligand-Induced Degradation (LID) domain resulting in the expression of a stable and functional fusion protein. The LID domain includes the FK506- and rapamycin-binding protein (FKBP) and a 19-amino acid degron fused to the C-terminus of FKBP. Administration of the small molecule Shield-1 binds tightly to FKBP thereby displacing the degron and inducing rapid and processive degradation of the LID domain and any fused partner protein. (Bonger et al., Nat. Chem. Biol. 7:531-37 (2011)).

In the degradation of HaloTag fusion proteins system via hydrophobic tagging, a hydrophobic moiety is appended to the surface of a protein, which is thought to mimic the partially denatured state of the protein. Bifunctional small molecules that bind a bacterial dehalogenase (HaloTag) are employed, and hydrophobic tagging of the HaloTag protein with an adamantyl moiety induces the degradation of cytosolic, isoprenylated, and transmembrane fusion proteins. (Neklesa et al., Nat. Chem. Biol. 7:538-43 (2011)).

In the degradation of HaloTag fusion proteins system via Halo PROTACs, heterobifunctional small molecules of a hexyl chloride HaloTag ligand covalently linked with a Von-Hippel-Lindau tumor suppressor ligand are used to target HaloTag fusion proteins to E3 ligase for ubiquitination and subsequent degradation by the proteasome. (Buckley et al., ACS Chem. Biol. 10:1831-37 (2015)).

In the degradation of dTAG fusion proteins via PROTACs system, POIs fused to $FKBP12^{F36V}$ are degraded via heterobifunctional small molecules that are $FKBP12^{F36V}$ ligands covalently linked via a linker sequence to a cereblon E3 ligase ligand to induce ubiquitination and subsequent degradation of the POI fusion protein by the proteasome. (Nabet et al., Nat. Chem. Biol. 14:431-41 (2018)). See also, International Publication numbers WO 2017/024318 and WO 2017/024319, each of which are incorporated herein by reference.

There remains a need to develop new compositions and methods for modulating protein abundance.

SUMMARY OF THE INVENTION

The present invention provides compositions that include a degron tag, and methods for modulating protein abundance in a target-specific manner via the degron tags. The invention may target endogenous and exogenous (e.g., therapeutic) proteins alike. As disclosed herein, degron tags are peptides that when fused to a target protein of interest (POI), transform the POI into a substrate for cereblon (CRBN)-dependent ubiquitination and degradation, which is induced by the administration of immunomodulatory drugs (IMiDs) or cereblon modulators (CMs). Without intending to be bound by any theory of operation, it is believed that IMiDs and CMs bind cereblon forming a complex (CRBN-IMiD or CRBN-CM) which has binding specificity for the degron tags. Consequently, degron tag-protein of interest fusion proteins ("degron-POI fusion proteins") become substrates for cereblon-dependent ubiquitination and degradation. Therefore, the degron tags of the present invention may be useful for targeted degradation of POIs.

Accordingly, a first aspect of the invention is directed to a degron tag which is a naturally or non-naturally occurring peptide that includes a first peptide fragment having an amino acid sequence that includes CXXX/-X/-CG (SEQ ID NO: 1) wherein X represents any amino acid and "(X/-)" means that the position in the peptide may be any amino acid or no amino acid, provided that there are either 2 or 4 amino acid residues between the cysteine residues wherein X represents any amino acid. The degron tag also includes a second peptide fragment, C-terminal to the first sequence, and which has an amino acid sequence HXXX(X/-)H/C (SEQ ID NO: 2), wherein X represents any amino acid and "(X/-)" means that the position in the peptide may be any amino acid or no amino acid. The degron tag binds a complex formed between CRBN and an IMiD or between CRBN and a CM.

Various naturally occurring proteins contain zinc finger regions (also known as zinc finger motifs) that include a beta-hairpin loop and an alpha-helix region. In some embodiments, the degron tag may include a first sequence derivable from or which is at least part of a first zinc finger region, and a second sequence derivable from or which is part of an α-helix region of a second zinc finger region. The first and second zinc finger regions may be the same or different, provided that the degron tag binds CRBN-IMiD or CRBN-CM.

Another aspect of the invention is directed to a fusion protein including a POI and a degron tag that binds CRBN-IMiD or CRBN-CM. In some embodiments, the degron tag may be located N-terminal to the POI, C-terminal to the POI or within the POI.

Other aspects of the invention are directed to nucleic acid molecules that include a sequence encoding non-naturally occurring degron tags, nucleic acid molecules encoding the fusion proteins, vectors containing the nucleic acid molecules, and cells transformed with the vectors. In some embodiments, the nucleic acid molecule encodes a fusion protein that includes a chimeric antigen receptor (CAR), which includes an extracellular ligand binding domain, a transmembrane domain, and a cytoplasmic domain including at least one intracellular signaling domain, and a degron tag. In some embodiments, the cell is an immune effector cell such as a T-cell transformed with a nucleic acid molecule encoding a CAR-degron tag fusion protein.

A further aspect of the invention is directed to a method of degrading a protein of interest that entails contacting a transgenic cell with an effective amount of an IMiD or a CM, wherein the cell produces a fusion protein including a protein of interest and at least one degron tag that binds a CRBN-IMiD complex or a CRBN-CM complex. The methods may be conducted in vivo or in vitro. The POIs may be exogenous or endogenous.

In vivo methods may serve as biological "safety switches" in order to inactivate POIs that are produced in a subject as a result of immune therapy. In some embodiments, the method entails administering an effective amount of an IMiD or CM, or a pharmaceutically acceptable salt or stereoisomer thereof, to a subject that has previously been treated via gene therapy whereby some endogenous cells express a fusion protein including a POI and a degron tag that binds CRBN-IMiD or CRBN-CM. In some embodiments, the subject has been administered immune effector cells such as autologous T-cells (CAR-T cells) which have been genetically modified to express a chimeric antigen receptor protein (CAR)-degron tag fusion protein, and is experiencing an adverse immune response (e.g., cytokine release syndrome or neurotoxicity) as a result of the therapy. In some other embodiments, the gene therapy includes gene knock-in, administration of viral vectors or clustered regularly interspaced short palindromic repeats (CRISPR)-mediated knock in.

Yet a further aspect of the invention is directed to a method of reducing gene overexpression in a subject including introducing into one or more relevant cells of the subject a nucleic acid sequence encoding a degron tag that is integrated genomically in-frame with a nucleic acid sequence of an endogenous protein associated with a disease due to overexpression of the endogenous protein; and administering to the subject an effective amount of an IMiD or CM. In some embodiments, the endogenous protein is associated with a disease that is a result of a gain of function mutation, amplification or increased expression, a monogenetic disease, a proteopathy, or a combination thereof.

A further aspect of the invention is directed to a method of evaluating the function of an endogenous protein or validating an endogenous protein as a target for therapy of a disease state including introducing into one or more relevant cells a nucleic acid sequence encoding a degron tag that is integrated genomically in-frame with a nucleic acid sequence of an endogenous protein suspected of being associated with a disease; and contacting the cells with an effective amount of an IMiD or CM. The methods may be conducted in vivo (e.g. in animal models) or in vitro (e.g. in cell cultures).

Any of the inventive methods may entail contacting the cell or administering to the subject an IMiD or CM which is thalidomide, pomalidomide, lenalidomide, CC-122, CC-220 or CC-885.

The present invention provides a simpler and more widely applicable method for chemical regulation of protein expression at the post-translational level. Advantages over prior methods may include: a) minimal modification of the target protein; b) relatively universal applicability to target proteins and cell types; and c) dose-dependent control by small molecule drugs with proven safety and bioavailability in mammals, and which in many embodiments are FDA-approved or which are in clinical trials.

BRIEF DESCRIPTION OF THE DRAWINGS

FIG. 411 is a photograph of a western blot showing Flag-$hsSALL4^{WT}$, Flag-$hsSALL4^{G600A}$, $hsSALL4^{G600N}$ and GAPDH protein levels after 24 hours of incubation with increasing concentrations of thalidomide or DMSO as a control.

FIG. 10 is an alignment of computationally optimized degron tags based on IKZF1, SEQ ID NOs: 90-139, using KALIGN+MView.

FIG. 11 is an alignment of naturally occurring sequences found in the proteins: IKZF2, GZF1, IKZF3, IKZF1, SALL4, ZNF653, ZFP91, ZNF692, ZNF827, ZBTB39, WIZ and ZNF98, SEQ ID NOs: 34-77, using KALIGN+MView.

FIG. 15B is an alignment of 23 putative lenalidomide-induced degrons (SEQ ID NOs: 151-176). Sequence differences versus IKZF3 ZF2 (SEQ ID NO: 151) are shown.

DETAILED DESCRIPTION OF THE INVENTION

Figure 1B:
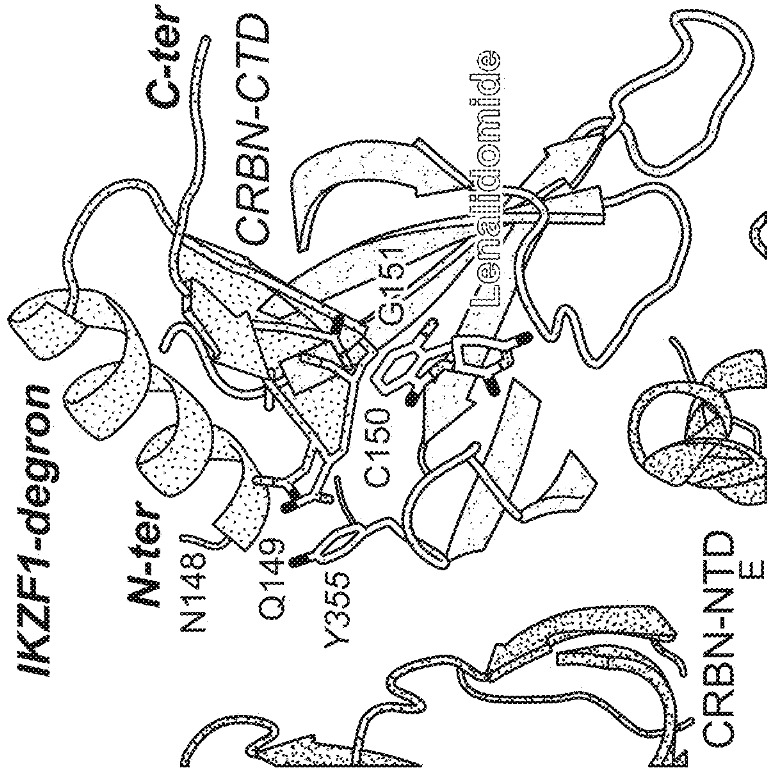
FIG. 1B is a depiction of a structural model of IKZF1 minimal degron bound to CRBN and lenalidomide (based on disclosure in Petzold et al., Nature 532:127-30 (2016)).
Figure 1A:
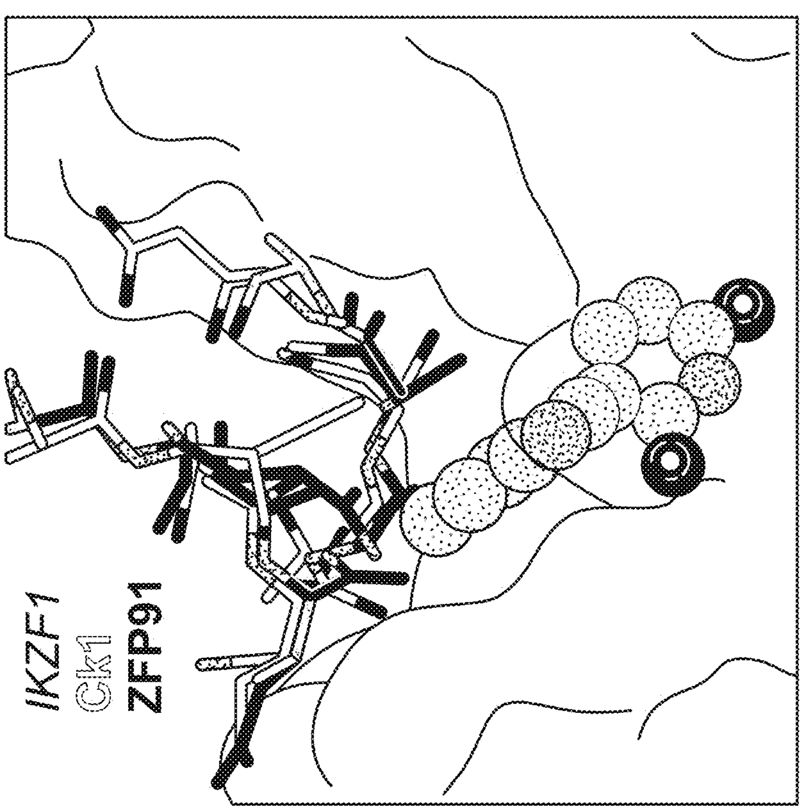
FIG. 1A is a depiction of the overlay of cereblon (CRBN)-immunomodulatory drug (IMiD) binding loop from Ck1α (PDB: 5fqd), IKZF1 (model) and ZFP91 (model).
Figure 1C:
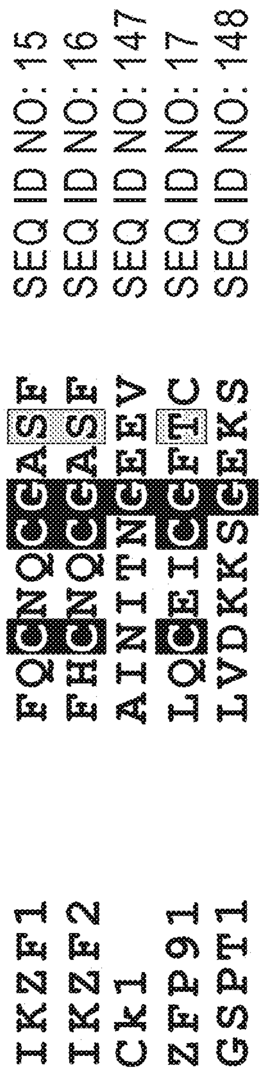
FIG. 1C is a multiple sequence alignment of the CRBN-IMiD binding region in IKZF1 (SEQ ID NO: 15), IKZF2 (SEQ ID NO: 16), Ck1α (SEQ ID NO: 147), ZFP91 IKZF2 (SEQ ID NO: 17) and GSPT1 (SEQ ID NO: 148) with essential residues highlighted. For IKZF1, Ck1α and ZFP91, the IMiD is lenalidomide (CRBN-IMiD complexes with thalidomide and pomalidomide also bind to these regions) (Petzold et al., Nature 532:127-30 (2016)), and for IKZF1, IKZF2 and GSPT1, the CM is CC-885 (Matyskiela et al., Nature 535:252-57 (2016)).
Figure 1D:
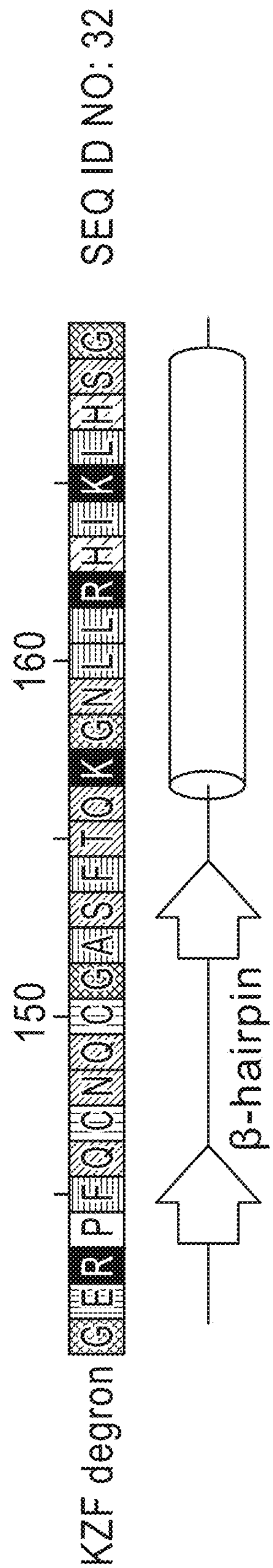
FIG. 1D shows the sequence and secondary structure of the IKZF degron tag (SEQ ID NO: 32).

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless stated otherwise, a "nucleotide sequence encoding an amino acid sequence" includes all nucleotide sequences that are degenerate versions of each other and that encode the same amino acid sequence.

The terms "peptide", "polypeptide", and "protein" are used herein consistent with their art-recognized meanings.

As used herein, the terms "peptide fragments", "protein domains", "peptide domains" and "domains" refer to amino acid sequences that are less than the full protein sequence of any protein mentioned herein. The terms "protein domains", "peptide domains" and "domains" are also more specifically used herein to refer to functional domains known in the art, e.g. zinc-finger domains, extracellular domains, intracellular domains, signaling domains, intracellular signaling domains, cytoplasmic domains and transmembrane domains.

A "vector" is a composition of matter which contains a nucleic acid and which can be used to deliver the nucleic acid to the interior of a cell. Numerous vectors are known in the art including linear polynucleotides, polynucleotides associated with ionic or amphiphilic compounds, plasmids and viruses. Thus, the term "vector" includes an autonomously replicating plasmid or a virus. The term should also be construed to include non-plasmid and non-viral compounds which facilitate transfer of nucleic acid into cells, such as, for example, polylysine compounds and liposomes. Representative examples of viral vectors include adenoviral vectors, adeno-associated virus vectors, lentivirus vectors and retroviral vectors.

Ranges: throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range including both integers and non-integers. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 etc. This applies regardless of the breadth of the range.

Degron Tags

Degron tags of the present invention are peptides generally having about 10 amino acids to about 70 amino acids, typically about 10 amino acids to about 50 amino acids, preferably about 10 amino acids to about 30 amino acids, and more preferably about 20 to about 30 amino acids. The degron tag includes a first peptide having an amino acid sequence CXXX/-X/-CG (SEQ ID NO: 1) wherein X represents any amino acid and "(X/-)" means that the position in the peptide may be any amino acid or no amino acid, provided that there are either 2 or 4 amino acid residues between the cysteins residues. The degron tag also includes a second peptide, C-terminal to the first peptide, and which has an amino acid sequence HXXX(X/-)H/C (SEQ ID NO: 2), wherein X represents any amino acid and "(X/-)" means that the position in the peptide may be any amino acid or no amino acid. The degron tag binds a complex formed between CRBN and an IMiD or between CRBN and a CM.

The first sequence may be derivable from or be at least a part of a first zinc finger region, and is referred to herein as the "β-hairpin portion" of the degron tag. The second sequence is derivable from or is at least a part of an α-helix region of a second zinc finger region, and is referred to herein as the "α-helix portion." The first and second zinc finger regions may be the same or different, provided that the degron tag binds cereblon (CRBN)-immunomodulatory drug (IMiD) or CRBN-cereblon modulator (CM). Thus, in some embodiments, the degron tag may include an entire β-hairpin loop and an entire α-helix region of the same or different zinc finger regions. Naturally occurring proteins that contain ZnF regions or domains are substrates for CRBN-IMiDs and CRBN-CMs.

Thus, degron tags of the present invention may have 100% sequence identity with a corresponding sequence in a native protein. In other embodiments, the degron tags contain at least one amino acid substitution, deletion or addition relative to the naturally occurring zinc finger region and have less than 100% sequence identity with a naturally occurring or native zinc finger region, e.g., from 70, 75, 80, 85, 90, 95, 96, 97, 98, or 99% sequence identity to a corresponding native zinc finger region, provided that the degron tag binds a CRBN-IMiD or CRBN-CM complex.

In some embodiments, the degron tag includes a β-hairpin portion of a first zinc finger region, and an α-helix portion of a second zinc finger region (wherein the ZnF's may be contained in the same or different naturally occurring proteins. Representative examples of proteins that contain zinc finger regions or domains that contain a β-hairpin loops that contain an amino acid sequence designated herein as SEQ ID NO: 1 and an α-helix region that contain the amino acid sequence designated herein as SEQ ID NO: 2 include Ikaros family zinc finger protein (IKZF)1, IKZF2, IKZF3, SALL4, ZFP91, GZF1, ZNF653, ZNF692, ZNF827, ZBTB39, WIZ and ZNF98. Representative human protein sequences of IKZF1 (SEQ ID NO:3), IKZF2 (SEQ ID NO:4), IKZF3 (SEQ ID NO:5), SALL4 (SEQ ID NO:6), ZFP91 (SEQ ID NO:7), GZF1 (SEQ ID NO:8), ZNF653 (SEQ ID NO:9), ZNF692 (SEQ ID NO:10), ZNF827 (SEQ ID NO:11), ZBTB39 (SEQ ID NO:12), WIZ (SEQ ID NO:13) and ZNF98 (SEQ ID NO:14) from which degron tags of the present invention may be derived are presented below. Zinc finger domains are indicated by capital letters; β-hairpin regions are indicated in bold and shading (which begin two residues before the second cysteine of CxxC motif and end five residues after the second cysteine), and α-helix regions are indicated in boxes (which begins at the sixth residue after the second cysteine of CxxC motif and continues to at least one residue after the second histidine in SEQ ID NO: 2).

An exemplary human IKZF1 (DNA-binding protein Ikaros; also referred to as Ikaros family zinc finger protein 1, also referred to as Lymphoid transcription factor LyF-1) amino acid sequence is set forth below (SEQ ID NO: 3; GenBank Accession No: Q13422, version 1):

```
  1 mdadegqdms qvsgkesppv sdtpdegdep mpipedlstt sggqqssksd rvvasnvkve
 61 tqsdeengra cemngeecae dlrmldasge kmngshrdqg ssalsgvggi rlpngkLKCD
121 ICGIICIGPN VLMVHKRSHt gerpFQCNQC GASFTQKGNL LRHIKLHsge kpFKCHLCNY
181 ACRRRDALTG HLRTHsvgkp HKCGYCGRSY KQRSSLEEHK ERCHnylesm glpgtlypvi
241 keetnhsema edlckigser slvldrlasn vakrkssmpq kflgdkglsd tpydssasye
301 kenemmkshv mdqainnain ylgaeslrpl vqtppggsev vpvispmyql hkplaegtpr
361 snhsaqdsav enllllskak lvpsereasp snscqdstdt esnneeqrsg liyltnhiap
421 harnglslke ehraydllra asensqdalr vvstsgeqmk vYKCEHCRVL FLDHVMYTIH
481 MGCHgfrdpF ECNMCGYHSQ DRYEFSSHIT RGEHrfhms
```

An exemplary human IKZF1 nucleic acid sequence is GenBank Accession No: NM_006060, version 6, incorporated herein by reference.

An exemplary human IKZF2 (Zinc finger protein Helios; also referred to as Ikaros family zinc finger protein 2) amino acid sequence is set forth below (SEQ ID NO: 4; GenBank Accession No: Q9UKS7, version 2):

```
  1 mdadegqdms qvsgkesppv sdtpdegdep mpipedlstt sggqqssksd rvvasnvkve
 61 tqsdeengra cemngeecae dlrmldasge kmngshrdqg ssalsgvggi rlpngkLKCD
121 ICGIICIGPN VLMVHKRSHt gerpFQCNQC GASFTQKGNL LRHIKLHsge kpFKCHLCNY
181 ACRRRDALTG HLRTHsvgkp HKCGYCGRSY KQRSSLEEHK ERCHnylesm glpgtlypvi
241 keetnhsema edlckigser slvldrlasn vakrkssmpq kflgdkglsd tpydssasye
301 kenemmkshv mdqainnain ylgaeslrpl vqtppggsev vpvispmyql hkplaegtpr
361 snhsaqdsav enllllskak lvpsereasp snscqdstdt esnneeqrsg liyltnhiap
421 harnglslke ehraydllra asensqdalr vvstsgeqmk vYKCEHCRVL FLDHVMYTIH
481 MGCHgfrdpF ECNMCGYHSQ DRYEFSSHIT RGEHrfhms
```

An exemplary human IKZF2 nucleic acid sequence is GenBank Accession No: NM_016260, version 2, incorporated herein by reference.

An exemplary human IKZF3 (Zinc finger protein Aiolos; also referred to as Ikaros family zinc finger protein 3) amino acid sequence is set forth below (SEQ ID NO: 5; GenBank Accession No: Q9UKT9, version 2):

```
  1 mediqtnael kstqeqsvpa esaavlndys ltkshemenv dsgegpaned edigddsmkv
 61 kdeyserden vlksepmgna eepeipysys reyneyenik lerhvvsfds srptsgkMNC
121 DVCGLSCISF NVLMVHKRSH tgerpFQCNQ CGASFTQKGN LLRHIKLHtg ekpFKCHLCN
181 YACQRRDALT GHLRTHsvek pYKCEFCGRS YKQRSSLEEH KERCRtflqs tdpgdtasae
241 arhikaemgs eralvldrla snvakrkssm pqkfigekrh cfdvnynssy myekeseliq
301 trmmdqainn aisylgaeal rplvqtppap tsemvpviss mypialtrae msngapqele
```

-continued

```
 361 kksihlpeks vpserglspn nsghdstdtd snheerqnhi yqqnhmvlsr arngmpllke
 421 vprsyellkp ppicprdsvk vinkegevmd vYRCDHCRVL FLDYVMFTIH MGCHgfrdpF
 481 ECNMCGYRSH DRYEFSSHIA RGEHrallk
```

An exemplary human IKZF3 nucleic acid sequence GenBank Accession No: KJ893290, version 1, incorporated herein by reference.

An exemplary human SALL4 (Sal-like protein 4; also referred to as Zinc finger protein 797) amino acid sequence is set forth below (SEQ ID NO: 6; GenBank Accession No: Q9UJQ4; version 1):

```
   1 msrrkqakpq hinseedqge qqpqqqtpef adaapaapaa gelgapvnhp gndevasede
  61 atvkrlrree thvcekccae ffsisefleh kknctknppv limndsegpv psedfsgavl
 121 shqptspgsk dchrenggss edmkekpdae svvylkteta lpptpqdisy lakgkvantn
 181 vtlqalrgtk vavnqrsada lpapvpgans ipwvleqilc lqqqqlqqiq lteqiriqvn
 241 mwashalhss gagadtlktl gshmsqqvsa avallsqkag sqglsldalk qaklphanip
 301 satsslspgl apftlkpdgt rvlpnvmsrl psallpqapg svlfqspfst valdtskkgk
 361 gkppnisavd vkpkdeaaly kHKCKYCSKV FGTDSSLQIH LRSHtgerpF VCSVCGHRFT
 421 TKGNLKVHFH RHpqvkanpq lfaefqdkva agngipyals vpdpidepsl sldskpvlvt
 481 tsvglpqnls sgtnpkdltg gslpgdlqpg pspeseggpt lpgvgpnyns praggfqgsg
 541 tpepgsetlk lqqlvenidk attdpNECLI CHRVLSCQSS LKMHYRTHtg erpFQCKICG
 601 RAFSTKGNLK THLGVHrtnt siktqHSCPI CQKKFTNAVM LQQHIRMHmg gqipntplpe
 661 npcdftgsep mtvgengstg aichddvies idveevssqe qpssssskvpt plpsihsasp
 721 tlgfammasl dapgkvgpap fnlqrqgsre ngsvesdglt ndssslmgdq eyqsrspdil
 781 ettsfqalsp ansqaesiks kspdagskae ssensrteme grsslpstfi rapptyvkve
 841 vpgtfvgpst lspgmtplla aqprrqakqH GCTRCGKNFS SASALQIHER THtgekpFVC
 901 NICGRAFTTK GNLKVHYMTH gannnsarrg rklaientma llgtdgkrvs eifpkeilap
 961 svnvdpvvwn qytsmlnggl avktneisvi qsggvptlpv slgatsvvnn atvskmdgsq
1021 sgisadvekp satdgvpkhq fphfleenki avs
```

An exemplary human SALL4 nucleic acid sequence is GenBank Accession No: NM_020436, version 4, incorporated herein by reference.

An exemplary human ZFP91 (E3 ubiquitin-protein ligase ZFP91; also referred to as RING-type E3 ubiquitin transferase ZFP91; also referred to Zinc finger protein 757) amino acid sequence is set forth below (SEQ ID NO: 7; GenBank Accession No: Q96JP5, version 1):

```
   1 mpgeteeprp peqqdqegge aakaapeepq qrppeavaaa pagttssrvl rggrdrgraa
  61 aaaaaaavsr rrkaeyprrr rsspsarppd vpgqqpqaak spspvqgkks prllciekvt
 121 tdkdpkeeke eeddsalpqe vsiaasrpsr gwrssrtsvs rhrdtentrs srsktgslql
 181 icksepntdq ldydvgeehq spggisseee eeeeeemlis eeeipfkddp rdetykphle
```

-continued 241 retpkprrks gkvkeekekk eikvevevev keeeneired eepprkrgrr rkddksprlp 301 krrkkppiqy VRCEMEGCGT VLAHPRYLQH HIKYQHllkk kYVCPHPSCG RLFRLQKQLL 361 RHAKHHtdqr dYICEYCARA FKSSHNLAVH RMIHtgekpL QCEICGFTCR QKASLNWHMK 421 KHdadsfyqF SCNICGKKFE KKDSVVAHKA KSHpevliae alaanagali tstdilgtnp 481 esltqpsdgq glpllpeplg nstsgeclll eaegmsksyc sgtervslma dgkifvgsgs 541 sggteglvmn sdilgattev liedsdsagp An exemplary human ZFP91 nucleic acid sequence is GenBank Accession No: NM_001197051, version 1, incorporated herein by reference.

An exemplary human GZF1 (GDNF-inducible zinc finger protein 1; also referred to as Zinc finger and BTB domain-containing protein 23; also referred to as Zinc finger protein 336) amino acid sequence is set forth below (SEQ ID NO: 8; GenBank Accession No: Q9H116, version 1):

1 mesgavlles ksspfnllhe mhelrllghl cdvtvsveyq gvrkdfmahk avlaatskff 61 kevflneksv dgtrtnvyln evqvadfasf lefvytakvq veedrvqrml evaeklkcld 121 lsetcfqlkk qmlesvllel qnfsesqeve vssgsqvsaa paprasvatd gphpsgltds 181 ldypgerasn gmssdlppkk skdkldkkke vvkppypkir rasgrlagrk vfveipkkky 241 trrlreqqkt aegdvgdyrc pqdqspdrvg temeqvskne gcqagaelee lskkagpeee 301 eeeeeedeeg ekkksnFKCS ICEKAFLYEK SFLKHSKHRH gvatevvYRC DTCGQTFANR 361 CNLKSHQRHV HsserhFPCE LCGKKFKRKK DVKRHVLQVH eggggerHRCG QCGKGLSSKT 421 ALRLHERTHt gdrpYGCTEC GARFSQPSAL KTHMRIHtge kpFVCDECGA RFTQNHMLIY 481 HKRCHtgerp FMCETCGKSF ASKEYLKHHN RIHtgskpFK CEVCFRTFAQ RNSLYQHIKV 541 HtgerpYCCD QCGKQFTQLN ALQRHRRIHt gerpFMCNAC GRTFTDKSTL RRHTSIHdkn 601 tpwksflviv dgspknddgh kteqpdeeyv ssklsdklls faenghfhnl aavqdtvptm 661 qenssadtac kaddsvvsqd tllattisel seltpqtdsm ptqlhslsnm e An exemplary human GZF1 nucleic acid sequence is GenBank Accession No: NM_001317012, version 1, incorporated herein by reference.

An exemplary human ZNF653 (Zinc finger protein 653; also referred to as Zinc finger protein Zip67) amino acid sequence is set forth below (SEQ ID NO: 9; GenBank Accession No: Q96CK0, version 1):

1 maeralepea eaeaeagagg eaaaeegaag rkargrprlt esdrarrrle srkkydvrrv 61 ylgeahgpwv dlrrrsgwsd aklaaylisl ergqrsgrhg kpweqvpkkp krkkrrrrnv 121 nclknvviwy edhkhrcpye phlaeldptf glyttavwqc eaghryfqdl hsplkplsds 181 dpdsdkvgng lvagssdsss sgsasdsees pegqpvkaaa aaaaatptsp vgssglitqe 241 gvhipfdvhh veslaeqgtp lcsnpagngp ealetvvcvp vpvqvgagps alfenvpqea 301 lgevvascpm pgmvpgsqvi iiagpgydal taegihlnma agsgvpgsgl geevpcamme 361 gvaaytqtep egsqpstmda tavagietkk ekedlcllkk eekeepvape lattvpesae -continued

```
421  peaeadgeel dgsdmsaiiy eipkepekrr rskrsrvmda dgllemFHCP YEGCSQVYVA
481  LSSFQNHVNL VHrkgktKVC PHPGCGKKFY LSNHLRRHMI IHsgvreFTC ETCGKSFKRK
541  NHLEVHRRTH tgetpLQCEI CGYQCRQRAS LNWHMKKHta evqynFTCDR CGKRFEKLDS
601  VKFHTLKSHp dhkpt
```

An exemplary human ZNF653 nucleic acid sequence GenBank Accession No: KJ895296, version 1, incorporated herein by reference.

An exemplary human ZNF692 (Zinc finger protein 692) amino acid sequence is set forth below (SEQ ID NO: 10; GenBank Accession No: Q9BU19, version 1):

```
  1  masspavdvs crrrekrrql darrskcrir lgghmeqwcl lkerlgfslh sqlakflldr
 61  ytssgcvlca gpeplppkgl qylvllshah srecslvpgl rgpggqdggl vwecsaghtf
121  swgpslsptp seapkpaslp httrrswcse atsgqeladl esehdertqe arlprrvgpp
181  petfpppgee egeeeednde deeemlsdas lwtyssspdd sepdaprllp spvtctpkeg
241  etppapaals splavpalsa sslssrappp aevrvqpqls rtpqaaqqte alastgsqaq
301  saptpawded taqigpkrir kaakrelMPC DFPGCGRIFS NRQYLNHHKK YQHihqksFS
361  CPEPACGKSF NFKKHLKEHM KLHsdtrdYI CEFCARSFRT SSNLVIHRRI HtgekpLQCE
421  ICGFTCRQKA SLNWHQRKHa etvaalrFPC EFCGKRFEKP DSVAAHRSKS Hpalllapqe
481  spsgplepcp sisapgplgs segsrpsasp qaptllpqq
```

An exemplary human ZNF692 nucleic acid sequence is GenBank Accession No: NM_001350072, version 1, incorporated herein by reference.

An exemplary human ZNF827 (Zinc finger protein 827) amino acid sequence is set forth below (SEQ ID NO: 11; GenBank Accession No: Q17R98, version 1):

```
  1  mprrkqeqpk rlpshvsrqe eaegelsege hwygnssetp seasygevqe nyklsledri
 61  qeqstspdts lgsttpssht lelvaldsev lrdslqcqdh lspgvsslcd ddpgsnkpls
121  snlrrlleag slkldaaata ngrvespvnv gsnlsfspps hhaqqlsvla rklaekqeqn
181  dqytpsnrfi wnqgkwlpns tttcslspds ailklkaaan avlqdksltr teetmrfesf
241  sspfssqsas stlaalskkv sersltpgqe hpppassfls lasmtssaal lkevaaraag
301  sllaekssll pedplpppps ekkpekvtpp pppppppppp pppqslelll lpvpkgrvsk
361  psnsaseees gkpFQCPICG LVIKRKSYWK RHMVIHtglk sHQCPLCPFR CARKDNLKSH
421  MKVHqhqdrg etFQCQLCPF TSSRHFSLKL HMRCHqhflr teakvkeeip dpdvkgsphl
481  sdsaclgqqr egggtelvgt mmtsntpert sqggagvspl lvkeepkedn glptsftlna
541  adrpanhtkl kdpseyvans asalfsqdis vkmasdflmk lsaanqkepm nlnfkvkeep
601  kegeslsttl prssyvfspe sevsapgvse dalkpqegkg svlrrdvsvk aasellmkls
661  aesyketqmv kikeepmevd iqdshvsisp srnvgystli grekteplqk mpegrvpper
721  nlfsqdisvk masellfqls ekvskehnht kentirttts pffsedtfrq spftsnskel
```

-continued

```
781 lpsdsvlhgr isapetekiv leagnglpsw kfndqlFPCD VCGKVFGRQQ TLSRHLSLHt

841 eerkYKCHLC PYAAKCRANL NQHLTVHsvk lvstdtediv savtsegsdg kkhpyyYSCH

901 VCGFETELNV QFVSHMSLHv dkeqwmfsIC CTACDFVTME EAEIKTHIGT KHtgedrktp

961 sesnspssss lsalsdsans kddsdgsqkn kggnnllvis vmpgsqpsln seekpekgFE

1021 CVFCNFVCKT KNMFERHLQI Hlitrm FECD VCHKFMKTPE QLLEHKKCHt vptgglnsgq

1081 w
```

An exemplary human ZNF827 nucleic acid sequence is GenBank Accession No: NM_001306215, version 1, incorporated herein by reference.

An exemplary human ZBTB39 (Zinc finger and BTB domain-containing protein 39) amino acid sequence is set forth below (SEQ ID NO: 12; GenBank Accession No: 015060, version1):

```
  1 mgmriklqst nhpnnllkel nkcrlsetmc dvtivvgsrs fpahkavlac aagyfqnlfl

 61 ntgldaarty vvdfitpanf ekvlsfvyts elftdlinvg viyevaerlg medllqachs

121 tfpdlestar akpltstses hsgtlscpsa epahplgelr gggdylgadr nyvlpsdagg

181 sykeeeknva sdanhslhlp qppppppkte dhdtpapfts ipsmmtqpll gtvstgiqts

241 tsscqpykvq sngdfsknsf ltpdnavdit tgtnsclsns ehskdpgfgq mdelqledlg

301 dddlqfedpa edigtteevi elsddsedel afgendnren kampcqvckk vlepniqlir

361 qhardhvdll tGNCKVCETH FQDRNSRVTH VLSHigiflF SCDMCETKFF TQWQLTLHRR

421 DGifenniiv hpndplpgkl glfsgaaspe lkcaacgkvl akdfhvvrgh ildhlnlkgQ

481 ACSVCDQRHL NLCSLMWHTL SHlgisvFSC SVCANSFVDW HLLEKHMAVH qsledalFHC

541 RLCSQSFKSE AAYRYHVSQH kcnsgldarp gfglqhpalq krklpaeefl geelalqgqp

601 gnskYSCKVC GKRFAHTSEF NYHRRIHtge kpYQCKVCHK FFRGRSTIKC HLKTHsgalm

661 YRCTVCGHYS STLNLMSKHV GVHkgslppd ftieqtfmyi ihskeadknp ds
```

An exemplary human ZBTB39 nucleic acid sequence is GenBank Accession No: KJ892870, version 1, incorporated herein by reference.

An exemplary human WIZ (Protein Wiz; also referred to as Widely-interspaced zinc finger-containing protein; also referred to as Zinc finger protein 803) amino acid sequence is set forth below (SEQ ID NO: 13; GenBank Accession No: 095785, version 2):

```
  1 megslagsla apdrpqgper lpgpapreni eggaeaaege ggifrstryl pvtkegprdi

611 dgrggisgt pdgrgpwehp lvqeagegil serrfedsvi vrtmkphael egsrrflhhr

121 geprllekha qgrprfdwlq dedeqgspqd aglhldlpaq ppplapfrrv fvpvedtpkt

181 ldmavvggre dledleglaq psewglptsa sevatqtwtv nseasverlq pllppirtgp

241 ylcelleeva egvaspdede deepavFPCI ECSIYFKQKE HLLEHMSQHr rapgqeppad
```

-continued 301 lapLACGECG WAFADPTALE QHRQLHqasr ekiieeiqkl kqvpgdegre arLQCPKCVF

361 GTNSSRAYVQ HAKLHmrepp gqttkepfgg ssgagspspe asallyqpyg aavglSACVF

421 CGFPAPSESL LREHVRLVHa hphweedgea yeedpasqpg tsqdahacfp dtavdyfgka 481 epslapmwre npagydpsla fgpgcqqlsi rdfplskpll hgtgqrplgr lafpstlast 541 pyslqlgrnk stvhpqglge rrrpwseeee eeeeedvvl tsemdfspen gvfsplatps 601 lipqaalelk qafrealqav eatqgqqqql rgmvpivlva klgpqvmaaa rvpprlqpee 661 lglagahpld fllldaplgg plgldtlldg dpamalkhee RKCPYCPDRF HNGIGLANHV 721 RGHlnrvgvs ynvrhfisae evkaierrfs fqkkkkvan fdpgtfslMR CDFCGAGFDT 781 RAGLSSHARA Hlrdfgitnw eltvspinil qellatsaae qppsplgrep ggppgsflts 841 rrprlpltvp fpptwaedpg paygdagslT TCEVCGACFE TRKGLSSHAR SHlrqlgvae 901 sessgapidl lyelvkqkgl pdahlglppg lakkssslke vvagaprpgl lslakpldap 961 avnkaikspp gfsakglghp pssplkktp lalagsptpk npedkspqls lsprpaspka 1021 gwpqsedegp lnltsgpepa rdIRCEFCGE FFENRKGLSS HARSHlrqmg vtewyvngsp 1081 idtlreilkr rtqsrpggpp nppgpspkal akmmggagpg sslearspsd lhisplakkl 1141 ppppgsplgh sptaspppta rkmfpglaap slpkklkpeq irveikreml pgalhgelhp 1201 segpwgapre dmtplnlssr aepvrdIRCE FCGEFFENRK GLSSHARSHl rqmgvtewsv 1261 ngspidtlre ilkkkskpcl ikkeppagdl apalaedgpp tvapgpvqsp lplsplagrp 1321 gkpgagpaqv prelsltpit gakpsatgyl gsvaakrplq edrllpaevk aktyiqtelp 1381 fkaktlhekt shssteACCE LCGLYFENRK ALASHARAHl rqfgvtewcv ngspietlse 1441 wikhrpqkvg ayrsyiqggr pftkkfrsag hgrdsdkrps lglapgglav vgrsaggepg 1501 peagraadgg erplaasppg tvkaeehqrq ninkferrqa rppdasaarg gedtndlqqk 1561 leevrqpppr vrpvpslvpr ppqtslvkfv gniytLKCRF CEVEFQGPLS IQEEWVRHLQ 1621 RHilemnfsk adpppeesqa pqaqtaaaea p An exemplary human WIZ nucleic acid sequence is GenBank Accession No: XM_005260008, version 3, incorporated herein by reference.

An exemplary human ZNF98 (Zinc finger protein 98; also referred to as Zinc finger protein 739; also referred to as Zinc finger protein F7175) amino acid sequence is set forth below (SEQ ID NO: 14; GenBank Accession No: A6NK75, version 4):

1 mpgplgslem gvltfrdval efsleewqcl dtaqqnlyrn vmlenyrnlv fvgiaaskpd 61 litcleqgke pwnvkrhemv teppvvysyf aqdlwpkqgk knyfqkvilr rykkcgrenl 121 qlrkycksmd eckvhkecyn glnqcltttq nkifqydkyv kvfhkfsnsn rhkightgkk 181 sFKCKECEKS FCMLSHLAQH KRIHsgekpY KCKECGKAYN EASNLSTHKR IHtgkkpYKC

241 EECGKAFNRL SHLTTHKIIH tgkkpYKCEE CGKAFNQSAN LTTHKRIHtg ekpYKCEECG

-continued

301 RAFSQSSTLT AHKIIHagek pYKCEECGKA FSQSSTLTTH HIIHtgekfY KCEECGKAFS

361 RLSHLTTHKR IHsgekpYKC EECGKAFKQS STLTTHKRIH agekfYKCEV CSKAFSRFSH

421 LTTHKRIHtg ekpYKCEECG KAFNLSSQLT THKIIHtgek pYKCEECGKA FNQSSTLSKH

481 KVIHtgekpY KCEECGKAFN QSSHLTTHKM IHtgekpYKC EECGKAFNNS SILNRHKMIH 541 tgeklykpes cnnacdniak iskykrncag ek An exemplary human ZNF98 nucleic acid sequence is GenBank Accession No: KJ900261, version 1, incorporated herein by reference.

Representative examples of β-hairpin portions having the amino acid sequence designated herein as SEQ ID NO: 1 and which are derivable from or at least part of a naturally occurring zinc finger region or domain include IKZF1: FQCNQCGASF (SEQ ID NO: 15), IKZF2: FHCNQCGASF (SEQ ID NO: 16), and ZFP91: LQCEICGFTC (SEQ ID NO: 17).

In some embodiments, the degron tag contains a β-hairpin portion having the amino acid sequence CXXX/-X/-CG that is present in a β-hairpin region of a first ZnF, e.g., any one of SEQ ID NOs: 3-14; and an α-helix portion having the amino acid sequence HXXX(X/-)H (SEQ ID NO: 2), that is present in an α-helix region of a second ZnF, e.g., any one of SEQ ID NOs: 3-14, wherein the first and second ZnF domains may be the same or different.

One such example is IKZF1 (Δ1-82/Δ197-238/Δ256-519): RMLDASGEKMNGSHRDQGSSALSGVGGIRLPNGKLKCDICGIICIGPNVLMVHKRSHTGERPFQCNQCGASFTQKGNLLRHIKLHSGEKPFKCIILCNYACRRRDALTGIILRTHSVIKE ETNIISEMAEDLCK (SEQ ID NO: 18). This degron tag contains a β-hairpin portion and an α-helix portion of each of ZnF1, ZnF2 and ZnF3 of the IKZF1 protein designated herein as SEQ ID NO: 1.

Additional examples of such degron tags include GERPFQCNQCGASFTTKGNLKVHFHRHPQVKAN (SEQ ID NO: 19) which contains a β-hairpin portion derivable from or which is contained in IKZF1 (SEQ ID NO: 3) and an α-helix portion derivable from or which is contained in SALL4 (SEQ ID NO: 6); GERPFVCSVCGHRFTQKGNLLRHIKLHS (SEQ ID NO: 20) which contains a β-hairpin portion derivable from or which is contained in SALL4 (SEQ ID NO: 6) and an α-helix portion derivable from or which is contained in IKZF1 (SEQ ID NO: 3); GEKPLQCEICGFTCRQKGNLLRHIKLHS (SEQ ID NO: 21) which contains a β-hairpin portion derivable from or which is contained in ZFP91 (SEQ ID NO: 7) and an α-helix portion derivable from or which is contained in IKZF1 (SEQ ID NO: 3); GERPFQCNQCGASFTQKASLNWHMKKH (SEQ ID NO: 22) which contains a β-hairpin portion derivable from or which is contained in IKZF1 (SEQ ID NO: 3) and an α-helix portion derivable from or which is contained in ZFP91 (SEQ ID NO: 7); GERPFVCSVCGHRFTQKASLNWHMKKH (SEQ ID NO: 23) which contains a β-hairpin portion derivable from or which is contained in SALL4 (SEQ ID NO: 6) and an α-helix portion derivable from or which is contained in ZFP91 (SEQ ID NO: 7); and GEKPLQCEICGFTCRTKGNLKVHFHRHPQVKAN (SEQ ID NO: 24) which contains a β-hairpin portion derivable from or which is contained in ZFP91 (SEQ ID NO: 7) and an α-helix portion derivable from or which is contained in SALL4 (SEQ ID NO: 6).

Further representative examples of degron tags of the present invention (further identified by corresponding naturally occurring zinc finger domains) include: GERPFQCNQCGASFTQKGNLLRHIKLHS (SEQ ID NO: 25) (1KZF1/3 ZnF2), RSHTGERPFVCSVCGHRFTTKGNLKVHFHRHPQVKAN (SEQ ID NO: 26)(SALL4 ZnF2), ALYKHKCKYCSKVFGTDSSLQIHLRSHTGERPFVCSVCGHRFTTKGNLKVHFHRHPQVK AN (SEQ ID NO: 27)(SALL4 ZnF1-2), MHYRTHTGERPFQCKICGRAFSTKGNLKTHLGVHRTNTSIKTQ (SEQ ID NO: 28) (SALL4 ZnF4), GEKPLQCEICGFTCRQKASLNWIIMKKH (SEQ ID NO: 29)(ZFP91 ZnF4), FQCNQCGASFTQKGNLLRIIIKLHSG (SEQ ID NO: 30)(IKZF1/3 ZnF2), GERPFQCNQCGASFTQKGNLLRHIKLHSGEKPFKCHLCNYACRRRDALTGHLRTHS (SEQ ID NO: 31)(IKZF1/3 ZnF2-3) and GERPFQCNQCGASFTQKGNLLRHIKLHSG (SEQ ID NO: 32)(IKZF).

Yet further representative degron tag sequences of the present invention may be represented by the sequence XXCXXCGXXXXXXXXXXXHXXX(X/-)(H/C) (SEQ ID NO: 33), wherein X represents any amino acid residue. The following degron tags include SEQ ID NO:33:

>IKZF2|140-162: (SEQ ID NO: 34)
FHCNQCGASFTQKGNLLRHIKLH

>GZF1|348-371: (SEQ ID NO: 35)
YRCDTCGQTFANRCNLKSHQRHVH

>GZF1|377-400: (SEQ ID NO: 36)
FPCELCGKKFKRKKDVKRHVLQVH

>GZF1|407-429: (SEQ ID NO: 37)
HRCGQCGKGLSSKTALRLHERTH

>GZF1|435-457: (SEQ ID NO: 38)
YGCTECGARFSQPSALKTHMRIH

>GZF1|463-485: (SEQ ID NO: 39)
FVCDECGARFTQNHMLIYHKRCH

>GZF1|491-513: (SEQ ID NO: 40)
FMCETCGKSFASKEYLKHHNRIH

>GZF1|1547-569: (SEQ ID NO: 41)
YCCDQCGKQFTQLNALQRHRRIH

-continued

>GZF1|575-597: (SEQ ID NO: 42)
FMCNACGRTFTDKSTLRRHTSIH

>IKZF3|146-168: (SEQ ID NO: 43)
FQCNQCGASFTQKGNLLRHIKLH

>IKZF3|118-140: (SEQ ID NO: 44)
MNCDVCGLSCISFNVLMVHKRSH

>IKZF3|202-224: (SEQ ID NO: 45)
YKCEFCGRSYKQRSSLEEHKERC

>IKZF1|145-167: (SEQ ID NO: 46)
FQCNQCGASFTQKGNLLRHIKLH

>IKZF1|117-139: (SEQ ID NO: 47)
LKCDICGIICIGPNVLMVHKRSH

>IKZF1|201-224: (SEQ ID NO: 48)
HKCGYCGRSYKQRSSLEEHKERCH

>SALL4|410-432: (SEQ ID NO: 49)
FVCSVCGHRFTTKGNLKVHFHRH

>SALL4|594-616: (SEQ ID NO: 50)
FQCKICGRAFSTKGNLKTHLGVH

>SALL4|870-892: (SEQ ID NO: 51)
HGCTRCGKNFSSASALQIHERTH

>SALL4|898-920: (SEQ ID NO: 52)
FVCNICGRAFTTKGNLKVHYMTH

>ZNF653|528-550: (SEQ ID NO: 53)
FTCETCGKSFKRKNHLEVHRRTH

>ZNF653|556-578: (SEQ ID NO: 54)
LQCEICGYQCRQRASLNWHMKKH

>ZNF653|586-609: (SEQ ID NO: 55)
FTCDRCGKRFEKLDSVKFHTLKSH

>ZFP91|400-422: (SEQ ID NO: 56)
LQCEICGFTCRQKASLNWHMKKH

>ZFP91|430-453: (SEQ ID NO: 57)
FSCNICGKKFEKKDSWAHKAKSH

>ZNF692|417-439: (SEQ ID NO: 58)
LQCEICGFTCRQKASLNWHQRKH

>ZNF692|448-471: (SEQ ID NO: 59)
FPCEFCGKRFEKPDSVAAHRSKSH

>ZNF827|374-396: (SEQ ID NO: 60)
FQCPICGLVDCRKSYWKRHMVIH

>ZNF827|817-839: (SEQ ID NO: 61)
FPCDVCGKVFGRQQTLSRHLSLH

-continued

>ZNF827|897-919: (SEQ ID NO: 62)
YSCHVCGFETELNVQFVSHMSLH

>ZBTB39|605-627: (SEQ ID NO: 63)
YSCKVCGKRFAHTSEFNYHRRIH

>ZBTB39|661-683: (SEQ ID NO: 64)
YRCTVCGHYSSTLNLMSKHVGVH

>WIZ|769-791: (SEQ ID NO: 65)
MRCDFCGAGFDTRAGLSSHARAH

>WIZ|304-326: (SEQ ID NO: 66)
LACGECGWAFADPTALEQHRQLH

>WIZ|870-892: (SEQ ID NO: 67)
TTCEVCGACFETRKGLSSHARSH

>ZNF827|897-919: (SEQ ID NO: 62)
YSCHVCGFETELNVQFVSHMSLH

>ZBTB39|605-627: (SEQ ID NO: 63)
YSCKVCGKRFAHTSEFNYHRRIH

>ZBTB39|661-683: (SEQ ID NO: 64)
YRCTVCGHYSSTLNLMSKHVGVH

>WIZ|769-791: (SEQ ID NO: 65)
MRCDFCGAGFDTRAGLSSHARAH

>WIZ|304-326: (SEQ ID NO: 66)
LACGECGWAFADPTALEQHRQLH

>WIZ|870-892: (SEQ ID NO: 67)
TTCEVCGACFETRKGLSSHARSH

>ZNF98|210-232: (SEQ ID NO: 68)
YKCKECGKAYNEASNLSTHKRIH

>ZNF98|238-260: (SEQ ID NO: 69)
YKCEECGKAFNRLSHLTTHKIIH

>ZNF98|266-288: (SEQ ID NO: 70)
YKCEECGKAFNQSANLTTHKRIH

>ZNF98|322-344: (SEQ ID NO: 71)
YKCEECGKAFSQSSTLTTHKIIH

>ZNF98|350-372: (SEQ ID NO: 72)
YKCEECGKAFSRLSHLTTHKRIH

>ZNF98|378-400: (SEQ ID NO: 73)
YKCEECGKAFKQSSTLTTHKRIH

>ZNF98|434-456: (SEQ ED NO: 74)
YKCEECGKAFNLSSQLTTHKIIH

>ZNF98|462-484: (SEQ ID NO: 75)
YKCEECGKAFNQSSTLSKHKVIH

-continued

>ZNF98|490-512:

(SEQ ID NO: 76)
YKCEECGKAFNQSSHLTTHKMIH

>ZNF98|518-540:

(SEQ ID NO: 77)
YKCEECGKAFNNSSILNRHKMIH

An alignment of SEQ ID NOs: 34-77 is shown in FIG. 11.

In some embodiments, the degron tag has the sequence XXCXXCGXXXXXXXXXXXHXXXH (SEQ ID NO: 78). Examples of specific degron tags embraced by SEQ ID NO: 78 include SEQ ID NOs: 34, 37-44, 46, 47, 49-54, 56, 58 and 60-77.

In some embodiments, the degron tag has the sequence XXCXXCGXXXXXXXXXXXIIXXXXH (SEQ ID NO: 79). Examples of specific degron tags defined by SEQ ID NO: 79 include SEQ ID NOs: 36, 37, 48, 55, 57, and 59.

In some embodiments, the degron tag has the sequence XXCXXCGXXXXXXXLXXHXXXH (SEQ ID NO: 80). Examples of specific degron tags defined by SEQ ID NO: 80 include SEQ ID NOs: 34, 37-44, 46, 47, 49-54, 56, 58, 61 and 65-77.

In some embodiments, the degron tag has the sequence XXCXXCGXXXXXXXLXXHXXXXII (SEQ ID NO: 81). Examples of specific degron tags defined by SEQ ID NO: 81 include SEQ ID NOs: 35 and 48.

In some embodiments, the degron tag has the sequence XXCXXCGXXFXXXXLXXHXXXH (SEQ ID NO: 82). Examples of specific degron tags defined by SEQ ID NO: 82 include SEQ ID NOs: 34, 38-43, 46, 49-53, 61, 65-67 and 69-77.

In some embodiments, the degron tag has the sequence XXCXXCGXXFXXXXLXXHXXXXH (SEQ ID NO: 83). An example of a specific degron tag defined by SEQ ID NO: 83 is SEQ ID NO: 35.

Figure 15A:
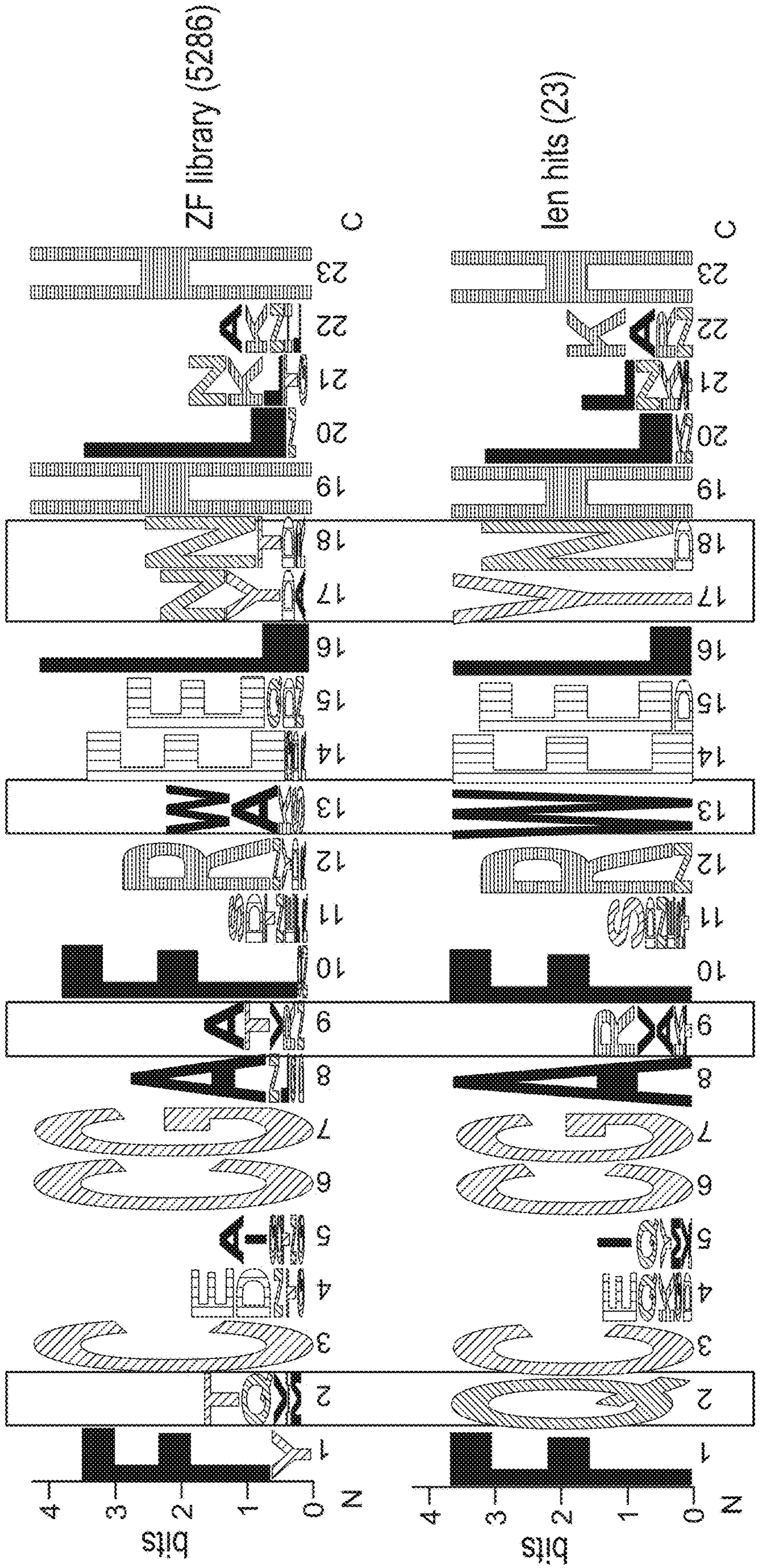
FIG. 15A is an image of logo plot sequence features of the unselected library and 23 ZFs significantly enriched in the GFPnegative gate with lenalidomide.

Yet further representative examples of degron tags are set forth in FIG. 15A-FIG. 15B and Tables 1-4 in the working examples. The first two sequences in FIG. 15B are controls: a fragment of the naturally occurring protein IKZF3, and a previously described hybrid of the naturally occurring proteins ZFP91 and IKZF3, respectively. The following sequences are "variants" derived from the Rosetta screen. In FIG. 15B, amino acids that match IKZF3 are denoted as "-", and those that mismatch are denoted with their amino acid code.

In some embodiments, the degron tag is a variant of a naturally occurring sequence such as in a human zinc finger domain. As used herein, a "variant" refers to a degron tag that contains a substitution, deletion, or addition of at least one amino acid relative to a naturally occurring sequence, provided that the variant substantially retains the same function as the corresponding naturally occurring sequence, which in the context of the present invention means that the variant is a substrate for a CRBN-IMiD complex or a CRBN-CM complex. The amino acid substitution, addition or deletion may be present in the portion of a degron tag derived from a β-hairpin, an α-helix, or both. As used herein, "variant" also includes degron tags that may be derived from species other than human, e.g. mouse, drosophila, chicken, non-human primate, etc. Degron tags disclosed above and which contain non-contiguous sequences and/or β-hairpin portions from a first protein and an α-helix portion from a second, different protein are examples of degron tags that are variants.

Additional representative examples of degron tags that are variants of naturally occurring sequences (e.g., and which contain at least one amino acid substitution) include SALL4 ZnF1-2 (S388N): ALYKHKCKYCNKVFGTDSSLQIHLRSHTGERPFVCSVCGHRFTTKGNLKVIIFIIRHPQVKAN (SEQ ID NO: 84), SALL4 ZnF4 (G600A): MHYRTHTGERPFQCKICARAFSTKGNLKTHLGVHRTNTSIKTQ (SEQ ID NO: 85) and SALL4 ZnF4 (G600N): MHYRTHTGERPFQCKICNRAFSTKGNLKTHLGVHRTNTSIKTQ (SEQ ID NO: 86).

Representative examples of degron tags that are variants of sequences in mouse and drosophila proteins include mmSALL4 ZnF2: RSHTGERPYVCPICGHRFTTKGNLKVHLQRHPEVK (SEQ ID NO: 87) and drSALL4 ZnF2: RSHTGERPFKCNICGNRFTTKGNLKVHFQRHKEKY (SEQ ID NO: 88), respectively.

In some embodiments, the degron tag is a variant of a zinc finger region or domain of IKZF1, and may be represented by the sequence XXXPXXCXXCGAXX- XRXXELX-XHLXXXXG (SEQ ID NO: 89), wherein X represents any amino acid residue. Representative examples of degron tags embraced by SEQ ID NO:89 are as follows:

(SEQ ID NO: 90)
RKRPFTCDSCGAAFDRAEELNNHLNAHTG;

(SEQ ID NO: 91)
RKRPFQCDRCGAAFDRAEELNNHLNAHTG (SEQ ID NO: 92)
RERPFQCDACGAAYDRAEELNNHLNAHTG (SEQ ID NO: 93)
RERPYQCDACGAAFDRAEELNNHLNAHSG (SEQ ID NO: 94)
RERPFQCDSCGAAFDRAEELNNHLNAHTG (SEQ ID NO: 95)
RKRPFQCDACGAAFDRSKELNDHLNAHTG (SEQ ID NO: 96)
RKRPFQCDSCGAAFNRSKELNDHLNAHTG (SEQ ID NO: 97)
RERPFMCDACGAAFNRSKELNDHLNAHSG (SEQ ID NO: 98)
RERPFQCDACGAAFDRAEELNDHLNKHTG (SEQ ID NO: 99)
RERPFVCTSCGAAFDRAEELNNHLNAHTG (SEQ ID NO: 100)
RERPFTCTACGAAFNRAEELNNHLNAHTG (SEQ ID NO: 101)
RERPFVCEMCGAAFDRAEELNNHLNAHTG (SEQ ID NO: 102)
RELPYVCDMCGAAFDRAEELNNHLNAHTG (SEQ ID NO: 103)
RERPFQCESCGAAFDRAEELNNHLNAHTG (SEQ ID NO: 104)
REMPYQCESCGAAFDRAEELNNHLNAHTG (SEQ ID NO: 105)
RERPFQCEYCGAAFDRAEELNNHLNALTG (SEQ ID NO: 106)
RERPFQCQYCGAAFDRAEELNNHLKNHTG

-continued (SEQ ID NO: 107)
REAPFQCESCGARFNRAEELNNHLNRHTG (SEQ ID NO: 108)
REAPFQCESCGARFNRAEELNNHLNNHTG (SEQ ID NO: 109)
RELPFQCESCGARFERAEELNYHLNVHTG (SEQ ID NO: 110)
XEMPFQCESCGARFNRAEELNNHLNAHTG (SEQ ID NO: 111)
REMPFQCESCGARFNRAEELNNHLNAHTG (SEQ ID NO: 112)
REMPFQCDSCGARFNRAEELNTHLNAHTG (SEQ ID NO: 113)
RKAPFQCDVCGARFNRAEELNYHLNTLTG (SEQ ID NO: 114)
REAPFQCDVCGARFNRAEELNYHLNLLTG (SEQ ID NO: 115)
RKTPFQCEVCGARFNRAEELNYHLNLLTG (SEQ ID NO: 116)
RKAPFQCEVCGARFNRAEELNTHLNILTG (SEQ ID NO: 117)
RKAPFQCEVCGARFNRAEELNTHLNILKG (SEQ ID NO: 118)
RKTPFQCDICGARFNRAEELNTHLNILTG (SEQ ID NO: 119)
RKIPFQCDVCGARFNRAEELNTHLNILTG (SEQ ID NO: 120)
RKAPFQCDVCGARFNRAEELNTHLNALTG (SEQ ID NO: 121)
RKAPFQCDVCGARFNRAEELNNHLNRLTG (SEQ ID NO: 122)
RKRPFQCEVCGARFNRAEELNNHLNALTG (SEQ ID NO: 123)
RKAPFQCEVCGARFNRAEELNNHLNALLG (SEQ ID NO: 124)
RERPFQCEVCGARFNRAEELNNHLNALTG (SEQ ID NO: 125)
RERPFQCEVCGARFNRAEELNNHLNALTG (SEQ ID NO: 126)
REAPFQCEVCGARFNRAEELNNHLNALTG (SEQ ID NO: 127)
RKAPFQCESCGARFNRWEELATHLNAHTG (SEQ ID NO: 128)
REAPFQCEMCGARFNRWEELASHLNAHTG (SEQ ID NO: 129)
RKMPFQCEVCGARFNRWEELANHLNALTG (SEQ ID NO: 130)
RKAPFQCDVCGARFNRKEELDDHLNKLTG (SEQ ID NO: 131)
REAPFQCDVCGARFNRKEELDTHLTKLTG (SEQ ID NO: 132)
REAPFQCEVCGARFNRKEELDNHLNNLTG (SEQ ID NO: 133)
REAPFQCDACGARFNRKEELDNHLNAHTG -continued (SEQ ID NO: 134)
REAPFQCDSCGARFNRAEELNNHLNAHTG (SEQ ID NO: 135)
REAPFQCDSCGARFNRAEELNNHLNAHTG (SEQ ID NO: 136)
REAPFQCDSCGARFNRAEELNNHLNAHTG (SEQ ID NO: 137)
REAPFQCDACGARFNRAEELNNHLNAHTG (SEQ ID NO: 138)
REAPFQCDACGARFNRAEELNNHLNAHTG (SEQ ID NO: 139)
REAPFQCEACGARFNRAEELNNHLNAHTG An alignment of SEQ ID NOs: 90-139 is shown in FIG. 10.

In some embodiments, the degron tag has the sequence R/XXXPFXCXXCGAXFXRXEELXXHLNXXTG (SEQ ID NO: 140). Examples of specific degron tags embraced by SEQ ID NO: 140 include: SEQ ID NOs: 90, 91, 94, 98-101, 103, 105, 107-116, 118-122, 124-130, and 132-139.

In some embodiments, the degron tag has the sequence R/XXXPFQCXXCGAXFXRAEELNXHLNXXTG (SEQ ID NO: 141). Examples of specific degron tags embraced by SEQ ID NO: 141 include: SEQ ID NOs: 91, 94, 98, 103, 105, 107, 108, 110-116, 118-122, 124-126 and 134-139.

In some embodiments, the degron tag has the sequence R/XXXPFQCXXCGAXFNRAEELNXHLNXXTG (SEQ ID NO: 142). Examples of specific degron tags embraced by SEQ ID NO: 142 include: SEQ ID NOs: 107, 108, 110-116, 118-122, 124-126 and 134-139. Degron tags having the amino acid sequences designated as SEQ ID NOs: 89-142 may be particularly suited for use in combination with the IMiD pomalidomide (commercially available under the tradename POMALYST®).

As disclosed above, the degron tags may include one or more amino acid residues N-terminal with respect to the β-hairpin portion, one or more amino acid residues between the β-hairpin portion and the α-helix portion, and one or more amino acid residues C-terminal with respect to the α-helix portion provided that the degron tag is a substrate for a CRBN-IMiD complex or a CRBN-CM complex. These additional amino acids may correspond to residues in the native zinc finger domains or be different provided that the degron tag maintains a zinc finger-like fold and exhibits the requisite binding properties as disclosed herein. In certain embodiments, e.g., with tags derived from IKZF1, the tags include a spacer of at least about 11 to about 12, 13, 14 or 15 amino acid residues between the β-hairpin portion and the α-helix portion and which contains at least one leucine residue, which is conserved across a large part of C2H2 zinc finger domains.

An example of such a spacer is shown in the following sequence: FQCNQCGASFTQKGNLLRHIKLHSG (SEQ ID NO: 30) (IKZF1/3 ZnF2).

Figure 22:
FIG. 22 is a schematic diagram of SEQ ID NO: 144.

In some embodiments, the degron tag may be a 27-mer peptide having the sequence: X E/K/V/T X P/A/K F/Y Q/V/T/K/R C E/D/Q V/I/S/Y/A C G A A/R/V/N/T F $X^{15}$ $X^{16}$ $X^{17}$ $X^{18}$ $X^{19}$ L $X^{21}$ $X^{22}$ H $X^{24}$ $X^{25}$ X II (SEQ ID NO: 143), wherein $X^5$ is N/D/S/E/K or another amino acid residue that imparts improved solubility; $X^{16}$ is R or Y or another amino acid residue that imparts improved solubility; $X^{17}$ is W/A/S or another amino acid residue that imparts improved solubility; $X^{18}$ is E or another amino acid residue that imparts improved solubility; $X^{19}$ is E or Q or another amino acid residue that imparts improved solubility; $X^{21}$ is N or Y or another amino acid residue that imparts improved solubility; $X^{22}$ is N/T/D/W or another amino acid residue that imparts improved solubility; $X^{24}$ is L or another amino acid residue that imparts improved solubility; $X^{25}$ is N/L/K/S/T or another amino acid residue that imparts improved solubility. An example is SEQ ID NO: 144 as shown in FIG. 22.

Fusion Proteins Containing Degron Tags

Genetically modified cells carry an inherent and potentially life-long hazard of cancerous transformations. Stem cells administered to regenerate tissues damaged by disease or treatment, correct congenital malformations, or rejuvenate aging tissues may have unknown risks (Mavroudi et al., J. Cancer Res. Ther. 2:22-33 (2014)). Likewise there could be unintended consequences from administering autologous cells modified ex vivo to act as in-patient factories to produce biological molecules, such as insulin, to alleviate the need for repeated injections (Sanlioglu et al., Expert Rev. Mol. Med. 14:e18 (2012)).

Safety switches (e.g., suicide genes) are of particular value in therapies dependent upon long-lived and/or proliferating cells. Moreover, suicide genes should be considered an adjunct to any clinical gene therapy in order to exploit their dual safety and monitoring functions. Many factors govern which suicide gene system is optimal. Among these are the anticipated urgency to rid a patient of the cells, whether it is better to be able to leave non-proliferating genetically modified cells intact or to kill all transduced cells, the overall potency of a particular system, the importance of bystander-cell killing, and immunogenicity.

The ability to degrade a particular endogenous protein of interest by creating POI-degron tag fusions and administering an IMiD or CM can be used to treat disorders wherein expression of a protein above certain threshold levels within the cell leads to a diseased state. Other applications of this technology include 1) targeted degradation of proteins where pathology is a function of gain of function mutation(s), 2) targeted degradation of proteins where pathology is a function of amplification or increased expression, 3) targeted degradation of proteins that are manifestations of monogenetic disease, 4) targeted degradation of proteins where genetic predisposition manifests over longer periods and often after alternative biological compensatory mechanisms are no longer adequate, for example, but not limited to, hypercholesterolemia and proteinopathies. In addition, POI-degron tag fusions can be used to evaluate the function of an endogenous protein or validate an endogenous protein as a target for therapy of a disease state.

Accordingly, the degron tags of the present invention can be utilized to produce a stably expressed endogenous protein-degron tag fusion protein or exogenous protein-degron tag fusion protein. Endogenous proteins originate within an organism, tissue or cell and is expressed by that same organism, tissue or cell, whereas exogenous proteins originate outside of an organism, tissue or cell and are introduced into the organism, tissue or cell.

Chimeric Antigen Receptor (CAR)-Degron Tag Fusions

Genetically modified T cells expressing chimeric antigen receptors (CAR-T therapy) have shown to have therapeutic efficacy in a number of cancers, including lymphoma (Till et al., Blood 119:3940-50 (2012)), chronic lymphocytic leukemia (Porter et al., N. Engl. J. Med. 365:725-33 (2011)), acute lymphoblastic leukemia (Grupp et al., N. Engl. J. Med. 368:1509-18 (2013)) and neuroblastoma (Louis et al., Blood 118:6050-56 (2011)). Two autologous CAR-T cell therapies (Kymriah™ and Yescarta™) have been approved by the FDA. In common, both are CD19-specific CAR-T cell therapies lysing CD19-positive targets (normal and malignant B lineage cells).

CAR-T therapy is not, however, without significant side effects. Although most adverse events with CAR-T are tolerable and acceptable, the administration of CAR-T cells has, in a number of cases, resulted in severe systemic inflammatory reactions, including cytokine release syndrome and tumor lysis syndrome (Xu et al., Leukemia Lymphoma 54:255-60 (2013)).

Cytokine release syndrome (CRS) is an inflammatory response clinically manifesting with fever, nausea, headache, tachycardia, hypotension, hypoxia, as well as cardiac and/or neurologic manifestations. Severe cytokine release syndrome is described as a cytokine storm, and can be fatal. CRS is believed to be a result of the sustained activation of a variety of cell types such as monocytes and macrophages, T cells and B cells, and is generally characterized by an increase in levels of TNFα and IFNγ within 1 to 2 hours of stimulus exposure, followed by increases in interleukin (IL)-6 and IL-10 and, in some cases, IL-2 and IL-8 (Doessegger et al., Nat. Clin. Transl. Immuno. 4:e39 (2015)).

Tumor lysis syndrome (TLS) is a metabolic syndrome that is caused by the sudden killing of tumor cells with chemotherapy, and subsequent release of cellular contents with the release of large amounts of potassium, phosphate, and nucleic acids into the systemic circulation. Catabolism of the nucleic acids to uric acid lease to hyperuricemia; the marked increase in uric acid excretion can result in the precipitation of uric acid in the renal tubules and renal vasoconstriction, impaired autoregulation, decreased renal flow, oxidation, and inflammation, resulting in acute kidney injury. Hyperphosphatemia with calcium phosphate deposition in the renal tubules can also cause acute kidney injury. High concentrations of both uric acid and phosphate potentiate the risk of acute kidney injury because uric acid precipitates more readily in the presence of calcium phosphate and vice versa that results in hyperkalemia, hyperphosphatemia, hypocalcemia, uremia, and acute renal failure. It usually occurs in patients with bulky, rapidly proliferating, treatment-responsive tumors (Wintrobe et al., "Complications of hematopoietic neoplasms" Wintrobe's Clinical Hematology, $11^{th}$: ed., Lippincott Williams & Wilkins, Vol. II, 1919-44 (2003)).

The dramatic clinical activity of CAR-T cell therapy presents a need to implement safety strategies to rapidly reverse or abort the T cell responses in patients undergoing CRS or associated adverse events.

Accordingly, the present invention includes fusion proteins that contain a CAR and at least one degron tag. The CARs of the present invention are further characterized in that they include an extracellular ligand binding domain capable of binding to an antigen, a transmembrane domain, and an intracellular domain in this order from the N-terminal side, wherein the intracellular domain includes at least one signaling domain. The degron tag(s) can be located at the N-terminus or between the extracellular binding domain and the transmembrane domain, provided that there is no disruption to antigen binding or insertion into the membrane. Similarly, degron tag(s) can be located at the C-terminus, between the transmembrane domain and the intracellular domain or between signaling domains when more than one is present, provided that there is no disruption of intracellular signaling or insertion into the membrane. The degron tag is preferably located at the C-terminus.

In one embodiment, the fusion protein includes a CAR which is tisagenlecleucel (Kymriah™) and a degron tag. Tisagenlecleucel is genetically modified, antigen-specific, autologous T cells that target CD19. The extracellular domain of the CAR is a murine anti-CD19 single chain antibody fragment (scFv) from murine monoclonal FMC63 hybridoma. The intracellular domain of the CAR is a T cell signaling domain derived from human CD3 and a co-stimulatory domain derived from human 4-1BB (CD137). The transmembrane domain and a spacer, located between the scFv domain and the transmembrane domain, are derived from human CD8α. Kymriah™ (tisagenlecleucel) is approved for the treatment of patients up to 25 years of age with B-cell precursor acute lymphoblastic leukemia (ALL) that is refractory or in relapse (R/R) and for the treatment of adults with R/R diffuse large B-cell lymphoma (DLBCL), the most common form of non-Hodgkin's lymphoma, as well as high grade B-cell lymphoma and DLBCL arising from follicular lymphoma. The degron tag may be any of the degron tags disclosed herein under the section entitled "Degron Tags".

In one embodiment, the fusion protein includes a CAR which is axicabtagene ciloleucel (Yescarta™) and a degron tag. Axicabtagene ciloleucel is genetically modified, antigen-specific, autologous T cells that target CD19. The extracellular domain of the CAR is a murine anti-CD19 single chain antibody fragment (scFv). The intracellular domain of the CAR is two signaling domains, one derived from human CD3(and one derived from human CD28. Yescarta™ (axicabtagene ciloleucel) is approved for the treatment of adults with RJR large B cell lymphoma including DLBCL not otherwise specified, primary mediastinal large B-cell lymphoma, high grade B-cell lymphoma, and DLBCL arising from follicular lymphoma. The degron tag may be any of the degron tags disclosed herein under the section entitled "Degron Tags".

The nucleic acid encoding the fusion protein containing the CAR and the degron tag can be easily prepared based on their respective amino acid sequences in accordance with conventional methods. For example, a base sequence encoding an amino acid sequence can be readily obtained from, for example, the aforementioned amino acid sequences or publicly available reference sequences, for example, NCBI RefSeq IDs or accession numbers of GenBank, for an amino acid sequence of each domain, and the nucleic acid of the present invention can be prepared using a standard molecular biological and/or chemical procedure. RefSeq IDs for commonly used CAR domains are known in the art, for example, U.S. Pat. No. 9,175,308 (which is incorporated herein by reference) discloses a number of specific amino acid sequences particularly used as CAR transmembrane and intracellular signaling domains. As one example, based on the base sequence, a nucleic acid can be synthesized, and the nucleic acid of the present invention can be prepared by combining DNA fragments which are obtained from a cDNA library using a polymerase chain reaction (PCR).

Immune effector cells expressing the CAR of the present invention can be engineered by introducing the nucleic acid encoding a CAR described above into a cell. In one embodiment, the step is carried out ex vivo. For example, a cell can be transformed ex vivo with a vector carrying the nucleic acid of the present invention to produce a cell expressing the CAR of the present invention.

Representative examples of immune effector cells include cytotoxic lymphocytes, T-cells, cytotoxic T-cells, T helper cells, Th17 T-cells, natural killer (NK) cells, natural killer T (NKT) cells, mast cells, dendritic cells, killer dendritic cells, or B cells derived from a mammal, for example, a human cell, or a cell derived from a non-human mammal such as a monkey, a mouse, a rat, a pig, a horse, or a dog. For example, a cell collected, isolated, purified or induced from a body fluid, a tissue or an organ such as blood (peripheral blood, umbilical cord blood etc.) or bone marrow can be used. A peripheral blood mononuclear cell (PBMC), an immune cell (a dendritic cell, a B cell, a hematopoietic stem cell, a macrophage, a monocyte, a NK cell or a hematopoietic cell (a neutrophil, a basophil)), an umbilical cord blood mononuclear cell, a fibroblast, a precursor adipocyte, a hepatocyte, a skin keratinocyte, a mesenchymal stem cell, an adipose stem cell, various cancer cell strains, or a neural stem cell can be used. In the present invention, use of a T-cell, a precursor cell of a T-cell (a hematopoietic stem cell, a lymphocyte precursor cell etc.) or a cell population containing them is preferable. Representative examples of T-cells include CD8-positive T-cells, CD4-positive T-cells, regulatory T-cells, cytotoxic T-cells, and tumor infiltrating lymphocytes. The cell population containing a T-cell and a precursor cell of a T-cell includes a PBMC. The aforementioned cells may be collected from a living body, obtained by expansion culture of a cell collected from a living body, or established as a cell strain. When transplantation of the produced CAR-expressing cell or a cell differentiated from the produced CAR-expressing cell into a living body is desired, it is preferable to introduce the nucleic acid into a cell collected from the living body itself or a conspecific living body thereof. Thus, the immune effector cells may be autologous or allogeneic.

The immune effector cells expressing the fusion protein containing the CAR and the degron tag can be used as a therapeutic agent for a disease. The therapeutic agent can be the cell expressing the CAR as an active ingredient, and may further include a suitable excipient. The disease against which the cell expressing the CAR is administered is not limited as long as the disease shows sensitivity to the transformed immune effector cells. Representative examples of diseases treatable with immune effector cells expressing nucleic acids encoding fusion proteins containing the CAR and a degron tag include cancer (blood cancer (leukemia), solid tumor, etc.), inflammatory disease/autoimmune disease (asthma, eczema), hepatitis, and infectious disease, e.g., the cause of which is a virus such as influenza and HIV, a bacterium, or a fungus, for example, tuberculosis, MRSA, VRE, and deep mycosis. The transformed immune effector cells bind to an antigen presented by a target cell that is desired to be decreased or eliminated for treatment of the aforementioned diseases, that is, a tumor antigen, a viral antigen, a bacterial antigen or the like is administered for treatment of these diseases. The cell of the present invention can also be utilized for prevention of an infectious disease after bone marrow transplantation or exposure to radiation, donor lymphocyte transfusion for the purpose of remission of recurrent leukemia, and the like. The immune effector cells may be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited. The cells may be injected directly into a tumor, lymph node, or site of infection.

In one embodiment, the antigen binding moiety portion of the CAR is designed to treat a particular cancer. For example, a CAR designed to target CD19 can be used to treat cancers and disorders including pre-B ALL (pediatric indication), adult ALL, mantle cell lymphoma, diffuse large B-cell lymphoma, and salvage post allogenic bone marrow transplantation.

When "an immunologically effective amount", "an anti-tumor effective amount", "a tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). In some embodiments, the CAR-degron tag expressing immune effector cells described herein may be administered at a dosage of $10^4$ to $10^9$ cells/kg body weight, preferably $10^5$ to $10^6$ cells/kg body weight, including all integer and non-integer values within those ranges. Cell compositions may also be administered multiple times at these dosages. The cells can be administered by using infusion techniques that are commonly known in immunotherapy (see, e.g., Rosenberg et al., N. Engl. J. Med. 319: 1676 (1988)). The optimal dosage and treatment regime for a particular patient can readily be determined by one skilled in the art of medicine by monitoring the patient for signs of disease and adjusting the treatment accordingly.

Further features of CAR proteins, nucleic acids encoding CAR proteins, immune effector cells expressing CARs and methods of using CAR expressing cells for the treatment of diseases are disclosed in U.S. Patent Application Publication 2018/0169109 A1, incorporated herein by reference.

Endogenous POIs-Degron Tag Fusions

In some aspects, the methods of the present invention are dire

In certain embodiments, a nucleic acid encoding a degron tag can be genomically inserted in-frame with a gene encoding a protein that is involved in a disorder. Representative examples of particular genes involved in disorders that may be targeted for degron tag insertion include alpha-1 antitrypsin (A1AT), apolipoprotein B (apoB), angiopoietin-like protein 3 (ANGPTL3), proprotein convertase subtilisin/kexin type 9 (PCSK9), apolipoprotein C3 (APOC3), catenin (CTNNB1), low density lipoprotein receptor (LDLR), C-reactive protein (CRP), apolipoprotein a (Apo(a)), Factor VII, Factor XI, antithrombin III (SERPINC1), phosphatidylinositol glycan class A (PIG-A), C5, alpha-1 antitrypsin (SERPINA1), hepcidin regulation (TMPRSS6), (delta-aminolevulinate synthase 1 (ALAS-1), acylCaA:diacylglycerol acyltransferase (DGAT), miR-122, miR-21, miR-155, miR-34a, prekallikrein (KLKB1), connective tissue growth factor (CCN2), intercellular adhesion molecule I (ICAM-1), glucagon receptor (GCGR), glucocorticoid receptor (GCCR), protein tyrosine phosphatase (PTP-1B), c-Raf kinase (RAF1), fibroblast growth factor receptor 4 (FGFR4), vascular adhesion molecule-1 (VCAM-1), very late antigen-4 (VLA-4), transthyretin (TTR), survival motor neuron 2 (SMN2), growth hormone receptor (GHR), dystrophia myotonic protein kinase (DMPK), cellular nucleic acid-binding protein (CNBP or ZNF9), clusterin (CLU), eukaryotic translation initiation factor 4E (eIF-4e), MDM2, MDM4, heat shock protein 27 (HSP 27), signal transduction and activator of transcription 3 protein (STAT3), vascular endothelial growth factor (VEGF), kinesin spindle protein (KIF11), hepatitis B genome, the androgen receptor (AR), Atonal homolog 1 (ATOH1), vascular endothelial growth factor receptor 1 (FLT1), retinoschism 1 (RS1), retinal pigment epithelium-specific 65 kDa protein (RPE65), Rab escort protein 1 (CHM), and the sodium channel, voltage gated, type X, alpha subunit (PN3 or SCN10A). Additional proteins of interest that may be targeted by degron tag insertion include proteins associated with gain of function mutations, for example, cancer causing proteins.

In particular embodiments, the protein of interest is apoB-100, ANGPTL3, PCSK9, APOC3, CRP, ApoA, Factor XI, Factor VII, antithrombin III, phosphatidylinositol glycan class A (PIG-A), the C5 component of complement, Alpha-1-antitrypsin (AIAT), TMPRSS6, ALAS-1, DGAT-2, KLB1, CCN2, ICAM, glucagon receptor, glucocorticoid receptor, PTP-1B, FGFR4, VCAM-1, VLA-4, GCCR, TTR, SMN1, GIR, DMPK, or sodium channel isoform Nav1.8.

In one embodiment, the degron tag is genomically integrated in-frame, either 5' or 3', into the gene encoding for an endogenous protein associated with a proteopathy. In one embodiment the degron tag is genomically integrated in-frame, either 5' or 3', into the gene encoding for an endogenous protein associated with a disorder such as Alzheimer's disease (Amyloid peptide (Ap); Tau protein), Cerebral β-amyloid angiopathy (Amyloid β peptide (Aβ)), Retinal ganglion cell degeneration in glaucoma (Amyloid β peptide (Ap)), Prion diseases (Prion protein), Parkinson's disease and other synucleinopathies (α-Synuclein), Tauopathies (Microtubule-associated protein tau (Tau protein)), Frontotemporal lobar degeneration (FTLD) (Ubi+, Tau-) (TDP-43), FTLD-FUS (Fused in sarcoma (FUS) protein), Amyotrophic lateral sclerosis (ALS) (Superoxide dismutase, TDP-43, FUS), Huntington's disease and other triplet repeat disorders (Proteins with tandem glutamine expansions), Familial British dementia (ABri), Familial Danish dementia (Adan), Hereditary cerebral hemorrhage with amyloidosis (Icelandic) (HCHWA-I) (Cystatin C), CADASIL (Notch3), Alexander disease (Glial fibrillary acidic protein (GFAP)), Seipinopathies (Seipin), Familial amyloidotic neuropathy, Senile systemic amyloidosis (Transthyretin), Serpinopathies (Serpins), AL (light chain) amyloidosis (primary systemic amyloidosis) (Monoclonal immunoglobulin light chains), AH (heavy chain) amyloidosis (Immunoglobulin heavy chains), AA (secondary) amyloidosis (Amyloid A protein), Type II diabetes (Islet amyloid polypeptide (IAPP; amylin)), Aortic medial amyloidosis (Medin (lactadherin)), ApoAl amyloidosis (Apolipoprotein AI), ApoAII amyloidosis (Apolipoprotein AII), ApoAIV amyloidosis (Apolipoprotein AIV), Familial amyloidosis of the Finnish type (FAF) (Gelsolin), Lysozyme amyloidosis (Lysozyme), Fibrinogen amyloidosis (Fibrinogen), Dialysis amyloidosis (Beta-2 microglobulin), Inclusion body myositis/myopathy (Amyloid β peptide (Aβ)), Cataracts (Crystallins), Retinitis pigmentosa with rhodopsin mutations (rhodopsin), Medullary thyroid carcinoma (Calcitonin), Cardiac atrial amyloidosis (Atrial natriuretic factor), Pituitary prolactinoma (Prolactin), Hereditary lattice corneal dystrophy (Keratoepithelin), Cutaneous lichen amyloidosis (Keratins), Mallory bodies (Keratin intermediate filament proteins), Corneal lactoferrin amyloidosis (Lactoferrin), Pulmonary alveolar proteinosis (Surfactant protein C (SP-C)), Odontogenic (Pindborg) tumor amyloid (Odontogenic ameloblast-associated protein), Seminal vesicle amyloid (Semenogelin I), Cystic Fibrosis (cystic fibrosis transmembrane conductance regulator (CFTR) protein), Sickle cell disease (Hemoglobin), and Critical illness myopathy (CIM) (Hyperproteolytic state of myosin ubiquitination).

In-frame insertion of the nucleic acid sequence encoding the degron tag can be performed or achieved by any known and effective genomic editing processes. In one aspect, the present invention utilizes the clustered regularly interspaced short palindromic repeats (CRISPR)-Cas9 system to produce knock-in endogenous protein-degron tag fusion proteins that are produced from the endogenous locus and are readily degraded in a reversible and dose-responsive fashion dependent on administration of an IMiD or CM. In certain embodiments, the CRISPR-Cas9 system is employed in order to insert an expression cassette for degron tag present in a homologous recombination (HR) "donor" sequence with the degron tag nucleic acid sequence serving as a "donor" sequence inserted into the genomic locus of a protein of interest during homologous recombination following CRISPR-Cas endonucleation. The HR targeting vector contains homology arms at the 5' and 3' end of the expression cassette homologous to the genomic DNA surrounding the targeting gene of interest locus. By fusing the nucleic acid sequence encoding the degron tag in frame with the target gene of interest, the resulting fusion protein contains a degron tag that is targeted by a CRBN-IMiD complex or a CRBN-CM complex.

A donor sequence can contain a non-homologous sequence flanked by two regions of homology to allow for efficient HR at the location of interest. Additionally, donor sequences can be a vector molecule containing sequences that are not homologous to the region of interest in cellular chromatin. A donor molecule can contain several, discontinuous regions of homology to cellular chromatin. For example, for targeted insertion of sequences not normally present in a region of interest, for example, the degron tags of the present invention, the sequences can be present in a donor nucleic acid molecule and flanked by regions of homology to the sequence in the region of interest. Alternatively, a donor molecule may be integrated into a cleaved target locus via non-homologous end joining (NHEJ) mechanisms. See, e.g., U.S. Patent Application Publications 2011/0207221 A1 and 2013/0326645 A1, the disclosures of all of which are incorporated herein by reference.

The donor degron tag encoding sequence for insertion can be DNA or RNA, single-stranded and/or double-stranded and can be introduced into a cell in linear or circular form. See, e.g., U.S. Patent Application Publications 2010/0047805 A1, 2011/0281361 A1, and 2011/0207221 A1, incorporated herein by reference. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. (See, e.g., Chang et al., Proc. Natl. Acad. Sci. 84:4959-4963 (1987) and Nehls et al., Science 272:886-889 (1996)). Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

The donor polynucleotide encoding a degron tag can be introduced into a cell as part of a vector molecule having additional sequences such as, for example, CRISPR-Cas sequences, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The present invention takes advantage of well-characterized insertion strategies, for example the clustered regularly interspaced short palindromic repeats (CRISPR)-Cas9 system. In general, the "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus. (See, e.g., Ruan et al., Sci. Rep. 5:14253 (2015); and Park et al., PLoS ONE 9(4):e95101 (2014)).

In some embodiments, the methods include modifying expression of a polynucleotide in a eukaryotic cell by introducing a nucleic acid encoding a degron tag.

In some embodiments, the polypeptides of the CRISPR-Cas system and donor sequence are administered or introduced to the cell. The nucleic acids typically are administered in the form of an expression vector, such as a viral expression vector. In some embodiments, the expression vector is a retroviral expression vector, an adenoviral expression vector, a DNA plasmid expression vector, or an adeno-associated virus (AAV) expression vector. In some embodiments, one or more polynucleotides encoding CRISPR-Cas system and donor sequence are delivered to the cell. In some embodiments, the delivery is by delivery of more than one vector.

Methods of delivering nucleic acid sequences to cells as described herein are described, for example, in U.S. Pat. Nos. 8,586,526; 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein.

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355, incorporated by reference herein, and lipofection reagents are sold commercially (e.g., Transfectam™ and Lipofectin™). Cationic and neutral lipids that are suitable for efficient receptor-recognition lipofection of polynucleotides include those described in WO 1991/17424 and WO 1991/16024, incorporated herein by reference. Delivery can be to cells (e.g. in vitro or ex vivo administration) or target tissues (e.g. in vivo administration).

The various polynucleotides as described herein may also be delivered using vectors containing sequences encoding one or more of compositions described herein. Any vector systems may be used including, but not limited to, plasmid vectors, retroviral vectors, lentiviral vectors, adenovirus vectors, poxvirus vectors; herpesvirus vectors and adeno-associated virus vectors, etc.

See, also, U.S. Pat. Nos. 6,534,261; 6,607,882; 6,824,978; 6,933,113; 6,979,539; 7,013,219; and 7,163,824, incorporated by reference herein.

At least six viral vector approaches are currently available for gene transfer in clinical trials, which utilize approaches that involve complementation of defective vectors by genes inserted into helper cell lines to generate the transducing agent. pLASN and MFG-S are examples of retroviral vectors that have been used in clinical trials. (Dunbar et al., Blood 85:3048-305 (1995); Kohn et al., Nat. Med. 1:1017-1023 (1995); Malech et al., PNAS 94(22):12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors. (Ellem et al., Immunol. Immunother. 44(1):10-20 (1997); and Dranoff et al., Hum. Gene Ther. 1:111-112 (1997)).

Vectors can be delivered in vivo by administration to an individual subject, typically by systemic administration (e.g., intravenous, intraperitoneal, intramuscular, intrathecal, intratracheal, subdermal, or intracranial infusion) or topical application. Alternatively, vectors can be delivered to cells ex vivo, such as cells explanted from an individual patient (e.g., lymphocytes, bone marrow aspirates or tissue biopsy) or universal donor hematopoietic stem cells, followed by reimplantation of the cells into a patient, usually after selection for cells which have incorporated the vector.

In some embodiments, non-CRISPR-CAS viral and non-viral based gene transfer methods can be used to insert nucleic acids encoding a degron tag in frame in the genomic locus of a protein of interest in mammalian cells or target tissues. Such methods can be used to administer nucleic acids encoding components of a zing finger protein (ZFP), zing finger nuclease (ZFN), transcription activator-like effector protein (TALE), and/or transcription activator-like effector nuclease (TALEN) system to cells in culture, or in a host organism including a donor sequence encoding a degron tag for in-frame insertion into the genomic locus of a protein of interest.

Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11:167-173 (1993); Miller, Nature 357:455-460 (1992); Van Brunt, Biotechnology 6(10):1149-1154 (1988); Vigne, Restor. Neurol. Neurosci. 8:35-36 (1995); Kremer & Perricaudet, British Medical Bulletin 51(1):31-44 (1995); and Yu et al., Gene Ther. 1:13-26 (1994).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Ther. 2:710-722 (1995); Ahmad et al., Cancer Res. 52:4817-4820 (1992); and U.S. Pat. Nos. 4,186,183, 4,217,344, 4,235,871, 4,261,975, 4,485,054, 4,501,728, 4,774,085, 4,837,028, and 4,946,787, incorporated herein by reference).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al., Nat. Biotechnol. 27(7):643 (2009)).

Further methods for creating fusion proteins including an endogenous protein and an exogenous protein fragment or domain (e.g., a degron tag) and methods of using them for the treatment of diseases are disclosed in US Patent Application Publication 2018/0179522 A1, incorporated herein by reference.

Pharmaceutical Compositions

The IMiD (immunomodulatory drugs) and CM (cereblon modulators) compounds of the present invention are known in the art, examples of which include thalidomide, pomalidomide, lenalidomide, CC-122, CC-220 and CC-885, or pharmaceutically acceptable salts thereof (e.g., HCl salt). The IMiD compounds, thalidomide (marketed under the name THALOMID®), lenalidomide (marketed under the name REVLIMID®) and pomalidomide (marketed under the name POMALYST®), have each been approved by the FDA for treatment of multiple myeloma (among other diseases). THALOMID®) is currently available as capsules containing 50 mg, 100 mg, 150 mg or 200 mg thalidomide. REVLIMID®) is currently available as capsules containing 2.5 mg, 5 mg, 10 mg, 15 mg, 20 mg or 25 mg lenalidomide. POMALYST®) is currently available as capsules containing 1 mg, 2 mg, 3 mg or 4 mg pomalidomide. The CM compounds CC-122, CC-220 and CC-885 are currently undergoing review by the FDA.

IMiD and CM compounds may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the IMiD and CM compounds include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

IMiD and CM compounds may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the IMiD and CM compounds may be used in the form of individual isomers and substantially free of other isomers, or in the form of a mixture of various isomers, e.g., racemic mixtures of stereoisomers.

In some embodiments, the IMiD or CM compound is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^{2}H$, may afford certain therapeutic advantages resulting from greater metabolic stability, for example, increased in vivo half-life or reduced dosage requirements, and thus may be advantageous in some circumstances.

In addition, IMiD and CM compounds embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Another aspect of the present invention is directed to a pharmaceutical composition that includes a therapeutically effective amount of an IMiD or CM compound, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may also include one or more pharmaceutically acceptable excipients.

Broadly, IMiD and CM compounds and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., *Remington: The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, IMiD and CM compounds are formulated for oral or intravenous administration (e.g., systemic intravenous injection).

Accordingly, IMiD and CM compounds may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). IMiD and CM compounds may also be formulated for rapid, intermediate or extended release.

Solid dosage forms for oral administration include capsules, tablets, pills, powders, and granules. In such solid dosage forms, the IMiD or CM compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, IMiD and CM compounds be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the IMiD or CM compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, IMiD and CM compounds may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The IMiD and CM compounds may be formulated for buccal or sublingual administration, examples of which include tablets, lozenges and gels.

The IMiD and CM compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

IMiD and CM compounds may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (Eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, 111. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" or "effective amount" refers to an amount of an IMiD or CM compound or a pharmaceutically acceptable salt or a stereoisomer thereof; or a composition including the IMiD or CM compound or a pharmaceutically acceptable salt or a stereoisomer thereof, effective in producing the desired therapeutic response. The term "therapeutically effective amount" includes the amount of the compound or a pharmaceutically acceptable salt or a stereoisomer thereof, when administered, may induce cereblon-mediated degradation of a protein of interest, including CARs, or in the case of CAR-T therapy may reducing or alleviate to some extent an adverse immune response, e.g., cytokine release syndrome (CRS) or a metabolic syndrome, e.g., tumor lysis syndrome (TLS).

In respect of the therapeutic amount of the IMiD or CM compound, the amount of the compound used for the treatment of a subject is low enough to avoid undue or severe side effects, within the scope of sound medical judgment can also be considered.

The total daily dosage of the IMiD and CM compounds and usage thereof may be decided in accordance with standard medical practice, e.g., by the attending physician using sound medical judgment. The specific therapeutically effective dose for any particular subject will depend upon any one or more of a variety of factors including the disease or disorder being treated and the severity thereof (e.g., its present status); the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, *Goodman and Gilman's, The Pharmacological Basis of Therapeutics, 10th ed.*, A. Gilman, J. Hardman and L. Limbird, eds., McGraw-Hill Press, 155-173, 2001).

IMiD and CM compounds may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosage may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg).

The methods of the present invention may entail administration of IMiD or CM compounds or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails at least one 28-day cycle which includes daily administration for 3 weeks (21 days) followed by a 7-day "off" period.

Pharmaceutical Kits

The present compositions and genetically modified cells may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the compound of the present invention or a pharmaceutical composition. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Example 1: Structural Model of IKZF1 Minimal Degron Bound to CRBN and Lenalidomide (FIG. 1B')

A detailed characterization of the CRBN-IMiD binding region in IKZF1 (FIG. 1A-FIG. 1D) is provided in Petzold et al., Nature 532:127-130 (2016), which is incorporated herein by reference.

Example 2: Degradation of Degron Tag-GFP N-Terminal Fusion Protein

Figure 2A:
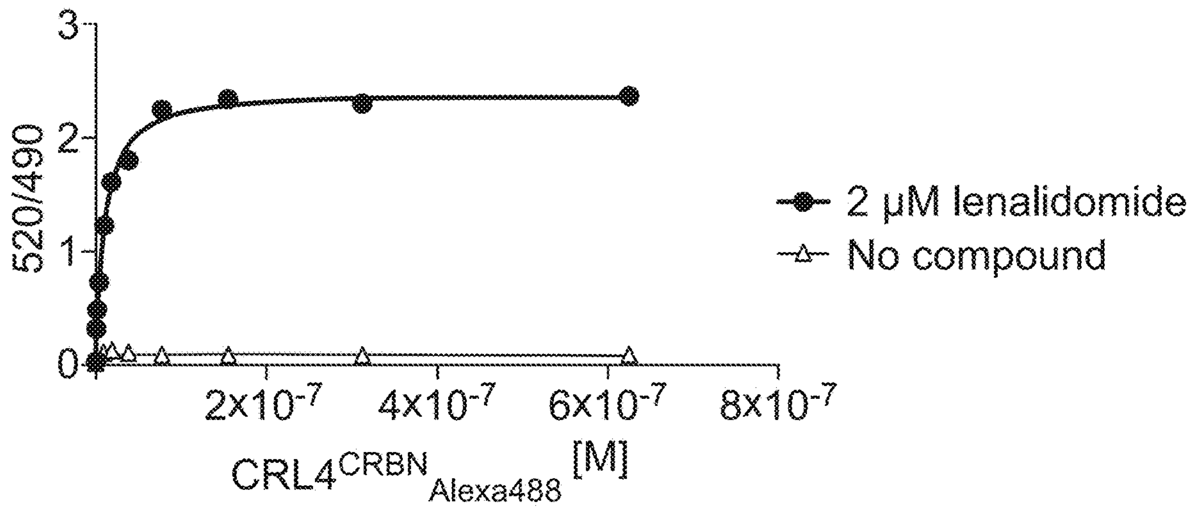
FIG. 2A is a graph showing the affinity of IKZF1 ZF2 for $CRL4^{CR}BN$ in the presence of lenalidomide by time-resolved fluorescence energy transfer (TR-FRET) (Petzold et al., Nature 532:127-30 (2016)).
Figure 2B:
FIG. 2B is a schematic diagram of a fluorescent reporter for fluorescence-activated cell sorting (FACS) assay.
Figure 2C:
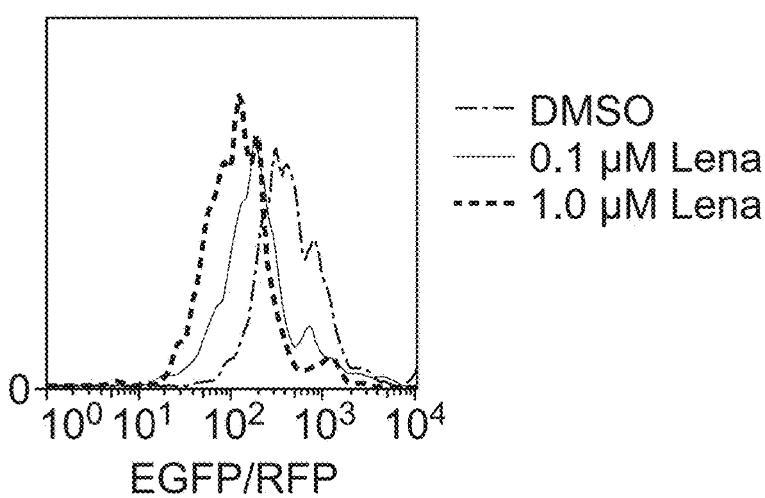
FIG. 2C is a plot of degradation of degron tag-GFP N-terminal fusion protein (degron tag was SEQ ID NO: 30) as measured by FACS.
Figure 3A:
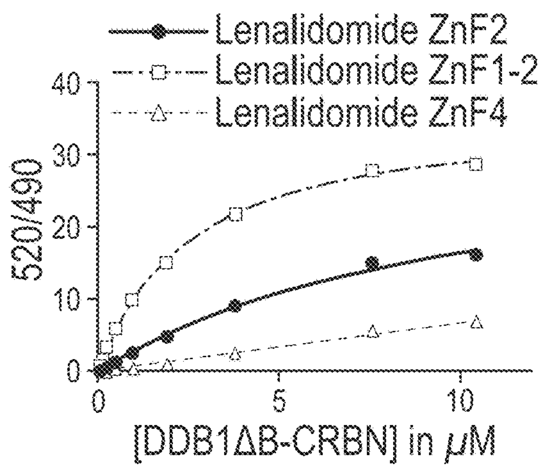
FIG. 3A is a graph of TR-FRET: titration of DDB1ΔB-$CRBN_{Spy\text{-}BodipyFL}$ to biotinylated $hsSALL4_{ZnF2}$, $hsSALL4_{ZnF1\text{-}2}$ and $hsSALL4_{ZnF4}$ at 100 nM and Terbium-Streptavidin at 4 nM in the presence of lenalidomide at 50 μM.
Figure 3B:
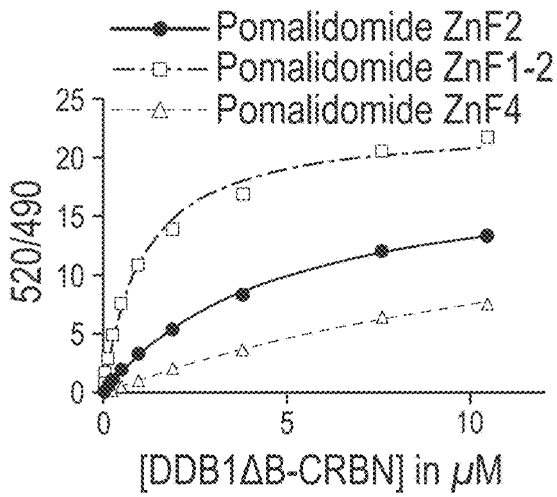
FIG. 3B is a graph of TR-FRET: titration of DDB1ΔB-$CRBN_{Spy\text{-}BodipyFL}$ to biotinylated $hsSALL4_{ZnF2}$, $hsSALL4_{ZnF1\text{-}2}$ and $hsSALL4_{ZnF4}$ at 100 nM and Terbium-Streptavidin at 4 nM in the presence of pomalidomide at 50 μM.
Figure 3C:
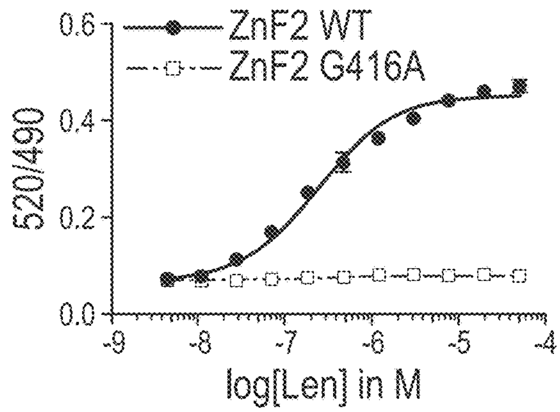
FIG. 3C is a graph of TR-FRET: titration of pomalidomide to DDB1ΔB-$CRBN_{Spy\text{-}BodipyFL}$ at 200 nM, $hsSALL4_{ZnF2}$, $mmSALL4_{ZnF2}$ and $drSALL4_{ZnF2}$ at 100 nM, and Terbium-Streptavidin at 4 nM.
Figure 3D:
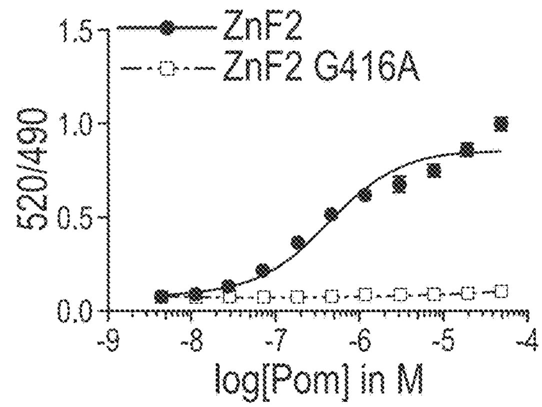
FIG. 3D is a graph of TR-FRET: titration of lenalidomide to DDB1ΔB-$CRBN_{Spy\text{-}BodipyFL}$ at 200 nM, $hsSALL4_{ZnF2}$, $mmSALL4_{ZnF2}$ and $drSALL4_{ZnF2}$ at 100 nM, and Terbium-Streptavidin at 4 nM.
Figure 3E:
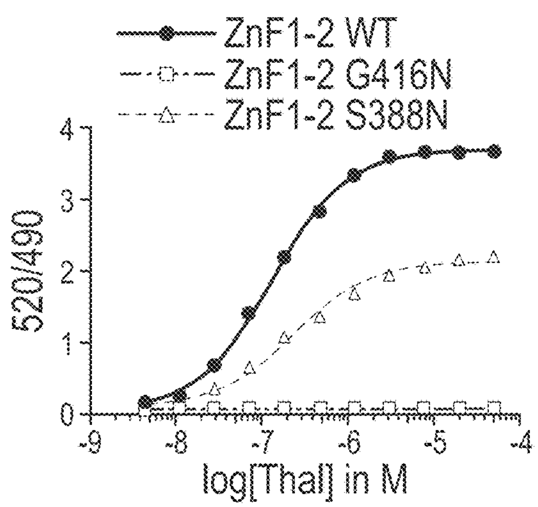
FIG. 3E is a graph of TR-FRET: titration of lenalidomide to DDB1ΔB-$CRBN_{Spy\text{-}BodipyFL}$ at 200 nM, ${hsSALL4_{ZnF2}}^{WT}$, ${hsSALL4_{ZnF2}}^{G416A}$ at 100 nM, and Terbium-Streptavidin at 4 nM.
Figure 3F:
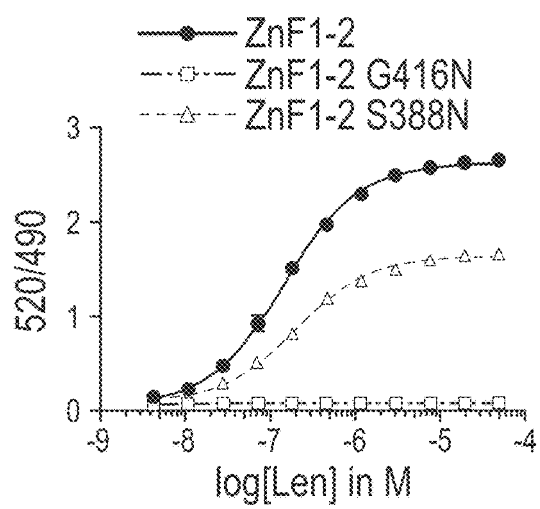
FIG. 3F is a graph of TR-FRET: titration of pomalidomide to DDB1ΔB-$CRBN_{Spy\text{-}BodipyFL}$ at 200 nM, ${hsSALL4_{ZnF2}}^{WT}$, ${hsSALL4_{ZnF2}}^{G416A}$ at 100 nM, and Terbium-Streptavidin at 4 nM.
Figure 3G:
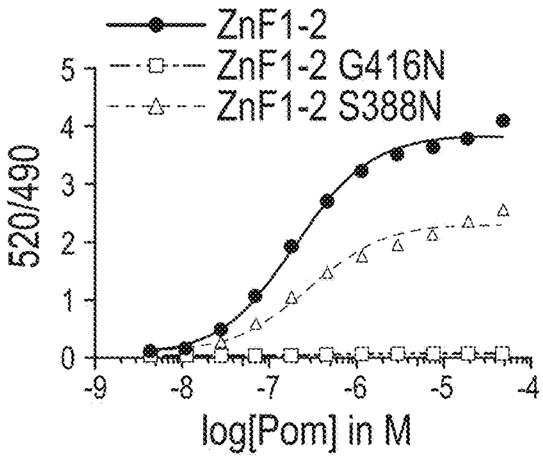
FIG. 3G is a graph of TR-FRET: titration of thalidomide to DDB1ΔB-$CRBN_{Spy\text{-}BodipyFL}$ at 200 nM, ${hsSALL4_{ZnF1\text{-}2}}^{WT}$, ${hsSALL4_{ZnF1\text{-}2}}^{G416N}$, ${hsSALL4_{ZnF2}}^{S388N}$ at 100 nM, and Terbium-Streptavidin at 4 nM.
Figure 3H:
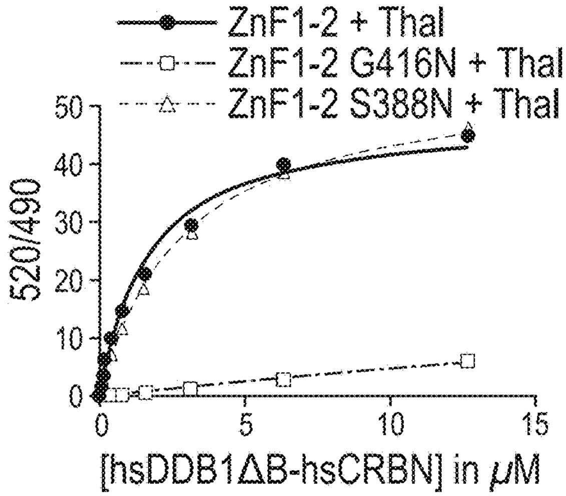
FIG. 3H is a graph of TR-FRET: titration of lenalidomide to DDB1ΔB-$CRBN_{Spy\text{-}BodipyFL}$ at 200 nM, ${hsSALL4_{ZnF1\text{-}2}}^{WT}$, ${hsSALL4_{ZnF1\text{-}2}}^{G416N}$, ${hsSALL4_{ZnF2}}^{S388N}$ at 100 nM, and Terbium-Streptavidin at 4 nM.
Figure 3I:
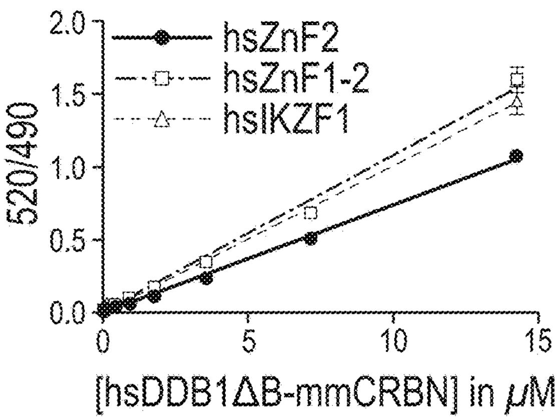
FIG. 3I is a graph of TR-FRET: titration of pomalidomide to DDB1ΔB-$CRBN_{Spy\text{-}BodipyFL}$ at 200 nM, ${hsSALL4_{ZnF1\text{-}2}}^{WT}$, ${hsSALL4_{ZnF1\text{-}2}}^{G416N}$, ${hsSALL4_{ZnF2}}^{S388N}$ at 100 nM, and Terbium-Streptavidin at 4 nM.
Figure 3J:
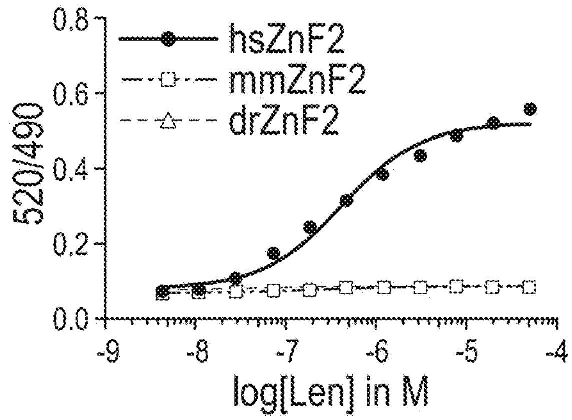
FIG. 3J is a graph of TR-FRET: titration of DDB1ΔB-$CRBN_{Spy\text{-}BodipyFL}$ to biotinylated $hsSALL4_{ZnF1\text{-}2}$, $hsSALL4_{ZnF1\text{-}2\ G416N}$ and $hsSALL4_{ZnF1\text{-}2\ S388N}$ at 100 nM and Terbium-Streptavidin at 4 nM in the presence of thalidomide at 50 μM.
Figure 3K:
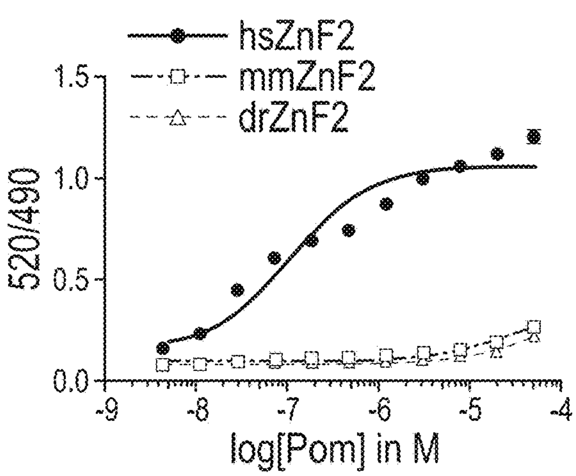
FIG. 3K is a graph of TR-FRET: titration of DDB1ΔB-$mmCRBN_{Spy\text{-}BodipyFL}$ to biotinylated $hsSALL4_{ZnF2}$, $hsSALL4_{ZnF1\text{-}2}$ and IKZF1A (Petzold et al., Nature 532: 127-130 (2016)) at 100 nM and Terbium-Streptavidin at 4 nM in the presence of thalidomide at 50 μM.

The degradation of degron tag-GFP N-terminal fusion protein, which was monitored by time-resolved fluorescence energy transfer (TR-FRET), is described in Petzold et al., Nature 532:127-130 (2016) (FIG. 2A-FIG. 2C).

Example 3: Biochemical Characterization of SALL4 Degron Binding to CRBN Using Time-Resolved Fluorescence Resonance Energy Transfer (TR-FRET)

Compounds in binding assays were dispensed into a 384-well microplate (Corning, 4514) using the D300e Digital Dispenser (HP) normalized to 1% DMSO and containing 100 nM biotinylated Strep-Avi-SALL4 (WT or mutant, see, FIG. 3A-FIG. 3K), 1 μM $His_6$-DDB1ΔB-$His_6$-$CRBN_{BODIPY\text{-}Spycatcher}$ and 4 nM terbium-coupled streptavidin (Invitrogen) in a buffer containing 50 mM Tris pH 7.5, 100 mM NaCl, 1 mM TCEP, 0.1% Pluronic F-68 solution (Sigma). Before TR-FRET measurements were conducted, the reactions were incubated for 15 minutes at room temperature (RT). After excitation of terbium fluorescence at 337 nm, emission at 490 nm (terbium) and 520 nm (boron-dipyrromethene (BODIPY)) were recorded with a 70 μs delay over 600 μs to reduce background fluorescence and the reaction was followed over 30×200 second cycles of each data point using a PHERAstar® FS microplate reader (BMG Labtech). The TR-FRET signal of each data point was extracted by calculating the 520/490 nm ratios. Data from three independent measurements (n=3), each calculated as an average of 5 technical replicates per well per experiment, was plotted and the half maximal effective concentrations $EC_{50}$ values calculated using variable slope equation in GraphPad Prism 7. Apparent affinities were determined by titrating Bodipy-FL labelled DDB1ΔB-CRBN to biotinylated Strep-Avi-SALL4 (constructs as indicated) at 100 nM, and terbium-streptavidin at 4 nM. The resulting data were fitted as described previously. (Petzold et al., Nature 532:127-130 (2016)).

Point mutations in the ZnF2 of SALL4 sequence are sufficient to abrogate IMiD induced CRBN binding in purified proteins (FIG. 3C-FIG. 3H). Specifically, G416A and G416N point mutations abrogated IMiD induced CRBN binding in purified proteins. Surprisingly, mutations in ZnF1 of ZnF1-2 SALL4 are still able to induce potent IMiD induced dimerization. Specifically, S388N mutation maintained IMiD induced CRBN binding in purified proteins.

Figure 4A:
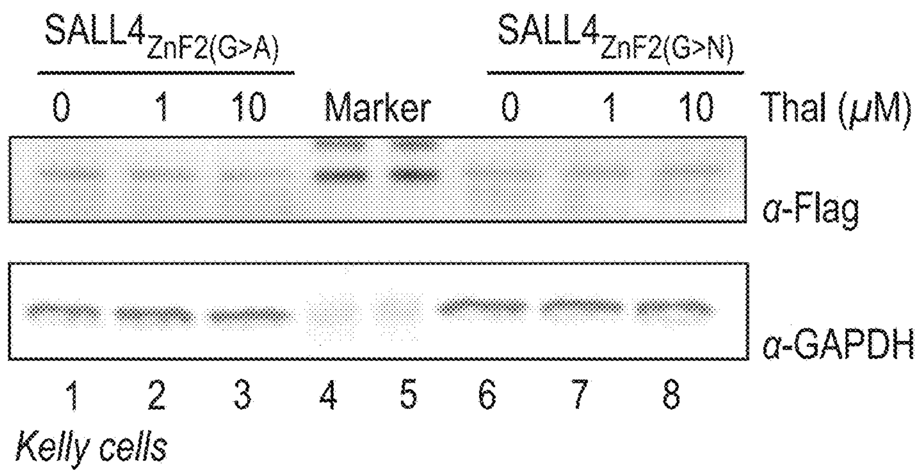
FIG. 4A is a photograph of a western blot showing Flag-$hsSALL4^{G416A}$, Flag-$hsSALL4^{G416N}$ and GAPDH protein levels after 24 hours of incubation with increasing concentrations of thalidomide or DMSO as a control (shown is one representative experiment out of three replicates).
Figure 4B:
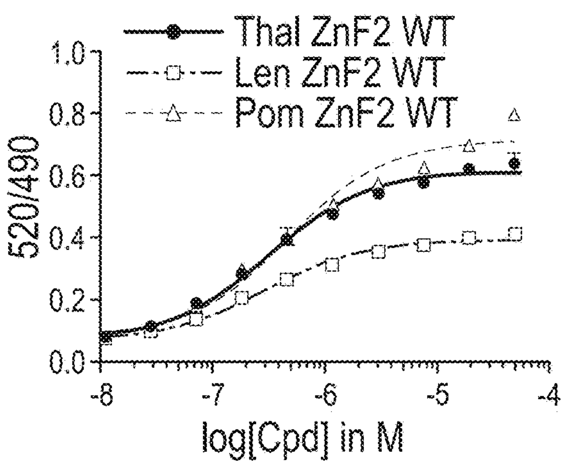
FIG. 4B is a graph of TR-FRET: titration of IMiD (thalidomide, lenalidomide and pomalidomide) to DDB1AB-$CRBN_{Spy\text{-}BodipyFL}$ at 200 nM, $hsSALL4_{ZnF2}$ at 100 nM, and Terbium-Streptavidin at 4 nM.
Figure 4C:
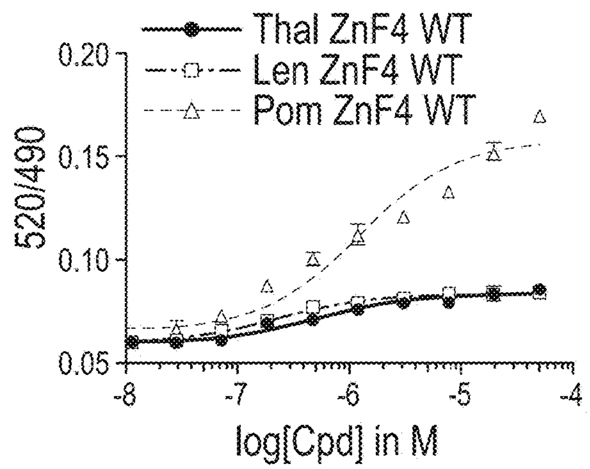
FIG. 4C is a graph of TR-FRET: titration of IMiD (thalidomide, lenalidomide and pomalidomide) to DDB1ΔB-$CRBN_{Spy\text{-}BodipyFL}$ at 1 μM, $hsSALL4_{ZnF4}$ at 100 nM, and Terbium-Streptavidin at 4 nM.
Figure 4D:
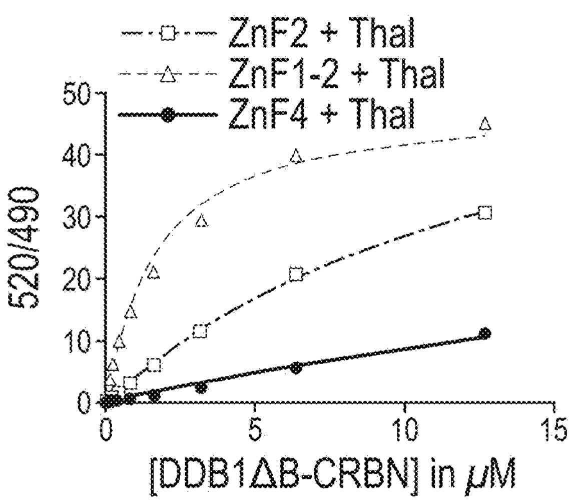
FIG. 4D is a graph of TR-FRET: titration of DDB1ΔB-$CRBN_{Spy\text{-}BodipyFL}$ to biotinylated $hsSALL4_{ZnF2}$, $hsSALL4_{ZnF1\text{-}2}$ or $hsSALL4_{ZnF4}$ at 100 nM and Terbium-Streptavidin at 4 nM in the presence of 50 μM thalidomide.
Figure 4E:
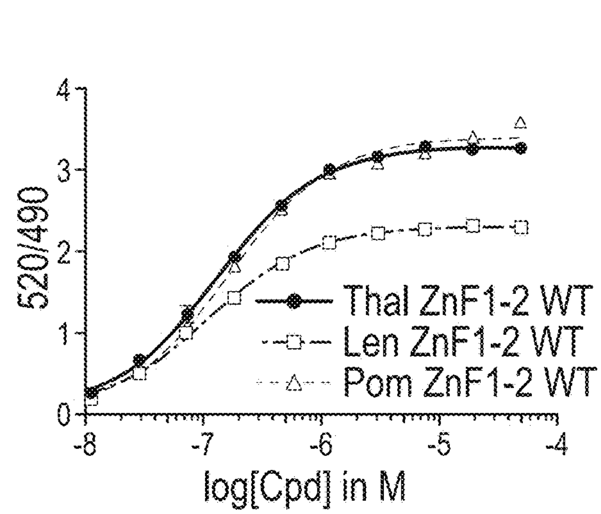
FIG. 4E is a graph of TR-FRET: titration of IMiD (thalidomide, lenalidomide and pomalidomide) to DDB1ΔB-$CRBN_{Spy\text{-}BodipyFL}$ at 200 nM, $hsSALL4_{ZnF1\text{-}2}$ at 100 nM, and Terbium-Streptavidin at 4 nM.
Figure 4F:
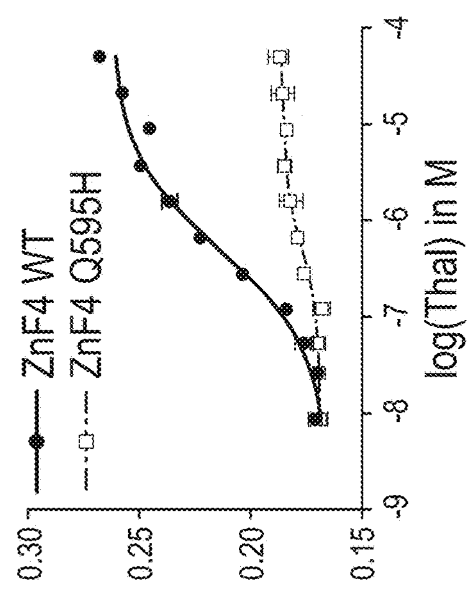
FIG. 4F is a graph of TR-FRET: titration of ${hsSALL4_{ZnF2}}^{G416A}$ mutant to DDB1ΔB-$CRBN_{Spy\text{-}BodipyFL}$ at 200 nM, $hsSALL4_{ZnF2}$ at 100 nM, and Terbium-Streptavidin at 4 nM.

Example 4: SALL4 ZnF2 is the Zinc Finger Responsible for IMiD-Dependent Binding to $CRL4^{CRBN}$ Kelly cells were transiently transfected with $hsSALL4^{G416A}$ or Flag-$hsSALL4^{G416N}$ were treated with increasing concentrations of thalidomide or DMSO as a control. Following 24 hours of incubation, SALL4 (α-Flag) and GAPDH protein levels were assessed by western blot analysis (FIG. 4A). (See, Example 7 for western blot method.)

Results are shown in FIG. 4A-FIG. 4H. The degron tags of SEQ ID NO's: 26-28 were validated in biochemical assays. SALL4 ZnF2 (SEQ ID NO: 26) and SALL4 ZnF1-2 (SEQ ID NO: 27) were sufficient to induce efficient dimerization, while SALL4 ZnF4 (SEQ ID NO: 28) binds with reduced affinity.

Mutations of key glycine 416 residue in Znf2 of SALL4 (G416A and G416N) disable degradation in cells (FIG. 4A). Surprisingly, mutations of conserved glycine in ZnF4 of SALL4 to alanine or asparagine have no effect on protein degradation (FIG. 4H).

Figure 4G:
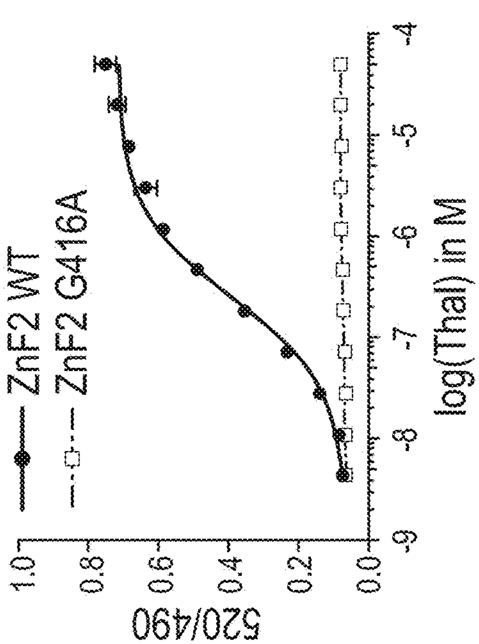
FIG. 4G is a graph of TR-FRET: titration of ${hsSALL4_{ZnF4}}^{Q595H}$ mutant to DDB1ΔB-$CRBN_{Spy\text{-}BodipyFL}$, at 1 μM, $hsSALL4_{ZnF4}$ at 100 nM, and Terbium-Streptavidin at 4 nM.
Figure 4H:
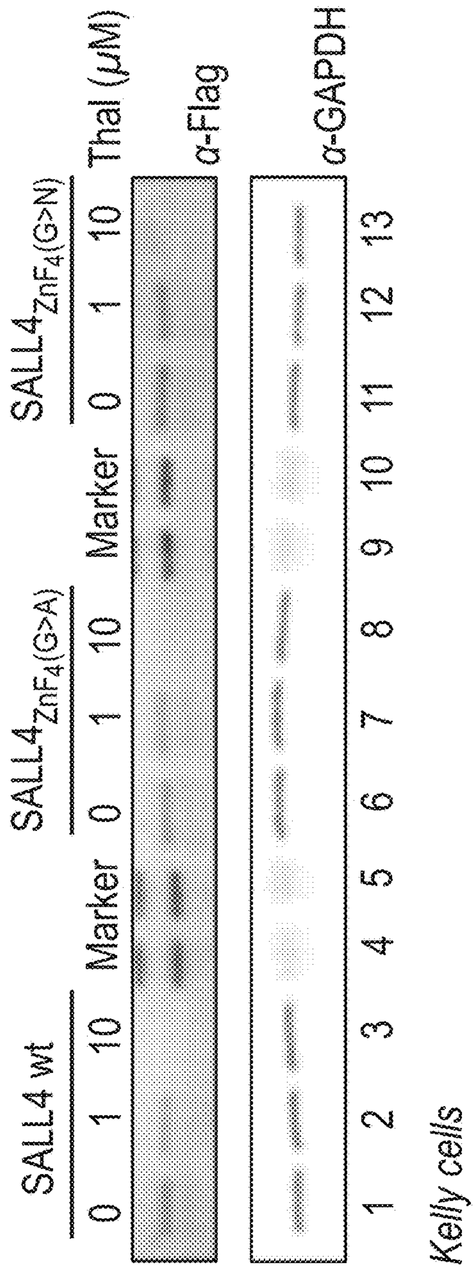
Figure 5:
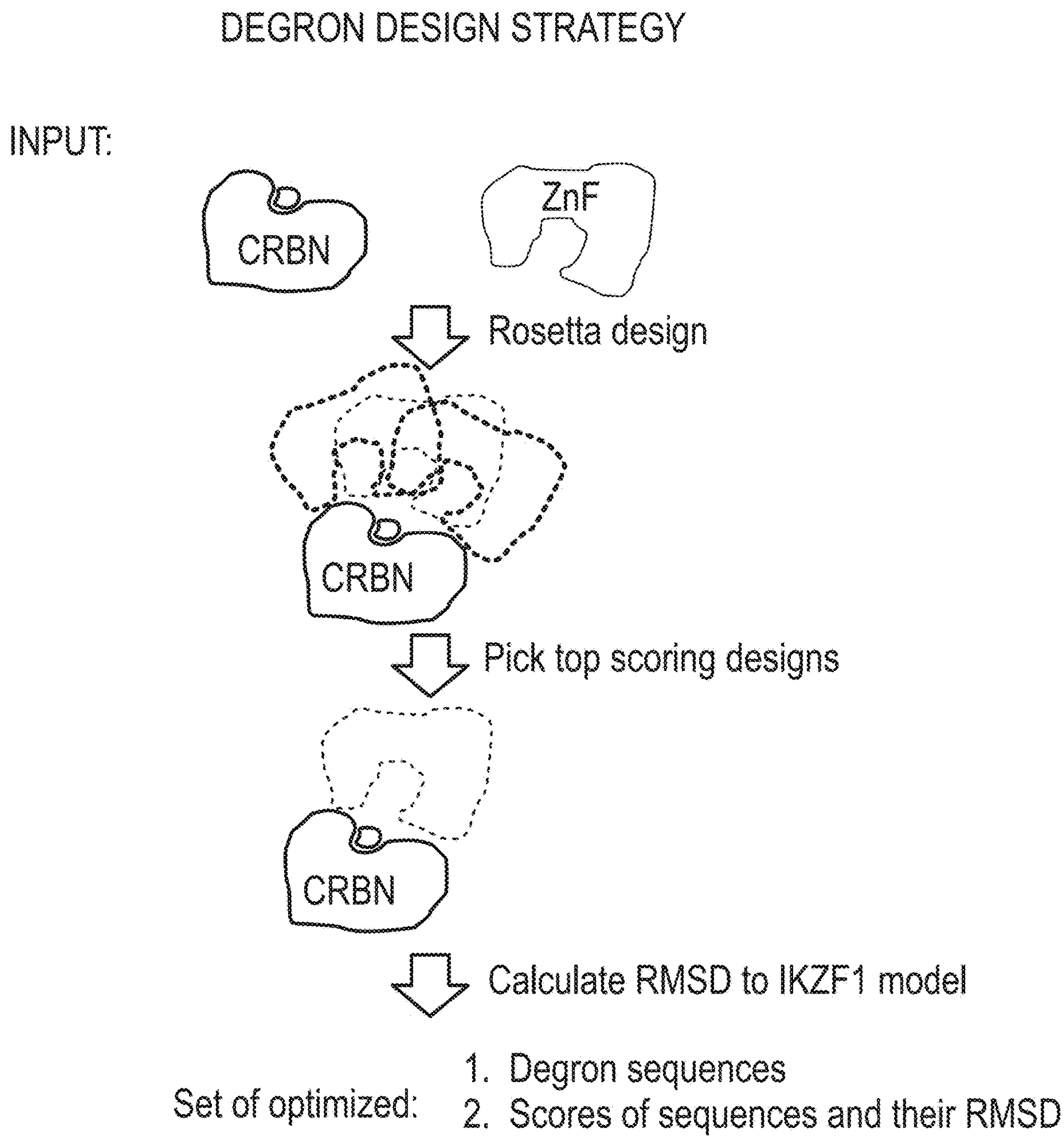
FIG. 5 is a depiction of the degron design strategy based on computational design of the amino acid sequence and subsequent scoring of the designs.
Figure 6:
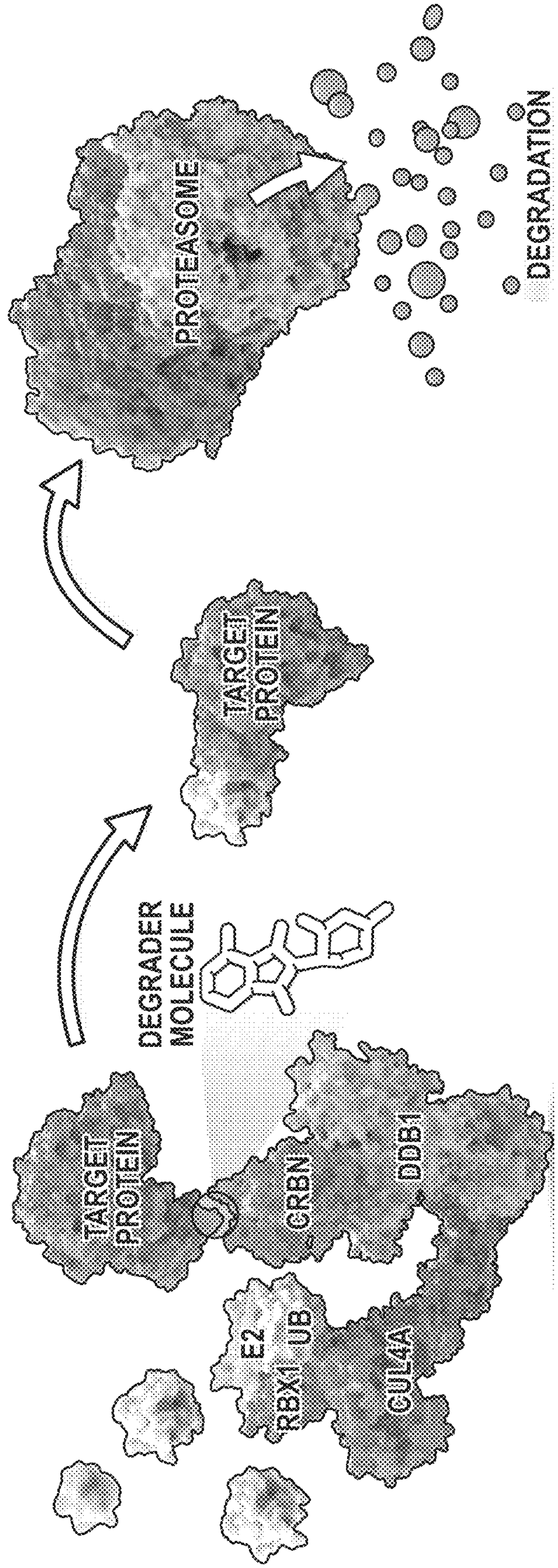
FIG. 6 is a depiction of IMiD induced protein degradation.
Figure 7:
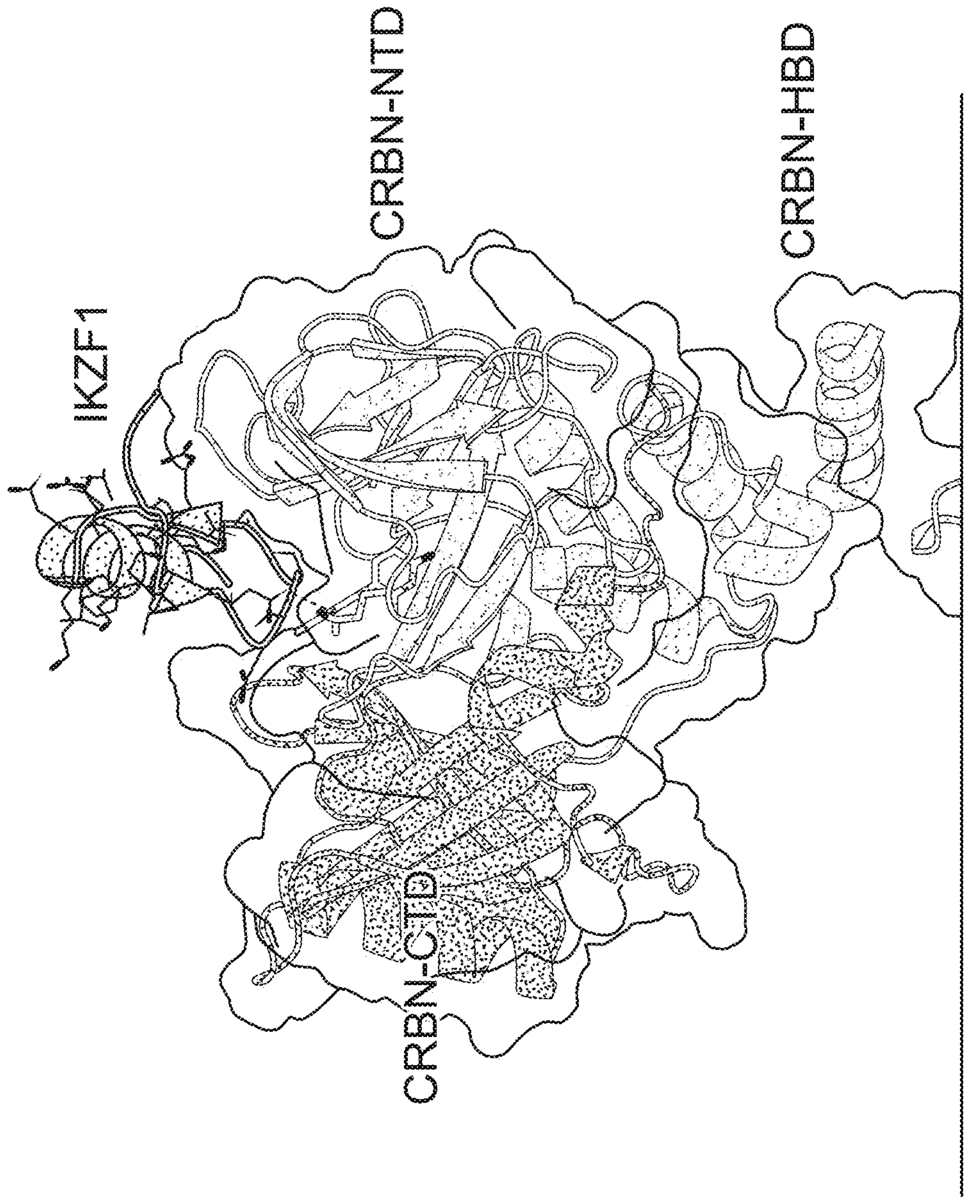
FIG. 7 is a depiction of IMiD induced ZnF binding to CRBN.
Figure 8:
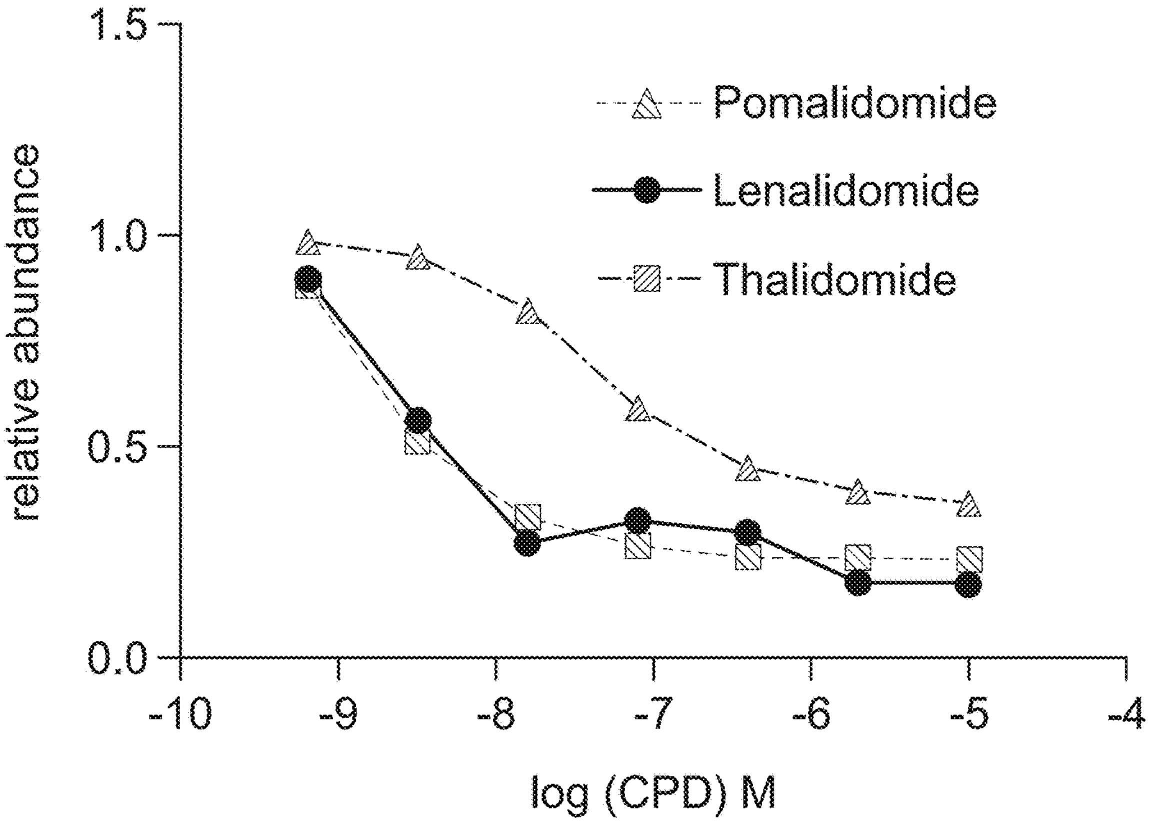
FIG. 8 is a graph of the relative abundance of a degron tag fusion protein of interest (degron-POI) showing cellular degradation in a reporter system induced by increasing amounts of IMiD.

Mutation of glutamine 595 residue in ZnF4 of SALL4 (Q595H) resulted in reduced binding affinity (FIG. 4G). TR-FRET: titration of IMiD (thalidomide) to DDB1ΔB-CRBNSpy-BodipyFL at 200 nM, hsSALL4ZnF2 and hsSALL4ZnF2G416A at 100 nM, and terbium-streptavidin at 4 nM.

Mutation of glutamine 595 residue in ZnF4 of SALL4 (Q59511) had no effect at the ability of the protein product to be degraded as confirmed by the western blot. Results are shown in FIG. 4H. Kelly cells transiently transfected with Flag-hsSALL4WT, Flag-hsSALL4G600A, or hsSALL4G600N were treated with increasing concentrations of thalidomide or DMSO as a control. Following 24 h of incubation, SALL4 (α-Flag) and GAPDH protein levels were assessed by western blot analysis (one representative experiment is shown out of three replicates).

Example 5: Compounds and Antibodies

Primary and secondary antibodies used included anti-FLAG 1:1000 (F1804, Sigma), anti-CRBN 1:500 (NBP1-91810, Novus Biologicals®) and anti-GAPDH at 1:10,000 dilution (G8795, Sigma), IRDye®680 Donkey anti-mouse at 1:10,000 dilution (926-68072, LI-COR®), IRDye®800 Goat anti-rabbit at 1:10,000 dilution (926-32211, LI-COR®).

Example 6: Cell Culture

Kelly cells were cultured in RPMI1640 supplemented with 10% dialyzed FBS.

Example 7: Western Blot

Cells were treated with compounds as indicated and incubated for 24 hours, or as indicated. Samples were run on 4-20% or Any kD™ SDS-PAGE Gels (Bio-rad), and transferred to polyvinylidene fluoride (PVDF) membranes using the iBlot® 2.0 dry blotting system (Thermo Fisher Scientific). Membranes were blocked with LI-COR® blocking solution (LI-COR®), and incubated with primary antibodies overnight, followed by three washes in LI-COR® blocking solution and incubation with secondary antibodies for one hour in the dark. After three final washes, the membranes were imaged on a LI-COR® fluorescent imaging station.

Example 8: Constructs and Protein Purification $_{His6}$DDB1ΔB(2), $_{His6\text{-}3c\text{-}Spy}$hsCRBN, $_{His6\text{-}3C\text{-}Spy}$mm-CRBN, $_{Strep\text{-}BirA}$hsSALL4590-618 (ZnF4), $_{Strep\text{-}BirA}$hsSALL4$^{Q595H}_{590\text{-}618}$ (ZnF4), $_{Strep\text{-}BirA}$hsSALL4$_{378\text{-}438}$ (ZnF1-2), $_{Strep\text{-}BirA}$hsSALL4$_{402\text{-}436}$ (ZnF2), $_{strep\text{-}BirA}$mm-SALL4$_{593\text{-}627}$ (ZnF4), $_{strep\text{-}BirA}$drSALL4$_{583\text{-}617}$ (ZnF2), and $_{strep\text{-}BirA}$IKZF1 (SEQ ID NO: 15) were subcloned into pAC-derived vectors. Mutant $_{strep\text{-}BirA}$hsSALL4$_{378\text{-}438}$ (ZnF1-2) and $_{Strep\text{-}BirA}$hsSALL4$_{402\text{-}436}$ (ZnF2) constructs were derived from these constructs using Q5 mutagenesis (NEB, USA). Recombinant proteins expressed in *Trichoplusia ni* High Five insect cells using the baculovirus expression system (Invitrogen™). For purification of DDB1ΔB-$CRBN_{SpyBodipyFL}$, cells were resuspended in buffer containing 50 mM tris(hydroxymethyl)aminomethane hydrochloride (Tris-HCl) pH 8.0, 200 mM NaCl, 1 mM tris(2-carboxyethyl)phosphine (TCEP), 1 mM phenylmethylsulfonyl fluoride (PMSF), 1× protease inhibitor cocktail (Sigma) and lysed by sonication. Cells expressing variations of $_{Strep\text{-}BirA}$SALL4 or IKZF1 (SEQ ID NO: 15) were lysed in the presence of 50 mM Tris-HCl pH 8.0, 500 mM NaCl, 1 mM TCEP, 1 mM PMSF and 1× protease inhibitor cocktail (Sigma). Following ultracentrifugation, the soluble fraction was passed over appropriate affinity resin Ni Sepharose® 6 Fast Flow affinity resin (GE Healthcare) or Strep-Tactin Sepharose® XT (IBA), and eluted with 50 mM Tris-HCl pH 8.0, 200 mM NaCl, 1 mM TCEP, 100 mM imidazole (Fischer Chemical) for $His_6$-tagged proteins or 50 mM Tris-HCl pH 8.0, 500 mM NaCl, 1 mM TCEP, 50 mM D-biotin (IBA) for Strep tagged proteins. Affinity-purified proteins were either further purified via ion exchange chromatography (POROS™ 50HQ) and subjected to size exclusion chromatography (SEC200 HiLoad™ 16/60, GE) ($_{His6}$DDB1ΔB-$_{His6\text{-}3c\text{-}Spy}$CRBN) or biotinylated over-night, concentrated and directly loaded on the size exclusion chromatography (ENRich™ SEC70 10/300, Bio-rad) in 50 mM 4-(2-hydroxyethyl)-1-piperazineethanesulfonic acid (HEPES) pH 7.4, 200 mM NaCl and 1 mM TCEP. Biotinylation of $_{Strep\text{-}BirA}$SALL4/$_{Strep\text{-}BirA}$IKZF1 constructs was performed as previously described (Cavadini et al., Nature 531:598-603 (2016)).

The protein-containing fractions were concentrated using ultrafiltration (Millipore™) flash frozen in liquid nitrogen, and stored at −80° C. or directly covalently labeled with BODIPY-FL-$SpyCatcher_{S50C}$ as described below.

Example 9: Spycatcher S50C mutant

Spycatcher (B. Zakeri et al., Proc. Natl. Acad. Sci. U.S.A 109:E690-697 (2012)) containing a Ser50Cys mutation was obtained as synthetic dsDNA fragment from IDT® (Integrated DNA Technologies) and subcloned as GST-TEV fusion protein in a pET-Duet™ derived vector. Spycatcher S50C was expressed in BL21 DE3 and cells were lysed in the presence of 50 mM Tris-HCl pH 8.0, 200 mM NaCl, 1 mM TCEP and 1 mM PMSF. Following ultracentrifugation, the soluble fraction was passed over Glutathione Sepharose® 4B (GE Healthcare) and eluted with wash buffer (50 mM Tris-HCl pH 8.0, 200 mM NaCl, 1 mM TCEP) supplemented with 10 mM glutathione (Fischer BioReagents). The affinity-purified protein was subjected to size exclusion chromatography, concentrated and flash frozen in liquid nitrogen.

Example 10: Labeling of Spycatcher with BODIPY-FL-Maleimide

Purified Spycatcherssac protein was incubated with DTT (8 mM) at 4° C. for 1 hour. DTT was removed using a ENRich SEC650 10/300 (Bio-rad) size exclusion column in a buffer containing 50 mM Tris pH 7.5 and 150 mM NaCl, 0.1 mM TCEP. BODIPY-FL-maleimide (Thermo Fisher®) was dissolved in 100% DMSO and mixed with Spycatcher$_{S50C}$ to achieve 2.5 molar excess of BODIPY-FL-maleimide. SpyCatcher$_{S50C}$ labeling was carried out at room temperature (RT) for 3 hours and stored overnight at 4° C. Labeled Spycatcher$_{S50C}$ was purified on an ENRich™ SEC650 10/300 (Bio-rad) size exclusion column in 50 mM Tris pH 7.5, 150 mM NaCl, 0.25 mM TCEP and 10% (v/v) glycerol, concentrated by ultrafiltration (Millipore™), flash frozen (~40 μM) in liquid nitrogen and stored at −80° C.

Example 11: BODIPY-FL-Spycatcher Labeling of CRBN-DDB1ΔB

Purified $_{His6}$DDB1ΔB-$_{His6\text{-}3c\text{-}Spy}$CRBN constructs (WT and V388I) were incubated overnight at 4° C. with BODIPY-FL-maleimide labeled SpyCatcher$_{S50c}$ protein at stoichiometric ratio. Protein was concentrated and loaded on the ENrich™ SEC 650 10/300 (Bio-rad) size exclusion column and the fluorescence monitored with absorption at 280 and 490 nm. Protein peak corresponding to the labeled protein was pooled, concentrated by ultrafiltration (Millipore™), flash frozen in liquid nitrogen and stored at −80° C.

Example 12: Validation of Degron Tag IKZF1 (Δ1-82/Δ197-238/Δ256-519) (SEQ ID NO: 18)

The non-naturally occurring degron tag of SEQ ID NO: 18 (IKZF1 (Δ1-82/Δ197-238/Δ256-519) was validated in biochemical and cellular assays as a GFP-fusion, a KRAS-fusion and in cells by flow cytometry.

Time-Resolved Fluorescence Resonance Energy Transfer (TR-FRET)

Compounds in dimerization assays were dispensed in a 384-well microplate (Corning, 4514) using D300e Digital Dispenser (HP) normalized to 2% DMSO into 80 nM biotinylated StrepII-avi-IKZF1A (See, Figure legends), 100 nM His$_6$-DDB1ΔB-His$_6$-CRBN$_{BODIPY\text{-}Spycatcher}$ and 2 nM terbium-coupled streptavidin (Invitrogen™) in a buffer containing 50 mM Tris pH 7.5, 200 mM NaCl, 0.1% Pluronic F-68 solution (Sigma) and 2% DMSO (4% DMSO final). Before TR-FRET measurements were conducted, the reactions were incubated for 15 min at RT. After excitation of terbium fluorescence at 337 nm, emission at 490 nm (terbium) and 520 nm (BODIPY) were recorded with a 70 s delay over 600 μs to reduce background fluorescence and the reaction was followed over 30 200 second cycles of each data point using a PHERAstar® FS microplate reader (BMG Labtech). The TR-FRET signal of each data point was extracted by calculating the 520/490 nm ratio. The 520/490 nm ratios in IKZF1Δ TR-FRET assays were plotted to calculate or IC$_{50}$ (for compound titrations) using GraphPad Prism 7 variable slope equation. The standard deviation in IKZF1A TR-FRET compound titrations was calculated from three independent replicates (n=3), or as an average of 5 technical replicates of single experiment for unlabeled protein titrations.

Potent dimerization was observed between CRBN-DDB1 dB and IKZF1 (SEQ ID NO: 18) as indicated in FIG. 12. Titration of the indicated molecules to DDB1ΔB-CRBN$_{SPYCATCHER\text{-}BODIPY}$, Terbium-streptavidin and IKZF1Δ$_{biotin}$. Data in this figure are presented as means±s.d. from three independent replicates (n=3).

Cellular Degradation Assays

IKZF1 (SEQ ID NO: 18, hereafter referred to as IKZF1Δ) was subcloned into mammalian pcDNA5/FRT Vector (Ampicillin and Hygromycin B resistant) modified to contain MCS-eGFP-P2A-mCherry. Stable cell lines expressing eGFP-IKZF1Δ fusion and mCherry reporter were generated using Flip-In™ 293 system. Plasmid (0.3 μg) and pOG44 (4.7 μg) DNA were pre-incubated in 100 μL of Opti-MEM I (Gibco, Life Technologies™) media containing 0.05 mg/ml Lipofectamine 2000 (Invitrogen™) for 20 min and added to Flip-In 293 cells containing 1.9 ml of DMEM media (Gibco, Life Technologies™) per well in a 6-well plate format (Falcon, 353046). Cells were propagated after 48 h and transferred into a 10 cm$^2$ plate (Corning, 430165) in DMEM media containing 50 μg/ml of Hygromycin B (REF 10687010, Invitrogen™) as a selection marker. Following 2-3 passage cycle FACS (FACSAria™ II, BD) was used to enrich for cells expressing eGFP and mCherry.

Cells were seeded at 30-50% confluency in either 24-, 48- or 96-well plates (3,524, 3,548 and 3,596, respectively; Costar) a day before compound treatment. Titrated compounds (see figure legends) were incubated with cells for 5 h following trypsinization and resuspension in DMEM media, transferred into 96-well plates (353910, Falcon) and analyzed by flow cytometer (Guava® easyCyte™ HT, Millipore™). Signal from at least 3,000 events per well was acquired, and the eGFP and mCherry florescence monitored. Data were analyzed using FlowJo™ (FlowJo™, LCC). Forward and side scatter outliers, frequently associated with cell debris, were removed leaving >90% of total cells, which was followed by removal of eGFP and mCherry signal outliers, leaving 88-90% of total cells, creating the set used for quantification. The eGFP protein abundance relative to mCherry was then quantified as a ten-fold amplified ratio for each individual cell using the formula: 10×eGFP/mCherry. The median of the ratio was then calculated per set, normalized to the median of the DMSO ratio.

Figure 9:
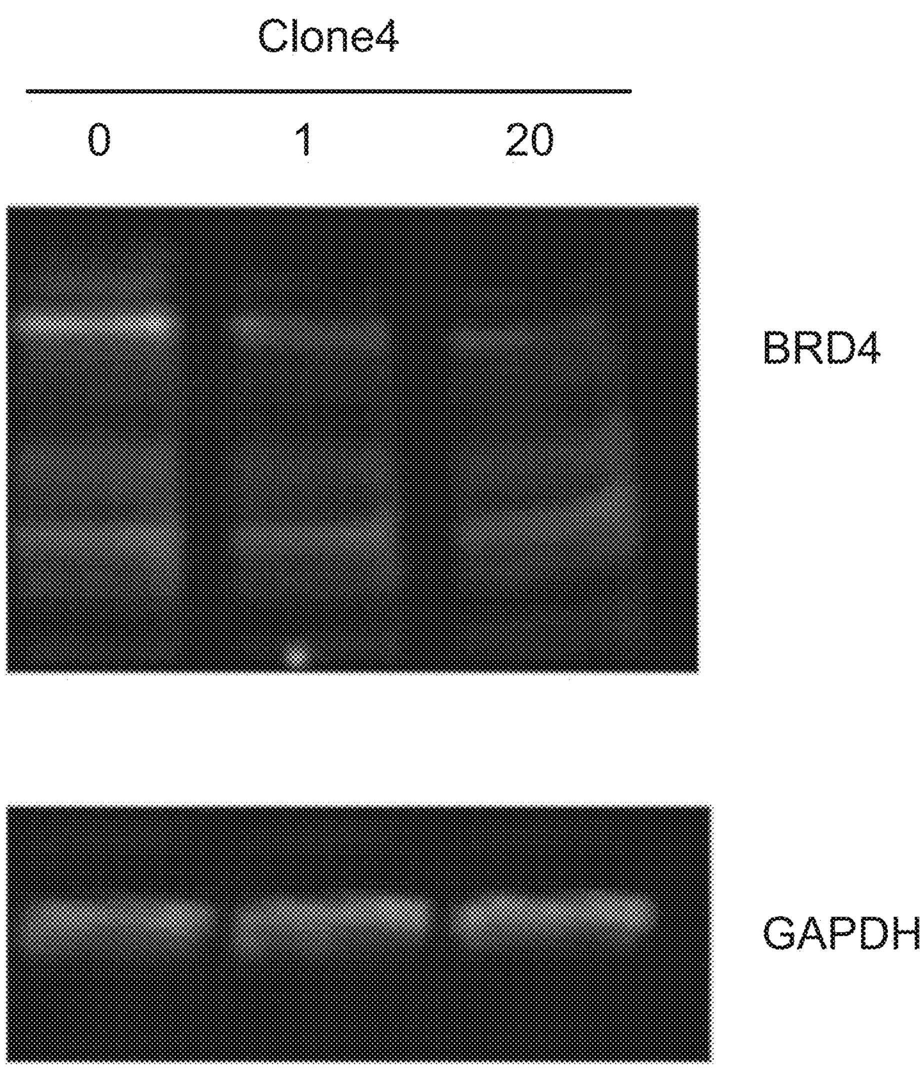
FIG. 9 is a photograph of a Western blot showing degradation of endogenous bromodomain-containing protein 4 (BRD4) by creating an N-terminus knock-in of IKZF1 degron tag at BRD4 locus using a nucleic acid sequence encoding SEQ ID NO: 30 and increasing amounts (1 and 20 μM) of lenalidomide.
Figure 12A:
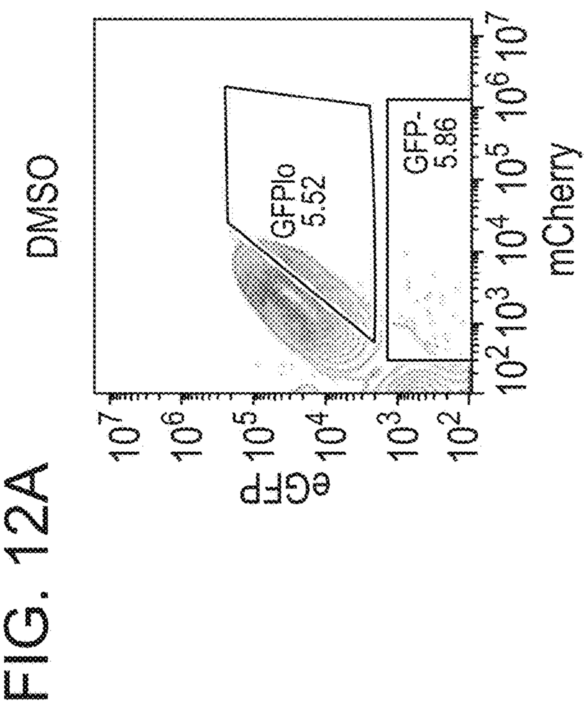
FIG. 12A is a graph of flow cytometry analysis of Jurkat T cells expressing a library of in silico designed C2H2 zinc fingers (ZF) in a protein degradation reporter with DMSO.
Figure 12B:
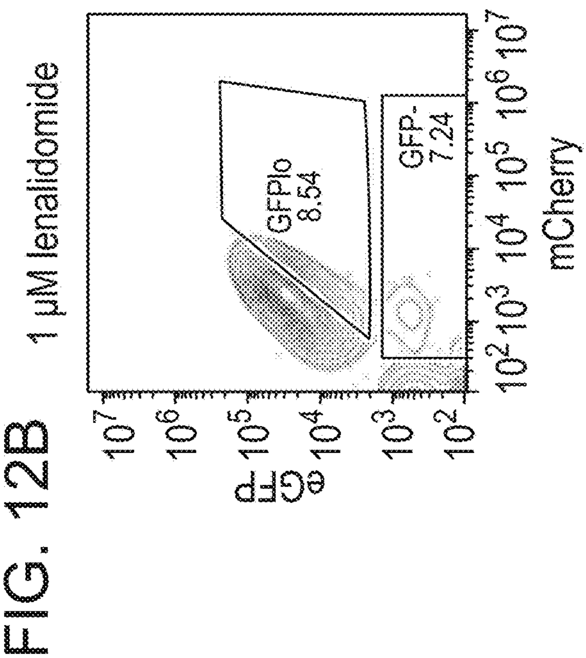
FIG. 12B is a graph of flow cytometry analysis of Jurkat T cells expressing a library of in silico designed C2H2 zinc fingers in a protein degradation reporter with 1 μM lenalidomide.
Figure 12C:
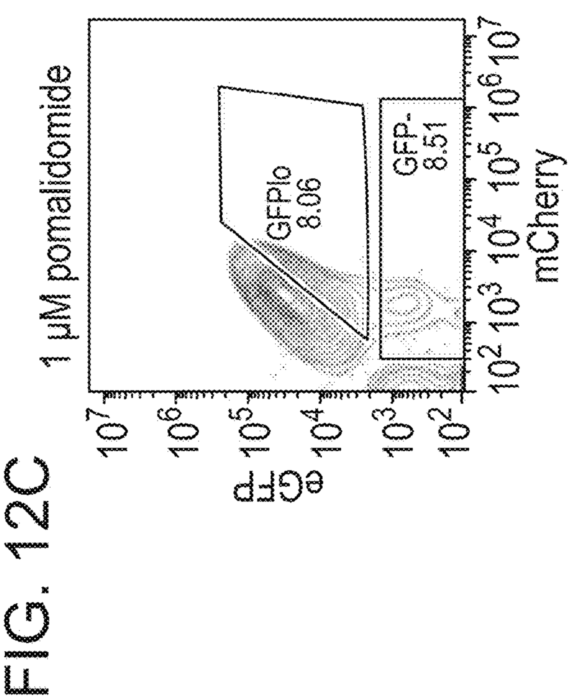
FIG. 12C is a graph of flow cytometry analysis of Jurkat T cells expressing a library of in silico designed C2H2 zinc fingers in a protein degradation reporter with 1 μM pomalidomide.
Figure 12D:
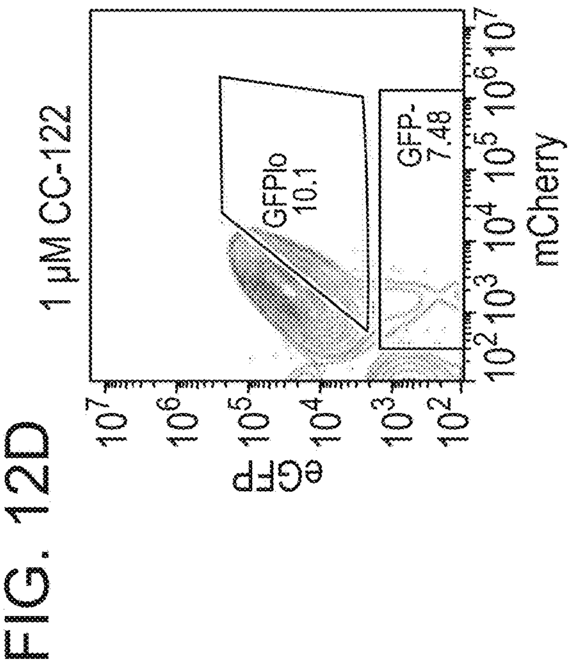
FIG. 12D is a graph of flow cytometry analysis of Jurkat T cells expressing a library of in silico designed C2H2 zinc fingers in a protein degradation reporter with 1 μM CC-122 (avadomide).
Figure 12E:
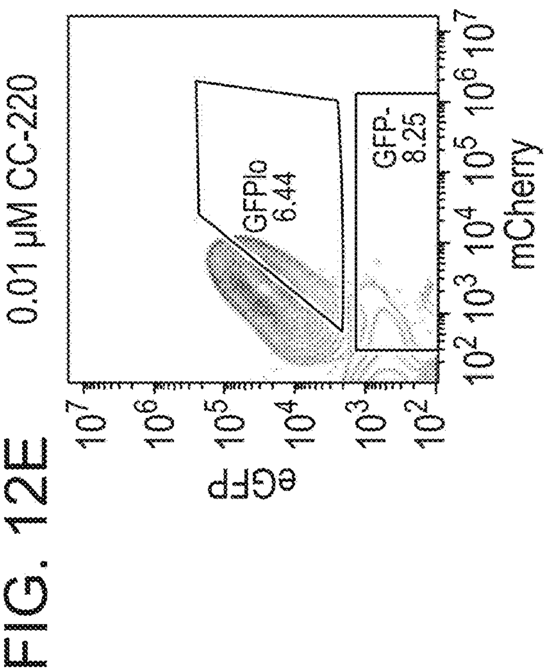
FIG. 12E is a graph of flow cytometry analysis of Jurkat T cells expressing a library of in silico designed C2H2 zinc fingers in a protein degradation reporter with 1 μM CC-220 (iberdimide).
Figure 13A:
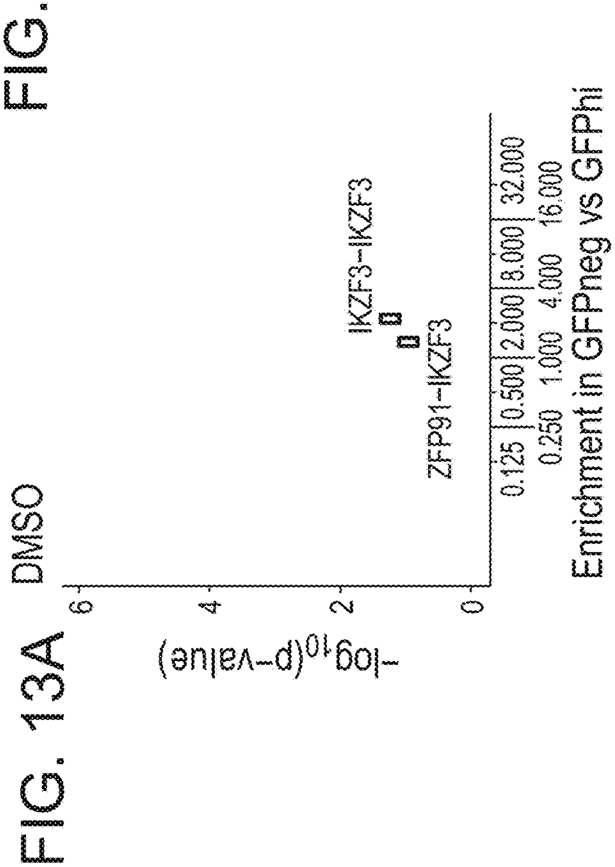
FIG. 13A is a waterfall plot of significance versus enrichment in GFP negative versus GFP high gates in cell populations encoding the ZF library based on GFP expression with DMSO.
Figure 13B:
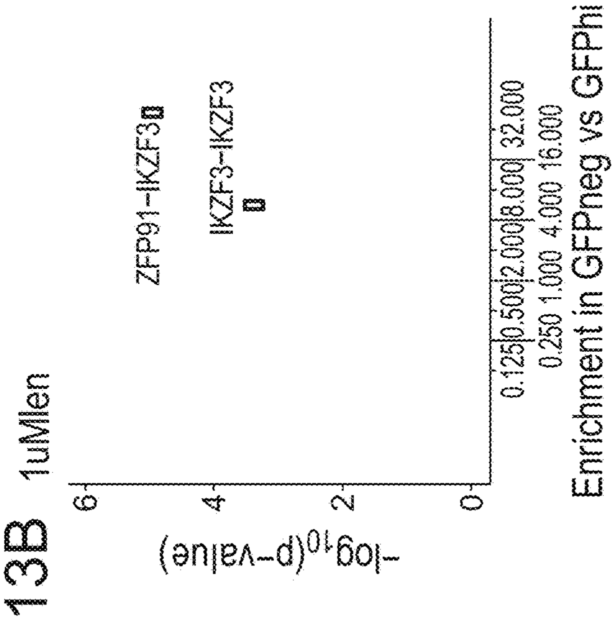
FIG. 13B is a waterfall plot of significance versus enrichment in GFP negative versus GFP high gates in cell populations encoding the ZF library based on GFP expression with 1 μM lenalidomide.
Figure 13C:
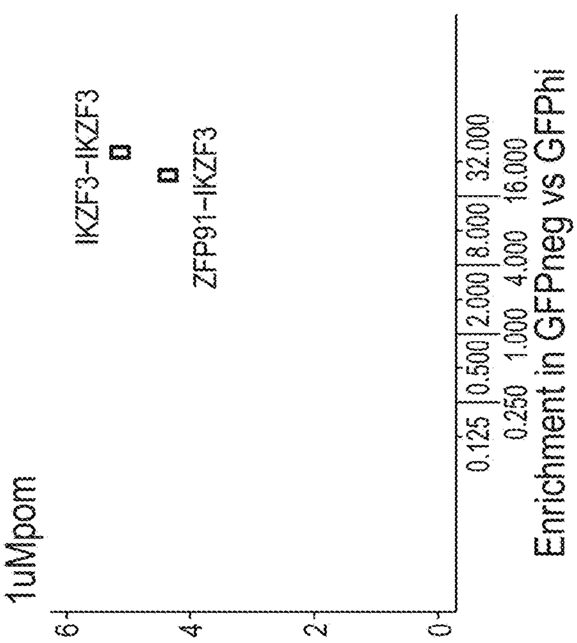
FIG. 13C is a waterfall plot of significance versus enrichment in GFP negative versus GFP high gates in cell populations encoding the ZF library based on GFP expression with 1 μM pomalidomide.
Figure 13D:
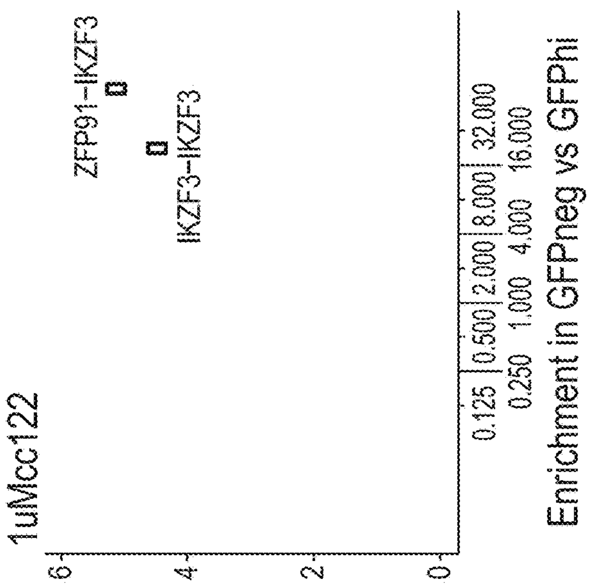
FIG. 13D is a waterfall plot of significance versus enrichment in GFP negative versus GFP high gates in cell populations encoding the ZF library based on GFP expression with 1 μM CC-122.
Figure 13E:
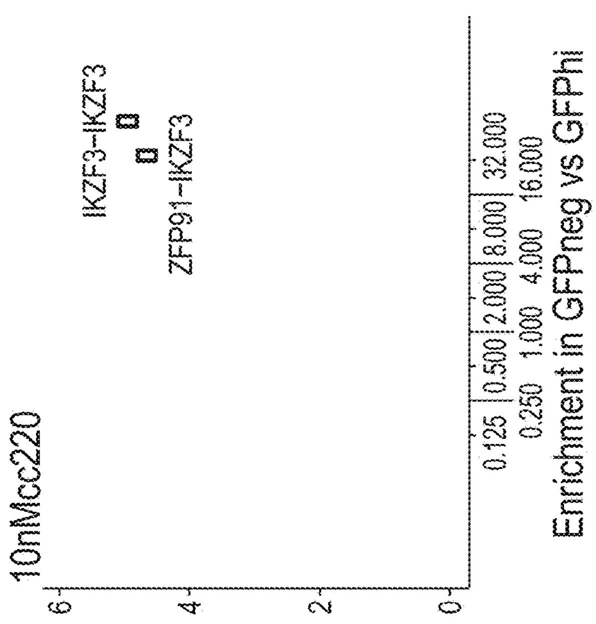
FIG. 13E is a waterfall plot of significance versus enrichment in GFP negative versus GFP high gates in cell populations encoding the ZF library based on GFP expression with 1 μM CC-220.

Representative data of potent degradation of eGFP-IKZF1Δ fusion by thalidomide, lenalidomide and pomalidomide is shown in FIG. 9. Quantitative assessment of cellular degradation of a IKZF1-EGFP reporter using flow cytometry analysis. Cells stably expressing IKZF1Δ-EGFP and mCherry were treated with increasing concentrations of the indicated molecules and the EGFP and mCherry signals followed using flow cytometry analysis. Data in this figure are presented as means±s.d. from four cell culture replicates (n=4).

Example 13: Validation of Degron Tag IKZF1/3 ZnF2 (SEQ ID NO: 25)

The degron tag of SEQ ID NO: 25 (IKZF1/3 ZnF2) was validated via a bromodomain-containing protein 4 (BRD4) knock-in assay.

For the generation of HEK293T BRD4 Degron Knockin cells, HEK293T cells were nucleofected using SF Cell Line 4D-Nucleofector™ X Kit L following manufacturer protocol (Lonza) with BRD4 sgRNA (TGGGATCACTAGCATGTCTG (SEQ ID NO: 145)) based Cas9 RNP complex (80 μmol) and 1Ig of pUC18 based plasmid with knock in donor DNA template (3 consecutive GFP 11 sites, followed by P2A site and Flag-Degron):

(SEQ ID NO: 146))

TCTGCTGACTGATATCTCACGGGGGCTCTTCTCTTCCTTTGTAGAGTGCCTGGT

GAAGAATGTGATGGGATCACTAATGAGGGATCATATGGTCCTCCATGAATACG

TCAACGCGGCCGGAATAACTGGCGGGAGTGGAGGGCGAGATCATATGGTTCTC

CACGAGTATGTCAACGCGGCCGGCATCACTGGAGGTTCAGGTGGGAGAGATCA

TATGGTCTTGCATGAATACGTGAATGCTGCGGGAATCACCGGGGGTAGCGGGG

GTAGAGATCATATGGTACTCCATGAATATGTAAACGCTGCGGGTATCACGGGT

GGCAGTGGAGGACGGGACCATATGGTCCTTCACGAATATGTGAATGCTGCGGG

CATAACGGGAGGATCCGGTGGTGGAAGCGGAGCTACTAACTTCAGCCTGCTGA

AGCAGGCTGGAGACGTGGAGGAGAACCCTGGACCTGACTACAAAGACGATGAC

GATAAAGGAGAACGGCCTTTTCAGTGCAATCAGTGCGGAGCCTCCTTTACTCA

AAAAGGCAACCTGCTGCGACACATTAAATTGCACAGCGGTGGAGGCGGCTCAG

GAGGTGGTGGTTCAGCGGAGAGCGGCCCTGGGACGAGATTGAGAAATCTGCC

AGTAATGGGGGATGGACTAGAAACTTCCCAAATGTCTACCTATAGTGAGTCGT

ATTA.

72 h post nucleofection, cells were transfected with 4 μg of pNTM-GFP1-10, and single clones isolated based on transient GFP-positive cells obtained by fluorescence assisted cell sorting (FACS). The degron DNA sequence is boxed (SEQ ID NO: 149)

(GGAGAACGGCCTTTTCAGTGCAATCAGTGCGGAGCCTCCTTTACTCAAA

AAGGCAACCTGCTGCGACACATTAAATTGCACAGC)

and has the amino

Example 14: Validation of Degron Tag IKZF1 (SEQ ID NO: 25)

Western Blot for Cellular BRD4 Degradation in IKZF1 Degron Cells

Degron-BRD4 cells were seeded at 90% confluency in 12 well plates (353043, Falcon), left to attach for 1.5 h, followed by the compound treatment for 5 h. Primary and secondary antibodies used included anti-BRD4 at 1:1000 dilution (A301-985A-M, Bethyl Laboratories, Lot: 6), anti-GAPDH at 1:10,000 dilution (G8795, Sigma, Lot: 065M4856V, Clone: GAPDH-71.1), IRDye®680 Donkey anti-mouse at 1:10,000 dilution (926-68072, LiCor®, Lot: C61116-05) and IRDye®800 Goat anti-rabbit at 1:10,000 dilution (926-32211, LiCor®, Lot: C70301-05).

FIG. 9 is a photograph of a Western blot showing degradation of BRD4 by creating an N-terminus knock-in of IKZF1 degron tag at BRD4 locus using a nucleic acid sequence encoding SEQ ID NO: 15 and increasing amounts (1 and 20 μM) of lenalidomide.

Example 15: Selection of the Zinc Finger Library Based on GFP Expression

The selection of the zinc finger library based on GFP expression was performed using flow cytometry.

The data illustrated in FIG. 12A-FIG. 12E show the flow cytometry analysis of Jurkat T cells expressing a library of in silico designed C2H2 zinc fingers in a protein degradation reporter. GFP low and GFP negative gates were provided across the evaluated drug conditions.

These findings illustrate that there was an increase in GFP negative and GFP low sequences in the thalidomide analog treated cells, as compared to vehicle control, consistent with drug-dependent degradation of a detectable subset of sequences in the zinc finger library.

Example 16: Selection of the Zinc Finger Library Based on GFP Expression

Jurkat cells expressing a library of 5826 C2H2 zinc fingers in the protein degradation reporter Cilantro 2 were treated with DMSO, lenalidomide, pomalidomide, iberdomide, or avadomide. eGFP+ and eGFP− cell populations were isolated by FACS in triplicate, and the relative frequency of individual zinc finger degronc (ZFs) was quantified with next-generation sequencing. Next-generation sequencing of sorted cell populations encoding the ZF library was based on GFP expression.

The results illustrated in FIG. 13A-FIG. 13E show identification of candidate thalidomide analog-responsive degrons by next-generation sequencing: waterfall plots summarizing next-generation sequencing of sorted cell populations encoding the ZF library based on GFP expression. Significance versus enrichment in GFP negative versus GFP high gates is plotted. Previously described positive control sequences are highlighted in red in FIG. 14. These findings indicate that numerous sequences in grey appeared to be more significantly enriched in the GFP negative versus GFP high sorted populations than the known degrons IKZF3 and ZFP91-IKZF3 in the presence of various thalidomide analogs, consistent with increased sensitivity to thalidomide analog-mediated degradation.

Seventy (70) thalolidome analog-regulated degrons or super degrons identified by next-generation sequencing (NGS) were selected. The selection criteria were as follows:

- Significantly enriched (FDR=0.001) in the GFPneg versus GFP+ sorts for at least 1 drug
- AND <2.5 enrichment in GFPneg versus GFP+ in DMSO condition (to remove unstable/endogenously degraded forms).

Sequence characteristics of thalidomide analog-regulated degrons identified by NGS are highlighted in FIG. 15A-FIG. 15B. These findings indicate that the 23 candidate lenalidomide-regulated novel variant super degrons converge on sequence features at the amino acid positions highlighted in blue (FIG. 15 A).

Figure 14:
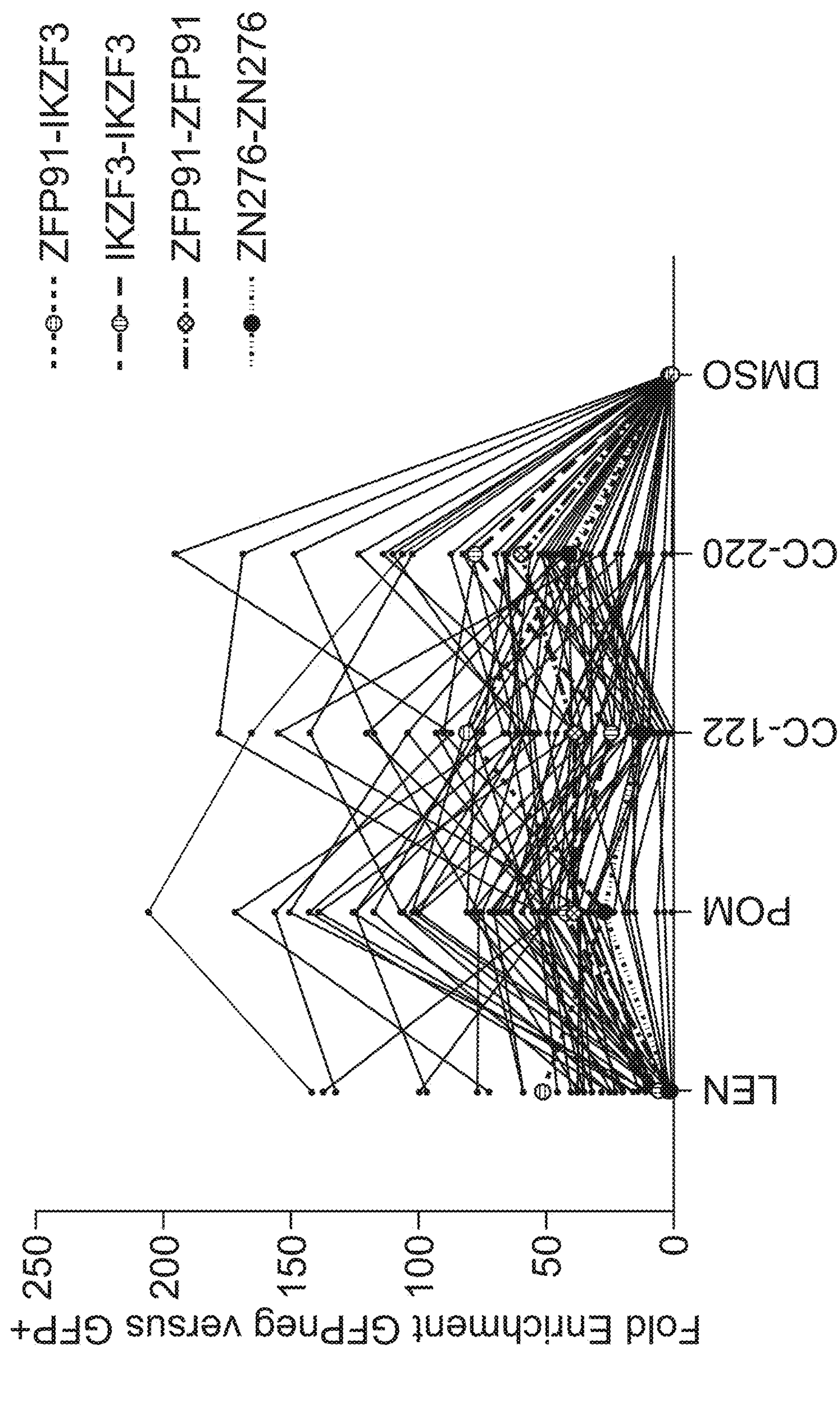
FIG. 14 is a graph of fold enrichment of candidate zinc finger degrons in GFP negative versus GFP high sorted populations. Previously described positive control degrons are highlighted.

Fold enrichment of candidate zinc finger degrons in GFP negative versus GFP high sorted populations is illustrated in FIG. 14. These sequences correspond to the 70 sequences chosen by the criteria listed above. Each sequence is connected with a line across all drug treatment conditions. These findings indicate that some novel variant sequences, in black, were more enriched in the GFPnegative versus GFPhigh gate with one or more thalidomide analog than the labeled controls.

Figure 16:
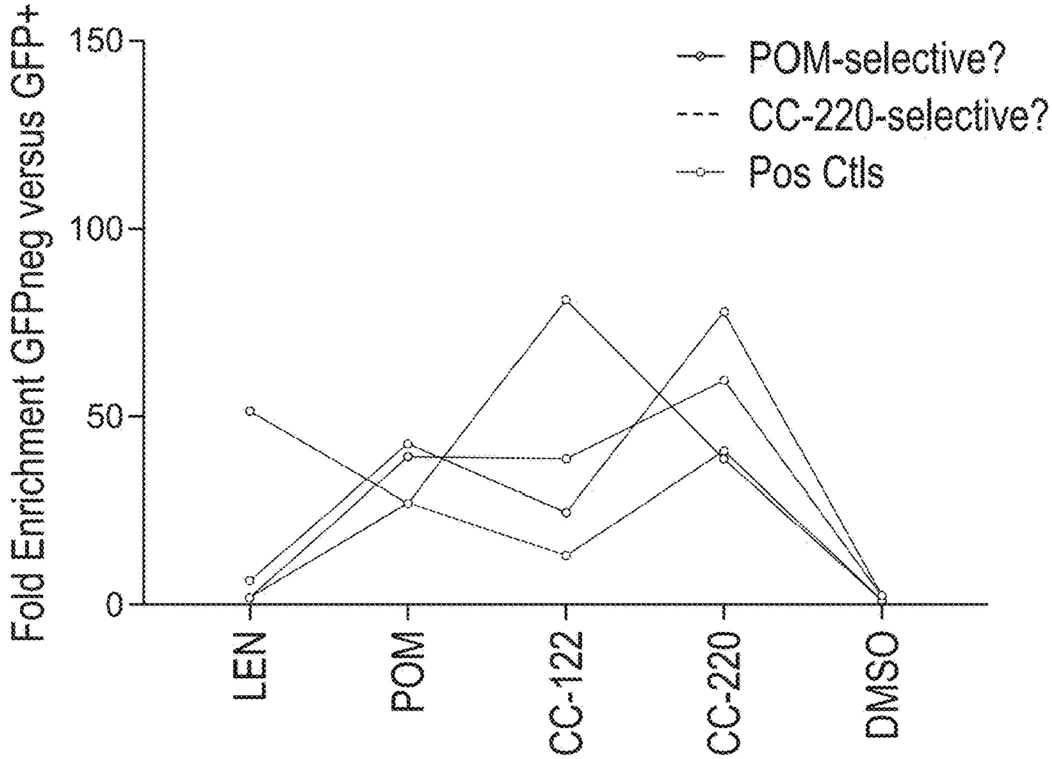
FIG. 16 is a graph of fold enrichment of candidate drug-selective zinc finger degrons in GFP negative versus GFP high sorted populations. Previously described positive control degrons are highlighted.

Fold enrichment of candidate drug-selective zinc finger degrons in GFP negative versus GFP high sorted populations is illustrated in FIG. 16. These findings indicate that a subset of sequences in blue and black were significantly enriched in GFPnegative versus GFPhigh gate for only one thalidomide analog, consistent with drug-selective degron function.

Known degrons degraded by all tested thalidomide analogs are labelled orange.

degradation reporter lentivector. A subset of novel variant ZFs in grey were more efficiently degraded than IKZF3 by one or more thalidomide analogs (FIG. 17A-FIG. 17D). A subset of novel variant ZFs in green were selectively degraded by CC-220 versus the other thalidomide analogs (FIG. 19A-FIG. 19D).

Figure 17A:
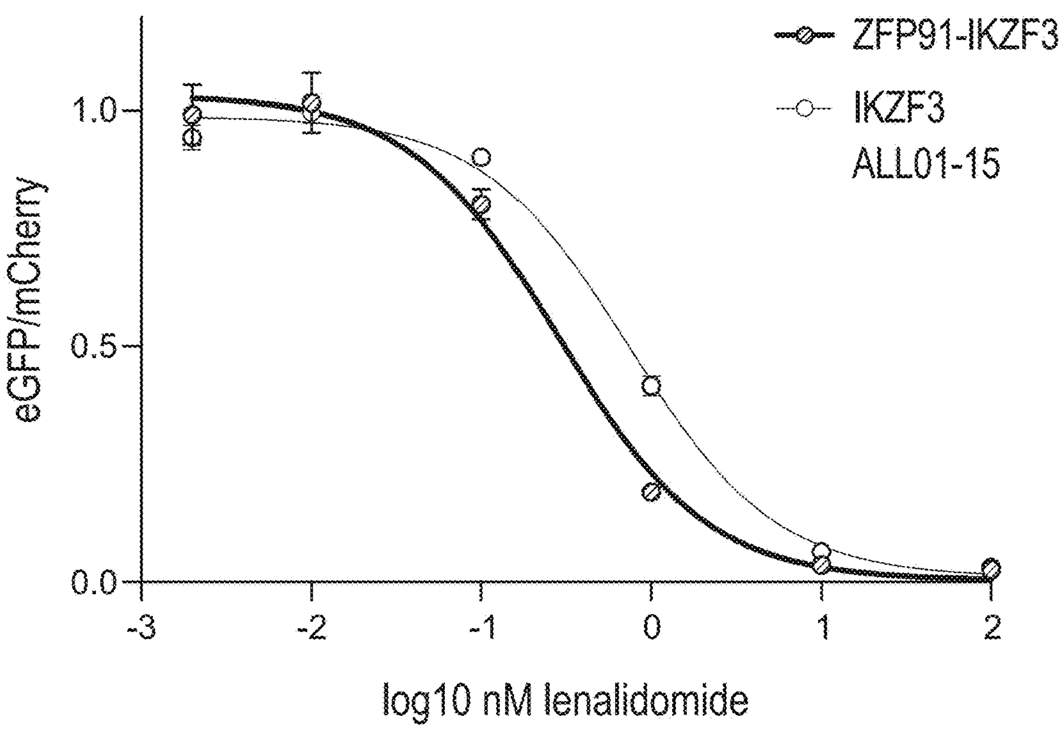
FIG. 17A is a graph of drug dependent degradation of Jurkat cells expressing IKZF3 and ZFP91-IKZF3 ZFs in the Artichoke protein degradation reporter lentivector with lenalidomide.
Figure 17B:
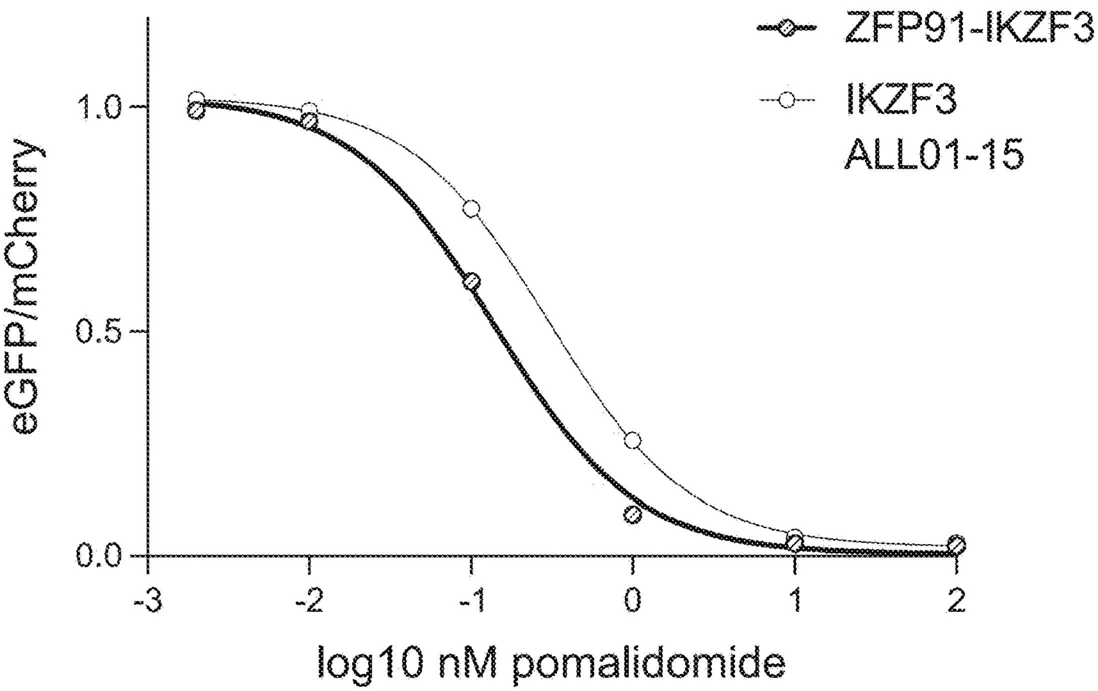
FIG. 17B is a graph of drug dependent degradation of Jurkat cells expressing IKZF3 and ZFP91-IKZF3 ZFs in the Artichoke protein degradation reporter lentivector with pomalidomide.
Figure 17C:
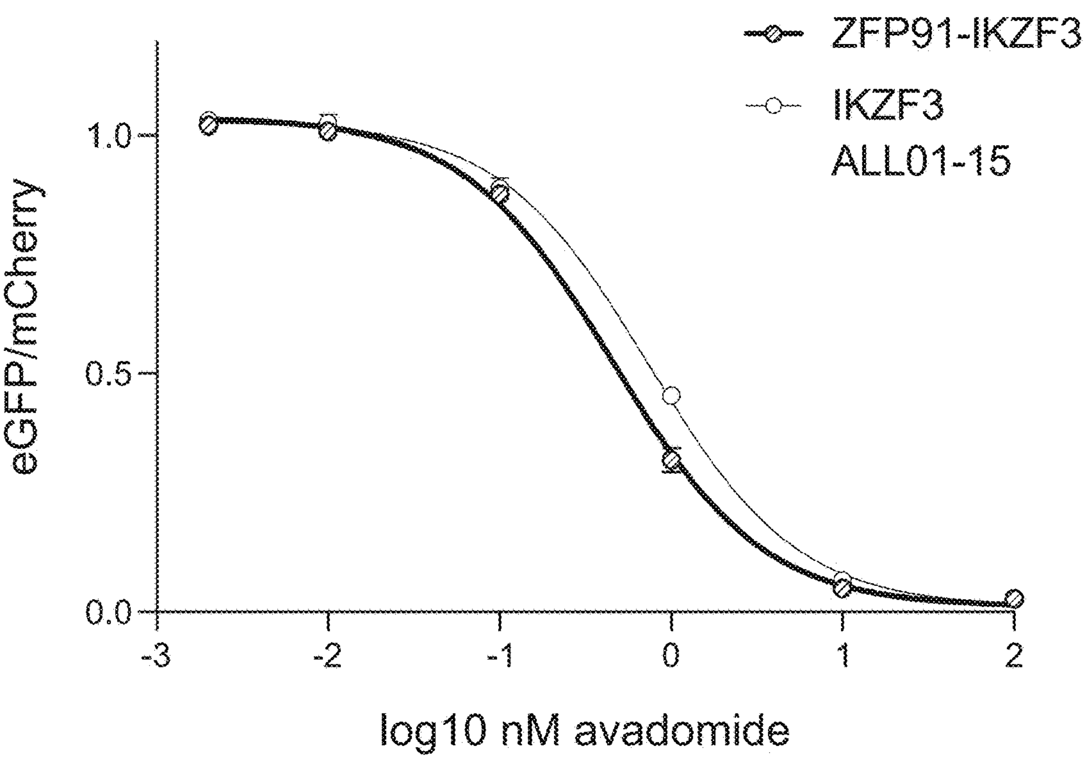
FIG. 17C is a graph of drug dependent degradation of Jurkat cells expressing IKZF3 and ZFP91-IKZF3 ZFs in the Artichoke protein degradation reporter lentivector with avadomide.
Figure 17D:
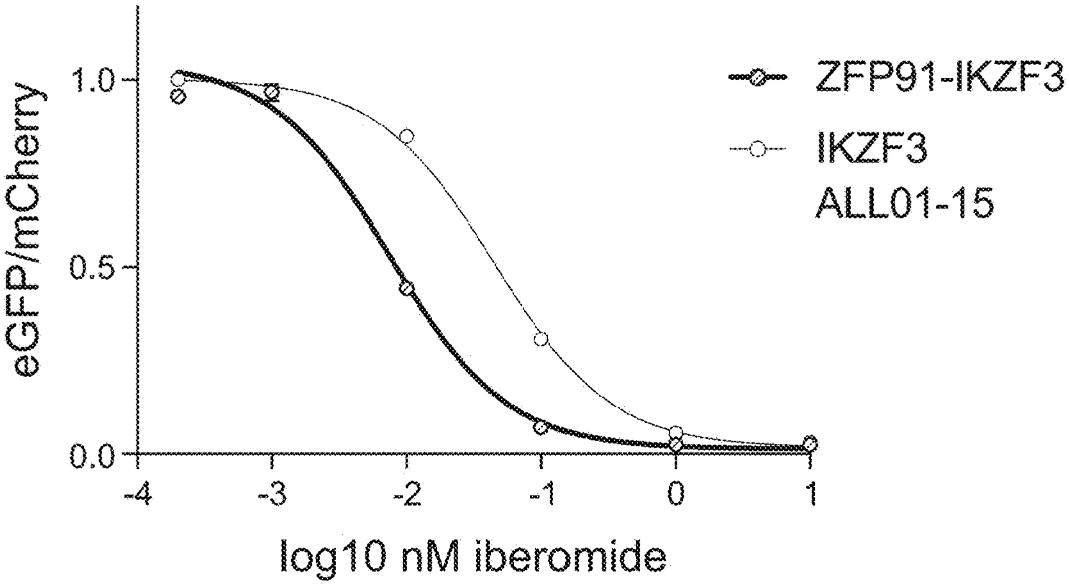
FIG. 17D is a graph of drug dependent degradation of Jurkat cells expressing IKZF3 and ZFP91-IKZF3 ZFs in the Artichoke protein degradation reporter lentivector with iberomide.
Figure 17E:
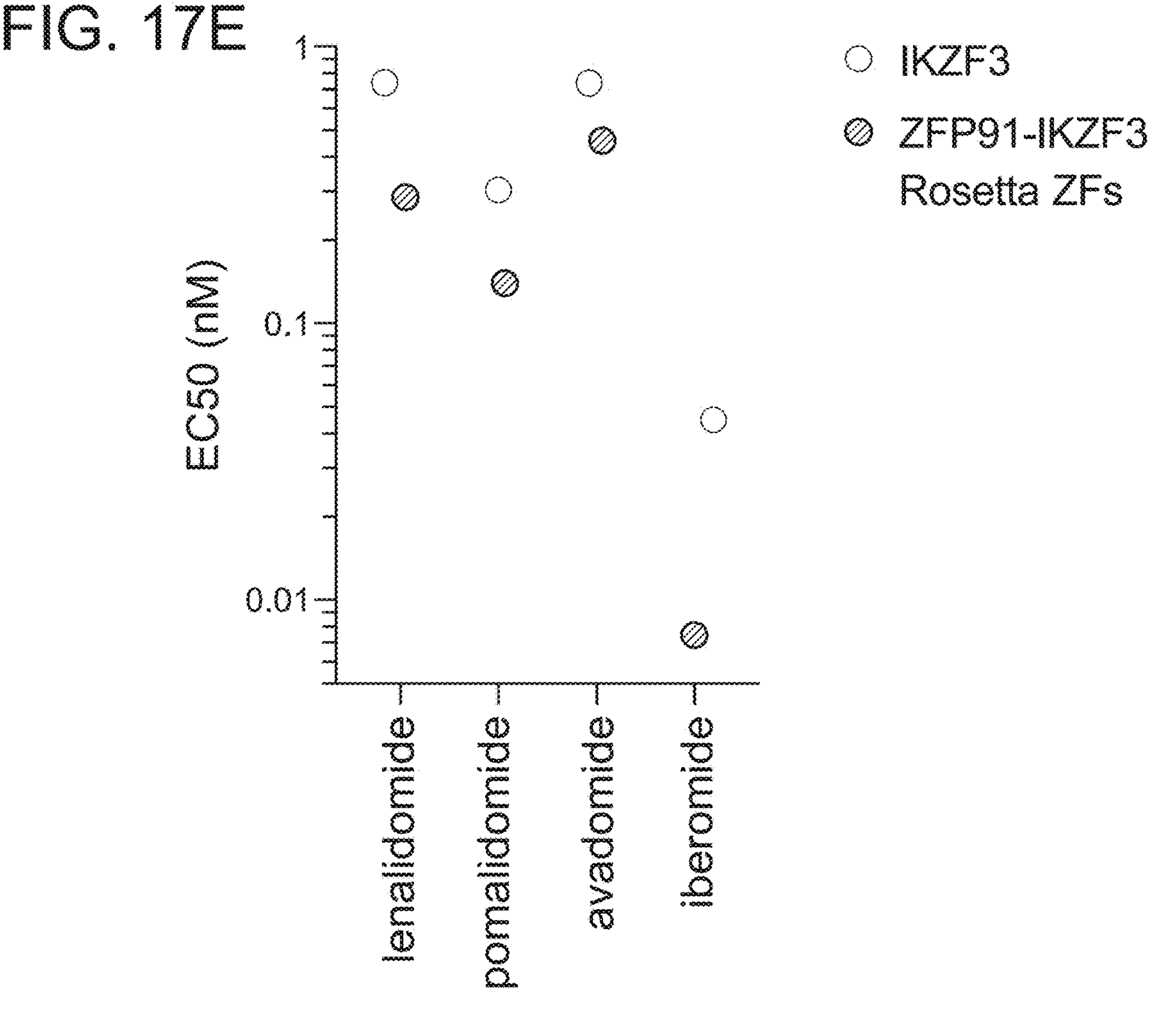
FIG. 17E is a graph of $EC_{50}$ values in Jurkat cells expressing IKZF3 and ZFP91-IKZF3 ZFs in the Artichoke protein degradation reporter lentivector with lenalidomide, pomalidomide, avadomide, and iberomide.

$EC_{50}$ values are summarized in FIG. 17E. These results indicate that a number of the new variant sequences validated as more efficiently degraded than IKZF3.

Figure 18:
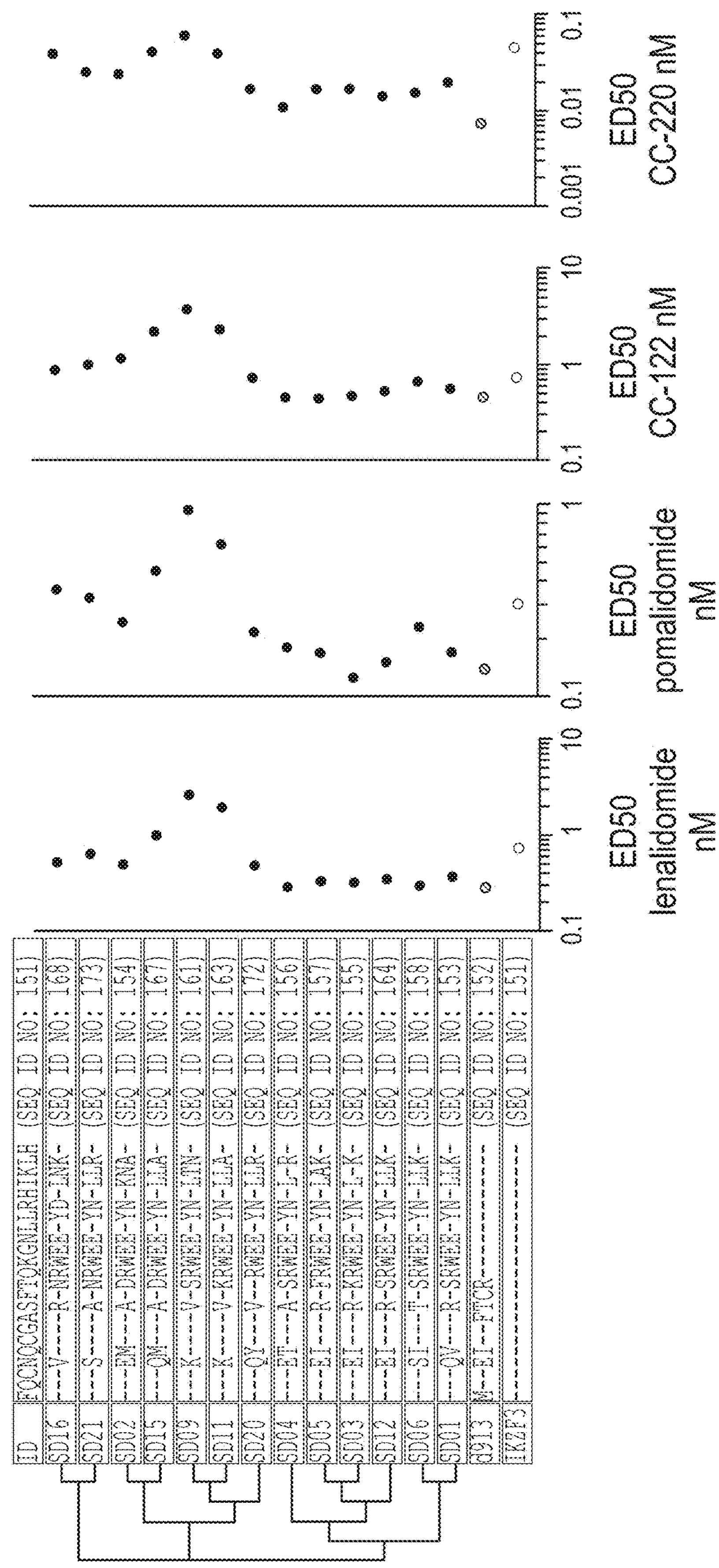
FIG. 18 is a diagram of sequence and degradation features for 15 in silico designed zinc fingers degraded by various thalidomide analogs. IKZF3 and d913 (ZFP91-IKZF3) are included as controls.
Figure 19A:
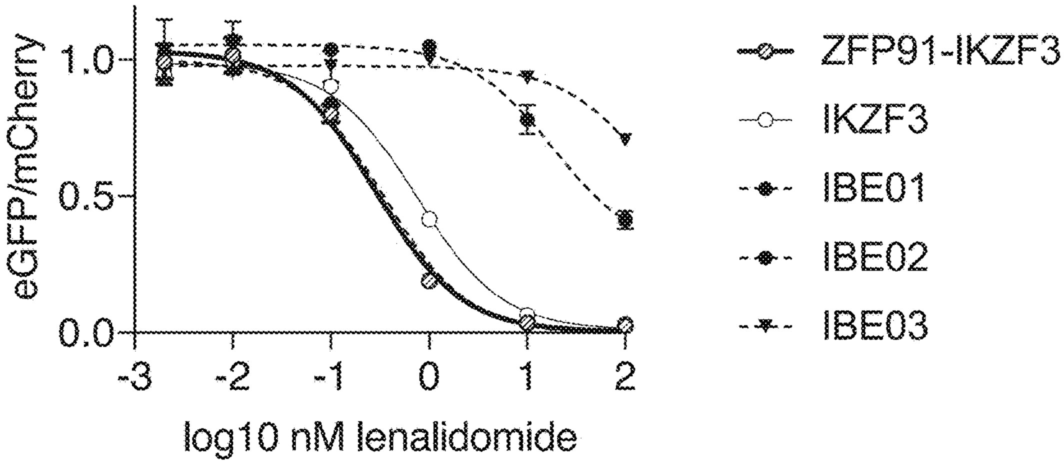
FIG. 19A is a graph of drug dependent degradation of Jurkat cells expressing IKZF3, ZFP91-IKZF3, IBE01 (CC220-01), IBE02 (CC220-02), and IBE03 (CC220-03) ZFs in the Artichoke protein degradation reporter lentivector with lenalidomide.
Figure 19B:
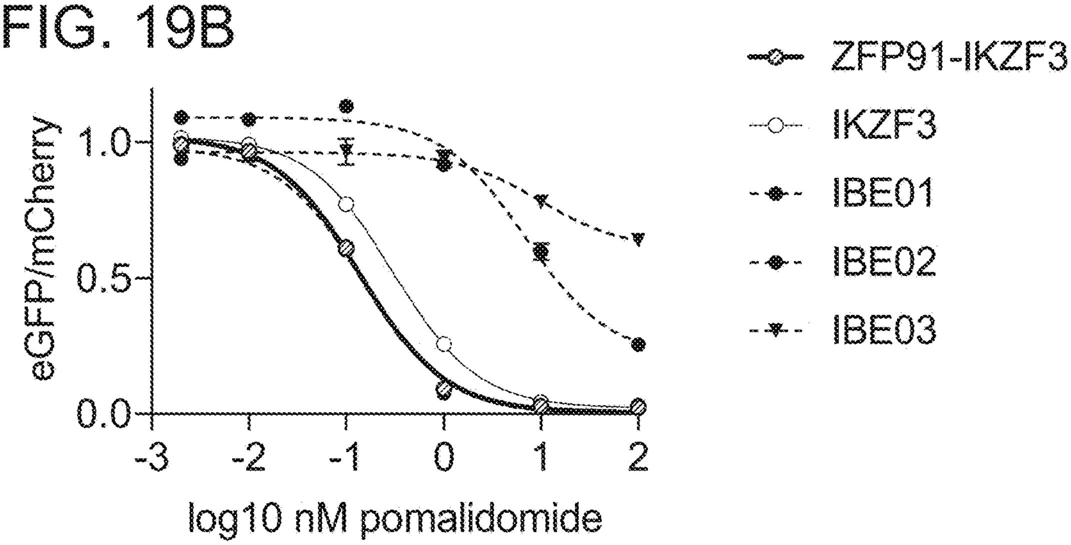
FIG. 19B is a graph of drug dependent degradation of Jurkat cells expressing IKZF3, ZFP91-IKZF3, IBE01, IBE02, and IBE03 ZFs in the Artichoke protein degradation reporter lentivector with pomalidomide.
Figure 19C:
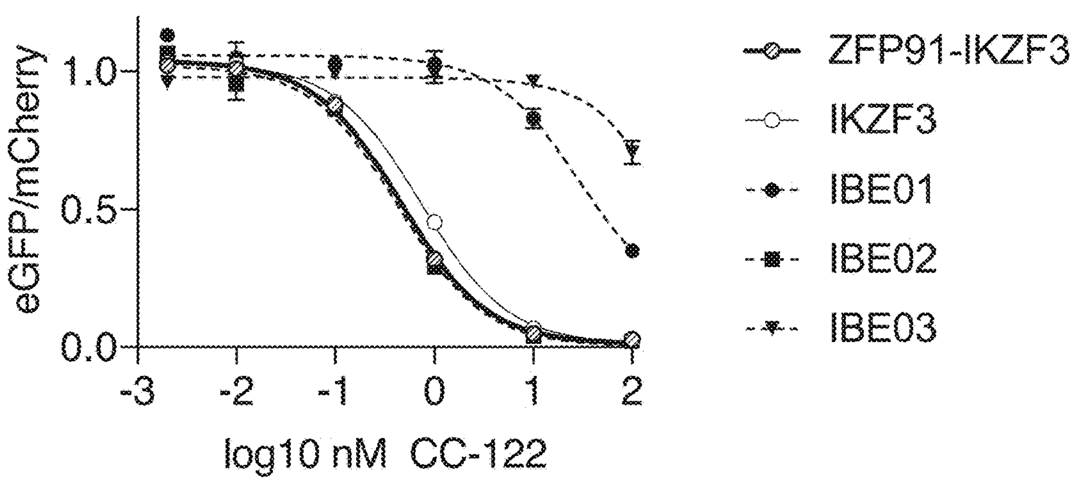
FIG. 19C is a graph of drug dependent degradation of Jurkat cells expressing IKZF3, ZFP91-IKZF3, IBE01, IBE02, and IBE03 ZFs in the Artichoke protein degradation reporter lentivector with avadomide.
Figure 19D:
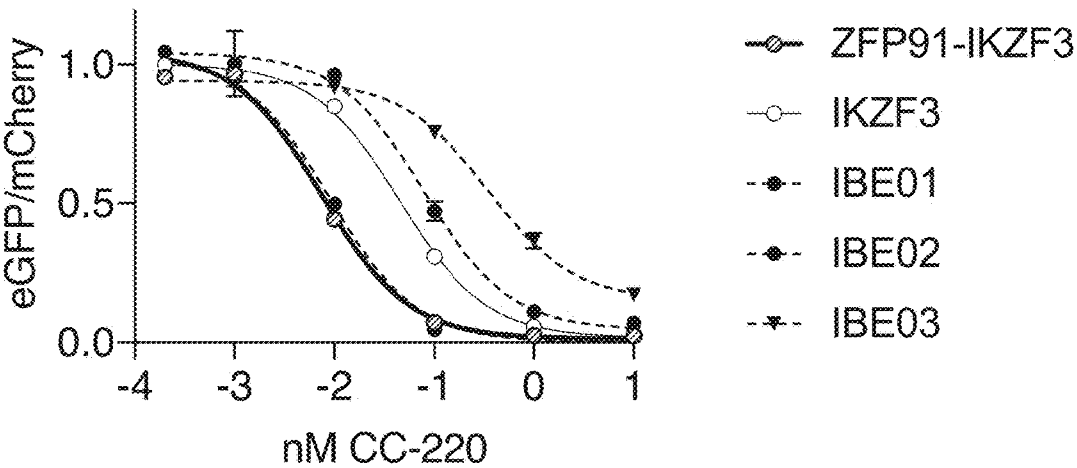
FIG. 19D is a graph of drug dependent degradation of Jurkat cells expressing IKZF3, ZFP91-IKZF3, IBE01, IBE02, and IBE03 ZFs in the Artichoke protein degradation reporter lentivector with iberomide.

Sequence and degradation features for 15 in silico designed zinc fingers degraded by various thalidomide analogs, including $EC_{50}$ values, are illustrated in FIG. 18. IKZF3 and d913 (ZFP91-IKZF3) are included as controls. These findings demonstrate that certain clusters of novel variant sequences had similar sensitivity to thalidomide analog-induced degradation.

Amino acid sequences for zinc finger degrons used in this experiment are set forth in Table 1.

TABLE 1

| ID | Gene | Sequence |
|---|---|---|
| POM01 | redo2-4ci3-hscrbn-pom-ikzf1_ikzf1_orun_982.prepack_019756_Rank_524 | FQCEYCGARFNRWEELYNHLLKH (SEQ ID NO: 177) |
| POM02 | redo-4ci3-hscrbn-pom-6b0o_6b0o_chaina_0001_0004_orun_547.prepack_011994_Rank_650 | YQCEICGARFNRWEELYNHLKNH (SEQ ID NO: 178) |
| POM03 | 4ci3-hscrbn-pom-6b0o_6b0o_chaina_0001_0007_orun_356.prepack_002330_Rank_340 | FQCEICGAAFSRWEELYNHLLAH (SEQ ID NO: 179) |
| POM04 | 4ci1-hscrbn-thal-6b0o_6b0o_chaina_0001_0007_orun_316.prepack_001977_Rank_655 | FQCEICGARFSRWEELYNHLSKH (SEQ ID NO: 180) |
| POM05 | redo-4ci3-hscrbn-pom-6b0o_6b0o_chaina_0001_0001_orun_1535.prepack_004827_Rank_779 | FQCEICGARFEYWEQLYNHLKNH (SEQ ID NO: 181) |
| CC22001 | redo2-4ci3-hscrbn-pom-ikzf1_ikzf1_orun_128.prepack_003206_Rank_1938 | FYCTQCGAAFDRWEELYNHLLNH (SEQ ID NO: 182) |
| CC22002 | Naa-ZFP91 Caa-redo2-4ci2-hscrbn-len-ikzf1_ikzf1_orun_1174.prepack_004080_Rank_5 | MQCEICGFTCRRAEELNTHLNKH (SEQ ID NO: 183) |
| CC22003 | 4ci1-hscrbn-thal-5vmu_5vmu_chaina_0001_0009_orun_275.prepack_001821_Rank_451 | FYCKQCGANFSRWEELYNHLKAH (SEQ ID NO: 184) |

Example 17: Validation of Candidate Zinc Finger Degrons in Artichoke Lentivector Jurkat cells expressing single candidate C2H2 zinc fingers in the protein degradation reporter Cilantro 2, or incorporated into a larger ZF array context (SGFNVLMVHKRSHTGERP-ZF-TGEKPFKCHLCNYACQRRDAL (SEQ ID NO: 188)) were treated in duplicate with DMSO or a concentration range of lenalidomide, pomalidomide, iberdomide, or avadomide, and eGFP expression was evaluated by flow cytometry.

The results illustrated in FIG. 17A-FIG. 17D and FIG. 19A-FIG. 19D show drug dependent degradation of Jurkat cells expressing individual ZFs in the Artichoke protein

Example 18: Validation of Candidate Zinc Finger Degrons in Cilantro 2 Lentivector The experimental procedure was as described in Example 16.

The results illustrated in FIG. 20A-FIG. 20D and FIG. 21A-FIG. 21D show drug dependent degradation of Jurkat cells expressing individual ZFs in the Cilantro 2 protein degradation reporter lentivector. The results illustrated in FIG. 20A-FIG. 20D demonstrate that a subset of novel variant sequences were more efficiently degraded than IKZF3. The results illustrated in FIG. 20A-FIG. 20D demonstrate that the novel variants sequences CC220-1/2/3 were more efficiently degraded by iberdomide (aka CC-220) than the indicated control sequences.

Figure 20A:
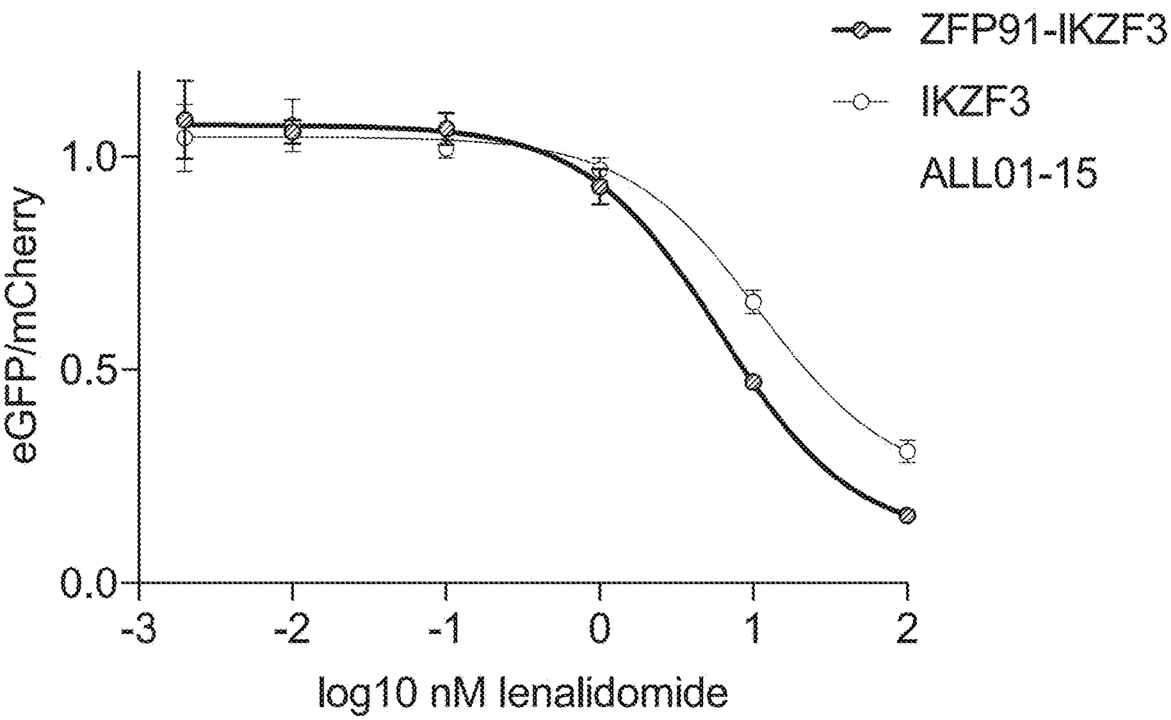
FIG. 20A is a graph of drug dependent degradation of Jurkat cells expressing IKZF3 and ZFP91-IKZF3 ZFs in the Cilantro 2 protein degradation reporter lentivector with lenalidomide.
Figure 20B:
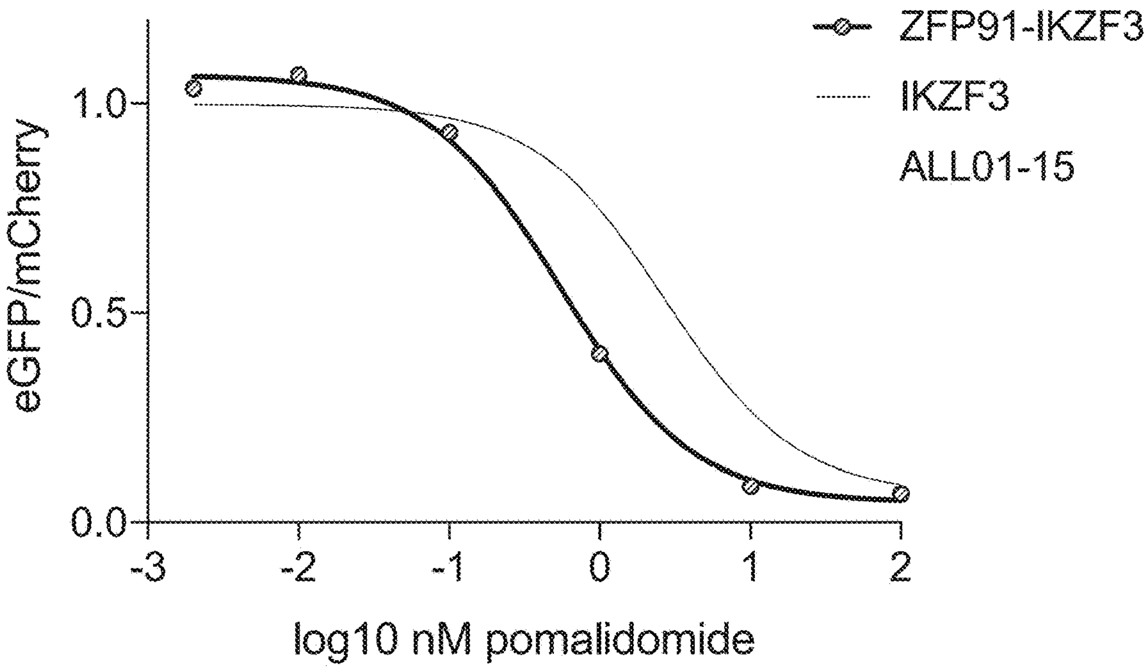
FIG. 20B is a graph of drug dependent degradation of Jurkat cells expressing IKZF3 and ZFP91-IKZF3 ZFs in the Cilantro 2 protein degradation reporter lentivector with pomalidomide.
Figure 20C:
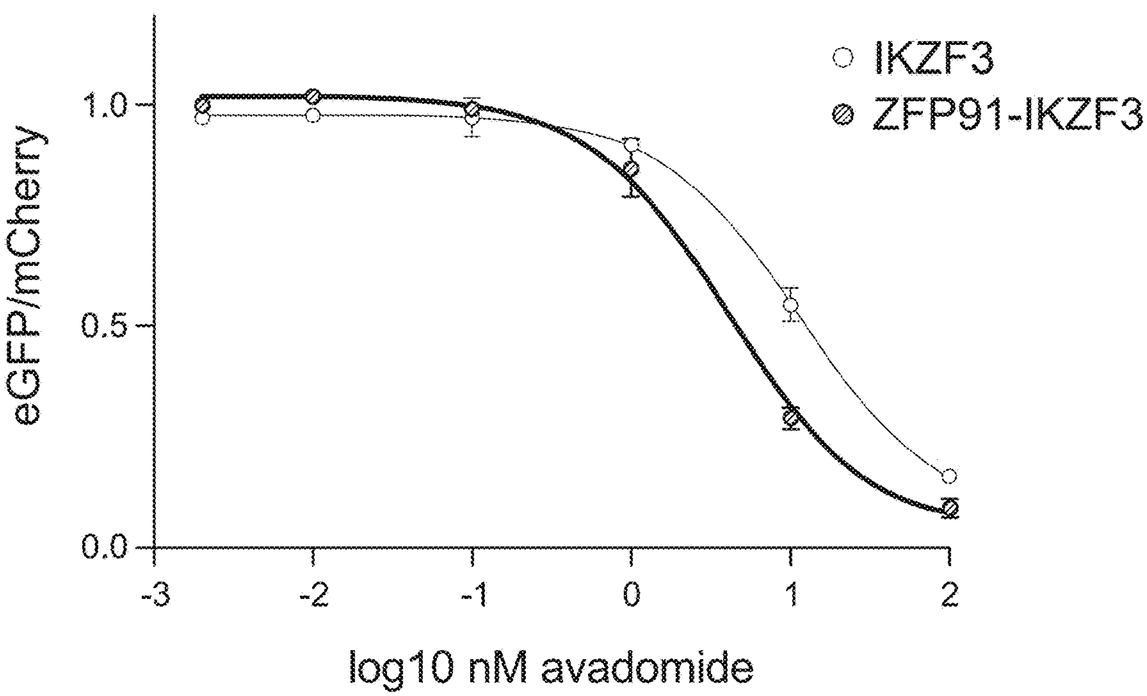
FIG. 20C is a graph of drug dependent degradation of Jurkat cells expressing IKZF3 and ZFP91-IKZF3 ZFs in the Cilantro 2 protein degradation reporter lentivector with avadomide.
Figure 20D:
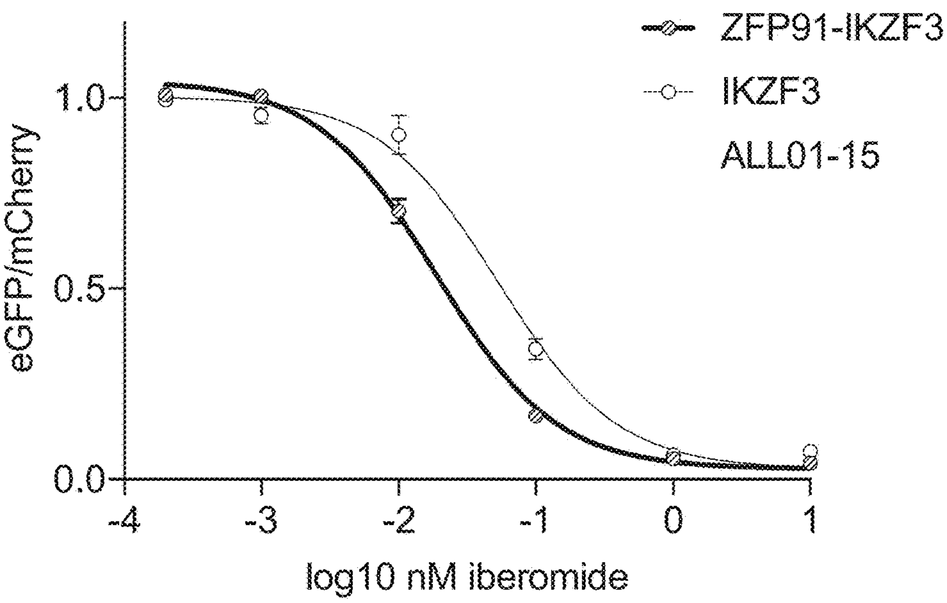
FIG. 20D is a graph of drug dependent degradation of Jurkat cells expressing IKZF3 and ZFP91-IKZF3 ZFs in the Cilantro 2 protein degradation reporter lentivector with iberomide.
Figure 20E:
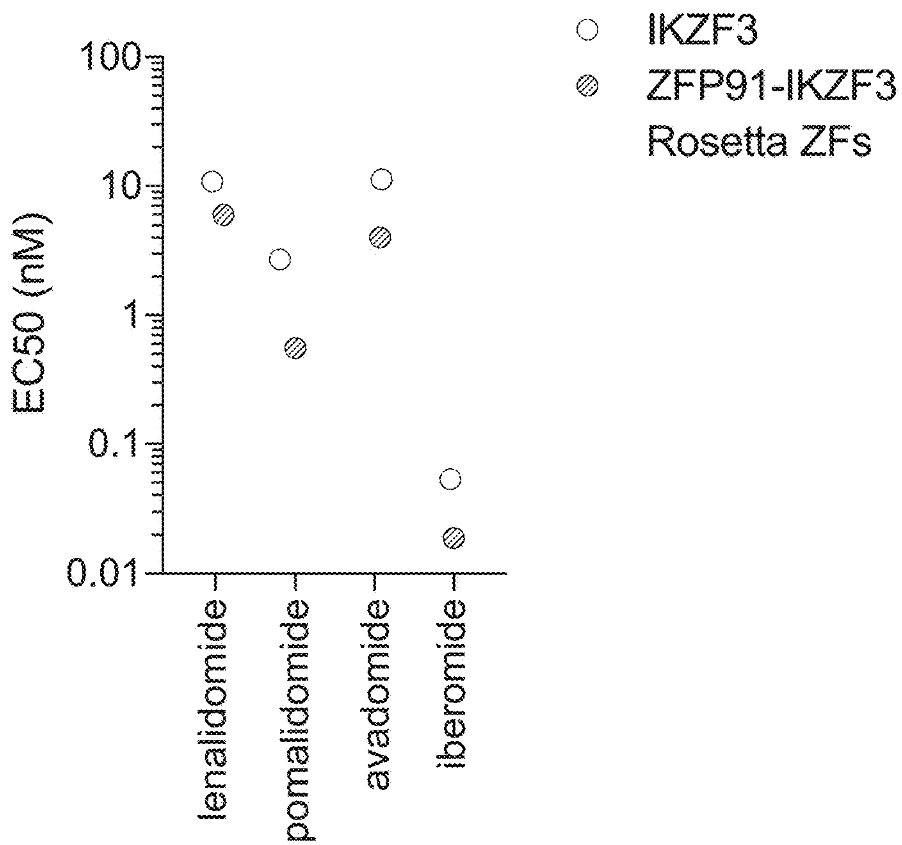
FIG. 20E is a graph of $EC_{50}$ values in Jurkat cells expressing IKZF3 and ZFP91-IKZF3 ZFs in the Cilantro 2 protein degradation reporter lentivector with lenalidomide, pomalidomide, avadomide, and iberomide.
Figure 21A:
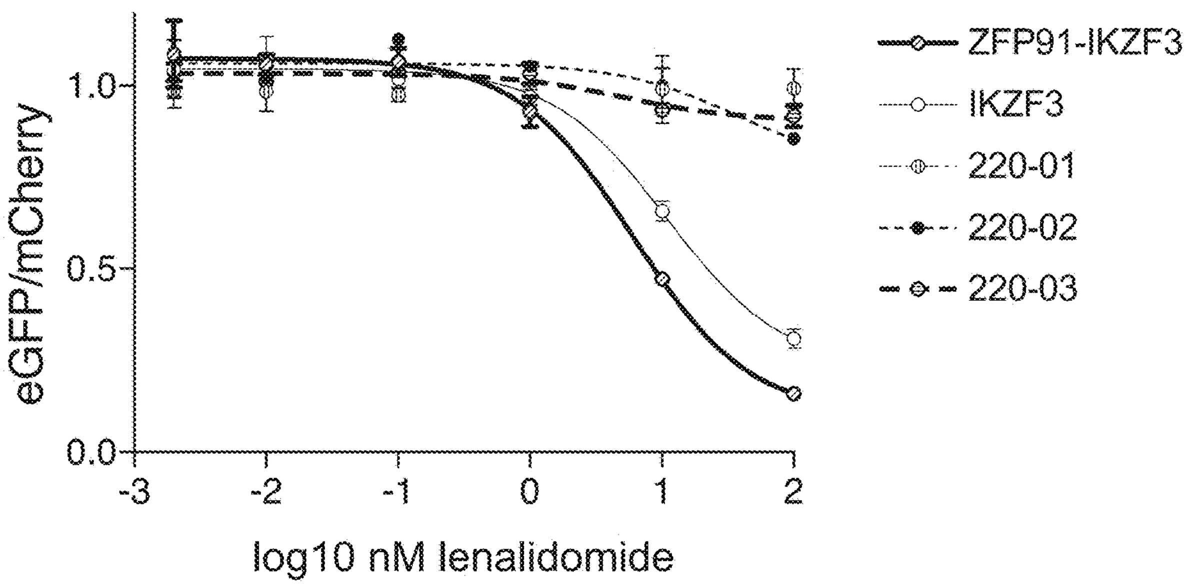
FIG. 21A is a graph of drug dependent degradation of Jurkat cells expressing IKZF3, ZFP91-IKZF3, CC220-01, CC220-02, and CC220-03 ZFs in the Cilantro 2 protein degradation reporter lentivector with lenalidomide.
Figure 21B:
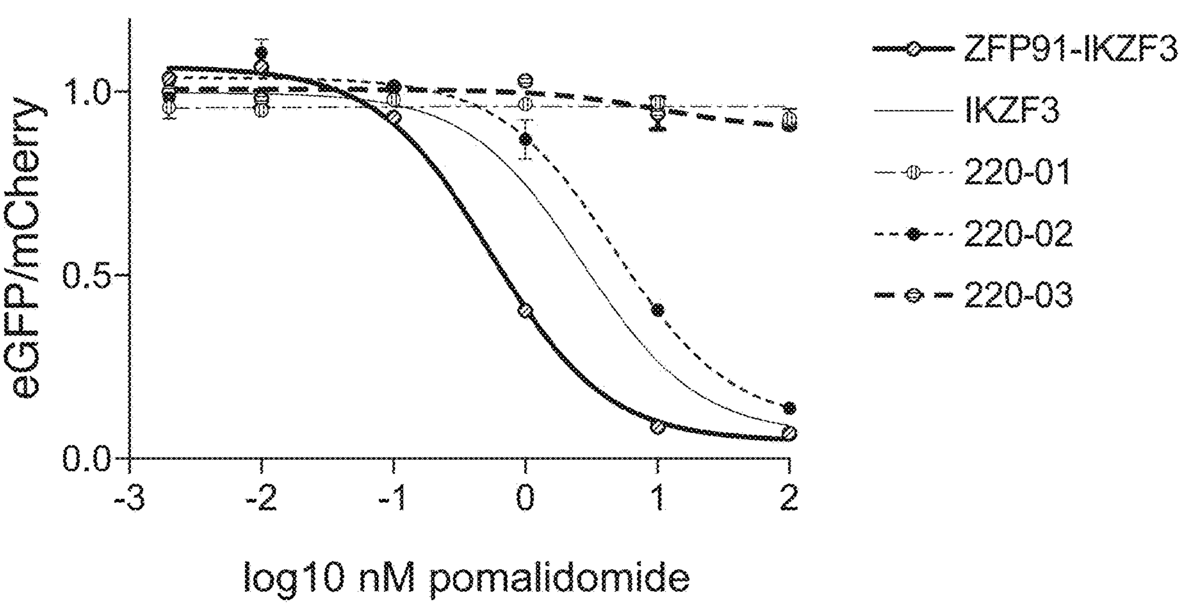
FIG. 21B is a graph of drug dependent degradation of Jurkat cells expressing IKZF3, ZFP91-IKZF3, CC220-01, CC220-02, and CC220-03 ZFs in the Cilantro 2 protein degradation reporter lentivector with pomalidomide.
Figure 21C:
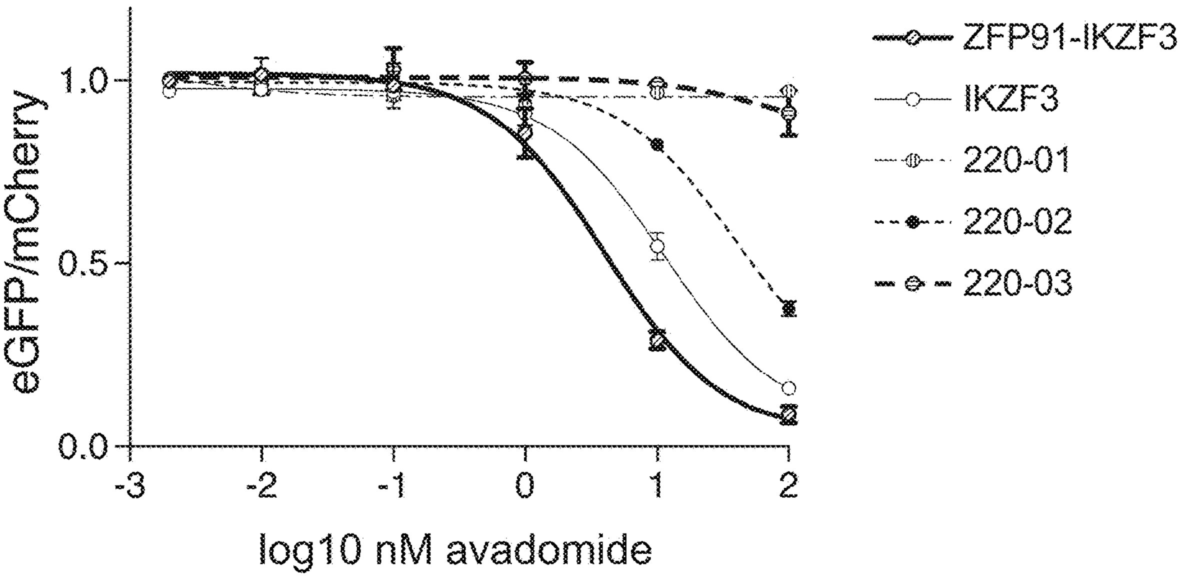
FIG. 21C is a graph of drug dependent degradation of Jurkat cells expressing IKZF3, ZFP91-IKZF3, CC220-01, CC220-02, and CC220-03 ZFs in the Cilantro 2 protein degradation reporter lentivector with avadomide.
Figure 21D:
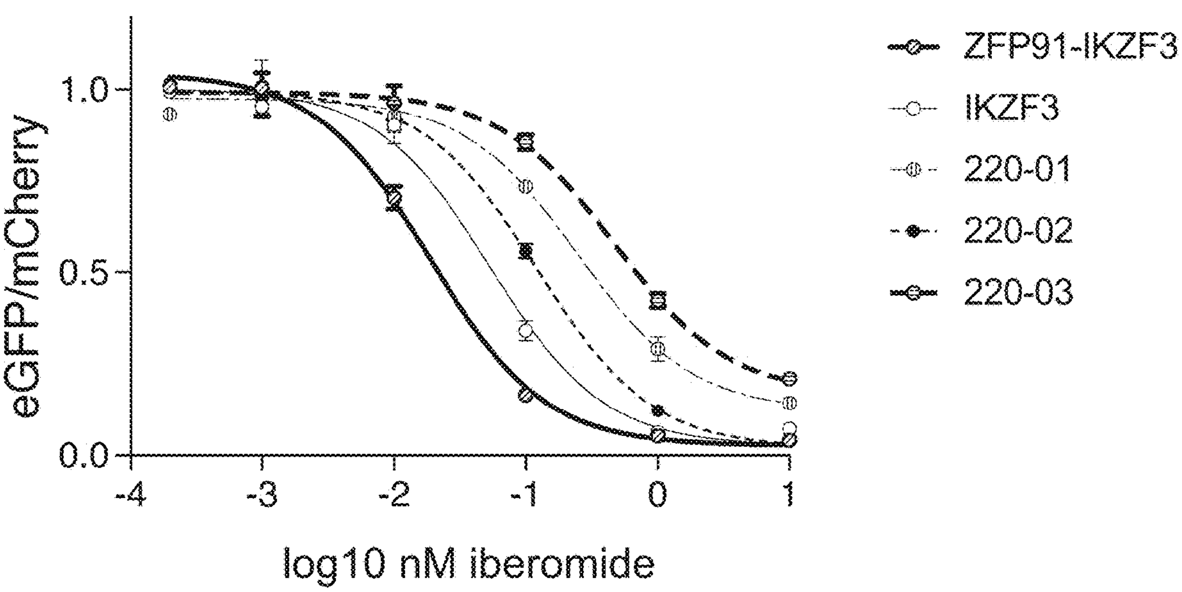
FIG. 21D is a graph of drug dependent degradation of Jurkat cells expressing IKZF3, ZFP91-IKZF3, CC220-01, CC220-02, and CC220-03 ZFs in the Cilantro 2 protein degradation reporter lentivector with iberomide.

$EC_{50}$ values are summarized in FIG. 20E. These results indicate that a number of the new variant sequences validated as more efficiently degraded than IKZF3 or ZFP91-IKZF3.

A summary of in silico designed ZF sequences and thalidomide-analog degradation $EC_{50}$ is set forth in Table 2.

TABLE 2

| Name Sequence | $EC_{50}$ | | | |
|---|---|---|---|---|
| | lenalidomide | pomalidomide | cc-122 | cc-220 |
| IKZF2FQCNQCGASFTQKGNLLRHIKLH (SEQ ID NO: 151) | 10.88 | 2.724 | 11.23 | 0.05367 |
| d913 MQCEICGFTCRQKGNLLRHIKLH (SEQ ID NO: 152) | 5.999 | 0.5538 | 4.018 | 0.01885 |
| PAN01FQCQVCGARFSRWEELYNHLLKH (SEQ ID NO: 153) | 2.156 | 0.6889 | 1.871 | 0.06991 |
| PAN02FQCQYCGAVFTRWEELYNHLLRH (SEQ ID NO: 172) | 4.738 | 1.006 | 4.437 | 0.06667 |
| PAN03FQCEMCGAAFDRWEELYNHKNAH (SEQ ID NO: 154) | 5.153 | 1.502 | 12.02 | 0.4044 |
| PAN04FQCNQCGASFTRWEELYNHLLRH (SEQ ID NO: 171) | 15.14 | 3.547 | 9.083 | 0.1348 |
| PAN05FQCKQCGAVFSRWEELYNHLTNH (SEQ ID NO: 161) | 4.463 | 1.195 | 7.753 | 0.05386 |
| PAN06FQCEICGARFKRWEELYNHLKKH (SEQ ID NO: 155) | 6.759 | 0.9589 | 2.77 | 0.1603 |
| PAN07FQCKQCGAVFSRWEELYNHLKNH (SEQ ID NO: 162) | 1.916 | 0.6012 | 4.775 | 0.04671 |
| PAN08FQCKQCGAVFKRWEELYNHLLAH (SEQ ID NO: 163) | 4.884 | 1.699 | 8.054 | 0.06198 |
| PAN09FQCEICGAAFSRWEELYNHLKRH (SEQ ID NO: 156) | 12.02 | 0.5962 | 2.62 | 0.07784 |
| PAN10FQCEICGARFSRWEELYNHLLKH (SEQ ID NO: 164) | 4.609 | 0.6173 | 2.562 | 0.1465 |
| PAN11FQCSQCGAAFNRWEELYNHLLRH (SEQ ID NO: 173) | 10.78 | 2.359 | 11.74 | 0.144 |
| PAN12FQCEICGARFFRWEEKYNHLAKH (SEQ ID NO: 157) | 14.61 | 1.033 | 3.176 | 0.3244 |
| PAN13FQCQMCGAAFDRWEELYNHLLAH (SEQ ID NO: 167) | 9.692 | 2.986 | 13.05 | 0.1915 |
| PAN14FQCSICGATFSRWEELYNHLLKH (SEQ ID NO: 158) | 13.74 | 1.839 | 3.986 | 0.1807 |
| PAN15FQCVQCGARFNRWEELYDHLNKH (SEQ ID NO: 168) | 4.637 | 0.8749 | 3.808 | 0.07327 |

These findings summarize the dose response relationships for drug-induced degradation of the indicated novel sequences, graphically presented in FIG. 20.

Amino acid sequences for zinc finger degrons CC220-01, CC220-02, and CC220-03, are set forth in Table 3.

TABLE 3

| ID | Gene | Sequence |
|---|---|---|
| CC220-01 (red) | redo2-4ci3-hscrbn-pom-ikzf1_ikzf1_orun_128. prepack_003206_Rank_1938 | FYCTQCGAAFDRWEELYNHLLNH (SEQ ID NO: 185) |

TABLE 3-continued

| ID | Gene | Sequence |
|---|---|---|
| CC220-02 (green) | Naa-ZFP91 Caa-redo2-4ci2-hscrbn-len-ikzf1_ikzf1_orun_1174. prepack_004080_Rank_5 | MQCEICGFTCRRAEELNTHLNKH (SEQ ID NO: 186) |
| CC220-03 (purple) | 4ci1-hscrbn-thal-5vmu_5vmu_chaina_0001_0009_orun_275. prepack_001821_Rank_451 | FYCKQCGANFSRWEELYNHLKAH (SEQ ID NO: 187) |

Nucleic acid sequences for zinc finger degrons used in the validation experiments are set forth in Table 4.

TABLE 4

| ID | Gene | Sequence |
|---|---|---|
| PAN09 (SD04) | redo-4ci3-hscrbn-pom-6b0o_6b0o_chatna_0001_0001_orun_53. prepack_011840_Rank_761 | TTCCAGTGCGAGATCTGCGGCGCTGCTTTCAGCCGGTGGGAGG AGCTGTACAACCACCTGAAGCGGCAC (SEQ ID NO: 188) |
| PAN06 (SD03) | 4ci3-h5crbn-pom-6b0o_6b0o_chaina_0001_0002_orun_445. prepack_003108_Rank_312 | TTCCAGTGCGAGATCTGCGGCGCTCGGTTCAAGCGGTGGGAGG AGCTGTACAACCACCTGAAGAAGCAC (SEQ ID NO: 189) |
| PAN03 (SD02) | 4ci1-hscrbn-thal-ikzf1_ikzf1_orun_132. prepack_000450_Rank_215 | TTCCAGTGCGAGATGTGCGGCGCTGCTTTCGACCGGTGGGAGG AGCTGTACAACCACAAGAACGCTCAC (SEQ ID NO: 190) |
| PAN14 (SD06) | redo2-4ci3-hscrbn-pom-6b0o_5b0o_chaina_0001_0008_orun_1192. prepack_001787_Rank_1877 | TTCCAGTGCAGCATCTGCGGCGCTACCTTCAGCCGGTGGGAGG AGCTGTACAACCACCTGCTGAAGCAC (SEQ ID NO: 191) |
| PAN01 (SD01) | 4ci1-hscrbn-thal-6b0o_6b0o_chains_0001_0005_orun_277. prepack_001633_Rank_469 | TTCCAGTGCCAGGTGTGCGGCGCTCGGTTCAGCCGGTGGGAGG AGCTGTACAACCACCTGCTGAAGCAC (SEQ ID NO: 192) |
| PAN12 (SD05) | redo-4ci3-hscrbn-pom-6b0o_6b0o_chaina_0001_0008_orun_576. prepack_012252_Rank_2030 | TTCCAGTGCGAGATCTGCGGCGCTCGGTTCTTCCGGTGGGAGG AGCTGTACAACCACCTGGCTAAGCAC (SEQ ID NO: 193) |
| | 4ci3-hscrbn-pom-6b0o_6b0o_chaina_0001_0008_orun_316. prepack_001980_Rank_331 | TTCCAGTGCGAGATCTGCGGCGCTCGGTTCAGCCGGTGGGAGG AGCTGTACAACCACCTGAACAAGCAC (SEQ ID NO: 194) |
| | redo2-4ci3-hscrbn-pom-6b0o_6b0o_chaina_0001_0005_orun_634. prepack_012759_Rank_1177 | TTCCAGTGCGAGATCTGCGGCGCTAAGTTCGAGAACTGGGAGG ACCTGTACAACCACCTGCTGAAGCAC (SEQ ID NO: 195) |
| PAM15 (SD16) | 4ci3-hscrbn-pom-ikzf1_ikzf1_orun_103. prepack_000139_Rank_778 | TTCCAGTGCGTGCAGTGCGGCGCTCGGTTCAACCGGTGGGAGG AGCTGTACGACCACCTGAACAAGCAC (SEQ ID NO: 196) |
| | 4ci1-hscrkn-thal-6b0o_6b0o_chaina_0001_0008_orun_72. prepack_003766_Rank_236 | TTCCAGTGCCAGGTGTGCGGCGCTCGGTTCAGCCGGTGGGAGG AGCTGTACAACCACCTGAGCAAGCAC (SEQ ID NO: 197) |
| PAM13 (SD15) | 4ci1-hscrbn-thal-ikzf1_ikzf1_orun_327. prepack_002586_Rank_233 | TTCCAGTGCCAGATGTGCGGCGCTGCTTTCGACCGGTGGGAGG AGCTGTACAACCACCTGCTGGCTCAC (SEQ ID NO: 198) |
| | redo-4ci3-hscrbn-pom-5vmu_5vmu_chaina_0001_0005_orun_632. prepack_024329_Rank_3068 | TTCCAGTGCAAGTACTGCGGCGCTGTGTTCAGCCGGTGGGAGG AGCTGTACAACCACCTGCTGGCTCAC (SEQ ID NO: 199) |
| PAN10 (SD12) | redo2-4ci2-hscrbn-len-6b0o_6b0o_chaina_0001_0005_orun_06. prepack_000085_Rank_158 | TTCCAGTGCGAGATCTGCGGCGCTCGGTTCAGCCGGTGGGAGG AGCTGTACAACCACCTGCTGAAGCAC (SEQ ID NO: 200) |
| PAN08 (SD11) | redo-4c13-hscrbn-pom-5vmu_5vmu_chaia_0001_0008_orun_1926. prepack_009328_Rank_4351 | TTCCAGTGCAAGCAGTGCGGCGCTGTGTTCAAGCGGTGGGAGG AGCTGTACAACCACCTGCTGGCTCAC (SEQ ID NO: 201) |
| PAN07 (SD10) | redo-4ci3-hscrbn-pom-5vmu_5vmu_chaina_0001_0009_orun_1438. prepack_004465_Rank_4272 | TTCCAGTGCAAGCAGTGCGGCGCTGTGTTCAGCCGGTGSGAGG AGCTGTACAACCACCTGAAGAACCAC (SEQ ID NO: 202) |

TABLE 4-continued

| ID | Gene | Sequence |
|---|---|---|
| PAN05 (SD09) | redo-4d3-hscrbn-pom-5vmu_5vmu_chaina_0001_0005_orun_173. prepack_007366_Rank_3104 | TTCCAGTGCAAGCAGTGCGGCGCTGTGTTCAGCCGGTGGGAGG AGCTGTACAACCACCTGACCAACCAC (SEQ ID NO: 203) |
| | 4ci1-hscrbn-thal-ikzf1_1kzf1_orun_102. prepack_000122_Rank_340 | TTCCAGTGCCAGTACTGCGGCGCTCGGTTCAACCGGTGGGAGG AGCTGTACGACCACCTGAACAAGCAC (SEQ ID NO: 204} |
| | 4ci1-hscrbn-thal-6b0o_6b0o_chaina_0001_0007_orun_311. prepack_001937_Rank_393 | TTCCAGTGCGAGATCTGCGGCGCTCGGTTCAGCCGGTGGGAGG AGCTGTACAACCACCTGAAGAACCAC (SEQ ID NO: 205) |
| PAN04 (SD19) | Naa-IKZF3 Caa-redo2-4ci2-hscrbn-len-ikzf1_ikzf1_orun_1480. prepack_010682_ Rank_2 | TTCCAGTGCAACCAGTGCGGCGCTAGCTTCACCCGGTGGGAGG AGCTGTACAACCACCTGCTGCGGCAC (SEQ ID NO: 206) |
| PAN02 (SD20) | 4ci1-hscrbn-thal-5vmu_5vmu_chaina_0001_0005_orun_153. prepack_000659_Rank_615 | TTCCAGTGCCAGTACTGCGGCGCTGTGTTCACCCGGTGGGAGG AGCTGTACAACCACCTGCTGCGGCAC (SEQ ID NO: 207) |
| PAN11 (SD21) | 4ci1-hserbn-thal-ifkzf1_ikzf1_orun_262. prepack_001873_Rank_276 | TTCCAGTGCAGCCAGTGCGGCGCTGCTTTCAACCGGTGGGAGG AGCTGTACAACCACCTGCTGCGGCAC (SEQ ID NO: 208) |
| | ZFP91-IKZF3 | CTGCAGTGCGAGATCTGCGGCTTCACCTGCCGGCAGAAGGGCA ACCTGCTGCGGCACATCAAGCTGCAC (SEQ ID NO: 209) |
| | redo2-4ci3-hscrbn-pom-5vmu_5vmu_chaina_0001_0005_orun_1179. prepack_001873_Rank_1631 | TTCACCTGCACCGCTTGCGGCGCTACCTTCACCCGGGCTGAGG AGCTGAACACCCACCTGAGCAAGCAC (SEQ ID NO: 210) |
| | redo-4ci3-hscrbn-pom-6b0o_6b0c_chaina_0001_0005_orun_466. prepack_0112S4_Rank_2785 | TTCCAGTGCGAGATCTGCGGCGCTCGGTTCGAGAACTGGGAGG ACCTGTACAACCACCTGCTGAAGCAC (SEQ ID NO: 211) |
| | redo-4ci3-hscrbrn-pom-5vmu_5vmu_chaina_0001_0008_orun_1600. prepack_006089_Rank_4286 | TTCCAGTGCGACAAGTGCGGCGCTAAGTTCGACCGGTGGGAGG AGCTGTACAACCACAACAACGCTCAC (SEQ ID NO: 212) |
| | 4ci3-hscrbn-pom-6b0o_6b0o_chaina_0001_0006_orun_409. prepack_002793_Rank_595 | TACCAGTGCGAGATCTGCGGCGCTACCTTCAGCCGGTGGGAGG AGCTGTACAACCACCTGAAGAAGCAC (SEQ ID NO: 213) |
| POM04 | 4ci1-hscrbn-thal-6b0o_6b0o_chaina_0001_0007_orun_316. prepack_001977_Rank_655 | TTCCAGTGCGAGATCTGCGGCGCTCGGTTCAGCCGGTGGGAGG AGCTGTACAACCACCTGAGCAAGCAC (SEQ ID NO: 214) |
| | N33-ZN653 Caa-4ci1-hscrbn-thal-5vmu_5vmu_chaina_0001_0005_orun_58. prepack_004105_Rank_4 | CTGCAGTGCGAGATCTGCGGCTACCAGTGCCGGCGGTGGGAGG AGCTGTACAACCACCTGCTGAAGCAC (SEQ ID NO: 215) |
| | redo2-4ci3-hscrbn-pom-6b0o_6b0o-chaina_0001_0003_orun_143. prepack_003891_Rank_1743 | TTCCAGTGCGAGATCTGCGGCGCTGCTTTCAGCCGGTGGGAGG AGCTGTACAACCACCTGAAGAACCAC (SEQ ID NO: 216) |
| | redo-4ci3-hscrbn-pom-5vmu_5vmu_chaina_0001_0008_orun_538. prepack_013398_Rank_2782 | TTCCAGTGCAAGCAGTGCGGCGCTGTGTTCACCCGGTGGGAGG AGCTGAAGACCCACCTGGACGCTCAC (SEQ ID NO: 217) |
| | 4ci1-hscrbn-thal-ikzf1_ikzf1_orun_184. prepack_001019_Rank_337 | TTCCAGTGCCAGTACTGCGGCGCTGCTTTCAACCGGTGGGAGG AGCTGTACAACCACCTGCTGAACCAC (SEQ ID NO: 218} |
| | redo2-4ci3-hscrbn-poro-6b0o_6b0o_chaina_0001_0002_orun_282. prepack_009662_Rank_473 | TFCACCTGCCAGATCTGCGGCGCTGCTTACGAGAACTGGGAGG ACCTGTACAACCACCTGAAGAAGCAC (SEQ ID NO: 219} |
| | 4ci3-hscrbn-pom-6b0o_6b0o_chaina_0001_0006_orun_405. prepack_002761_Rank_270 | TTCCAGTGCGAGATCTGCGGCGCTCGGTTCAGCCGGTGGGAGG AGCTGTACAACCACCTGGCTAAGCAC (SEQ ID NO: 220} |
| | 4ci3-hscrbn-pom-ikzf1_ikzf1_orun_280. prepack_002077_Rank_537 | TTCCAGTGCACCAAGTGCGGCGCTCGGTTCAACCGGTGGGAGG AGCTGTACAACCACGACCTGGCTCAC (SEQ ID NO: 221} |
| | 4ci1-hscrbn-thal-6b0o_6b0o_chaina_0001_0002_orun_156. prepack_000567_Rank_391 | TACCAGTGCGAGATCTGCGGCGCTCGGTTCAGCCGGTGGGAGG AGCTGTACAACCACCTGAAGAAGCAC (SEQ ID NO: 222} |

TABLE 4-continued

| ID | Gene | Sequence |
| --- | --- | --- |
| | redo-4ci3-hscrbn-pom-6b0o_6b0o_chaina_0001_0006_orun_1514.prepack_004648_Rank_574 | TTCCAGTGCGAGATCTGCGGCGCTAAGTTCAGCCGGTGGGAGGAGCTGTACAACCACCTGAACCTGCAC (SEQ ID NO: 223} |
| | 4ci1-hscrbn-thal-5vmu_5vmu_chaina_0001_0008_orun_06.prepack_000053_Rank_250 | TTCCAGTGCCAGTACTGCGGCGCTGTGTTCACCCGGTGGGAGGAGCTGTACAACCACCTGCTGAACCAC (SEQ ID NO: 224} |
| | Naa-ZFP91 Caa-4ci1-hscrbn-thal-ikzf1_ikzf1_orun_169.prepack_000854_Rank_7 | CTGCAGTGCGAGATCTGCGGCTTCACCTGCCGGCGGTGGGAGGAGCTGTACAACCACCTGCTGAACCAC (SEQ ID NO: 225} |
| | Naa-ZN276 Caa-4ci1-hscrbn-thal-5vmu_5vmu_chaina_0001_0005_orun_58.prepack_004105_Rank_4 | CTGCAGTGCGAGGTGTGCGGCTTCCAGTGCCGGCGGTGGGAGGAGCTGTACAACCACCTGCTGAAGCAC (SEQ ID NO: 226} |
| | 4ci1-hscrbn-pom-ikzf1_ik2f1_orun_381.prepack_003192_Rank_264 | TTCCAGTGCGAGATGTGCGGCGCTCGGTTCAACCGGTGGGAGGAGCTGTACAACCACCTGCGGGCTCAC (SEQ ID NO: 227} |
| | redo-4ci3-hscrbn-pom-6b0o_6b0o_chaina_0001_0003_orun_593.prepack_012399_Rank_742 | TTCCAGTGCGAGATCTGCGGCGCTGCTTTCGAGAACTGGGAGGACCTGTACAACCACCTGAAGAAGCAC (SEQ ID NO: 228} |
| | redo-4ci3-hscrbn-pom-6b0o_6b0o_chaina_0001_0008_orun_1994.prepack_008901_Rank_2692 | TTCCAGTGCAGCATCTGCGGCGCTACCTTCAGCCGGTGGGAGGAGCTGTACAACCACCTGAGCAAGCAC (SEQ ID NO: 229} |
| | redo2-4ci3-hscrbn-pom-ikzf1_ikzf1_orun_312.prepack_012416_Rank_502 | TACCAGTGCGAGTACTGCGGCGCTCGGTTCAACCGGTGGGAGGAGCTGTACAACCACCTGCTGAAGCAC (SEQ ID NO: 230} |
| | redo-4ci3-hscrbn-pom-5vmu_5vmu_chaina_0001_0009_orun_1913.prepack_009203_Rank_4602 | TTCCAGTGCCAGTACTGCGGCGCTGTGTTCGCTCGGTGGGAGGAGCTGTACAACCACCTGCTGAACCAC (SEQ ID NO: 231} |
| | redo2-4cl2-hscrbn-len-6b0o_6b0o_chaina_0001_0004_orun_282.prepack_009572_Rank_147 | TACCAGTGCGAGATCTGCGGCGCTCGGTTCGACCGGTGGGAGGAGCTGTACAACCACCTGAAGAACCAC (SEQ ID NO: 232} |
| POM05 | redo-4ci3-hscrbn-pom-6b0o_6b0o_chaina_0001_0001_orun_1535.prepack_004827_Rank_79 | TTCCAGTGCGAGATCTGCGGCGCTCGGTTCGAGTACTGGGAGCAGCTGTACAACCACCTGAAGAACCAC (SEQ ID NO: 233} |
| POM01 | redo2-4ci3-hscrbn-pom-ikzf1_ikzf1_orun_982.prepack_019756_Rank_524 | TTCCAGTGCGAGTACTGCGGCGCTCGGTTCAACCGGTGGGAGGAGCTGTACAACCACCTGCTGAAGCAC (SEQ ID NO: 234) |
| POM02 | redo-4ci3-hscrbn-pom-6b0o_5b0o_chaina_0001_0004_orun_547.prepack_011934_Rank_650 | TACCAGTGCGAGATCTGCGGCGCTCGGTTCAACCGGTGGGAGGAGCTGTACAACCACCTGAAGAACCAC (SEQ ID NO: 235} |
| POM03 | 4ci3-hscrbn-pom-6b0o_6b0o_chaina_0001_0007_orun_356.prepack_002330_Rank_340 | TTCCAGTGCGAGATCTGCGGCGCTGCTTTCAGCCGGTGGGAGGAGCTGTACAACCACCTGCTGGCTCAC (SEQ ID NO: 236) |
| | redo2-4ci3-hscrbn-pom-6b0o_6b0o_chaina_0001_0008_orun_1212.prepack_001971_Rank_1974 | TTCCAGTGCACCATCTGCGGCGCTACCTTCGACAAGTGGGAGAACCTGTACAACCACCTGAACCTGCAC (SEQ ID NO: 237) |
| | 4ci3-hscrbn-pom-6b0o_6b0o_chaina_0001_0006_orun_257.prepack_001459_Rank_364 | TACCAGTGCTACATCTGCGGCGCTGCTTTCGACAAGTGGGAGCTGCTGTACAACCACCTGAAGAAGCAC (SEQ ID NO: 238) |
| CC220-01 | redo2-4ci3-hscrbn-pom-ikzf1_ikzf1_orun_128.prepack_003206_Rank_1938 | TTCTACTGCACCCAGTGCGGCGCTGCTTTCGACCGGTGGGAGGAGCTGTACAACCACCTGCTGAACCAC (SEQ ID NO: 239} |
| CC220-02 | Naa-ZFP91 Caa-redo2-4ci2-hscrbn-len-ikzf1_ikzf1_orun_1174.prepack_004080_Rank_5 | CTGCAGTGCGAGATCTGCGGCTTCACCTGCCGGCGGGCTGAGGAGCTGAACACCCACCTGAACAAGCAC (SEQ ID NO: 240} |
| CC220-03 | 4ci1-hscrbn-thal-5vmu_5vmu_chaina_0001_0009_orun_275.prepack_001821_Rank_451 | TTCTACTGCAAGCAGTGCGGCGCTAACTTCAGCCGGTGGGAGGAGCTGTACAACCACCTGAAGGCTCAC (SEQ ID NO: 241} |

TABLE 4-continued

| ID | Gene | Sequence |
|---|---|---|
| CC220-04 | redo-4ci3-hscrbn-pom-5vmu_5vmu_chaina_0001_0009_orun_1912. prepack_009194_Rank_3636 | TTCCAGTGCAAGCAGTGCGGCGCTGTGTTCAGCCGGGCTGAGGAGCTGAACAAGCACCTGACCGCTCAC (SEQ ID NO: 242) |
| | redo-4ci3-hscrbn-pom-5vmu_5vmu_chaina_0001_0005_orun_1627. prepack_006346_Rank_1563 | TTCCAGTGCCGGCAGTGCGGCGCTGTGTTCAGCCGGGCTGAGGAGCTGAACAAGCACCTGAACCTGCAC (SEQ ID NO: 243) |
| | 4ci1-hscrbn-thal-ikzf1_ikzf1_orun_440. prepack_003831_Rank_375 | TTCCAGTGCCAGTACTGCGGCGCTGCTTTCAACCGGTGGGAGGAGCTGTACGACCACCTGAACAAGCAC (SEQ ID NO: 244} |
| | redo2-4ci3-hscrbn-pom-5vmu_5vmu_chaina_0001_0009_orun_432. prepack_012362_Rank_1015 | TTCCAGTGCCAGTACTGCGGCGCTGTGTGGAAGCGGTGGGAGGAGCTGTACAACCACCTGCTGGCTCAC (SEQ ID NO: 245) |
| | 4ci1-hscrbn-thal-6b0o_6b0o_chaina_0001_0006_orun_96. prepack_003956_Rank_201 | TTCCAGTGCGAGATCTGCGGCGCTGCTTTCAGCCGGTGGGAGGAGCTGTACAACCACCTGCTGATGCAC (SEQ ID NO: 246} |
| | 4ci1-hscrbn-thal-ikzf1_ikzf1_orun_450. prepack_003933_Rank_180 | TTCCAGTGCCAGTACTGCGGCGCTGCTTTCAACCGGTGGGAGGAGCTGTACAACCACCTGCTGGCTCAC (SEQ ID NO: 247) |
| | Naa-ZN276 Caa-redo2-4ci3-hscrbn-pom-ikzf1_ikzf1_orun_1151. prepack_001784_Rank_3 | CTGCAGTGCGAGGTGTGCGGCTTCCAGTGCCGGCGGTGGGAGGAGCTGTACAACCACCTGACCAAGCAC (SEQ ID NO: 248) |
| | redo-4ci3-hscrbn-pom-5vmu_5vmu_chaina_0001_0008_orun_1226. prepack_002352_Rank_4643 | TTCCAGTGCGACCAGTGCGGCGCTGTGTTCGACCGGTGGGAGGAGCTGTACAACCACCTGAACCGGCAC (SEQ ID NO: 249) |
| | IKZF3-IKZF3 | TTCCAGTGCAACCAGTGCGGCGCTAGCTTCACCCAGAAGGGCAACCTGCTGCGGCACATCAAGCTGCAC (SEQ ID NO: 250) |
| | ZN276-ZN276 | CTGCAGTGCGAGGTGTGCGGCTTCCAGTGCCGGCAGCGGGCTAGCCTGAAGTACCACATGACCAAGCAC (SEQ ID NO: 251) |
| | ZFP91-ZFP91 | CTGCAGTGCGAGATCTGCGGCTTCACCTGCCGGCAGAAGGCTAGCCTGAACTGGCACATGAAGAAGCAC (SEQ ID NO: 252) |
| | 4ci1-hscrbn-thal-6b0o_6b0o_chaina_0001_0007_orun_116. prepack_000221_Rank_520 | TTCCAGTGCCAGATCTGCGGCGCTGCTTTCAACCGGTGGGAGGAGCTGTACAACCACCTGCTGATGCAC (SEQ ID NO: 253) |
| | redo2-4ci3-hscrbn-pom-ikzf1_ikzf1_orun_1485. prepack_005474_Rank_961 | TTCCAGTGCGAGATGTGCGGCGCTCGGTTCGACCGGTGGGAGGAGCTGTACAACCACCTGAACGCTCAC (SEQ ID NO: 254) |
| | 4ci3-hscrbn-pom-ikzf1_ikzf1_orun_39. prepack_003276_Rank_413 | TTCCAGTGCCAGTACTGCGGCGCTGCTTTCGACCGGTGGGAGGAGCTGTACAACCACCTGCTGAACCAC (SEQ ID NO: 255) |
| | 4ci1-hscrbn-thal-ikzf1_ikzf1_orun_257. prepack_001821_Rank_207 | TTCCAGTGCGAGATGTGCGGCGCTGCTTTCGACCGGTGGGAGGAGCTGTACAACCACCTGAACGCTCAC (SEQ ID NO: 256) |
| | Naa-IKZF3 Caa-4ci1-hscrbn-thal-5vmu_5vmu_chaina_0001_0005_orun_58. prepack_004105_Rank_4 | TTCCAGTGCAACCAGTGCGGCGCTAGCTTCACCCGGTGGGAGGAGCTGTACAACCACCTGCTGAAGCAC (SEQ ID NO: 257) |

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A degron tag comprising a non-naturally occurring peptide which has the amino acid sequence of any one of (SEQ ID NO: 153) FQCQVCGARFSRWEELYNHLLKH, (SEQ ID NO: 154) FQCEMCGAAFDRWEELYNHKNAH, (SEQ ID NO: 155) FQCEICGARFKRWEELYNHLKKH, (SEQ ID NO: 156) FQCEICGAAFSRWEELYNHLKRH, (SEQ ID NO: 157) FQCEICGARFFRWEELYNHLAKH, (SEQ ID NO: 158) FQCSICGATFSRWEELYNHLLKH, (SEQ ID NO: 159) FQCEICGARFSRWEELYNHLNKH, (SEQ ID NO: 160) FQCEICGAKFENWEDLYNHLLKH, (SEQ ID NO: 161) FQCKQCGAVFSRWEELYNHLTNH, (SEQ ID NO: 162) FQCKQCGAVFSRWEELYNHLKNH, (SEQ ID NO: 163) FQCKQCGAVFKRWEELYNHLLAH, (SEQ ID NO: 164) FQCEICGARFSRWEELYNHLLKH, (SEQ ID NO: 165) FQCQVCGARFSRWEELYNHLSKH, (SEQ ID NO: 166) FQCQYCGARFNRWEELYDHLNKH, (SEQ ID NO: 167) FQCQMCGAAFDRWEELYNHLLAH, (SEQ ID NO: 168) FQCVQCGARFNRWEELYDHLNKH, -continued (SEQ ID NO: 169) FQCKYCGAVFSRWEELYNHLLAH, (SEQ ID NO: 170) FQCEICGARFSRWEELYNHLKNH, (SEQ ID NO: 171) FQCNQCGASFTRWEELYNHLLRH, (SEQ ID NO: 172) FQCQYCGAVFTRWEELYNHLLRH, (SEQ ID NO: 173) FQCSQCGAAFNRWEELYNHLLRH, (SEQ ID NO: 174) FQCDKCGAKFDRWEELYNHNNAH, (SEQ ID NO: 175) FQCEICGARFENWEDLYNHLLKH, (SEQ ID NO: 176) FTCTACGATFTRAEELNTHLSKH, (SEQ ID NO: 177) FQCEYCGARFNRWEELYNHLLKH, (SEQ ID NO: 178) YQCEICGARFNRWEELYNHLKNH, (SEQ ID NO: 179) FQCEICGAAFSRWEELYNHLLAH, (SEQ ID NO: 180) FQCEICGARFSRWEELYNHLSKH, (SEQ ID NO: 181) FQCEICGARFEYWEQLYNHLKNH, (SEQ ID NO: 182) FYCTQCGAAFDRWEELYNHLLNH, (SEQ ID NO: 183) MQCEICGFTCRRAEELNTHLNKH, or (SEQ ID NO: 184) FYCKQCGANFSRWEELYNHLKAH.

2. A fusion protein comprising a protein of interest and at least one degron tag according to claim 1.

3. The fusion of claim 2, wherein the degron tag domain is located N- or C-terminal to the protein of interest.

4. The fusion protein of claim 2, wherein said protein of interest is selected from the group consisting of: chimeric antigen receptors (CAR), bromodomain-containing protein 4 (BRD4), $KRAS^{G12V}$, apolipoprotein B (apoB)-100, angiopoietin-like protein 3 (ANGPTL3), proprotein convertase subtilisin/kexin type 9 (PCSK9), apolipoprotein C3 (APOC3), C-reactive protein (CRP), apolipoprotein A (ApoA), Factor XI, Factor VII, antithrombin III, phosphatidylinositol glycan class A (PIG-A), C5 component of complement, Alpha-1-antitrypsin (A1AT), hepcidin regulation TMPRSS6, delta-aminolevulinate synthase 1 (ALAS-1), acylCaA:diacylglycerol acyltransferase (DGAT)-2, prekallikrein (KLKB1), connective tissue growth factor (CCN2), intercellular adhesion molecule-1 (ICAM-1), glucagon receptor (GCGR), glucocorticoid receptor (GCCR), protein tyrosine phosphatase (PTP-1B), c-Raf kinase (RAF1), fibroblast growth factor receptor 4 (FGFR4), vascular adhesion molecule-1 (VCAM-1), very late antigen-4 (VLA-4), transthyretin (TTR), survival motor neuron 2 (SMN2), growth hormone receptor GHR, dystrophia myotonic protein kinase (DMPK), sodium channel isoform Nav1.8, Tau protein, Amyloid R peptide (A3), Prion protein, α-Synuclein, TDP-43, Fused in sarcoma (FUS) protein, Superoxide dismutase, Proteins with tandem glutamine expansions, Cystatin C, Notch3, Glial fibrillary acidic protein (GFAP), Seipin, Transthyretin, Serpins, Monoclonal immunoglobulin light chains, Immunoglobulin heavy chains, Amyloid A protein, Islet amyloid polypeptide (IAPP; amylin), Medin (lactadherin), Apolipoprotein AI, Apolipoprotein AII, Apolipoprotein AIV, Gelsolin, Lysozyme, Fibrinogen, Beta-2 microglobulin, Crystallins, rhodopsin, Calcitonin, Atrial natriuretic factor, Prolactin, Keratoepithelin, Keratins, Keratin intermediate filament proteins, Lactoferrin, Surfactant protein C (SP-C), Odontogenic ameloblast-associated protein, Semenogelin I, cystic fibrosis transmembrane conductance regulator (CFTR) protein, Hemoglobin, and Hyperproteolytic state of myosin ubiquitination.

5. The fusion protein of claim 2, which comprises a CAR protein comprising, from N-terminus to C-terminus:

a) an extracellular ligand binding domain;

b) a transmembrane domain;

c) a cytoplasmic domain comprising at least one intracellular signaling domain; and d) the at least one degron tag according to claim 1.

6. The fusion protein of claim 5, wherein said extracellular ligand binding domain binds a tumor associated antigen.

7. The fusion protein of claim 6, wherein said tumor associated antigen is CD19.

8. The fusion protein of claim 5, wherein said a)-c) comprise tisagenlecleucel CAR or axicabtagene ciloleucel CAR.

9. The fusion protein of claim 2, further comprising one or more amino acid residues N-terminal with respect to the degron tag and/or one or more amino acid residues C-terminal with respect to the degron tag.

10. A non-naturally occurring nucleic acid sequence encoding the degron tag of claim 1 or a fusion protein comprising a protein of interest and at least one degron tag according to claim 1.

11. A nucleic acid sequence encoding the fusion protein of claim 2.

12. A vector comprising the nucleic acid sequence of claim 11.

13. A cell which expresses the nucleic acid of claim 11.

14. The cell of claim 13, which is an immune effector cell.

15. The cell of claim 14, which is a T-cell.

16. The cell of claim 13, which is a mammalian cell.

17. The cell of claim 16, which is a human or rodent cell.

18. A method of degrading a protein of interest comprising:

contacting a cell in vitro or in vivo with an effective amount of an immunomodulatory drug (IMiD) or a cereblon modulator (CM), wherein the cell expresses a nucleic acid encoding a fusion protein comprising a protein of interest and at least one degron tag according to claim 1.

19. The method of claim 18, wherein said IMiD or CM is thalidomide, pomalidomide, lenalidomide, CC-122, CC-220 or CC-885.

20. A method of degrading a protein of interest comprising:

administering an effective amount of an IMiD or CM to a subject, wherein the subject has previously been treated via gene therapy causing at least some endogenous cells to express a nucleic acid encoding a fusion protein comprising a protein of interest and at least one degron tag according to claim 1.

21. The method of claim 20, wherein said gene therapy comprises gene knock-in, administration of viral vectors or clustered regularly interspaced short palindromic repeats (CRISPR)-mediated knock in.

22. A method of degrading a chimeric antigen receptor protein comprising:

administering an effective amount of an IMiD or CM to a subject, wherein the subject has previously been treated with allogeneic or autologous immune effector cells that express a nucleic acid encoding a fusion protein comprising the CAR and at least one degron tag according to claim 1.

23. A method of reducing gene overexpression in a subject, comprising:

transforming one or more relevant cells of the subject with an exogenous nucleic acid sequence encoding the degron tag of claim 1, wherein the nucleic acid sequence is integrated genomically in-frame with a nucleic acid sequence encoding an endogenous protein associated with a disease due to overexpression of the endogenous protein; wherein expression of the thus modified nucleic acid produces a fusion protein that contains in-frame the degron tag and the endogenous protein, and administering to the subject an effective amount of an IMiD or CM.

24. The method of claim 23, wherein the degron tag is located N-or C-terminal to the endogenous protein.

* * * * *

SEQUENCE LISTING

<160> NUMBER OF SEQ ID NOS: 257

<210> SEQ ID NO 1
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: wherein the Xaa represents any amino acid
<220> FEATURE:
<221> NAME/KEY: misc_feature
<222> LOCATION: (4)..(5)
<223> OTHER INFORMATION: wherein the Xaa means that the position in the peptide may be any amino acid or no amino acid, provided that there are either 2 or 4 amino acid residues between the cysteins residues.

<400> SEQUENCE: 1

```
Cys Xaa Xaa Xaa Xaa Cys Gly
1               5
```

<210> SEQ ID NO 2
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: wherein the Xaa represents any amino acid
<220> FEATURE:
<221> NAME/KEY: misc_feature
<222> LOCATION: (5)..(5)
<223> OTHER INFORMATION: wherein the Xaa means that the position in the peptide may be any amino acid or no amino acid, provided that there are either 2 or 4 amino acid residues between the cysteins residues.
<220> FEATURE:
<221> NAME/KEY: misc_feature
<222> LOCATION: (6)..(6)
<223> OTHER INFORMATION: wherein the Xaa represents histidine (His) or cysteine (Cys).

<400> SEQUENCE: 2

```
His Xaa Xaa Xaa Xaa Xaa
1               5
```

<210> SEQ ID NO 3
<211> LENGTH: 519
<212> TYPE: PRT
<213> ORGANISM: Artificial Sequence
<220> FEATURE:
<223> OTHER INFORMATION: Synthetic polypeptide

<400> SEQUENCE: 3

```
Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80
```

-continued

```
Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Thr Leu Tyr Pro Val Ile
225                 230                 235                 240

Lys Glu Glu Thr Asn His Ser Glu Met Ala Glu Asp Leu Cys Lys Ile
                245                 250                 255

Gly Ser Glu Arg Ser Leu Val Leu Asp Arg Leu Ala Ser Asn Val Ala
            260                 265                 270

Lys Arg Lys Ser Ser Met Pro Gln Lys Phe Leu Gly Asp Lys Gly Leu
        275                 280                 285

Ser Asp Thr Pro Tyr Asp Ser Ser Ala Ser Tyr Glu Lys Glu Asn Glu
    290                 295                 300

Met Met Lys Ser His Val Met Asp Gln Ala Ile Asn Asn Ala Ile Asn
305                 310                 315                 320

Tyr Leu Gly Ala Glu Ser Leu Arg Pro Leu Val Gln Thr Pro Pro Gly
                325                 330                 335

Gly Ser Glu Val Val Pro Val Ile Ser Pro Met Tyr Gln Leu His Lys
            340                 345                 350

Pro Leu Ala Glu Gly Thr Pro Arg Ser Asn His Ser Ala Gln Asp Ser
        355                 360                 365

Ala Val Glu Asn Leu Leu Leu Leu Ser Lys Ala Lys Leu Val Pro Ser
    370                 375                 380

Glu Arg Glu Ala Ser Pro Ser Asn Ser Cys Gln Asp Ser Thr Asp Thr
385                 390                 395                 400

Glu Ser Asn Asn Glu Glu Gln Arg Ser Gly Leu Ile Tyr Leu Thr Asn
                405                 410                 415

His Ile Ala Pro His Ala Arg Asn Gly Leu Ser Leu Lys Glu Glu His
            420                 425                 430

Arg Ala Tyr Asp Leu Leu Arg Ala Ala Ser Glu Asn Ser Gln Asp Ala
        435                 440                 445

Leu Arg Val Val Ser Thr Ser Gly Glu Gln Met Lys Val Tyr Lys Cys
    450                 455                 460

Glu His Cys Arg Val Leu Phe Leu Asp His Val Met Tyr Thr Ile His
465                 470                 475                 480

Met Gly Cys His Gly Phe Arg Asp Pro Phe Glu Cys Asn Met Cys Gly
                485                 490                 495
```

```
Tyr His Ser Gln Asp Arg Tyr Glu Phe Ser Ser His Ile Thr Arg Gly
            500                 505                 510

Glu His Arg Phe His Met Ser
        515


<210> SEQ ID NO 4
<211> LENGTH: 519
<212> TYPE: PRT
<213> ORGANISM: Artificial Sequence
<220> FEATURE:
<223> OTHER INFORMATION: Synthetic polypeptide

<400> SEQUENCE: 4

Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Thr Leu Tyr Pro Val Ile
225                 230                 235                 240

Lys Glu Glu Thr Asn His Ser Glu Met Ala Glu Asp Leu Cys Lys Ile
                245                 250                 255

Gly Ser Glu Arg Ser Leu Val Leu Asp Arg Leu Ala Ser Asn Val Ala
            260                 265                 270

Lys Arg Lys Ser Ser Met Pro Gln Lys Phe Leu Gly Asp Lys Gly Leu
        275                 280                 285

Ser Asp Thr Pro Tyr Asp Ser Ser Ala Ser Tyr Glu Lys Glu Asn Glu
    290                 295                 300

Met Met Lys Ser His Val Met Asp Gln Ala Ile Asn Asn Ala Ile Asn
305                 310                 315                 320

Tyr Leu Gly Ala Glu Ser Leu Arg Pro Leu Val Gln Thr Pro Pro Gly
                325                 330                 335
```

-continued

```
Gly Ser Glu Val Val Pro Val Ile Ser Pro Met Tyr Gln Leu His Lys
            340                 345                 350

Pro Leu Ala Glu Gly Thr Pro Arg Ser Asn His Ser Ala Gln Asp Ser
        355                 360                 365

Ala Val Glu Asn Leu Leu Leu Leu Ser Lys Ala Lys Leu Val Pro Ser
    370                 375                 380

Glu Arg Glu Ala Ser Pro Ser Asn Ser Cys Gln Asp Ser Thr Asp Thr
385                 390                 395                 400

Glu Ser Asn Asn Glu Glu Gln Arg Ser Gly Leu Ile Tyr Leu Thr Asn
                405                 410                 415

His Ile Ala Pro His Ala Arg Asn Gly Leu Ser Leu Lys Glu Glu His
            420                 425                 430

Arg Ala Tyr Asp Leu Leu Arg Ala Ala Ser Glu Asn Ser Gln Asp Ala
        435                 440                 445

Leu Arg Val Val Ser Thr Ser Gly Glu Gln Met Lys Val Tyr Lys Cys
    450                 455                 460

Glu His Cys Arg Val Leu Phe Leu Asp His Val Met Tyr Thr Ile His
465                 470                 475                 480

Met Gly Cys His Gly Phe Arg Asp Pro Phe Glu Cys Asn Met Cys Gly
                485                 490                 495

Tyr His Ser Gln Asp Arg Tyr Glu Phe Ser Ser His Ile Thr Arg Gly
            500                 505                 510

Glu His Arg Phe His Met Ser
        515
```

<210> SEQ ID NO 5
<211> LENGTH: 509
<212> TYPE: PRT
<213> ORGANISM: Artificial Sequence
<220> FEATURE:
<223> OTHER INFORMATION: Synthetic polypeptide

<400> SEQUENCE: 5

```
Met Glu Asp Ile Gln Thr Asn Ala Glu Leu Lys Ser Thr Gln Glu Gln
1               5                   10                  15

Ser Val Pro Ala Glu Ser Ala Ala Val Leu Asn Asp Tyr Ser Leu Thr
            20                  25                  30

Lys Ser His Glu Met Glu Asn Val Asp Ser Gly Glu Gly Pro Ala Asn
        35                  40                  45

Glu Asp Glu Asp Ile Gly Asp Asp Ser Met Lys Val Lys Asp Glu Tyr
    50                  55                  60

Ser Glu Arg Asp Glu Asn Val Leu Lys Ser Glu Pro Met Gly Asn Ala
65                  70                  75                  80

Glu Glu Pro Glu Ile Pro Tyr Ser Tyr Ser Arg Glu Tyr Asn Glu Tyr
                85                  90                  95

Glu Asn Ile Lys Leu Glu Arg His Val Val Ser Phe Asp Ser Ser Arg
            100                 105                 110

Pro Thr Ser Gly Lys Met Asn Cys Asp Val Cys Gly Leu Ser Cys Ile
        115                 120                 125

Ser Phe Asn Val Leu Met Val His Lys Arg Ser His Thr Gly Glu Arg
    130                 135                 140

Pro Phe Gln Cys Asn Gln Cys Gly Ala Ser Phe Thr Gln Lys Gly Asn
145                 150                 155                 160

Leu Leu Arg His Ile Lys Leu His Thr Gly Glu Lys Pro Phe Lys Cys
                165                 170                 175
```

-continued

```
His Leu Cys Asn Tyr Ala Cys Gln Arg Arg Asp Ala Leu Thr Gly His
            180                 185                 190

Leu Arg Thr His Ser Val Glu Lys Pro Tyr Lys Cys Glu Phe Cys Gly
        195                 200                 205

Arg Ser Tyr Lys Gln Arg Ser Ser Leu Glu Glu His Lys Glu Arg Cys
    210                 215                 220

Arg Thr Phe Leu Gln Ser Thr Asp Pro Gly Asp Thr Ala Ser Ala Glu
225                 230                 235                 240

Ala Arg His Ile Lys Ala Glu Met Gly Ser Glu Arg Ala Leu Val Leu
                245                 250                 255

Asp Arg Leu Ala Ser Asn Val Ala Lys Arg Lys Ser Ser Met Pro Gln
            260                 265                 270

Lys Phe Ile Gly Glu Lys Arg His Cys Phe Asp Val Asn Tyr Asn Ser
        275                 280                 285

Ser Tyr Met Tyr Glu Lys Glu Ser Glu Leu Ile Gln Thr Arg Met Met
    290                 295                 300

Asp Gln Ala Ile Asn Asn Ala Ile Ser Tyr Leu Gly Ala Glu Ala Leu
305                 310                 315                 320

Arg Pro Leu Val Gln Thr Pro Pro Ala Pro Thr Ser Glu Met Val Pro
                325                 330                 335

Val Ile Ser Ser Met Tyr Pro Ile Ala Leu Thr Arg Ala Glu Met Ser
            340                 345                 350

Asn Gly Ala Pro Gln Glu Leu Glu Lys Lys Ser Ile His Leu Pro Glu
        355                 360                 365

Lys Ser Val Pro Ser Glu Arg Gly Leu Ser Pro Asn Asn Ser Gly His
    370                 375                 380

Asp Ser Thr Asp Thr Asp Ser Asn His Glu Glu Arg Gln Asn His Ile
385                 390                 395                 400

Tyr Gln Gln Asn His Met Val Leu Ser Arg Ala Arg Asn Gly Met Pro
                405                 410                 415

Leu Leu Lys Glu Val Pro Arg Ser Tyr Glu Leu Leu Lys Pro Pro Pro
            420                 425                 430

Ile Cys Pro Arg Asp Ser Val Lys Val Ile Asn Lys Glu Gly Glu Val
        435                 440                 445

Met Asp Val Tyr Arg Cys Asp His Cys Arg Val Leu Phe Leu Asp Tyr
    450                 455                 460

Val Met Phe Thr Ile His Met Gly Cys His Gly Phe Arg Asp Pro Phe
465                 470                 475                 480

Glu Cys Asn Met Cys Gly Tyr Arg Ser His Asp Arg Tyr Glu Phe Ser
                485                 490                 495

Ser His Ile Ala Arg Gly Glu His Arg Ala Leu Leu Lys
            500                 505
```

<210> SEQ ID NO 6
<211> LENGTH: 1053
<212> TYPE: PRT
<213> ORGANISM: Artificial Sequence
<220> FEATURE:
<223> OTHER INFORMATION: Synthetic polypeptide

<400> SEQUENCE: 6

```
Met Ser Arg Arg Lys Gln Ala Lys Pro Gln His Ile Asn Ser Glu Glu
1               5                   10                  15

Asp Gln Gly Glu Gln Gln Pro Gln Gln Gln Thr Pro Glu Phe Ala Asp
            20                  25                  30
```

-continued

```
Ala Ala Pro Ala Ala Pro Ala Ala Gly Glu Leu Gly Ala Pro Val Asn
        35                  40                  45

His Pro Gly Asn Asp Glu Val Ala Ser Glu Asp Glu Ala Thr Val Lys
    50                  55                  60

Arg Leu Arg Arg Glu Glu Thr His Val Cys Glu Lys Cys Cys Ala Glu
65                  70                  75                  80

Phe Phe Ser Ile Ser Glu Phe Leu Glu His Lys Lys Asn Cys Thr Lys
                85                  90                  95

Asn Pro Pro Val Leu Ile Met Asn Asp Ser Glu Gly Pro Val Pro Ser
            100                 105                 110

Glu Asp Phe Ser Gly Ala Val Leu Ser His Gln Pro Thr Ser Pro Gly
        115                 120                 125

Ser Lys Asp Cys His Arg Glu Asn Gly Gly Ser Ser Glu Asp Met Lys
    130                 135                 140

Glu Lys Pro Asp Ala Glu Ser Val Val Tyr Leu Lys Thr Glu Thr Ala
145                 150                 155                 160

Leu Pro Pro Thr Pro Gln Asp Ile Ser Tyr Leu Ala Lys Gly Lys Val
                165                 170                 175

Ala Asn Thr Asn Val Thr Leu Gln Ala Leu Arg Gly Thr Lys Val Ala
            180                 185                 190

Val Asn Gln Arg Ser Ala Asp Ala Leu Pro Ala Pro Val Pro Gly Ala
        195                 200                 205

Asn Ser Ile Pro Trp Val Leu Glu Gln Ile Leu Cys Leu Gln Gln Gln
    210                 215                 220

Gln Leu Gln Gln Ile Gln Leu Thr Glu Gln Ile Arg Ile Gln Val Asn
225                 230                 235                 240

Met Trp Ala Ser His Ala Leu His Ser Ser Gly Ala Gly Ala Asp Thr
                245                 250                 255

Leu Lys Thr Leu Gly Ser His Met Ser Gln Gln Val Ser Ala Ala Val
            260                 265                 270

Ala Leu Leu Ser Gln Lys Ala Gly Ser Gln Gly Leu Ser Leu Asp Ala
        275                 280                 285

Leu Lys Gln Ala Lys Leu Pro His Ala Asn Ile Pro Ser Ala Thr Ser
    290                 295                 300

Ser Leu Ser Pro Gly Leu Ala Pro Phe Thr Leu Lys Pro Asp Gly Thr
305                 310                 315                 320

Arg Val Leu Pro Asn Val Met Ser Arg Leu Pro Ser Ala Leu Leu Pro
                325                 330                 335

Gln Ala Pro Gly Ser Val Leu Phe Gln Ser Pro Phe Ser Thr Val Ala
            340                 345                 350

Leu Asp Thr Ser Lys Lys Gly Lys Gly Lys Pro Pro Asn Ile Ser Ala
        355                 360                 365

Val Asp Val Lys Pro Lys Asp Glu Ala Ala Leu Tyr Lys His Lys Cys
    370                 375                 380

Lys Tyr Cys Ser Lys Val Phe Gly Thr Asp Ser Ser Leu Gln Ile His
385                 390                 395                 400

Leu Arg Ser His Thr Gly Glu Arg Pro Phe Val Cys Ser Val Cys Gly
                405                 410                 415

His Arg Phe Thr Thr Lys Gly Asn Leu Lys Val His Phe His Arg His
            420                 425                 430

Pro Gln Val Lys Ala Asn Pro Gln Leu Phe Ala Glu Phe Gln Asp Lys
        435                 440                 445

Val Ala Ala Gly Asn Gly Ile Pro Tyr Ala Leu Ser Val Pro Asp Pro
```

-continued

```
    450                 455                 460

Ile Asp Glu Pro Ser Leu Ser Leu Asp Ser Lys Pro Val Leu Val Thr
465                 470                 475                 480

Thr Ser Val Gly Leu Pro Gln Asn Leu Ser Ser Gly Thr Asn Pro Lys
                485                 490                 495

Asp Leu Thr Gly Gly Ser Leu Pro Gly Asp Leu Gln Pro Gly Pro Ser
            500                 505                 510

Pro Glu Ser Glu Gly Gly Pro Thr Leu Pro Gly Val Gly Pro Asn Tyr
        515                 520                 525

Asn Ser Pro Arg Ala Gly Gly Phe Gln Gly Ser Gly Thr Pro Glu Pro
    530                 535                 540

Gly Ser Glu Thr Leu Lys Leu Gln Gln Leu Val Glu Asn Ile Asp Lys
545                 550                 555                 560

Ala Thr Thr Asp Pro Asn Glu Cys Leu Ile Cys His Arg Val Leu Ser
                565                 570                 575

Cys Gln Ser Ser Leu Lys Met His Tyr Arg Thr His Thr Gly Glu Arg
            580                 585                 590

Pro Phe Gln Cys Lys Ile Cys Gly Arg Ala Phe Ser Thr Lys Gly Asn
        595                 600                 605

Leu Lys Thr His Leu Gly Val His Arg Thr Asn Thr Ser Ile Lys Thr
    610                 615                 620

Gln His Ser Cys Pro Ile Cys Gln Lys Lys Phe Thr Asn Ala Val Met
625                 630                 635                 640

Leu Gln Gln His Ile Arg Met His Met Gly Gly Gln Ile Pro Asn Thr
                645                 650                 655

Pro Leu Pro Glu Asn Pro Cys Asp Phe Thr Gly Ser Glu Pro Met Thr
            660                 665                 670

Val Gly Glu Asn Gly Ser Thr Gly Ala Ile Cys His Asp Asp Val Ile
        675                 680                 685

Glu Ser Ile Asp Val Glu Glu Val Ser Ser Gln Glu Ala Pro Ser Ser
    690                 695                 700

Ser Ser Lys Val Pro Thr Pro Leu Pro Ser Ile His Ser Ala Ser Pro
705                 710                 715                 720

Thr Leu Gly Phe Ala Met Met Ala Ser Leu Asp Ala Pro Gly Lys Val
                725                 730                 735

Gly Pro Ala Pro Phe Asn Leu Gln Arg Gln Gly Ser Arg Glu Asn Gly
            740                 745                 750

Ser Val Glu Ser Asp Gly Leu Thr Asn Asp Ser Ser Ser Leu Met Gly
        755                 760                 765

Asp Gln Glu Tyr Gln Ser Arg Ser Pro Asp Ile Leu Glu Thr Thr Ser
    770                 775                 780

Phe Gln Ala Leu Ser Pro Ala Asn Ser Gln Ala Glu Ser Ile Lys Ser
785                 790                 795                 800

Lys Ser Pro Asp Ala Gly Ser Lys Ala Glu Ser Ser Glu Asn Ser Arg
                805                 810                 815

Thr Glu Met Glu Gly Arg Ser Ser Leu Pro Ser Thr Phe Ile Arg Ala
            820                 825                 830

Pro Pro Thr Tyr Val Lys Val Glu Val Pro Gly Thr Phe Val Gly Pro
        835                 840                 845

Ser Thr Leu Ser Pro Gly Met Thr Pro Leu Leu Ala Ala Gln Pro Arg
    850                 855                 860

Arg Gln Ala Lys Gln His Gly Cys Thr Arg Cys Gly Lys Asn Phe Ser
865                 870                 875                 880
```

```
Ser Ala Ser Ala Leu Gln Ile His Glu Arg Thr His Thr Gly Glu Lys
                885                 890                 895

Pro Phe Val Cys Asn Ile Cys Gly Arg Ala Phe Thr Thr Lys Gly Asn
            900                 905                 910

Leu Lys Val His Tyr Met Thr His Gly Ala Asn Asn Asn Ser Ala Arg
        915                 920                 925

Arg Gly Arg Lys Leu Ala Ile Glu Asn Thr Met Ala Leu Leu Gly Thr
    930                 935                 940

Asp Gly Lys Arg Val Ser Glu Ile Phe Pro Lys Glu Ile Leu Ala Pro
945                 950                 955                 960

Ser Val Asn Val Asp Pro Val Val Trp Asn Gln Tyr Thr Ser Met Leu
                965                 970                 975

Asn Gly Gly Leu Ala Val Lys Thr Asn Glu Ile Ser Val Ile Gln Ser
            980                 985                 990

Gly Gly Val Pro Thr Leu Pro Val  Ser Leu Gly Ala Thr  Ser Val Val
        995                 1000                1005

Asn Asn  Ala Thr Val Ser Lys  Met Asp Gly Ser Gln  Ser Gly Ile
    1010                1015                1020

Ser Ala  Asp Val Glu Lys Pro  Ser Ala Thr Asp Gly  Val Pro Lys
    1025                1030                1035

His Gln  Phe Pro His Phe Leu  Glu Glu Asn Lys Ile  Ala Val Ser
    1040                1045                1050


<210> SEQ ID NO 7
<211> LENGTH: 570
<212> TYPE: PRT
<213> ORGANISM: Artificial Sequence
<220> FEATURE:
<223> OTHER INFORMATION: Synthetic polypeptide

<400> SEQUENCE: 7

Met Pro Gly Glu Thr Glu Glu Pro Arg Pro Pro Glu Gln Gln Asp Gln
1               5                   10                  15

Glu Gly Gly Glu Ala Ala Lys Ala Ala Pro Glu Glu Pro Gln Gln Arg
            20                  25                  30

Pro Pro Glu Ala Val Ala Ala Ala Pro Ala Gly Thr Thr Ser Ser Arg
        35                  40                  45

Val Leu Arg Gly Gly Arg Asp Arg Gly Arg Ala Ala Ala Ala Ala Ala
    50                  55                  60

Ala Ala Ala Val Ser Arg Arg Arg Lys Ala Glu Tyr Pro Arg Arg Arg
65                  70                  75                  80

Arg Ser Ser Pro Ser Ala Arg Pro Pro Asp Val Pro Gly Gln Gln Pro
                85                  90                  95

Gln Ala Ala Lys Ser Pro Ser Pro Val Gln Gly Lys Lys Ser Pro Arg
            100                 105                 110

Leu Leu Cys Ile Glu Lys Val Thr Thr Asp Lys Asp Pro Lys Glu Glu
        115                 120                 125

Lys Glu Glu Glu Asp Asp Ser Ala Leu Pro Gln Glu Val Ser Ile Ala
    130                 135                 140

Ala Ser Arg Pro Ser Arg Gly Trp Arg Ser Ser Arg Thr Ser Val Ser
145                 150                 155                 160

Arg His Arg Asp Thr Glu Asn Thr Arg Ser Ser Arg Ser Lys Thr Gly
                165                 170                 175

Ser Leu Gln Leu Ile Cys Lys Ser Glu Pro Asn Thr Asp Gln Leu Asp
            180                 185                 190
```

-continued

```
Tyr Asp Val Gly Glu Glu His Gln Ser Pro Gly Gly Ile Ser Ser Glu
        195                 200                 205

Glu Glu Glu Glu Glu Glu Glu Glu Met Leu Ile Ser Glu Glu Glu Ile
    210                 215                 220

Pro Phe Lys Asp Asp Pro Arg Asp Glu Thr Tyr Lys Pro His Leu Glu
225                 230                 235                 240

Arg Glu Thr Pro Lys Pro Arg Arg Lys Ser Gly Lys Val Lys Glu Glu
                245                 250                 255

Lys Glu Lys Lys Glu Ile Lys Val Glu Val Glu Val Glu Val Lys Glu
            260                 265                 270

Glu Glu Asn Glu Ile Arg Glu Asp Glu Glu Pro Pro Arg Lys Arg Gly
        275                 280                 285

Arg Arg Arg Lys Asp Asp Lys Ser Pro Arg Leu Pro Lys Arg Arg Lys
    290                 295                 300

Lys Pro Pro Ile Gln Tyr Val Arg Cys Glu Met Glu Gly Cys Gly Thr
305                 310                 315                 320

Val Leu Ala His Pro Arg Tyr Leu Gln His His Ile Lys Tyr Gln His
                325                 330                 335

Leu Leu Lys Lys Lys Tyr Val Cys Pro His Pro Ser Cys Gly Arg Leu
            340                 345                 350

Phe Arg Leu Gln Lys Gln Leu Leu Arg His Ala Lys His His Thr Asp
        355                 360                 365

Gln Arg Asp Tyr Ile Cys Glu Tyr Cys Ala Arg Ala Phe Lys Ser Ser
    370                 375                 380

His Asn Leu Ala Val His Arg Met Ile His Thr Gly Glu Lys Pro Leu
385                 390                 395                 400

Gln Cys Glu Ile Cys Gly Phe Thr Cys Arg Gln Lys Ala Ser Leu Asn
                405                 410                 415

Trp His Met Lys Lys His Asp Ala Asp Ser Phe Tyr Gln Phe Ser Cys
            420                 425                 430

Asn Ile Cys Gly Lys Lys Phe Glu Lys Lys Asp Ser Val Val Ala His
        435                 440                 445

Lys Ala Lys Ser His Pro Glu Val Leu Ile Ala Glu Ala Leu Ala Ala
    450                 455                 460

Asn Ala Gly Ala Leu Ile Thr Ser Thr Asp Ile Leu Gly Thr Asn Pro
465                 470                 475                 480

Glu Ser Leu Thr Gln Pro Ser Asp Gly Gln Gly Leu Pro Leu Leu Pro
                485                 490                 495

Glu Pro Leu Gly Asn Ser Thr Ser Gly Glu Cys Leu Leu Leu Glu Ala
            500                 505                 510

Glu Gly Met Ser Lys Ser Tyr Cys Ser Gly Thr Glu Arg Val Ser Leu
        515                 520                 525

Met Ala Asp Gly Lys Ile Phe Val Gly Ser Gly Ser Ser Gly Gly Thr
    530                 535                 540

Glu Gly Leu Val Met Asn Ser Asp Ile Leu Gly Ala Thr Thr Glu Val
545                 550                 555                 560

Leu Ile Glu Asp Ser Asp Ser Ala Gly Pro
                565                 570
```

<210> SEQ ID NO 8
<211> LENGTH: 570
<212> TYPE: PRT
<213> ORGANISM: Artificial Sequence
<220> FEATURE:

-continued

<223> OTHER INFORMATION: Synthetic polypeptide

<400> SEQUENCE: 8

```
Met Pro Gly Glu Thr Glu Glu Pro Arg Pro Pro Glu Gln Gln Asp Gln
1               5                   10                  15

Glu Gly Gly Glu Ala Ala Lys Ala Ala Pro Glu Glu Pro Gln Gln Arg
            20                  25                  30

Pro Pro Glu Ala Val Ala Ala Ala Pro Ala Gly Thr Thr Ser Ser Arg
        35                  40                  45

Val Leu Arg Gly Gly Arg Asp Arg Gly Arg Ala Ala Ala Ala Ala Ala
    50                  55                  60

Ala Ala Ala Val Ser Arg Arg Arg Lys Ala Glu Tyr Pro Arg Arg Arg
65                  70                  75                  80

Arg Ser Ser Pro Ser Ala Arg Pro Pro Asp Val Pro Gly Gln Gln Pro
                85                  90                  95

Gln Ala Ala Lys Ser Pro Ser Pro Val Gln Gly Lys Lys Ser Pro Arg
            100                 105                 110

Leu Leu Cys Ile Glu Lys Val Thr Thr Asp Lys Asp Pro Lys Glu Glu
        115                 120                 125

Lys Glu Glu Glu Asp Asp Ser Ala Leu Pro Gln Glu Val Ser Ile Ala
    130                 135                 140

Ala Ser Arg Pro Ser Arg Gly Trp Arg Ser Ser Arg Thr Ser Val Ser
145                 150                 155                 160

Arg His Arg Asp Thr Glu Asn Thr Arg Ser Ser Arg Ser Lys Thr Gly
                165                 170                 175

Ser Leu Gln Leu Ile Cys Lys Ser Glu Pro Asn Thr Asp Gln Leu Asp
            180                 185                 190

Tyr Asp Val Gly Glu Glu His Gln Ser Pro Gly Gly Ile Ser Ser Glu
        195                 200                 205

Glu Glu Glu Glu Glu Glu Glu Glu Met Leu Ile Ser Glu Glu Glu Ile
    210                 215                 220

Pro Phe Lys Asp Asp Pro Arg Asp Glu Thr Tyr Lys Pro His Leu Glu
225                 230                 235                 240

Arg Glu Thr Pro Lys Pro Arg Arg Lys Ser Gly Lys Val Lys Glu Glu
                245                 250                 255

Lys Glu Lys Lys Glu Ile Lys Val Glu Val Glu Val Glu Val Lys Glu
            260                 265                 270

Glu Glu Asn Glu Ile Arg Glu Asp Glu Glu Pro Pro Arg Lys Arg Gly
        275                 280                 285

Arg Arg Arg Lys Asp Asp Lys Ser Pro Arg Leu Pro Lys Arg Arg Lys
    290                 295                 300

Lys Pro Pro Ile Gln Tyr Val Arg Cys Glu Met Glu Gly Cys Gly Thr
305                 310                 315                 320

Val Leu Ala His Pro Arg Tyr Leu Gln His His Ile Lys Tyr Gln His
                325                 330                 335

Leu Leu Lys Lys Lys Tyr Val Cys Pro His Pro Ser Cys Gly Arg Leu
            340                 345                 350

Phe Arg Leu Gln Lys Gln Leu Leu Arg His Ala Lys His His Thr Asp
        355                 360                 365

Gln Arg Asp Tyr Ile Cys Glu Tyr Cys Ala Arg Ala Phe Lys Ser Ser
    370                 375                 380

His Asn Leu Ala Val His Arg Met Ile His Thr Gly Glu Lys Pro Leu
385                 390                 395                 400
```

```
Gln Cys Glu Ile Cys Gly Phe Thr Cys Arg Gln Lys Ala Ser Leu Asn
                405                 410                 415

Trp His Met Lys Lys His Asp Ala Asp Ser Phe Tyr Gln Phe Ser Cys
                420                 425                 430

Asn Ile Cys Gly Lys Lys Phe Glu Lys Lys Asp Ser Val Val Ala His
        435                 440                 445

Lys Ala Lys Ser His Pro Glu Val Leu Ile Ala Glu Ala Leu Ala Ala
    450                 455                 460

Asn Ala Gly Ala Leu Ile Thr Ser Thr Asp Ile Leu Gly Thr Asn Pro
465                 470                 475                 480

Glu Ser Leu Thr Gln Pro Ser Asp Gly Gln Gly Leu Pro Leu Leu Pro
                485                 490                 495

Glu Pro Leu Gly Asn Ser Thr Ser Gly Glu Cys Leu Leu Leu Glu Ala
            500                 505                 510

Glu Gly Met Ser Lys Ser Tyr Cys Ser Gly Thr Glu Arg Val Ser Leu
        515                 520                 525

Met Ala Asp Gly Lys Ile Phe Val Gly Ser Gly Ser Ser Gly Gly Thr
    530                 535                 540

Glu Gly Leu Val Met Asn Ser Asp Ile Leu Gly Ala Thr Thr Glu Val
545                 550                 555                 560

Leu Ile Glu Asp Ser Asp Ser Ala Gly Pro
                565                 570


<210> SEQ ID NO 9
<211> LENGTH: 615
<212> TYPE: PRT
<213> ORGANISM: Artificial Sequence
<220> FEATURE:
<223> OTHER INFORMATION: Synthetic polypeptide

<400> SEQUENCE: 9

Met Ala Glu Arg Ala Leu Glu Pro Glu Ala Glu Ala Glu Ala Glu Ala
1               5                   10                  15

Gly Ala Gly Gly Glu Ala Ala Ala Glu Glu Gly Ala Ala Gly Arg Lys
            20                  25                  30

Ala Arg Gly Arg Pro Arg Leu Thr Glu Ser Asp Arg Ala Arg Arg Arg
        35                  40                  45

Leu Glu Ser Arg Lys Lys Tyr Asp Val Arg Arg Val Tyr Leu Gly Glu
    50                  55                  60

Ala His Gly Pro Trp Val Asp Leu Arg Arg Arg Ser Gly Trp Ser Asp
65                  70                  75                  80

Ala Lys Leu Ala Ala Tyr Leu Ile Ser Leu Glu Arg Gly Gln Arg Ser
                85                  90                  95

Gly Arg His Gly Lys Pro Trp Glu Gln Val Pro Lys Lys Pro Lys Arg
            100                 105                 110

Lys Lys Arg Arg Arg Arg Asn Val Asn Cys Leu Lys Asn Val Val Ile
        115                 120                 125

Trp Tyr Glu Asp His Lys His Arg Cys Pro Tyr Glu Pro His Leu Ala
    130                 135                 140

Glu Leu Asp Pro Thr Phe Gly Leu Tyr Thr Thr Ala Val Trp Gln Cys
145                 150                 155                 160

Glu Ala Gly His Arg Tyr Phe Gln Asp Leu His Ser Pro Leu Lys Pro
                165                 170                 175

Leu Ser Asp Ser Asp Pro Asp Ser Asp Lys Val Gly Asn Gly Leu Val
            180                 185                 190
```

```
Ala Gly Ser Ser Asp Ser Ser Ser Ser Gly Ser Ala Ser Asp Ser Glu
        195                 200                 205

Glu Ser Pro Glu Gly Gln Pro Val Lys Ala Ala Ala Ala Ala Ala Ala
    210                 215                 220

Ala Thr Pro Thr Ser Pro Val Gly Ser Ser Gly Leu Ile Thr Gln Glu
225                 230                 235                 240

Gly Val His Ile Pro Phe Asp Val His His Val Glu Ser Leu Ala Glu
                245                 250                 255

Gln Gly Thr Pro Leu Cys Ser Asn Pro Ala Gly Asn Gly Pro Glu Ala
            260                 265                 270

Leu Glu Thr Val Val Cys Val Pro Val Pro Val Gln Val Gly Ala Gly
        275                 280                 285

Pro Ser Ala Leu Phe Glu Asn Val Pro Gln Glu Ala Leu Gly Glu Val
    290                 295                 300

Val Ala Ser Cys Pro Met Pro Gly Met Val Pro Gly Ser Gln Val Ile
305                 310                 315                 320

Ile Ile Ala Gly Pro Gly Tyr Asp Ala Leu Thr Ala Glu Gly Ile His
                325                 330                 335

Leu Asn Met Ala Ala Gly Ser Gly Val Pro Gly Ser Gly Leu Gly Glu
            340                 345                 350

Glu Val Pro Cys Ala Met Met Glu Gly Val Ala Ala Tyr Thr Gln Thr
        355                 360                 365

Glu Pro Glu Gly Ser Gln Pro Ser Thr Met Asp Ala Thr Ala Val Ala
    370                 375                 380

Gly Ile Glu Thr Lys Lys Glu Lys Glu Asp Leu Cys Leu Leu Lys Lys
385                 390                 395                 400

Glu Glu Lys Glu Glu Pro Val Ala Pro Glu Leu Ala Thr Thr Val Pro
                405                 410                 415

Glu Ser Ala Glu Pro Glu Ala Glu Ala Asp Gly Glu Glu Leu Asp Gly
            420                 425                 430

Ser Asp Met Ser Ala Ile Ile Tyr Glu Ile Pro Lys Glu Pro Glu Lys
        435                 440                 445

Arg Arg Arg Ser Lys Arg Ser Arg Val Met Asp Ala Asp Gly Leu Leu
    450                 455                 460

Glu Met Phe His Cys Pro Tyr Glu Gly Cys Ser Gln Val Tyr Val Ala
465                 470                 475                 480

Leu Ser Ser Phe Gln Asn His Val Asn Leu Val His Arg Lys Gly Lys
                485                 490                 495

Thr Lys Val Cys Pro His Pro Gly Cys Gly Lys Lys Phe Tyr Leu Ser
            500                 505                 510

Asn His Leu Arg Arg His Met Ile Ile His Ser Gly Val Arg Glu Phe
        515                 520                 525

Thr Cys Glu Thr Cys Gly Lys Ser Phe Lys Arg Lys Asn His Leu Glu
    530                 535                 540

Val His Arg Arg Thr His Thr Gly Glu Thr Pro Leu Gln Cys Glu Ile
545                 550                 555                 560

Cys Gly Tyr Gln Cys Arg Gln Arg Ala Ser Leu Asn Trp His Met Lys
                565                 570                 575

Lys His Thr Ala Glu Val Gln Tyr Asn Phe Thr Cys Asp Arg Cys Gly
            580                 585                 590

Lys Arg Phe Glu Lys Leu Asp Ser Val Lys Phe His Thr Leu Lys Ser
        595                 600                 605

His Pro Asp His Lys Pro Thr
```

```
    610                 615


<210> SEQ ID NO 10
<211> LENGTH: 519
<212> TYPE: PRT
<213> ORGANISM: Artificial Sequence
<220> FEATURE:
<223> OTHER INFORMATION: Synthetic polypeptide

<400> SEQUENCE: 10

Met Ala Ser Ser Pro Ala Val Asp Val Ser Cys Arg Arg Arg Glu Lys
1               5                   10                  15

Arg Arg Gln Leu Asp Ala Arg Arg Ser Lys Cys Arg Ile Arg Leu Gly
            20                  25                  30

Gly His Met Glu Gln Trp Cys Leu Leu Lys Glu Arg Leu Gly Phe Ser
        35                  40                  45

Leu His Ser Gln Leu Ala Lys Phe Leu Leu Asp Arg Tyr Thr Ser Ser
    50                  55                  60

Gly Cys Val Leu Cys Ala Gly Pro Glu Pro Leu Pro Pro Lys Gly Leu
65                  70                  75                  80

Gln Tyr Leu Val Leu Leu Ser His Ala His Ser Arg Glu Cys Ser Leu
                85                  90                  95

Val Pro Gly Leu Arg Gly Pro Gly Gly Gln Asp Gly Gly Leu Val Trp
            100                 105                 110

Glu Cys Ser Ala Gly His Thr Phe Ser Trp Gly Pro Ser Leu Ser Pro
        115                 120                 125

Thr Pro Ser Glu Ala Pro Lys Pro Ala Ser Leu Pro His Thr Thr Arg
    130                 135                 140

Arg Ser Trp Cys Ser Glu Ala Thr Ser Gly Gln Glu Leu Ala Asp Leu
145                 150                 155                 160

Glu Ser Glu His Asp Glu Arg Thr Gln Glu Ala Arg Leu Pro Arg Arg
                165                 170                 175

Val Gly Pro Pro Pro Glu Thr Phe Pro Pro Pro Gly Glu Glu Glu Gly
            180                 185                 190

Glu Glu Glu Glu Asp Asn Asp Glu Asp Glu Glu Glu Met Leu Ser Asp
        195                 200                 205

Ala Ser Leu Trp Thr Tyr Ser Ser Ser Pro Asp Asp Ser Glu Pro Asp
    210                 215                 220

Ala Pro Arg Leu Leu Pro Ser Pro Val Thr Cys Thr Pro Lys Glu Gly
225                 230                 235                 240

Glu Thr Pro Pro Ala Pro Ala Ala Leu Ser Ser Pro Leu Ala Val Pro
                245                 250                 255

Ala Leu Ser Ala Ser Ser Leu Ser Ser Arg Ala Pro Pro Pro Ala Glu
            260                 265                 270

Val Arg Val Gln Pro Gln Leu Ser Arg Thr Pro Gln Ala Ala Gln Gln
        275                 280                 285

Thr Glu Ala Leu Ala Ser Thr Gly Ser Gln Ala Gln Ser Ala Pro Thr
    290                 295                 300

Pro Ala Trp Asp Glu Asp Thr Ala Gln Ile Gly Pro Lys Arg Ile Arg
305                 310                 315                 320

Lys Ala Ala Lys Arg Glu Leu Met Pro Cys Asp Phe Pro Gly Cys Gly
                325                 330                 335

Arg Ile Phe Ser Asn Arg Gln Tyr Leu Asn His His Lys Lys Tyr Gln
            340                 345                 350

His Ile His Gln Lys Ser Phe Ser Cys Pro Glu Pro Ala Cys Gly Lys
```

```
        355                 360                 365

Ser Phe Asn Phe Lys Lys His Leu Lys Glu His Met Lys Leu His Ser
    370                 375                 380

Asp Thr Arg Asp Tyr Ile Cys Glu Phe Cys Ala Arg Ser Phe Arg Thr
385                 390                 395                 400

Ser Ser Asn Leu Val Ile His Arg Arg Ile His Thr Gly Glu Lys Pro
                405                 410                 415

Leu Gln Cys Glu Ile Cys Gly Phe Thr Cys Arg Gln Lys Ala Ser Leu
            420                 425                 430

Asn Trp His Gln Arg Lys His Ala Glu Thr Val Ala Ala Leu Arg Phe
        435                 440                 445

Pro Cys Glu Phe Cys Gly Lys Arg Phe Glu Lys Pro Asp Ser Val Ala
    450                 455                 460

Ala His Arg Ser Lys Ser His Pro Ala Leu Leu Leu Ala Pro Gln Glu
465                 470                 475                 480

Ser Pro Ser Gly Pro Leu Glu Pro Cys Pro Ser Ile Ser Ala Pro Gly
                485                 490                 495

Pro Leu Gly Ser Ser Glu Gly Ser Arg Pro Ser Ala Ser Pro Gln Ala
            500                 505                 510

Pro Thr Leu Leu Pro Gln Gln
        515


<210> SEQ ID NO 11
<211> LENGTH: 1081
<212> TYPE: PRT
<213> ORGANISM: Artificial Sequence
<220> FEATURE:
<223> OTHER INFORMATION: Synthetic polypeptide

<400> SEQUENCE: 11

Met Pro Arg Arg Lys Gln Glu Gln Pro Lys Arg Leu Pro Ser His Val
1               5                   10                  15

Ser Arg Gln Glu Glu Ala Glu Gly Glu Leu Ser Glu Gly Glu His Trp
            20                  25                  30

Tyr Gly Asn Ser Ser Glu Thr Pro Ser Glu Ala Ser Tyr Gly Glu Val
        35                  40                  45

Gln Glu Asn Tyr Lys Leu Ser Leu Glu Asp Arg Ile Gln Glu Gln Ser
    50                  55                  60

Thr Ser Pro Asp Thr Ser Leu Gly Ser Thr Thr Pro Ser Ser His Thr
65                  70                  75                  80

Leu Glu Leu Val Ala Leu Asp Ser Glu Val Leu Arg Asp Ser Leu Gln
                85                  90                  95

Cys Gln Asp His Leu Ser Pro Gly Val Ser Ser Leu Cys Asp Asp Asp
            100                 105                 110

Pro Gly Ser Asn Lys Pro Leu Ser Ser Asn Leu Arg Arg Leu Leu Glu
        115                 120                 125

Ala Gly Ser Leu Lys Leu Asp Ala Ala Ala Thr Ala Asn Gly Arg Val
    130                 135                 140

Glu Ser Pro Val Asn Val Gly Ser Asn Leu Ser Phe Ser Pro Pro Ser
145                 150                 155                 160

His His Ala Gln Gln Leu Ser Val Leu Ala Arg Lys Leu Ala Glu Lys
                165                 170                 175

Gln Glu Gln Asn Asp Gln Tyr Thr Pro Ser Asn Arg Phe Ile Trp Asn
            180                 185                 190

Gln Gly Lys Trp Leu Pro Asn Ser Thr Thr Thr Cys Ser Leu Ser Pro
```

-continued

```
        195                 200                 205

Asp Ser Ala Ile Leu Lys Leu Lys Ala Ala Ala Asn Ala Val Leu Gln
    210                 215                 220

Asp Lys Ser Leu Thr Arg Thr Glu Glu Thr Met Arg Phe Glu Ser Phe
225                 230                 235                 240

Ser Ser Pro Phe Ser Ser Gln Ser Ala Ser Ser Thr Leu Ala Ala Leu
                245                 250                 255

Ser Lys Lys Val Ser Glu Arg Ser Leu Thr Pro Gly Gln Glu His Pro
            260                 265                 270

Pro Pro Ala Ser Ser Phe Leu Ser Leu Ala Ser Met Thr Ser Ser Ala
        275                 280                 285

Ala Leu Leu Lys Glu Val Ala Ala Arg Ala Ala Gly Ser Leu Leu Ala
    290                 295                 300

Glu Lys Ser Ser Leu Leu Pro Glu Asp Pro Leu Pro Pro Pro Pro Ser
305                 310                 315                 320

Glu Lys Lys Pro Glu Lys Val Thr Pro Pro Pro Pro Pro Pro Pro Pro
                325                 330                 335

Pro Pro Pro Pro Pro Pro Pro Gln Ser Leu Glu Leu Leu Leu Leu Pro
            340                 345                 350

Val Pro Lys Gly Arg Val Ser Lys Pro Ser Asn Ser Ala Ser Glu Glu
        355                 360                 365

Glu Ser Gly Lys Pro Phe Gln Cys Pro Ile Cys Gly Leu Val Ile Lys
    370                 375                 380

Arg Lys Ser Tyr Trp Lys Arg His Met Val Ile His Thr Gly Leu Lys
385                 390                 395                 400

Ser His Gln Cys Pro Leu Cys Pro Phe Arg Cys Ala Arg Lys Asp Asn
                405                 410                 415

Leu Lys Ser His Met Lys Val His Gln His Gln Asp Arg Gly Glu Thr
            420                 425                 430

Phe Gln Cys Gln Leu Cys Pro Phe Thr Ser Ser Arg His Phe Ser Leu
        435                 440                 445

Lys Leu His Met Arg Cys His Gln His Phe Leu Arg Thr Glu Ala Lys
    450                 455                 460

Val Lys Glu Glu Ile Pro Asp Pro Asp Val Lys Gly Ser Pro His Leu
465                 470                 475                 480

Ser Asp Ser Ala Cys Leu Gly Gln Gln Arg Glu Gly Gly Gly Thr Glu
                485                 490                 495

Leu Val Gly Thr Met Met Thr Ser Asn Thr Pro Glu Arg Thr Ser Gln
            500                 505                 510

Gly Gly Ala Gly Val Ser Pro Leu Leu Val Lys Glu Glu Pro Lys Glu
        515                 520                 525

Asp Asn Gly Leu Pro Thr Ser Phe Thr Leu Asn Ala Ala Asp Arg Pro
    530                 535                 540

Ala Asn His Thr Lys Leu Lys Asp Pro Ser Glu Tyr Val Ala Asn Ser
545                 550                 555                 560

Ala Ser Ala Leu Phe Ser Gln Asp Ile Ser Val Lys Met Ala Ser Asp
                565                 570                 575

Phe Leu Met Lys Leu Ser Ala Ala Asn Gln Lys Glu Pro Met Asn Leu
            580                 585                 590

Asn Phe Lys Val Lys Glu Glu Pro Lys Glu Gly Glu Ser Leu Ser Thr
        595                 600                 605

Thr Leu Pro Arg Ser Ser Tyr Val Phe Ser Pro Glu Ser Glu Val Ser
    610                 615                 620
```

Ala Pro Gly Val Ser Glu Asp Ala Leu Lys Pro Gln Glu Gly Lys Gly
625 630 635 640

Ser Val Leu Arg Arg Asp Val Ser Val Lys Ala Ala Ser Glu Leu Leu
645 650 655

Met Lys Leu Ser Ala Glu Ser Tyr Lys Glu Thr Gln Met Val Lys Ile
660 665 670

Lys Glu Glu Pro Met Glu Val Asp Ile Gln Asp Ser His Val Ser Ile
675 680 685

Ser Pro Ser Arg Asn Val Gly Tyr Ser Thr Leu Ile Gly Arg Glu Lys
690 695 700

Thr Glu Pro Leu Gln Lys Met Pro Glu Gly Arg Val Pro Pro Glu Arg
705 710 715 720

Asn Leu Phe Ser Gln Asp Ile Ser Val Lys Met Ala Ser Glu Leu Leu
725 730 735

Phe Gln Leu Ser Glu Lys Val Ser Lys Glu His Asn His Thr Lys Glu
740 745 750

Asn Thr Ile Arg Thr Thr Thr Ser Pro Phe Phe Ser Glu Asp Thr Phe
755 760 765

Arg Gln Ser Pro Phe Thr Ser Asn Ser Lys Glu Leu Leu Pro Ser Asp
770 775 780

Ser Val Leu His Gly Arg Ile Ser Ala Pro Glu Thr Glu Lys Ile Val
785 790 795 800

Leu Glu Ala Gly Asn Gly Leu Pro Ser Trp Lys Phe Asn Asp Gln Leu
805 810 815

Phe Pro Cys Asp Val Cys Gly Lys Val Phe Gly Arg Gln Gln Thr Leu
820 825 830

Ser Arg His Leu Ser Leu His Thr Glu Glu Arg Lys Tyr Lys Cys His
835 840 845

Leu Cys Pro Tyr Ala Ala Lys Cys Arg Ala Asn Leu Asn Gln His Leu
850 855 860

Thr Val His Ser Val Lys Leu Val Ser Thr Asp Thr Glu Asp Ile Val
865 870 875 880

Ser Ala Val Thr Ser Glu Gly Ser Asp Gly Lys Lys His Pro Tyr Tyr
885 890 895

Tyr Ser Cys His Val Cys Gly Phe Glu Thr Glu Leu Asn Val Gln Phe
900 905 910

Val Ser His Met Ser Leu His Val Asp Lys Glu Gln Trp Met Phe Ser
915 920 925

Ile Cys Cys Thr Ala Cys Asp Phe Val Thr Met Glu Glu Ala Glu Ile
930 935 940

Lys Thr His Ile Gly Thr Lys His Thr Gly Glu Asp Arg Lys Thr Pro
945 950 955 960

Ser Glu Ser Asn Ser Pro Ser Ser Ser Ser Leu Ser Ala Leu Ser Asp
965 970 975

Ser Ala Asn Ser Lys Asp Asp Ser Asp Gly Ser Gln Lys Asn Lys Gly
980 985 990

Gly Asn Asn Leu Leu Val Ile Ser Val Met Pro Gly Ser Gln Pro Ser
995 1000 1005

Leu Asn Ser Glu Glu Lys Pro Glu Lys Gly Phe Glu Cys Val Phe
1010 1015 1020

Cys Asn Phe Val Cys Lys Thr Lys Asn Met Phe Glu Arg His Leu
1025 1030 1035

-continued

```
Gln Ile  His Leu Ile Thr Arg  Met Phe Glu Cys Asp  Val Cys His
    1040                1045                1050

Lys Phe  Met Lys Thr Pro Glu  Gln Leu Leu Glu His  Lys Lys Cys
    1055                1060                1065

His Thr  Val Pro Thr Gly Gly  Leu Asn Ser Gly Gln  Trp
    1070                1075                1080


<210> SEQ ID NO 12
<211> LENGTH: 712
<212> TYPE: PRT
<213> ORGANISM: Artificial Sequence
<220> FEATURE:
<223> OTHER INFORMATION: Synthetic polypeptide

<400> SEQUENCE: 12

Met Gly Met Arg Ile Lys Leu Gln Ser Thr Asn His Pro Asn Asn Leu
1               5                   10                  15

Leu Lys Glu Leu Asn Lys Cys Arg Leu Ser Glu Thr Met Cys Asp Val
            20                  25                  30

Thr Ile Val Val Gly Ser Arg Ser Phe Pro Ala His Lys Ala Val Leu
        35                  40                  45

Ala Cys Ala Ala Gly Tyr Phe Gln Asn Leu Phe Leu Asn Thr Gly Leu
    50                  55                  60

Asp Ala Ala Arg Thr Tyr Val Val Asp Phe Ile Thr Pro Ala Asn Phe
65                  70                  75                  80

Glu Lys Val Leu Ser Phe Val Tyr Thr Ser Glu Leu Phe Thr Asp Leu
                85                  90                  95

Ile Asn Val Gly Val Ile Tyr Glu Val Ala Glu Arg Leu Gly Met Glu
            100                 105                 110

Asp Leu Leu Gln Ala Cys His Ser Thr Phe Pro Asp Leu Glu Ser Thr
        115                 120                 125

Ala Arg Ala Lys Pro Leu Thr Ser Thr Ser Glu Ser His Ser Gly Thr
    130                 135                 140

Leu Ser Cys Pro Ser Ala Glu Pro Ala His Pro Leu Gly Glu Leu Arg
145                 150                 155                 160

Gly Gly Gly Asp Tyr Leu Gly Ala Asp Arg Asn Tyr Val Leu Pro Ser
                165                 170                 175

Asp Ala Gly Gly Ser Tyr Lys Glu Glu Glu Lys Asn Val Ala Ser Asp
            180                 185                 190

Ala Asn His Ser Leu His Leu Pro Gln Pro Pro Pro Pro Pro Pro Lys
        195                 200                 205

Thr Glu Asp His Asp Thr Pro Ala Pro Phe Thr Ser Ile Pro Ser Met
    210                 215                 220

Met Thr Gln Pro Leu Leu Gly Thr Val Ser Thr Gly Ile Gln Thr Ser
225                 230                 235                 240

Thr Ser Ser Cys Gln Pro Tyr Lys Val Gln Ser Asn Gly Asp Phe Ser
                245                 250                 255

Lys Asn Ser Phe Leu Thr Pro Asp Asn Ala Val Asp Ile Thr Thr Gly
            260                 265                 270

Thr Asn Ser Cys Leu Ser Asn Ser Glu His Ser Lys Asp Pro Gly Phe
        275                 280                 285

Gly Gln Met Asp Glu Leu Gln Leu Glu Asp Leu Gly Asp Asp Asp Leu
    290                 295                 300

Gln Phe Glu Asp Pro Ala Glu Asp Ile Gly Thr Thr Glu Glu Val Ile
305                 310                 315                 320
```

-continued

```
Glu Leu Ser Asp Asp Ser Glu Asp Glu Leu Ala Phe Gly Glu Asn Asp
                325                 330                 335

Asn Arg Glu Asn Lys Ala Met Pro Cys Gln Val Cys Lys Lys Val Leu
            340                 345                 350

Glu Pro Asn Ile Gln Leu Ile Arg Gln His Ala Arg Asp His Val Asp
        355                 360                 365

Leu Leu Thr Gly Asn Cys Lys Val Cys Glu Thr His Phe Gln Asp Arg
    370                 375                 380

Asn Ser Arg Val Thr His Val Leu Ser His Ile Gly Ile Phe Leu Phe
385                 390                 395                 400

Ser Cys Asp Met Cys Glu Thr Lys Phe Phe Thr Gln Trp Gln Leu Thr
                405                 410                 415

Leu His Arg Arg Asp Gly Ile Phe Glu Asn Asn Ile Ile Val His Pro
            420                 425                 430

Asn Asp Pro Leu Pro Gly Lys Leu Gly Leu Phe Ser Gly Ala Ala Ser
        435                 440                 445

Pro Glu Leu Lys Cys Ala Ala Cys Gly Lys Val Leu Ala Lys Asp Phe
    450                 455                 460

His Val Val Arg Gly His Ile Leu Asp His Leu Asn Leu Lys Gly Gln
465                 470                 475                 480

Ala Cys Ser Val Cys Asp Gln Arg His Leu Asn Leu Cys Ser Leu Met
                485                 490                 495

Trp His Thr Leu Ser His Leu Gly Ile Ser Val Phe Ser Cys Ser Val
            500                 505                 510

Cys Ala Asn Ser Phe Val Asp Trp His Leu Leu Glu Lys His Met Ala
        515                 520                 525

Val His Gln Ser Leu Glu Asp Ala Leu Phe His Cys Arg Leu Cys Ser
    530                 535                 540

Gln Ser Phe Lys Ser Glu Ala Ala Tyr Arg Tyr His Val Ser Gln His
545                 550                 555                 560

Lys Cys Asn Ser Gly Leu Asp Ala Arg Pro Gly Phe Gly Leu Gln His
                565                 570                 575

Pro Ala Leu Gln Lys Arg Lys Leu Pro Ala Glu Glu Phe Leu Gly Glu
            580                 585                 590

Glu Leu Ala Leu Gln Gly Gln Pro Gly Asn Ser Lys Tyr Ser Cys Lys
        595                 600                 605

Val Cys Gly Lys Arg Phe Ala His Thr Ser Glu Phe Asn Tyr His Arg
    610                 615                 620

Arg Ile His Thr Gly Glu Lys Pro Tyr Gln Cys Lys Val Cys His Lys
625                 630                 635                 640

Phe Phe Arg Gly Arg Ser Thr Ile Lys Cys His Leu Lys Thr His Ser
                645                 650                 655

Gly Ala Leu Met Tyr Arg Cys Thr Val Cys Gly His Tyr Ser Ser Thr
            660                 665                 670

Leu Asn Leu Met Ser Lys His Val Gly Val His Lys Gly Ser Leu Pro
        675                 680                 685

Pro Asp Phe Thr Ile Glu Gln Thr Phe Met Tyr Ile Ile His Ser Lys
    690                 695                 700

Glu Ala Asp Lys Asn Pro Asp Ser
705                 710
```

<210> SEQ ID NO 13
<211> LENGTH: 1651
<212> TYPE: PRT

```
<213> ORGANISM: Artificial Sequence
<220> FEATURE:
<223> OTHER INFORMATION: Synthetic polypeptide

<400> SEQUENCE: 13

Met Glu Gly Ser Leu Ala Gly Ser Leu Ala Ala Pro Asp Arg Pro Gln
1               5                   10                  15

Gly Pro Glu Arg Leu Pro Gly Pro Ala Pro Arg Glu Asn Ile Glu Gly
            20                  25                  30

Gly Ala Glu Ala Ala Glu Gly Glu Gly Gly Ile Phe Arg Ser Thr Arg
        35                  40                  45

Tyr Leu Pro Val Thr Lys Glu Gly Pro Arg Asp Ile Leu Asp Gly Arg
    50                  55                  60

Gly Gly Ile Ser Gly Thr Pro Asp Gly Arg Gly Pro Trp Glu His Pro
65                  70                  75                  80

Leu Val Gln Glu Ala Gly Glu Gly Ile Leu Ser Glu Arg Arg Phe Glu
                85                  90                  95

Asp Ser Val Ile Val Arg Thr Met Lys Pro His Ala Glu Leu Glu Gly
            100                 105                 110

Ser Arg Arg Phe Leu His His Arg Gly Glu Pro Arg Leu Leu Glu Lys
        115                 120                 125

His Ala Gln Gly Arg Pro Arg Phe Asp Trp Leu Gln Asp Glu Asp Glu
    130                 135                 140

Gln Gly Ser Pro Gln Asp Ala Gly Leu His Leu Asp Leu Pro Ala Gln
145                 150                 155                 160

Pro Pro Pro Leu Ala Pro Phe Arg Arg Val Phe Val Pro Val Glu Asp
                165                 170                 175

Thr Pro Lys Thr Leu Asp Met Ala Val Val Gly Gly Arg Glu Asp Leu
            180                 185                 190

Glu Asp Leu Glu Gly Leu Ala Gln Pro Ser Glu Trp Gly Leu Pro Thr
        195                 200                 205

Ser Ala Ser Glu Val Ala Thr Gln Thr Trp Thr Val Asn Ser Glu Ala
    210                 215                 220

Ser Val Glu Arg Leu Gln Pro Leu Leu Pro Pro Ile Arg Thr Gly Pro
225                 230                 235                 240

Tyr Leu Cys Glu Leu Leu Glu Glu Val Ala Glu Gly Val Ala Ser Pro
                245                 250                 255

Asp Glu Asp Glu Asp Glu Glu Pro Ala Val Phe Pro Cys Ile Glu Cys
            260                 265                 270

Ser Ile Tyr Phe Lys Gln Lys Glu His Leu Leu Glu His Met Ser Gln
        275                 280                 285

His Arg Arg Ala Pro Gly Gln Glu Pro Pro Ala Asp Leu Ala Pro Leu
    290                 295                 300

Ala Cys Gly Glu Cys Gly Trp Ala Phe Ala Asp Pro Thr Ala Leu Glu
305                 310                 315                 320

Gln His Arg Gln Leu His Gln Ala Ser Arg Glu Lys Ile Ile Glu Glu
                325                 330                 335

Ile Gln Lys Leu Lys Gln Val Pro Gly Asp Glu Gly Arg Glu Ala Arg
            340                 345                 350

Leu Gln Cys Pro Lys Cys Val Phe Gly Thr Asn Ser Ser Arg Ala Tyr
        355                 360                 365

Val Gln His Ala Lys Leu His Met Arg Glu Pro Pro Gly Gln Thr Thr
    370                 375                 380

Lys Glu Pro Phe Gly Gly Ser Ser Gly Ala Gly Ser Pro Ser Pro Glu
```

-continued

```
385                 390                 395                 400

Ala Ser Ala Leu Leu Tyr Gln Pro Tyr Gly Ala Ala Val Gly Leu Ser
                405                 410                 415

Ala Cys Val Phe Cys Gly Phe Pro Ala Pro Ser Glu Ser Leu Leu Arg
            420                 425                 430

Glu His Val Arg Leu Val His Ala His Pro His Trp Glu Glu Asp Gly
        435                 440                 445

Glu Ala Tyr Glu Glu Asp Pro Ala Ser Gln Pro Gly Thr Ser Gln Asp
    450                 455                 460

Ala His Ala Cys Phe Pro Asp Thr Ala Val Asp Tyr Phe Gly Lys Ala
465                 470                 475                 480

Glu Pro Ser Leu Ala Pro Met Trp Arg Glu Asn Pro Ala Gly Tyr Asp
                485                 490                 495

Pro Ser Leu Ala Phe Gly Pro Gly Cys Gln Gln Leu Ser Ile Arg Asp
            500                 505                 510

Phe Pro Leu Ser Lys Pro Leu Leu His Gly Thr Gly Gln Arg Pro Leu
        515                 520                 525

Gly Arg Leu Ala Phe Pro Ser Thr Leu Ala Ser Thr Pro Tyr Ser Leu
    530                 535                 540

Gln Leu Gly Arg Asn Lys Ser Thr Val His Pro Gln Gly Leu Gly Glu
545                 550                 555                 560

Arg Arg Arg Pro Trp Ser Glu Glu Glu Glu Glu Glu Glu Glu Glu Glu
                565                 570                 575

Asp Val Val Leu Thr Ser Glu Met Asp Phe Ser Pro Glu Asn Gly Val
            580                 585                 590

Phe Ser Pro Leu Ala Thr Pro Ser Leu Ile Pro Gln Ala Ala Leu Glu
        595                 600                 605

Leu Lys Gln Ala Phe Arg Glu Ala Leu Gln Ala Val Glu Ala Thr Gln
    610                 615                 620

Gly Gln Gln Gln Gln Leu Arg Gly Met Val Pro Ile Val Leu Val Ala
625                 630                 635                 640

Lys Leu Gly Pro Gln Val Met Ala Ala Ala Arg Val Pro Pro Arg Leu
                645                 650                 655

Gln Pro Glu Glu Leu Gly Leu Ala Gly Ala His Pro Leu Asp Phe Leu
            660                 665                 670

Leu Leu Asp Ala Pro Leu Gly Gly Pro Leu Gly Leu Asp Thr Leu Leu
        675                 680                 685

Asp Gly Asp Pro Ala Met Ala Leu Lys His Glu Glu Arg Lys Cys Pro
    690                 695                 700

Tyr Cys Pro Asp Arg Phe His Asn Gly Ile Gly Leu Ala Asn His Val
705                 710                 715                 720

Arg Gly His Leu Asn Arg Val Gly Val Ser Tyr Asn Val Arg His Phe
                725                 730                 735

Ile Ser Ala Glu Glu Val Lys Ala Ile Glu Arg Arg Phe Ser Phe Gln
            740                 745                 750

Lys Lys Lys Lys Lys Val Ala Asn Phe Asp Pro Gly Thr Phe Ser Leu
        755                 760                 765

Met Arg Cys Asp Phe Cys Gly Ala Gly Phe Asp Thr Arg Ala Gly Leu
    770                 775                 780

Ser Ser His Ala Arg Ala His Leu Arg Asp Phe Gly Ile Thr Asn Trp
785                 790                 795                 800

Glu Leu Thr Val Ser Pro Ile Asn Ile Leu Gln Glu Leu Leu Ala Thr
                805                 810                 815
```

```
Ser Ala Ala Glu Gln Pro Pro Ser Pro Leu Gly Arg Glu Pro Gly Gly
            820                 825                 830

Pro Pro Gly Ser Phe Leu Thr Ser Arg Arg Pro Arg Leu Pro Leu Thr
        835                 840                 845

Val Pro Phe Pro Pro Thr Trp Ala Glu Asp Pro Gly Pro Ala Tyr Gly
    850                 855                 860

Asp Ala Gln Ser Leu Thr Thr Cys Glu Val Cys Gly Ala Cys Phe Glu
865                 870                 875                 880

Thr Arg Lys Gly Leu Ser Ser His Ala Arg Ser His Leu Arg Gln Leu
                885                 890                 895

Gly Val Ala Glu Ser Glu Ser Ser Gly Ala Pro Ile Asp Leu Leu Tyr
            900                 905                 910

Glu Leu Val Lys Gln Lys Gly Leu Pro Asp Ala His Leu Gly Leu Pro
        915                 920                 925

Pro Gly Leu Ala Lys Lys Ser Ser Ser Leu Lys Glu Val Val Ala Gly
    930                 935                 940

Ala Pro Arg Pro Gly Leu Leu Ser Leu Ala Lys Pro Leu Asp Ala Pro
945                 950                 955                 960

Ala Val Asn Lys Ala Ile Lys Ser Pro Pro Gly Phe Ser Ala Lys Gly
                965                 970                 975

Leu Gly His Pro Pro Ser Ser Pro Leu Leu Lys Lys Thr Pro Leu Ala
            980                 985                 990

Leu Ala Gly Ser Pro Thr Pro Lys  Asn Pro Glu Asp Lys  Ser Pro Gln
        995                 1000                1005

Leu Ser  Leu Ser Pro Arg Pro  Ala Ser Pro Lys Ala  Gln Trp Pro
    1010                1015                1020

Gln Ser  Glu Asp Glu Gly Pro  Leu Asn Leu Thr Ser  Gly Pro Glu
    1025                1030                1035

Pro Ala  Arg Asp Ile Arg Cys  Glu Phe Cys Gly Glu  Phe Phe Glu
    1040                1045                1050

Asn Arg  Lys Gly Leu Ser Ser  His Ala Arg Ser His  Leu Arg Gln
    1055                1060                1065

Met Gly  Val Thr Glu Trp Tyr  Val Asn Gly Ser Pro  Ile Asp Thr
    1070                1075                1080

Leu Arg  Glu Ile Leu Lys Arg  Arg Thr Gln Ser Arg  Pro Gly Gly
    1085                1090                1095

Pro Pro  Asn Pro Pro Gly Pro  Ser Pro Lys Ala Leu  Ala Lys Met
    1100                1105                1110

Met Gly  Gly Ala Gly Pro Gly  Ser Ser Leu Glu Ala  Arg Ser Pro
    1115                1120                1125

Ser Asp  Leu His Ile Ser Pro  Leu Ala Lys Lys Leu  Pro Pro Pro
    1130                1135                1140

Pro Gly  Ser Pro Leu Gly His  Ser Pro Thr Ala Ser  Pro Pro Pro
    1145                1150                1155

Thr Ala  Arg Lys Met Phe Pro  Gly Leu Ala Ala Pro  Ser Leu Pro
    1160                1165                1170

Lys Lys  Leu Lys Pro Glu Gln  Ile Arg Val Glu Ile  Lys Arg Glu
    1175                1180                1185

Met Leu  Pro Gly Ala Leu His  Gly Glu Leu His Pro  Ser Glu Gly
    1190                1195                1200

Pro Trp  Gly Ala Pro Arg Glu  Asp Met Thr Pro Leu  Asn Leu Ser
    1205                1210                1215
```

```
Ser Arg  Ala Glu Pro Val Arg  Asp Ile Arg Cys Glu  Phe Cys Gly
    1220                 1225                 1230

Glu Phe  Phe Glu Asn Arg Lys  Gly Leu Ser Ser His  Ala Arg Ser
    1235                 1240                 1245

His Leu  Arg Gln Met Gly Val  Thr Glu Trp Ser Val  Asn Gly Ser
    1250                 1255                 1260

Pro Ile  Asp Thr Leu Arg Glu  Ile Leu Lys Lys Lys  Ser Lys Pro
    1265                 1270                 1275

Cys Leu  Ile Lys Lys Glu Pro  Pro Ala Gly Asp Leu  Ala Pro Ala
    1280                 1285                 1290

Leu Ala  Glu Asp Gly Pro Pro  Thr Val Ala Pro Gly  Pro Val Gln
    1295                 1300                 1305

Ser Pro  Leu Pro Leu Ser Pro  Leu Ala Gly Arg Pro  Gly Lys Pro
    1310                 1315                 1320

Gly Ala  Gly Pro Ala Gln Val  Pro Arg Glu Leu Ser  Leu Thr Pro
    1325                 1330                 1335

Ile Thr  Gly Ala Lys Pro Ser  Ala Thr Gly Tyr Leu  Gly Ser Val
    1340                 1345                 1350

Ala Ala  Lys Arg Pro Leu Gln  Glu Asp Arg Leu Leu  Pro Ala Glu
    1355                 1360                 1365

Val Lys  Ala Lys Thr Tyr Ile  Gln Thr Glu Leu Pro  Phe Lys Ala
    1370                 1375                 1380

Lys Thr  Leu His Glu Lys Thr  Ser His Ser Ser Thr  Glu Ala Cys
    1385                 1390                 1395

Cys Glu  Leu Cys Gly Leu Tyr  Phe Glu Asn Arg Lys  Ala Leu Ala
    1400                 1405                 1410

Ser His  Ala Arg Ala His Leu  Arg Gln Phe Gly Val  Thr Glu Trp
    1415                 1420                 1425

Cys Val  Asn Gly Ser Pro Ile  Glu Thr Leu Ser Glu  Trp Ile Lys
    1430                 1435                 1440

His Arg  Pro Gln Lys Val Gly  Ala Tyr Arg Ser Tyr  Ile Gln Gly
    1445                 1450                 1455

Gly Arg  Pro Phe Thr Lys Lys  Phe Arg Ser Ala Gly  His Gly Arg
    1460                 1465                 1470

Asp Ser  Asp Lys Arg Pro Ser  Leu Gly Leu Ala Pro  Gly Gly Leu
    1475                 1480                 1485

Ala Val  Val Gly Arg Ser Ala  Gly Gly Glu Pro Gly  Pro Glu Ala
    1490                 1495                 1500

Gly Arg  Ala Ala Asp Gly Gly  Glu Arg Pro Leu Ala  Ala Ser Pro
    1505                 1510                 1515

Pro Gly  Thr Val Lys Ala Glu  Glu His Gln Arg Gln  Asn Ile Asn
    1520                 1525                 1530

Lys Phe  Glu Arg Arg Gln Ala  Arg Pro Pro Asp Ala  Ser Ala Ala
    1535                 1540                 1545

Arg Gly  Gly Glu Asp Thr Asn  Asp Leu Gln Gln Lys  Leu Glu Glu
    1550                 1555                 1560

Val Arg  Gln Pro Pro Pro Arg  Val Arg Pro Val Pro  Ser Leu Val
    1565                 1570                 1575

Pro Arg  Pro Pro Gln Thr Ser  Leu Val Lys Phe Val  Gly Asn Ile
    1580                 1585                 1590

Tyr Thr  Leu Lys Cys Arg Phe  Cys Glu Val Glu Phe  Gln Gly Pro
    1595                 1600                 1605

Leu Ser  Ile Gln Glu Glu Trp  Val Arg His Leu Gln  Arg His Ile
```

```
    1610                1615                1620

Leu Glu  Met Asn Phe Ser Lys  Ala Asp Pro Pro Pro  Glu Glu Ser
    1625                1630                1635

Gln Ala  Pro Gln Ala Gln Thr  Ala Ala Ala Glu Ala  Pro
    1640                1645                1650


<210> SEQ ID NO 14
<211> LENGTH: 572
<212> TYPE: PRT
<213> ORGANISM: Artificial Sequence
<220> FEATURE:
<223> OTHER INFORMATION: Synthetic polypeptide

<400> SEQUENCE: 14

Met Pro Gly Pro Leu Gly Ser Leu Glu Met Gly Val Leu Thr Phe Arg
1               5                   10                  15

Asp Val Ala Leu Glu Phe Ser Leu Glu Glu Trp Gln Cys Leu Asp Thr
            20                  25                  30

Ala Gln Gln Asn Leu Tyr Arg Asn Val Met Leu Glu Asn Tyr Arg Asn
        35                  40                  45

Leu Val Phe Val Gly Ile Ala Ala Ser Lys Pro Asp Leu Ile Thr Cys
    50                  55                  60

Leu Glu Gln Gly Lys Glu Pro Trp Asn Val Lys Arg His Glu Met Val
65                  70                  75                  80

Thr Glu Pro Pro Val Val Tyr Ser Tyr Phe Ala Gln Asp Leu Trp Pro
                85                  90                  95

Lys Gln Gly Lys Lys Asn Tyr Phe Gln Lys Val Ile Leu Arg Thr Tyr
            100                 105                 110

Lys Lys Cys Gly Arg Glu Asn Leu Gln Leu Arg Lys Tyr Cys Lys Ser
        115                 120                 125

Met Asp Glu Cys Lys Val His Lys Glu Cys Tyr Asn Gly Leu Asn Gln
    130                 135                 140

Cys Leu Thr Thr Thr Gln Asn Lys Ile Phe Gln Tyr Asp Lys Tyr Val
145                 150                 155                 160

Lys Val Phe His Lys Phe Ser Asn Ser Asn Arg His Lys Ile Gly His
                165                 170                 175

Thr Gly Lys Lys Ser Phe Lys Cys Lys Glu Cys Glu Lys Ser Phe Cys
            180                 185                 190

Met Leu Ser His Leu Ala Gln His Lys Arg Ile His Ser Gly Glu Lys
        195                 200                 205

Pro Tyr Lys Cys Lys Glu Cys Gly Lys Ala Tyr Asn Glu Ala Ser Asn
    210                 215                 220

Leu Ser Thr His Lys Arg Ile His Thr Gly Lys Lys Pro Tyr Lys Cys
225                 230                 235                 240

Glu Glu Cys Gly Lys Ala Phe Asn Arg Leu Ser His Leu Thr Thr His
                245                 250                 255

Lys Ile Ile His Thr Gly Lys Lys Pro Tyr Lys Cys Glu Glu Cys Gly
            260                 265                 270

Lys Ala Phe Asn Gln Ser Ala Asn Leu Thr Thr His Lys Arg Ile His
        275                 280                 285

Thr Gly Glu Lys Pro Tyr Lys Cys Glu Glu Cys Gly Arg Ala Phe Ser
    290                 295                 300

Gln Ser Ser Thr Leu Thr Ala His Lys Ile Ile His Ala Gly Glu Lys
305                 310                 315                 320

Pro Tyr Lys Cys Glu Glu Cys Gly Lys Ala Phe Ser Gln Ser Ser Thr
```

```
                325                 330                 335

Leu Thr Thr His Lys Ile Ile His Thr Gly Glu Lys Phe Tyr Lys Cys
            340                 345                 350

Glu Glu Cys Gly Lys Ala Phe Ser Arg Leu Ser His Leu Thr Thr His
        355                 360                 365

Lys Arg Ile His Ser Gly Glu Lys Pro Tyr Lys Cys Glu Glu Cys Gly
    370                 375                 380

Lys Ala Phe Lys Gln Ser Ser Thr Leu Thr Thr His Lys Arg Ile His
385                 390                 395                 400

Ala Gly Glu Lys Phe Tyr Lys Cys Glu Val Cys Ser Lys Ala Phe Ser
                405                 410                 415

Arg Phe Ser His Leu Thr Thr His Lys Arg Ile His Thr Gly Glu Lys
            420                 425                 430

Pro Tyr Lys Cys Glu Glu Cys Gly Lys Ala Phe Asn Leu Ser Ser Gln
        435                 440                 445

Leu Thr Thr His Lys Ile Ile His Thr Gly Glu Lys Pro Tyr Lys Cys
    450                 455                 460

Glu Glu Cys Gly Lys Ala Phe Asn Gln Ser Ser Thr Leu Ser Lys His
465                 470                 475                 480

Lys Val Ile His Thr Gly Glu Lys Pro Tyr Lys Cys Glu Glu Cys Gly
                485                 490                 495

Lys Ala Phe Asn Gln Ser Ser His Leu Thr Thr His Lys Met Ile His
            500                 505                 510

Thr Gly Glu Lys Pro Tyr Lys Cys Glu Glu Cys Gly Lys Ala Phe Asn
        515                 520                 525

Asn Ser Ser Ile Leu Asn Arg His Lys Met Ile His Thr Gly Glu Lys
    530                 535                 540

Leu Tyr Lys Pro Glu Ser Cys Asn Asn Ala Cys Asp Asn Ile Ala Lys
545                 550                 555                 560

Ile Ser Lys Tyr Lys Arg Asn Cys Ala Gly Glu Lys
                565                 570


<210> SEQ ID NO 15
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 15

Phe Gln Cys Asn Gln Cys Gly Ala Ser Phe
1               5                   10


<210> SEQ ID NO 16
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 16

Phe His Cys Asn Gln Cys Gly Ala Ser Phe
1               5                   10


<210> SEQ ID NO 17
<211> LENGTH: 10
<212> TYPE: PRT
<213> ORGANISM: Artificial Sequence
<220> FEATURE:
```

<223> OTHER INFORMATION: Synthetic polypeptide

<400> SEQUENCE: 17

```
Leu Gln Cys Glu Ile Cys Gly Phe Thr Cys
1               5                   10
```

<210> SEQ ID NO 18
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 18

```
Arg Met Leu Asp Ala Ser Gly Glu Lys Met Asn Gly Ser His Arg Asp
1               5                   10                  15

Gln Gly Ser Ser Ala Leu Ser Gly Val Gly Gly Ile Arg Leu Pro Asn
            20                  25                  30

Gly Lys Leu Lys Cys Asp Ile Cys Gly Ile Ile Cys Ile Gly Pro Asn
        35                  40                  45

Val Leu Met Val His Lys Arg Ser His Thr Gly Glu Arg Pro Phe Gln
    50                  55                  60

Cys Asn Gln Cys Gly Ala Ser Phe Thr Gln Lys Gly Asn Leu Leu Arg
65                  70                  75                  80

His Ile Lys Leu His Ser Gly Glu Lys Pro Phe Lys Cys His Leu Cys
                85                  90                  95

Asn Tyr Ala Cys Arg Arg Arg Asp Ala Leu Thr Gly His Leu Arg Thr
            100                 105                 110

His Ser Val Ile Lys Glu Glu Thr Asn His Ser Glu Met Ala Glu Asp
        115                 120                 125

Leu Cys Lys
    130
```

<210> SEQ ID NO 19
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 19

```
Gly Glu Arg Pro Phe Gln Cys Asn Gln Cys Gly Ala Ser Phe Thr Thr
1               5                   10                  15

Lys Gly Asn Leu Lys Val His Phe His Arg His Pro Gln Val Lys Ala
            20                  25                  30

Asn
```

<210> SEQ ID NO 20
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 20

```
Gly Glu Arg Pro Phe Val Cys Ser Val Cys Gly His Arg Phe Thr Gln
1               5                   10                  15

Lys Gly Asn Leu Leu Arg His Ile Lys Leu His Ser
            20                  25
```

<210> SEQ ID NO 21
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 21

Gly Glu Lys Pro Leu Gln Cys Glu Ile Cys Gly Phe Thr Cys Arg Gln
1               5                   10                  15

Lys Gly Asn Leu Leu Arg His Ile Lys Leu His Ser
            20                  25

<210> SEQ ID NO 22
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 22

Gly Glu Arg Pro Phe Gln Cys Asn Gln Cys Gly Ala Ser Phe Thr Gln
1               5                   10                  15

Lys Ala Ser Leu Asn Trp His Met Lys Lys His
            20                  25

<210> SEQ ID NO 23
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 23

Gly Glu Arg Pro Phe Val Cys Ser Val Cys Gly His Arg Phe Thr Gln
1               5                   10                  15

Lys Ala Ser Leu Asn Trp His Met Lys Lys His
            20                  25

<210> SEQ ID NO 24
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 24

Gly Glu Lys Pro Leu Gln Cys Glu Ile Cys Gly Phe Thr Cys Arg Thr
1               5                   10                  15

Lys Gly Asn Leu Lys Val His Phe His Arg His Pro Gln Val Lys Ala
            20                  25                  30

Asn

<210> SEQ ID NO 25
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 25

Gly Glu Arg Pro Phe Gln Cys Asn Gln Cys Gly Ala Ser Phe Thr Gln
1               5                   10                  15

Lys Gly Asn Leu Leu Arg His Ile Lys Leu His Ser

```
            20                  25


<210> SEQ ID NO 26
<211> LENGTH: 37
<212> TYPE: PRT
<213> ORGANISM: Artificial Sequence
<220> FEATURE:
<223> OTHER INFORMATION: Synthetic polypeptide

<400> SEQUENCE: 26

Arg Ser His Thr Gly Glu Arg Pro Phe Val Cys Ser Val Cys Gly His
1               5                   10                  15

Arg Phe Thr Thr Lys Gly Asn Leu Lys Val His Phe His Arg His Pro
            20                  25                  30

Gln Val Lys Ala Asn
        35


<210> SEQ ID NO 27
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 27

Ala Leu Tyr Lys His Lys Cys Lys Tyr Cys Ser Lys Val Phe Gly Thr
1               5                   10                  15

Asp Ser Ser Leu Gln Ile His Leu Arg Ser His Thr Gly Glu Arg Pro
            20                  25                  30

Phe Val Cys Ser Val Cys Gly His Arg Phe Thr Thr Lys Gly Asn Leu
        35                  40                  45

Lys Val His Phe His Arg His Pro Gln Val Lys Ala Asn
    50                  55                  60


<210> SEQ ID NO 28
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 28

Met His Tyr Arg Thr His Thr Gly Glu Arg Pro Phe Gln Cys Lys Ile
1               5                   10                  15

Cys Gly Arg Ala Phe Ser Thr Lys Gly Asn Leu Lys Thr His Leu Gly
            20                  25                  30

Val His Arg Thr Asn Thr Ser Ile Lys Thr Gln
        35                  40


<210> SEQ ID NO 29
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 29

Gly Glu Lys Pro Leu Gln Cys Glu Ile Cys Gly Phe Thr Cys Arg Gln
1               5                   10                  15

Lys Ala Ser Leu Asn Trp His Met Lys Lys His
            20                  25
```

<210> SEQ ID NO 30
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 30

```
Phe Gln Cys Asn Gln Cys Gly Ala Ser Phe Thr Gln Lys Gly Asn Leu
1               5                   10                  15

Leu Arg His Ile Lys Leu His Ser Gly
            20                  25
```

<210> SEQ ID NO 31
<211> LENGTH: 56
<212> TYPE: PRT
<213> ORGANISM: Artificial Sequence
<220> FEATURE:
<223> OTHER INFORMATION: Synthetic polypeptide

<400> SEQUENCE: 31

```
Gly Glu Arg Pro Phe Gln Cys Asn Gln Cys Gly Ala Ser Phe Thr Gln
1               5                   10                  15

Lys Gly Asn Leu Leu Arg His Ile Lys Leu His Ser Gly Glu Lys Pro
            20                  25                  30

Phe Lys Cys His Leu Cys Asn Tyr Ala Cys Arg Arg Arg Asp Ala Leu
        35                  40                  45

Thr Gly His Leu Arg Thr His Ser
    50                  55
```

<210> SEQ ID NO 32
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 32

```
Gly Glu Arg Pro Phe Gln Cys Asn Gln Cys Gly Ala Ser Phe Thr Gln
1               5                   10                  15

Lys Gly Asn Leu Leu Arg His Ile Lys Leu His Ser Gly
            20                  25
```

<210> SEQ ID NO 33
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: wherein the Xaa represents any amino acid
<220> FEATURE:
<221> NAME/KEY: misc_feature
<222> LOCATION: (4)..(18)
<223> OTHER INFORMATION: wherein the Xaa represents any amino acid
<220> FEATURE:
<221> NAME/KEY: misc_feature
<222> LOCATION: (20)..(22)
<223> OTHER INFORMATION: wherein the Xaa represents any amino acid
<220> FEATURE:
<221> NAME/KEY: misc_feature
<222> LOCATION: (23)..(23)
<223> OTHER INFORMATION: wherein the Xaa means that the position in the peptide may be any amino acid or no amino acid, provided that there are either 2 or 4 amino acid residues between the cysteins residues.

```
<220> FEATURE:
<221> NAME/KEY: misc_feature
<222> LOCATION: (24)..(24)
<223> OTHER INFORMATION: wherein the Xaa represents histidine (His) or
      cysteine (Cys).

<400> SEQUENCE: 33

Xaa Xaa Cys Xaa Xaa Cys Gly Xaa Xaa Xaa Xaa Xaa Xaa Xaa Xaa Xaa
1               5                   10                  15

Xaa Xaa His Xaa Xaa Xaa Xaa Xaa
            20


<210> SEQ ID NO 34
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 34

Phe His Cys Asn Gln Cys Gly Ala Ser Phe Thr Gln Lys Gly Asn Leu
1               5                   10                  15

Leu Arg His Ile Lys Leu His
            20


<210> SEQ ID NO 35
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 35

Tyr Arg Cys Asp Thr Cys Gly Gln Thr Phe Ala Asn Arg Cys Asn Leu
1               5                   10                  15

Lys Ser His Gln Arg His Val His
            20


<210> SEQ ID NO 36
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 36

Phe Pro Cys Glu Leu Cys Gly Lys Lys Phe Lys Arg Lys Lys Asp Val
1               5                   10                  15

Lys Arg His Val Leu Gln Val His
            20


<210> SEQ ID NO 37
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 37

His Arg Cys Gly Gln Cys Gly Lys Gly Leu Ser Ser Lys Thr Ala Leu
1               5                   10                  15

Arg Leu His Glu Arg Thr His
            20
```

```
<210> SEQ ID NO 38
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 38

Tyr Gly Cys Thr Glu Cys Gly Ala Arg Phe Ser Gln Pro Ser Ala Leu
1               5                   10                  15

Lys Thr His Met Arg Ile His
            20


<210> SEQ ID NO 39
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 39

Phe Val Cys Asp Glu Cys Gly Ala Arg Phe Thr Gln Asn His Met Leu
1               5                   10                  15

Ile Tyr His Lys Arg Cys His
            20


<210> SEQ ID NO 40
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 40

Phe Met Cys Glu Thr Cys Gly Lys Ser Phe Ala Ser Lys Glu Tyr Leu
1               5                   10                  15

Lys His His Asn Arg Ile His
            20


<210> SEQ ID NO 41
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 41

Tyr Cys Cys Asp Gln Cys Gly Lys Gln Phe Thr Gln Leu Asn Ala Leu
1               5                   10                  15

Gln Arg His Arg Arg Ile His
            20


<210> SEQ ID NO 42
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 42

Phe Met Cys Asn Ala Cys Gly Arg Thr Phe Thr Asp Lys Ser Thr Leu
1               5                   10                  15

Arg Arg His Thr Ser Ile His
            20
```

<210> SEQ ID NO 43
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 43

```
Phe Gln Cys Asn Gln Cys Gly Ala Ser Phe Thr Gln Lys Gly Asn Leu
1               5                   10                  15

Leu Arg His Ile Lys Leu His
            20
```

<210> SEQ ID NO 44
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 44

```
Met Asn Cys Asp Val Cys Gly Leu Ser Cys Ile Ser Phe Asn Val Leu
1               5                   10                  15

Met Val His Lys Arg Ser His
            20
```

<210> SEQ ID NO 45
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 45

```
Tyr Lys Cys Glu Phe Cys Gly Arg Ser Tyr Lys Gln Arg Ser Ser Leu
1               5                   10                  15

Glu Glu His Lys Glu Arg Cys
            20
```

<210> SEQ ID NO 46
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 46

```
Phe Gln Cys Asn Gln Cys Gly Ala Ser Phe Thr Gln Lys Gly Asn Leu
1               5                   10                  15

Leu Arg His Ile Lys Leu His
            20
```

<210> SEQ ID NO 47
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 47

```
Leu Lys Cys Asp Ile Cys Gly Ile Ile Cys Ile Gly Pro Asn Val Leu
1               5                   10                  15

Met Val His Lys Arg Ser His
            20
```

<210> SEQ ID NO 48
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 48

```
His Lys Cys Gly Tyr Cys Gly Arg Ser Tyr Lys Gln Arg Ser Ser Leu
1               5                   10                  15

Glu Glu His Lys Glu Arg Cys His
            20
```

<210> SEQ ID NO 49
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 49

```
Phe Val Cys Ser Val Cys Gly His Arg Phe Thr Thr Lys Gly Asn Leu
1               5                   10                  15

Lys Val His Phe His Arg His
            20
```

<210> SEQ ID NO 50
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 50

```
Phe Gln Cys Lys Ile Cys Gly Arg Ala Phe Ser Thr Lys Gly Asn Leu
1               5                   10                  15

Lys Thr His Leu Gly Val His
            20
```

<210> SEQ ID NO 51
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 51

```
His Gly Cys Thr Arg Cys Gly Lys Asn Phe Ser Ser Ala Ser Ala Leu
1               5                   10                  15

Gln Ile His Glu Arg Thr His
            20
```

<210> SEQ ID NO 52
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 52

```
Phe Val Cys Asn Ile Cys Gly Arg Ala Phe Thr Thr Lys Gly Asn Leu
1               5                   10                  15

Lys Val His Tyr Met Thr His
```

```
            20


<210> SEQ ID NO 53
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 53

Phe Thr Cys Glu Thr Cys Gly Lys Ser Phe Lys Arg Lys Asn His Leu
1               5                   10                  15

Glu Val His Arg Arg Thr His
            20


<210> SEQ ID NO 54
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 54

Leu Gln Cys Glu Ile Cys Gly Tyr Gln Cys Arg Gln Arg Ala Ser Leu
1               5                   10                  15

Asn Trp His Met Lys Lys His
            20


<210> SEQ ID NO 55
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 55

Phe Thr Cys Asp Arg Cys Gly Lys Arg Phe Glu Lys Leu Asp Ser Val
1               5                   10                  15

Lys Phe His Thr Leu Lys Ser His
            20


<210> SEQ ID NO 56
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 56

Leu Gln Cys Glu Ile Cys Gly Phe Thr Cys Arg Gln Lys Ala Ser Leu
1               5                   10                  15

Asn Trp His Met Lys Lys His
            20


<210> SEQ ID NO 57
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 57

Phe Ser Cys Asn Ile Cys Gly Lys Lys Phe Glu Lys Lys Asp Ser Val
1               5                   10                  15
```

Val Ala His Lys Ala Lys Ser His
            20

<210> SEQ ID NO 58
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 58

Leu Gln Cys Glu Ile Cys Gly Phe Thr Cys Arg Gln Lys Ala Ser Leu
1               5                   10                  15

Asn Trp His Gln Arg Lys His
            20

<210> SEQ ID NO 59
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 59

Phe Pro Cys Glu Phe Cys Gly Lys Arg Phe Glu Lys Pro Asp Ser Val
1               5                   10                  15

Ala Ala His Arg Ser Lys Ser His
            20

<210> SEQ ID NO 60
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 60

Phe Gln Cys Pro Ile Cys Gly Leu Val Ile Lys Arg Lys Ser Tyr Trp
1               5                   10                  15

Lys Arg His Met Val Ile His
            20

<210> SEQ ID NO 61
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 61

Phe Pro Cys Asp Val Cys Gly Lys Val Phe Gly Arg Gln Gln Thr Leu
1               5                   10                  15

Ser Arg His Leu Ser Leu His
            20

<210> SEQ ID NO 62
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 62

Tyr Ser Cys His Val Cys Gly Phe Glu Thr Glu Leu Asn Val Gln Phe
1               5                   10                  15

Val Ser His Met Ser Leu His
20

<210> SEQ ID NO 63
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 63

Tyr Ser Cys Lys Val Cys Gly Lys Arg Phe Ala His Thr Ser Glu Phe
1 5 10 15

Asn Tyr His Arg Arg Ile His
20

<210> SEQ ID NO 64
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 64

Tyr Arg Cys Thr Val Cys Gly His Tyr Ser Ser Thr Leu Asn Leu Met
1 5 10 15

Ser Lys His Val Gly Val His
20

<210> SEQ ID NO 65
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 65

Met Arg Cys Asp Phe Cys Gly Ala Gly Phe Asp Thr Arg Ala Gly Leu
1 5 10 15

Ser Ser His Ala Arg Ala His
20

<210> SEQ ID NO 66
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 66

Leu Ala Cys Gly Glu Cys Gly Trp Ala Phe Ala Asp Pro Thr Ala Leu
1 5 10 15

Glu Gln His Arg Gln Leu His
20

<210> SEQ ID NO 67
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 67

Thr Thr Cys Glu Val Cys Gly Ala Cys Phe Glu Thr Arg Lys Gly Leu

-continued

```
1               5                   10                  15

Ser Ser His Ala Arg Ser His
            20


<210> SEQ ID NO 68
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 68

Tyr Lys Cys Lys Glu Cys Gly Lys Ala Tyr Asn Glu Ala Ser Asn Leu
1               5                   10                  15

Ser Thr His Lys Arg Ile His
            20


<210> SEQ ID NO 69
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 69

Tyr Lys Cys Glu Glu Cys Gly Lys Ala Phe Asn Arg Leu Ser His Leu
1               5                   10                  15

Thr Thr His Lys Ile Ile His
            20


<210> SEQ ID NO 70
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 70

Tyr Lys Cys Glu Glu Cys Gly Lys Ala Phe Asn Gln Ser Ala Asn Leu
1               5                   10                  15

Thr Thr His Lys Arg Ile His
            20


<210> SEQ ID NO 71
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 71

Tyr Lys Cys Glu Glu Cys Gly Lys Ala Phe Ser Gln Ser Ser Thr Leu
1               5                   10                  15

Thr Thr His Lys Ile Ile His
            20


<210> SEQ ID NO 72
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 72
```

Tyr Lys Cys Glu Glu Cys Gly Lys Ala Phe Ser Arg Leu Ser His Leu
1               5                   10                  15

Thr Thr His Lys Arg Ile His
            20

<210> SEQ ID NO 73
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 73

Tyr Lys Cys Glu Glu Cys Gly Lys Ala Phe Lys Gln Ser Ser Thr Leu
1               5                   10                  15

Thr Thr His Lys Arg Ile His
            20

<210> SEQ ID NO 74
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 74

Tyr Lys Cys Glu Glu Cys Gly Lys Ala Phe Asn Leu Ser Ser Gln Leu
1               5                   10                  15

Thr Thr His Lys Ile Ile His
            20

<210> SEQ ID NO 75
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 75

Tyr Lys Cys Glu Glu Cys Gly Lys Ala Phe Asn Gln Ser Ser Thr Leu
1               5                   10                  15

Ser Lys His Lys Val Ile His
            20

<210> SEQ ID NO 76
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 76

Tyr Lys Cys Glu Glu Cys Gly Lys Ala Phe Asn Gln Ser Ser His Leu
1               5                   10                  15

Thr Thr His Lys Met Ile His
            20

<210> SEQ ID NO 77
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 77

```
Tyr Lys Cys Glu Glu Cys Gly Lys Ala Phe Asn Asn Ser Ser Ile Leu
1               5                   10                  15

Asn Arg His Lys Met Ile His
            20


<210> SEQ ID NO 78
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: wherein the Xaa represents any amino acid
<220> FEATURE:
<221> NAME/KEY: misc_feature
<222> LOCATION: (4)..(5)
<223> OTHER INFORMATION: wherein the Xaa represents any amino acid
<220> FEATURE:
<221> NAME/KEY: misc_feature
<222> LOCATION: (8)..(18)
<223> OTHER INFORMATION: wherein the Xaa represents any amino acid
<220> FEATURE:
<221> NAME/KEY: misc_feature
<222> LOCATION: (20)..(22)
<223> OTHER INFORMATION: wherein the Xaa represents any amino acid

<400> SEQUENCE: 78

Xaa Xaa Cys Xaa Xaa Cys Gly Xaa Xaa Xaa Xaa Xaa Xaa Xaa Xaa Xaa
1               5                   10                  15

Xaa Xaa His Xaa Xaa Xaa His
            20


<210> SEQ ID NO 79
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: wherein the Xaa represents any amino acid
<220> FEATURE:
<221> NAME/KEY: misc_feature
<222> LOCATION: (4)..(5)
<223> OTHER INFORMATION: wherein the Xaa represents any amino acid
<220> FEATURE:
<221> NAME/KEY: misc_feature
<222> LOCATION: (8)..(18)
<223> OTHER INFORMATION: wherein the Xaa represents any amino acid
<220> FEATURE:
<221> NAME/KEY: misc_feature
<222> LOCATION: (20)..(23)
<223> OTHER INFORMATION: wherein the Xaa represents any amino acid

<400> SEQUENCE: 79

Xaa Xaa Cys Xaa Xaa Cys Gly Xaa Xaa Xaa Xaa Xaa Xaa Xaa Xaa Xaa
1               5                   10                  15

Xaa Xaa His Xaa Xaa Xaa Xaa His
            20


<210> SEQ ID NO 80
<211> LENGTH: 22
<212> TYPE: PRT
<213> ORGANISM: Artificial Sequence
<220> FEATURE:
<223> OTHER INFORMATION: Synthetic polypeptide
<220> FEATURE:
```

```
<221> NAME/KEY: misc_feature
<222> LOCATION: (1)..(2)
<223> OTHER INFORMATION: wherein the Xaa represents any amino acid
<220> FEATURE:
<221> NAME/KEY: misc_feature
<222> LOCATION: (4)..(5)
<223> OTHER INFORMATION: wherein the Xaa represents any amino acid
<220> FEATURE:
<221> NAME/KEY: misc_feature
<222> LOCATION: (8)..(14)
<223> OTHER INFORMATION: wherein the Xaa represents any amino acid
<220> FEATURE:
<221> NAME/KEY: misc_feature
<222> LOCATION: (16)..(17)
<223> OTHER INFORMATION: wherein the Xaa represents any amino acid
<220> FEATURE:
<221> NAME/KEY: misc_feature
<222> LOCATION: (19)..(21)
<223> OTHER INFORMATION: wherein the Xaa represents any amino acid

<400> SEQUENCE: 80

Xaa Xaa Cys Xaa Xaa Cys Gly Xaa Xaa Xaa Xaa Xaa Xaa Xaa Leu Xaa
1               5                   10                  15

Xaa His Xaa Xaa Xaa His
            20


<210> SEQ ID NO 81
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: wherein the Xaa represents any amino acid
<220> FEATURE:
<221> NAME/KEY: misc_feature
<222> LOCATION: (4)..(5)
<223> OTHER INFORMATION: wherein the Xaa represents any amino acid
<220> FEATURE:
<221> NAME/KEY: misc_feature
<222> LOCATION: (8)..(14)
<223> OTHER INFORMATION: wherein the Xaa represents any amino acid
<220> FEATURE:
<221> NAME/KEY: misc_feature
<222> LOCATION: (16)..(17)
<223> OTHER INFORMATION: wherein the Xaa represents any amino acid
<220> FEATURE:
<221> NAME/KEY: misc_feature
<222> LOCATION: (19)..(22)
<223> OTHER INFORMATION: wherein the Xaa represents any amino acid

<400> SEQUENCE: 81

Xaa Xaa Cys Xaa Xaa Cys Gly Xaa Xaa Xaa Xaa Xaa Xaa Xaa Leu Xaa
1               5                   10                  15

Xaa His Xaa Xaa Xaa Xaa His
            20


<210> SEQ ID NO 82
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: wherein the Xaa represents any amino acid
<220> FEATURE:
<221> NAME/KEY: misc_feature
<222> LOCATION: (4)..(5)
<223> OTHER INFORMATION: wherein the Xaa represents any amino acid
```

<220> FEATURE:
<221> NAME/KEY: misc_feature
<222> LOCATION: (8)..(9)
<223> OTHER INFORMATION: wherein the Xaa represents any amino acid
<220> FEATURE:
<221> NAME/KEY: misc_feature
<222> LOCATION: (11)..(14)
<223> OTHER INFORMATION: wherein the Xaa represents any amino acid
<220> FEATURE:
<221> NAME/KEY: misc_feature
<222> LOCATION: (16)..(17)
<223> OTHER INFORMATION: wherein the Xaa represents any amino acid
<220> FEATURE:
<221> NAME/KEY: misc_feature
<222> LOCATION: (19)..(21)
<223> OTHER INFORMATION: wherein the Xaa represents any amino acid

<400> SEQUENCE: 82

```
Xaa Xaa Cys Xaa Xaa Cys Gly Xaa Xaa Phe Xaa Xaa Xaa Xaa Leu Xaa
1               5                   10                  15

Xaa His Xaa Xaa Xaa His
            20
```

<210> SEQ ID NO 83
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: wherein the Xaa represents any amino acid
<220> FEATURE:
<221> NAME/KEY: misc_feature
<222> LOCATION: (4)..(5)
<223> OTHER INFORMATION: wherein the Xaa represents any amino acid
<220> FEATURE:
<221> NAME/KEY: misc_feature
<222> LOCATION: (8)..(9)
<223> OTHER INFORMATION: wherein the Xaa represents any amino acid
<220> FEATURE:
<221> NAME/KEY: misc_feature
<222> LOCATION: (11)..(14)
<223> OTHER INFORMATION: wherein the Xaa represents any amino acid
<220> FEATURE:
<221> NAME/KEY: misc_feature
<222> LOCATION: (16)..(17)
<223> OTHER INFORMATION: wherein the Xaa represents any amino acid
<220> FEATURE:
<221> NAME/KEY: misc_feature
<222> LOCATION: (19)..(22)
<223> OTHER INFORMATION: wherein the Xaa represents any amino acid

<400> SEQUENCE: 83

```
Xaa Xaa Cys Xaa Xaa Cys Gly Xaa Xaa Phe Xaa Xaa Xaa Xaa Leu Xaa
1               5                   10                  15

Xaa His Xaa Xaa Xaa Xaa His
            20
```

<210> SEQ ID NO 84
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 84

```
Ala Leu Tyr Lys His Lys Cys Lys Tyr Cys Asn Lys Val Phe Gly Thr
1               5                   10                  15

Asp Ser Ser Leu Gln Ile His Leu Arg Ser His Thr Gly Glu Arg Pro
```

-continued

```
            20                  25                  30

Phe Val Cys Ser Val Cys Gly His Arg Phe Thr Thr Lys Gly Asn Leu
        35                  40                  45

Lys Val His Phe His Arg His Pro Gln Val Lys Ala Asn
    50                  55                  60


<210> SEQ ID NO 85
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 85

Met His Tyr Arg Thr His Thr Gly Glu Arg Pro Phe Gln Cys Lys Ile
1               5                   10                  15

Cys Ala Arg Ala Phe Ser Thr Lys Gly Asn Leu Lys Thr His Leu Gly
            20                  25                  30

Val His Arg Thr Asn Thr Ser Ile Lys Thr Gln
        35                  40


<210> SEQ ID NO 86
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 86

Met His Tyr Arg Thr His Thr Gly Glu Arg Pro Phe Gln Cys Lys Ile
1               5                   10                  15

Cys Asn Arg Ala Phe Ser Thr Lys Gly Asn Leu Lys Thr His Leu Gly
            20                  25                  30

Val His Arg Thr Asn Thr Ser Ile Lys Thr Gln
        35                  40


<210> SEQ ID NO 87
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 87

Arg Ser His Thr Gly Glu Arg Pro Tyr Val Cys Pro Ile Cys Gly His
1               5                   10                  15

Arg Phe Thr Thr Lys Gly Asn Leu Lys Val His Leu Gln Arg His Pro
            20                  25                  30

Glu Val Lys
        35


<210> SEQ ID NO 88
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 88

Arg Ser His Thr Gly Glu Arg Pro Phe Lys Cys Asn Ile Cys Gly Asn
1               5                   10                  15

Arg Phe Thr Thr Lys Gly Asn Leu Lys Val His Phe Gln Arg His Lys
```

```
            20                  25                  30

Glu Lys Tyr
        35


<210> SEQ ID NO 89
<211> LENGTH: 29
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(3)
<223> OTHER INFORMATION: wherein the Xaa represents any amino acid
<220> FEATURE:
<221> NAME/KEY: misc_feature
<222> LOCATION: (5)..(6)
<223> OTHER INFORMATION: wherein the Xaa represents any amino acid
<220> FEATURE:
<221> NAME/KEY: misc_feature
<222> LOCATION: (8)..(9)
<223> OTHER INFORMATION: wherein the Xaa represents any amino acid
<220> FEATURE:
<221> NAME/KEY: misc_feature
<222> LOCATION: (13)..(15)
<223> OTHER INFORMATION: wherein the Xaa represents any amino acid
<220> FEATURE:
<221> NAME/KEY: misc_feature
<222> LOCATION: (17)..(18)
<223> OTHER INFORMATION: wherein the Xaa represents any amino acid
<220> FEATURE:
<221> NAME/KEY: misc_feature
<222> LOCATION: (21)..(22)
<223> OTHER INFORMATION: wherein the Xaa represents any amino acid
<220> FEATURE:
<221> NAME/KEY: misc_feature
<222> LOCATION: (25)..(28)
<223> OTHER INFORMATION: wherein the Xaa represents any amino acid

<400> SEQUENCE: 89

Xaa Xaa Xaa Pro Xaa Xaa Cys Xaa Xaa Cys Gly Ala Xaa Xaa Xaa Arg
1               5                   10                  15

Xaa Xaa Glu Leu Xaa Xaa His Leu Xaa Xaa Xaa Xaa Gly
            20                  25


<210> SEQ ID NO 90
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 90

Arg Lys Arg Pro Phe Thr Cys Asp Ser Cys Gly Ala Ala Phe Asp Arg
1               5                   10                  15

Ala Glu Glu Leu Asn Asn His Leu Asn Ala His Thr Gly
            20                  25


<210> SEQ ID NO 91
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 91

Arg Lys Arg Pro Phe Gln Cys Asp Arg Cys Gly Ala Ala Phe Asp Arg
1               5                   10                  15

Ala Glu Glu Leu Asn Asn His Leu Asn Ala His Thr Gly
```

20 25

<210> SEQ ID NO 92
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 92

Arg Glu Arg Pro Phe Gln Cys Asp Ala Cys Gly Ala Ala Tyr Asp Arg
1 5 10 15

Ala Glu Glu Leu Asn Asn His Leu Asn Ala His Thr Gly
20 25

<210> SEQ ID NO 93
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 93

Arg Glu Arg Pro Tyr Gln Cys Asp Ala Cys Gly Ala Ala Phe Asp Arg
1 5 10 15

Ala Glu Glu Leu Asn Asn His Leu Asn Ala His Ser Gly
20 25

<210> SEQ ID NO 94
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 94

Arg Glu Arg Pro Phe Gln Cys Asp Ser Cys Gly Ala Ala Phe Asp Arg
1 5 10 15

Ala Glu Glu Leu Asn Asn His Leu Asn Ala His Thr Gly
20 25

<210> SEQ ID NO 95
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 95

Arg Lys Arg Pro Phe Gln Cys Asp Ala Cys Gly Ala Ala Phe Asp Arg
1 5 10 15

Ser Lys Glu Leu Asn Asp His Leu Asn Ala His Thr Gly
20 25

<210> SEQ ID NO 96
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 96

Arg Lys Arg Pro Phe Gln Cys Asp Ser Cys Gly Ala Ala Phe Asn Arg
1 5 10 15

-continued

Ser Lys Glu Leu Asn Asp His Leu Asn Ala His Thr Gly
20 25

<210> SEQ ID NO 97
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 97

Arg Glu Arg Pro Phe Met Cys Asp Ala Cys Gly Ala Ala Phe Asn Arg
1 5 10 15

Ser Lys Glu Leu Asn Asp His Leu Asn Ala His Ser Gly
20 25

<210> SEQ ID NO 98
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 98

Arg Glu Arg Pro Phe Gln Cys Asp Ala Cys Gly Ala Ala Phe Asp Arg
1 5 10 15

Ala Glu Glu Leu Asn Asp His Leu Asn Lys His Thr Gly
20 25

<210> SEQ ID NO 99
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 99

Arg Glu Arg Pro Phe Val Cys Thr Ser Cys Gly Ala Ala Phe Asp Arg
1 5 10 15

Ala Glu Glu Leu Asn Asn His Leu Asn Ala His Thr Gly
20 25

<210> SEQ ID NO 100
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 100

Arg Glu Arg Pro Phe Thr Cys Thr Ala Cys Gly Ala Ala Phe Asn Arg
1 5 10 15

Ala Glu Glu Leu Asn Asn His Leu Asn Ala His Thr Gly
20 25

<210> SEQ ID NO 101
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 101

Arg Glu Arg Pro Phe Val Cys Glu Met Cys Gly Ala Ala Phe Asp Arg
1 5 10 15

Ala Glu Glu Leu Asn Asn His Leu Asn Ala His Thr Gly
            20                  25

<210> SEQ ID NO 102
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 102

Arg Glu Leu Pro Tyr Val Cys Asp Met Cys Gly Ala Ala Phe Asp Arg
1               5                   10                  15

Ala Glu Glu Leu Asn Asn His Leu Asn Ala His Thr Gly
            20                  25

<210> SEQ ID NO 103
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 103

Arg Glu Arg Pro Phe Gln Cys Glu Ser Cys Gly Ala Ala Phe Asp Arg
1               5                   10                  15

Ala Glu Glu Leu Asn Asn His Leu Asn Ala His Thr Gly
            20                  25

<210> SEQ ID NO 104
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 104

Arg Glu Met Pro Tyr Gln Cys Glu Ser Cys Gly Ala Ala Phe Asp Arg
1               5                   10                  15

Ala Glu Glu Leu Asn Asn His Leu Asn Ala His Thr Gly
            20                  25

<210> SEQ ID NO 105
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 105

Arg Glu Arg Pro Phe Gln Cys Glu Tyr Cys Gly Ala Ala Phe Asp Arg
1               5                   10                  15

Ala Glu Glu Leu Asn Asn His Leu Asn Ala Leu Thr Gly
            20                  25

<210> SEQ ID NO 106
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 106

Arg Glu Arg Pro Phe Gln Cys Gln Tyr Cys Gly Ala Ala Phe Asp Arg

```
1               5                   10                  15

Ala Glu Glu Leu Asn Asn His Leu Lys Asn His Thr Gly
            20                  25


<210> SEQ ID NO 107
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 107

Arg Glu Ala Pro Phe Gln Cys Glu Ser Cys Gly Ala Arg Phe Asn Arg
1               5                   10                  15

Ala Glu Glu Leu Asn Asn His Leu Asn Arg His Thr Gly
            20                  25


<210> SEQ ID NO 108
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 108

Arg Glu Ala Pro Phe Gln Cys Glu Ser Cys Gly Ala Arg Phe Asn Arg
1               5                   10                  15

Ala Glu Glu Leu Asn Asn His Leu Asn Asn His Thr Gly
            20                  25


<210> SEQ ID NO 109
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 109

Arg Glu Leu Pro Phe Gln Cys Glu Ser Cys Gly Ala Arg Phe Glu Arg
1               5                   10                  15

Ala Glu Glu Leu Asn Tyr His Leu Asn Val His Thr Gly
            20                  25


<210> SEQ ID NO 110
<211> LENGTH: 29
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 110

Xaa Glu Met Pro Phe Gln Cys Glu Ser Cys Gly Ala Arg Phe Asn Arg
1               5                   10                  15

Ala Glu Glu Leu Asn Asn His Leu Asn Ala His Thr Gly
            20                  25


<210> SEQ ID NO 111
<211> LENGTH: 29
<212> TYPE: PRT
<213> ORGANISM: Artificial Sequence
<220> FEATURE:
```

<223> OTHER INFORMATION: Synthetic polypeptide

<400> SEQUENCE: 111

Arg Glu Met Pro Phe Gln Cys Glu Ser Cys Gly Ala Arg Phe Asn Arg
1               5                   10                  15

Ala Glu Glu Leu Asn Asn His Leu Asn Ala His Thr Gly
            20                  25

<210> SEQ ID NO 112
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 112

Arg Glu Met Pro Phe Gln Cys Asp Ser Cys Gly Ala Arg Phe Asn Arg
1               5                   10                  15

Ala Glu Glu Leu Asn Thr His Leu Asn Ala His Thr Gly
            20                  25

<210> SEQ ID NO 113
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 113

Arg Lys Ala Pro Phe Gln Cys Asp Val Cys Gly Ala Arg Phe Asn Arg
1               5                   10                  15

Ala Glu Glu Leu Asn Tyr His Leu Asn Thr Leu Thr Gly
            20                  25

<210> SEQ ID NO 114
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 114

Arg Glu Ala Pro Phe Gln Cys Asp Val Cys Gly Ala Arg Phe Asn Arg
1               5                   10                  15

Ala Glu Glu Leu Asn Tyr His Leu Asn Leu Leu Thr Gly
            20                  25

<210> SEQ ID NO 115
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 115

Arg Lys Thr Pro Phe Gln Cys Glu Val Cys Gly Ala Arg Phe Asn Arg
1               5                   10                  15

Ala Glu Glu Leu Asn Tyr His Leu Asn Leu Leu Thr Gly
            20                  25

<210> SEQ ID NO 116
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 116

Arg Lys Ala Pro Phe Gln Cys Glu Val Cys Gly Ala Arg Phe Asn Arg
1 5 10 15

Ala Glu Glu Leu Asn Thr His Leu Asn Ile Leu Thr Gly
20 25

<210> SEQ ID NO 117
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 117

Arg Lys Ala Pro Phe Gln Cys Glu Val Cys Gly Ala Arg Phe Asn Arg
1 5 10 15

Ala Glu Glu Leu Asn Thr His Leu Asn Ile Leu Lys Gly
20 25

<210> SEQ ID NO 118
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 118

Arg Lys Thr Pro Phe Gln Cys Asp Ile Cys Gly Ala Arg Phe Asn Arg
1 5 10 15

Ala Glu Glu Leu Asn Thr His Leu Asn Ile Leu Thr Gly
20 25

<210> SEQ ID NO 119
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 119

Arg Lys Ile Pro Phe Gln Cys Asp Val Cys Gly Ala Arg Phe Asn Arg
1 5 10 15

Ala Glu Glu Leu Asn Thr His Leu Asn Ile Leu Thr Gly
20 25

<210> SEQ ID NO 120
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 120

Arg Lys Ala Pro Phe Gln Cys Asp Val Cys Gly Ala Arg Phe Asn Arg
1 5 10 15

Ala Glu Glu Leu Asn Thr His Leu Asn Ala Leu Thr Gly
20 25

<210> SEQ ID NO 121
<211> LENGTH: 29
<212> TYPE: PRT

<213> ORGANISM: Artificial Sequence
<220> FEATURE:
<223> OTHER INFORMATION: Synthetic polypeptide

<400> SEQUENCE: 121

Arg Lys Ala Pro Phe Gln Cys Asp Val Cys Gly Ala Arg Phe Asn Arg
1               5                   10                  15

Ala Glu Glu Leu Asn Asn His Leu Asn Arg Leu Thr Gly
            20                  25

<210> SEQ ID NO 122
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 122

Arg Lys Arg Pro Phe Gln Cys Glu Val Cys Gly Ala Arg Phe Asn Arg
1               5                   10                  15

Ala Glu Glu Leu Asn Asn His Leu Asn Ala Leu Thr Gly
            20                  25

<210> SEQ ID NO 123
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 123

Arg Lys Ala Pro Phe Gln Cys Glu Val Cys Gly Ala Arg Phe Asn Arg
1               5                   10                  15

Ala Glu Glu Leu Asn Asn His Leu Asn Ala Leu Leu Gly
            20                  25

<210> SEQ ID NO 124
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 124

Arg Glu Arg Pro Phe Gln Cys Glu Val Cys Gly Ala Arg Phe Asn Arg
1               5                   10                  15

Ala Glu Glu Leu Asn Asn His Leu Asn Ala Leu Thr Gly
            20                  25

<210> SEQ ID NO 125
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 125

Arg Glu Arg Pro Phe Gln Cys Glu Val Cys Gly Ala Arg Phe Asn Arg
1               5                   10                  15

Ala Glu Glu Leu Asn Asn His Leu Asn Ala Leu Thr Gly
            20                  25

<210> SEQ ID NO 126
<211> LENGTH: 29

<212> TYPE: PRT
<213> ORGANISM: Artificial Sequence
<220> FEATURE:
<223> OTHER INFORMATION: Synthetic polypeptide

<400> SEQUENCE: 126

```
Arg Glu Ala Pro Phe Gln Cys Glu Val Cys Gly Ala Arg Phe Asn Arg
1               5                   10                  15

Ala Glu Glu Leu Asn Asn His Leu Asn Ala Leu Thr Gly
            20                  25
```

<210> SEQ ID NO 127
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 127

```
Arg Lys Ala Pro Phe Gln Cys Glu Ser Cys Gly Ala Arg Phe Asn Arg
1               5                   10                  15

Trp Glu Glu Leu Ala Thr His Leu Asn Ala His Thr Gly
            20                  25
```

<210> SEQ ID NO 128
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 128

```
Arg Glu Ala Pro Phe Gln Cys Glu Met Cys Gly Ala Arg Phe Asn Arg
1               5                   10                  15

Trp Glu Glu Leu Ala Ser His Leu Asn Ala His Thr Gly
            20                  25
```

<210> SEQ ID NO 129
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 129

```
Arg Lys Met Pro Phe Gln Cys Glu Val Cys Gly Ala Arg Phe Asn Arg
1               5                   10                  15

Trp Glu Glu Leu Ala Asn His Leu Asn Ala Leu Thr Gly
            20                  25
```

<210> SEQ ID NO 130
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 130

```
Arg Lys Ala Pro Phe Gln Cys Asp Val Cys Gly Ala Arg Phe Asn Arg
1               5                   10                  15

Lys Glu Glu Leu Asp Asp His Leu Asn Lys Leu Thr Gly
            20                  25
```

<210> SEQ ID NO 131

<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 131

```
Arg Glu Ala Pro Phe Gln Cys Asp Val Cys Gly Ala Arg Phe Asn Arg
1               5                   10                  15

Lys Glu Glu Leu Asp Thr His Leu Thr Lys Leu Thr Gly
            20                  25
```

<210> SEQ ID NO 132
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 132

```
Arg Glu Ala Pro Phe Gln Cys Glu Val Cys Gly Ala Arg Phe Asn Arg
1               5                   10                  15

Lys Glu Glu Leu Asp Asn His Leu Asn Asn Leu Thr Gly
            20                  25
```

<210> SEQ ID NO 133
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 133

```
Arg Glu Ala Pro Phe Gln Cys Asp Ala Cys Gly Ala Arg Phe Asn Arg
1               5                   10                  15

Lys Glu Glu Leu Asp Asn His Leu Asn Ala His Thr Gly
            20                  25
```

<210> SEQ ID NO 134
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 134

```
Arg Glu Ala Pro Phe Gln Cys Asp Ser Cys Gly Ala Arg Phe Asn Arg
1               5                   10                  15

Ala Glu Glu Leu Asn Asn His Leu Asn Ala His Thr Gly
            20                  25
```

<210> SEQ ID NO 135
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 135

```
Arg Glu Ala Pro Phe Gln Cys Asp Ser Cys Gly Ala Arg Phe Asn Arg
1               5                   10                  15

Ala Glu Glu Leu Asn Asn His Leu Asn Ala His Thr Gly
            20                  25
```

```
<210> SEQ ID NO 136
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 136

Arg Glu Ala Pro Phe Gln Cys Asp Ser Cys Gly Ala Arg Phe Asn Arg
1               5                   10                  15

Ala Glu Glu Leu Asn Asn His Leu Asn Ala His Thr Gly
            20                  25


<210> SEQ ID NO 137
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 137

Arg Glu Ala Pro Phe Gln Cys Asp Ala Cys Gly Ala Arg Phe Asn Arg
1               5                   10                  15

Ala Glu Glu Leu Asn Asn His Leu Asn Ala His Thr Gly
            20                  25


<210> SEQ ID NO 138
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 138

Arg Glu Ala Pro Phe Gln Cys Asp Ala Cys Gly Ala Arg Phe Asn Arg
1               5                   10                  15

Ala Glu Glu Leu Asn Asn His Leu Asn Ala His Thr Gly
            20                  25


<210> SEQ ID NO 139
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 139

Arg Glu Ala Pro Phe Gln Cys Glu Ala Cys Gly Ala Arg Phe Asn Arg
1               5                   10                  15

Ala Glu Glu Leu Asn Asn His Leu Asn Ala His Thr Gly
            20                  25


<210> SEQ ID NO 140
<211> LENGTH: 29
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: wherein the Xaa represents arginine (Arg) or
      any amino acid
<220> FEATURE:
<221> NAME/KEY: misc_feature
<222> LOCATION: (2)..(3)
<223> OTHER INFORMATION: wherein the Xaa represents any amino acid
```

```
<220> FEATURE:
<221> NAME/KEY: misc_feature
<222> LOCATION: (6)..(6)
<223> OTHER INFORMATION: wherein the Xaa represents any amino acid
<220> FEATURE:
<221> NAME/KEY: misc_feature
<222> LOCATION: (8)..(9)
<223> OTHER INFORMATION: wherein the Xaa represents any amino acid
<220> FEATURE:
<221> NAME/KEY: misc_feature
<222> LOCATION: (13)..(13)
<223> OTHER INFORMATION: wherein the Xaa represents any amino acid
<220> FEATURE:
<221> NAME/KEY: misc_feature
<222> LOCATION: (15)..(15)
<223> OTHER INFORMATION: wherein the Xaa represents any amino acid
<220> FEATURE:
<221> NAME/KEY: misc_feature
<222> LOCATION: (17)..(17)
<223> OTHER INFORMATION: wherein the Xaa represents any amino acid
<220> FEATURE:
<221> NAME/KEY: misc_feature
<222> LOCATION: (21)..(22)
<223> OTHER INFORMATION: wherein the Xaa represents any amino acid
<220> FEATURE:
<221> NAME/KEY: misc_feature
<222> LOCATION: (26)..(27)
<223> OTHER INFORMATION: wherein the Xaa represents any amino acid

<400> SEQUENCE: 140

Xaa Xaa Xaa Pro Phe Xaa Cys Xaa Xaa Cys Gly Ala Xaa Phe Xaa Arg
1               5                   10                  15

Xaa Glu Glu Leu Xaa Xaa His Leu Asn Xaa Xaa Thr Gly
            20                  25


<210> SEQ ID NO 141
<211> LENGTH: 29
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: wherein the Xaa represents arginine (Arg) or
      any amino acid
<220> FEATURE:
<221> NAME/KEY: misc_feature
<222> LOCATION: (2)..(3)
<223> OTHER INFORMATION: wherein the Xaa represents any amino acid
<220> FEATURE:
<221> NAME/KEY: misc_feature
<222> LOCATION: (8)..(9)
<223> OTHER INFORMATION: wherein the Xaa represents any amino acid
<220> FEATURE:
<221> NAME/KEY: misc_feature
<222> LOCATION: (13)..(13)
<223> OTHER INFORMATION: wherein the Xaa represents any amino acid
<220> FEATURE:
<221> NAME/KEY: misc_feature
<222> LOCATION: (15)..(15)
<223> OTHER INFORMATION: wherein the Xaa represents any amino acid
<220> FEATURE:
<221> NAME/KEY: misc_feature
<222> LOCATION: (22)..(22)
<223> OTHER INFORMATION: wherein the Xaa represents any amino acid
<220> FEATURE:
<221> NAME/KEY: misc_feature
<222> LOCATION: (26)..(27)
<223> OTHER INFORMATION: wherein the Xaa represents any amino acid

<400> SEQUENCE: 141

Xaa Xaa Xaa Pro Phe Gln Cys Xaa Xaa Cys Gly Ala Xaa Phe Xaa Arg
1               5                   10                  15
```

```
Ala Glu Glu Leu Asn Xaa His Leu Asn Xaa Xaa Thr Gly
            20                  25


<210> SEQ ID NO 142
<211> LENGTH: 29
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: wherein the Xaa represents arginine (Arg) or
      any amino acid
<220> FEATURE:
<221> NAME/KEY: misc_feature
<222> LOCATION: (2)..(3)
<223> OTHER INFORMATION: wherein the Xaa represents any amino acid
<220> FEATURE:
<221> NAME/KEY: misc_feature
<222> LOCATION: (8)..(9)
<223> OTHER INFORMATION: wherein the Xaa represents any amino acid
<220> FEATURE:
<221> NAME/KEY: misc_feature
<222> LOCATION: (13)..(13)
<223> OTHER INFORMATION: wherein the Xaa represents any amino acid
<220> FEATURE:
<221> NAME/KEY: misc_feature
<222> LOCATION: (22)..(22)
<223> OTHER INFORMATION: wherein the Xaa represents any amino acid
<220> FEATURE:
<221> NAME/KEY: misc_feature
<222> LOCATION: (26)..(27)
<223> OTHER INFORMATION: wherein the Xaa represents any amino acid

<400> SEQUENCE: 142

Xaa Xaa Xaa Pro Phe Gln Cys Xaa Xaa Cys Gly Ala Xaa Phe Asn Arg
1               5                   10                  15

Ala Glu Glu Leu Asn Xaa His Leu Asn Xaa Xaa Thr Gly
            20                  25


<210> SEQ ID NO 143
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: wherein the Xaa represents any amino acid
<220> FEATURE:
<221> NAME/KEY: misc_feature
<222> LOCATION: (2)..(2)
<223> OTHER INFORMATION: wherein the Xaa represents glutamic acid (Glu),
      lysine (Lys), valine (Val), or threonine (Thr)
<220> FEATURE:
<221> NAME/KEY: misc_feature
<222> LOCATION: (3)..(3)
<223> OTHER INFORMATION: wherein the Xaa represents any amino acid
<220> FEATURE:
<221> NAME/KEY: misc_feature
<222> LOCATION: (4)..(4)
<223> OTHER INFORMATION: wherein the Xaa represents proline (Pro),
      alanine (Ala), or lisine (Lys)
<220> FEATURE:
<221> NAME/KEY: misc_feature
<222> LOCATION: (5)..(5)
<223> OTHER INFORMATION: wherein the Xaa represents phenylalanine (Phe)
      or tyrosine (Tyr)
<220> FEATURE:
<221> NAME/KEY: misc_feature
<222> LOCATION: (6)..(6)
<223> OTHER INFORMATION: wherein the Xaa represents glutamine (Gln),
      valine (Val), threonine (Thr), lysine (Lys), or arginine (Arg)
```

-continued

<220> FEATURE:
<221> NAME/KEY: misc_feature
<222> LOCATION: (8)..(8)
<223> OTHER INFORMATION: wherein the Xaa represents glutamic acid (Glu), aspartic acid (Asp), or glutamine (Gln)
<220> FEATURE:
<221> NAME/KEY: misc_feature
<222> LOCATION: (9)..(9)
<223> OTHER INFORMATION: wherein the Xaa represents valine (Val), isoleucine (Ile), serine (Ser), tyrosine (Tyr), or alanine (Ala)
<220> FEATURE:
<221> NAME/KEY: misc_feature
<222> LOCATION: (13)..(13)
<223> OTHER INFORMATION: wherein the Xaa represents alanine (Ala), arginine (Arg), valine (Val), asparagine (Asn), or tyrosine (Tyr)
<220> FEATURE:
<221> NAME/KEY: misc_feature
<222> LOCATION: (15)..(15)
<223> OTHER INFORMATION: wherein the Xaa represents asparagine (Asn), aspartic acid (Asp), serine (Ser), glutamic acid (Glu), lysine (Lys), or another amino acid residue that imparts improved solubility
<220> FEATURE:
<221> NAME/KEY: misc_feature
<222> LOCATION: (16)..(16)
<223> OTHER INFORMATION: wherein the Xaa represents arginine (Arg), or tyrosine (Tyr), or another amino acid residue that imparts improved solubility
<220> FEATURE:
<221> NAME/KEY: misc_feature
<222> LOCATION: (17)..(17)
<223> OTHER INFORMATION: wherein the Xaa represents tryptophan (Trp), alanine (Ala), or serine (Ser), or another amino acid residue that imparts improved solubility
<220> FEATURE:
<221> NAME/KEY: misc_feature
<222> LOCATION: (18)..(18)
<223> OTHER INFORMATION: wherein the Xaa represents glutamic acid or another amino acid residue that imparts improved solubility
<220> FEATURE:
<221> NAME/KEY: misc_feature
<222> LOCATION: (19)..(19)
<223> OTHER INFORMATION: wherein the Xaa represents glutamic acid (Glu) or glutamine (Gln) or another amino acid residue that imparts improved solubility
<220> FEATURE:
<221> NAME/KEY: misc_feature
<222> LOCATION: (21)..(21)
<223> OTHER INFORMATION: wherein the Xaa represents asparagine (Asn) or tyrosine (Tyr) or another amino acid residue that imparts improved solubility
<220> FEATURE:
<221> NAME/KEY: misc_feature
<222> LOCATION: (22)..(22)
<223> OTHER INFORMATION: wherein the Xaa represents asparagine (Asn), threonine (Thr), aspartic acid (Asp), or tryptophan (Trp), or another amino acid residue that imparts improved solubility
<220> FEATURE:
<221> NAME/KEY: misc_feature
<222> LOCATION: (24)..(24)
<223> OTHER INFORMATION: wherein the Xaa represents leucine (Leu) or another amino acid residue that imparts improved solubility
<220> FEATURE:
<221> NAME/KEY: misc_feature
<222> LOCATION: (25)..(25)
<223> OTHER INFORMATION: wherein the Xaa represents asparagine (Asn), leucine (Leu), lysine (Lys), serine (Ser), or threonine (Thr), or another amino acid residue that imparts improved solubility
<220> FEATURE:
<221> NAME/KEY: misc_feature
<222> LOCATION: (26)..(26)
<223> OTHER INFORMATION: wherein the Xaa represents any amino acid

<400> SEQUENCE: 143

```
Xaa Xaa Xaa Xaa Xaa Xaa Cys Xaa Xaa Cys Gly Ala Xaa Phe Xaa Xaa
1               5                   10                  15

Xaa Xaa Xaa Leu Xaa Xaa His Xaa Xaa Xaa His
```

```
            20                  25


<210> SEQ ID NO 144
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 144

Arg Glu Arg Pro Phe Gln Cys Asn Gln Cys Gly Ala Ser Phe Thr Gln
1               5                   10                  15

Lys Gly Asn Leu Leu Arg His Ile Lys Leu His
            20                  25


<210> SEQ ID NO 145
<211> LENGTH: 20
<212> TYPE: DNA
<213> ORGANISM: Artificial Sequence
<220> FEATURE:
<223> OTHER INFORMATION: Synthetic polypeptide

<400> SEQUENCE: 145

tgggatcact agcatgtctg                                                  20


<210> SEQ ID NO 146
<211> LENGTH: 693
<212> TYPE: DNA
<213> ORGANISM: Artificial Sequence
<220> FEATURE:
<223> OTHER INFORMATION: Synthetic polypeptide

<400> SEQUENCE: 146

tctgctgact gatatctcac gggggctctt ctcttccttt gtagagtgcc tggtgaagaa      60

tgtgatggga tcactaatga gggatcatat ggtcctccat gaatacgtca acgcggccgg     120

aataactggc gggagtggag ggcgagatca tatggttctc cacgagtatg tcaacgcggc     180

cggcatcact ggaggttcag gtgggagaga tcatatggtc ttgcatgaat acgtgaatgc     240

tgcgggaatc accgggggta gcgggggtag agatcatatg gtactccatg aatatgtaaa     300

cgctgcgggt atcacgggtg gcagtggagg acgggaccat atggtccttc acgaatatgt     360

gaatgctgcg ggcataacgg gaggatccgg tggtggaagc ggagctacta acttcagcct     420

gctgaagcag gctggagacg tggaggagaa ccctggacct gactacaaag acgatgacga     480

taaaggagaa cggccttttc agtgcaatca gtgcggagcc tcctttactc aaaaaggcaa     540

cctgctgcga cacattaaat tgcacagcgg tggaggcggc tcaggaggtg gtggttcagc     600

ggagagcggc cctgggacga gattgagaaa tctgccagta atgggggatg gactagaaac     660

ttcccaaatg tctacctata gtgagtcgta tta                                  693


<210> SEQ ID NO 147
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 147

Ala Ile Asn Ile Thr Asn Gly Glu Glu Val
1               5                   10


<210> SEQ ID NO 148
```

<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 148

Leu Val Asp Lys Lys Ser Gly Glu Lys Ser
1 5 10

<210> SEQ ID NO 149
<211> LENGTH: 84
<212> TYPE: DNA
<213> ORGANISM: Artificial Sequence
<220> FEATURE:
<223> OTHER INFORMATION: Synthetic polypeptide

<400> SEQUENCE: 149
ggagaacggc cttttcagtg caatcagtgc ggagcctcct ttactcaaaa aggcaacctg 60
ctgcgacaca ttaaattgca cagc 84

<210> SEQ ID NO 150

<400> SEQUENCE: 150

000

<210> SEQ ID NO 151
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 151

Phe Gln Cys Asn Gln Cys Gly Ala Ser Phe Thr Gln Lys Gly Asn Leu
1 5 10 15

Leu Arg His Ile Lys Leu His
20

<210> SEQ ID NO 152
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 152

Met Gln Cys Glu Ile Cys Gly Phe Thr Cys Arg Gln Lys Gly Asn Leu
1 5 10 15

Leu Arg His Ile Lys Leu His
20

<210> SEQ ID NO 153
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 153

Phe Gln Cys Gln Val Cys Gly Ala Arg Phe Ser Arg Trp Glu Glu Leu
1 5 10 15

Tyr Asn His Leu Leu Lys His
20

<210> SEQ ID NO 154
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 154

Phe Gln Cys Glu Met Cys Gly Ala Ala Phe Asp Arg Trp Glu Glu Leu
1 5 10 15

Tyr Asn His Lys Asn Ala His
20

<210> SEQ ID NO 155
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 155

Phe Gln Cys Glu Ile Cys Gly Ala Arg Phe Lys Arg Trp Glu Glu Leu
1 5 10 15

Tyr Asn His Leu Lys Lys His
20

<210> SEQ ID NO 156
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 156

Phe Gln Cys Glu Ile Cys Gly Ala Ala Phe Ser Arg Trp Glu Glu Leu
1 5 10 15

Tyr Asn His Leu Lys Arg His
20

<210> SEQ ID NO 157
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 157

Phe Gln Cys Glu Ile Cys Gly Ala Arg Phe Phe Arg Trp Glu Glu Leu
1 5 10 15

Tyr Asn His Leu Ala Lys His
20

<210> SEQ ID NO 158
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 158

Phe Gln Cys Ser Ile Cys Gly Ala Thr Phe Ser Arg Trp Glu Glu Leu
1 5 10 15

Tyr Asn His Leu Leu Lys His

20

<210> SEQ ID NO 159
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 159

Phe Gln Cys Glu Ile Cys Gly Ala Arg Phe Ser Arg Trp Glu Glu Leu
1 5 10 15

Tyr Asn His Leu Asn Lys His
20

<210> SEQ ID NO 160
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 160

Phe Gln Cys Glu Ile Cys Gly Ala Lys Phe Glu Asn Trp Glu Asp Leu
1 5 10 15

Tyr Asn His Leu Leu Lys His
20

<210> SEQ ID NO 161
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 161

Phe Gln Cys Lys Gln Cys Gly Ala Val Phe Ser Arg Trp Glu Glu Leu
1 5 10 15

Tyr Asn His Leu Thr Asn His
20

<210> SEQ ID NO 162
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 162

Phe Gln Cys Lys Gln Cys Gly Ala Val Phe Ser Arg Trp Glu Glu Leu
1 5 10 15

Tyr Asn His Leu Lys Asn His
20

<210> SEQ ID NO 163
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 163

Phe Gln Cys Lys Gln Cys Gly Ala Val Phe Lys Arg Trp Glu Glu Leu
1 5 10 15

Tyr Asn His Leu Leu Ala His
20

<210> SEQ ID NO 164
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 164

Phe Gln Cys Glu Ile Cys Gly Ala Arg Phe Ser Arg Trp Glu Glu Leu
1 5 10 15

Tyr Asn His Leu Leu Lys His
20

<210> SEQ ID NO 165
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 165

Phe Gln Cys Gln Val Cys Gly Ala Arg Phe Ser Arg Trp Glu Glu Leu
1 5 10 15

Tyr Asn His Leu Ser Lys His
20

<210> SEQ ID NO 166
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 166

Phe Gln Cys Gln Tyr Cys Gly Ala Arg Phe Asn Arg Trp Glu Glu Leu
1 5 10 15

Tyr Asp His Leu Asn Lys His
20

<210> SEQ ID NO 167
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 167

Phe Gln Cys Gln Met Cys Gly Ala Ala Phe Asp Arg Trp Glu Glu Leu
1 5 10 15

Tyr Asn His Leu Leu Ala His
20

<210> SEQ ID NO 168
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 168

Phe Gln Cys Val Gln Cys Gly Ala Arg Phe Asn Arg Trp Glu Glu Leu
1 5 10 15

Tyr Asp His Leu Asn Lys His
20

<210> SEQ ID NO 169
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 169

Phe Gln Cys Lys Tyr Cys Gly Ala Val Phe Ser Arg Trp Glu Glu Leu
1 5 10 15

Tyr Asn His Leu Leu Ala His
20

<210> SEQ ID NO 170
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 170

Phe Gln Cys Glu Ile Cys Gly Ala Arg Phe Ser Arg Trp Glu Glu Leu
1 5 10 15

Tyr Asn His Leu Lys Asn His
20

<210> SEQ ID NO 171
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 171

Phe Gln Cys Asn Gln Cys Gly Ala Ser Phe Thr Arg Trp Glu Glu Leu
1 5 10 15

Tyr Asn His Leu Leu Arg His
20

<210> SEQ ID NO 172
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 172

Phe Gln Cys Gln Tyr Cys Gly Ala Val Phe Thr Arg Trp Glu Glu Leu
1 5 10 15

Tyr Asn His Leu Leu Arg His
20

<210> SEQ ID NO 173
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 173

Phe Gln Cys Ser Gln Cys Gly Ala Ala Phe Asn Arg Trp Glu Glu Leu

```
1               5                   10                  15

Tyr Asn His Leu Leu Arg His
            20


<210> SEQ ID NO 174
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 174

Phe Gln Cys Asp Lys Cys Gly Ala Lys Phe Asp Arg Trp Glu Glu Leu
1               5                   10                  15

Tyr Asn His Asn Asn Ala His
            20


<210> SEQ ID NO 175
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 175

Phe Gln Cys Glu Ile Cys Gly Ala Arg Phe Glu Asn Trp Glu Asp Leu
1               5                   10                  15

Tyr Asn His Leu Leu Lys His
            20


<210> SEQ ID NO 176
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 176

Phe Thr Cys Thr Ala Cys Gly Ala Thr Phe Thr Arg Ala Glu Glu Leu
1               5                   10                  15

Asn Thr His Leu Ser Lys His
            20


<210> SEQ ID NO 177
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 177

Phe Gln Cys Glu Tyr Cys Gly Ala Arg Phe Asn Arg Trp Glu Glu Leu
1               5                   10                  15

Tyr Asn His Leu Leu Lys His
            20


<210> SEQ ID NO 178
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 178
```

-continued

```
Tyr Gln Cys Glu Ile Cys Gly Ala Arg Phe Asn Arg Trp Glu Glu Leu
1               5                   10                  15

Tyr Asn His Leu Lys Asn His
            20


<210> SEQ ID NO 179
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 179

Phe Gln Cys Glu Ile Cys Gly Ala Ala Phe Ser Arg Trp Glu Glu Leu
1               5                   10                  15

Tyr Asn His Leu Leu Ala His
            20


<210> SEQ ID NO 180
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 180

Phe Gln Cys Glu Ile Cys Gly Ala Arg Phe Ser Arg Trp Glu Glu Leu
1               5                   10                  15

Tyr Asn His Leu Ser Lys His
            20


<210> SEQ ID NO 181
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 181

Phe Gln Cys Glu Ile Cys Gly Ala Arg Phe Glu Tyr Trp Glu Gln Leu
1               5                   10                  15

Tyr Asn His Leu Lys Asn His
            20


<210> SEQ ID NO 182
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 182

Phe Tyr Cys Thr Gln Cys Gly Ala Ala Phe Asp Arg Trp Glu Glu Leu
1               5                   10                  15

Tyr Asn His Leu Leu Asn His
            20


<210> SEQ ID NO 183
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 183
```

```
Met Gln Cys Glu Ile Cys Gly Phe Thr Cys Arg Arg Ala Glu Glu Leu
1               5                   10                  15

Asn Thr His Leu Asn Lys His
            20


<210> SEQ ID NO 184
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 184

Phe Tyr Cys Lys Gln Cys Gly Ala Asn Phe Ser Arg Trp Glu Glu Leu
1               5                   10                  15

Tyr Asn His Leu Lys Ala His
            20


<210> SEQ ID NO 185
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 185

Phe Tyr Cys Thr Gln Cys Gly Ala Ala Phe Asp Arg Trp Glu Glu Leu
1               5                   10                  15

Tyr Asn His Leu Leu Asn His
            20


<210> SEQ ID NO 186
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 186

Met Gln Cys Glu Ile Cys Gly Phe Thr Cys Arg Arg Ala Glu Glu Leu
1               5                   10                  15

Asn Thr His Leu Asn Lys His
            20


<210> SEQ ID NO 187
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 187

Phe Tyr Cys Lys Gln Cys Gly Ala Asn Phe Ser Arg Trp Glu Glu Leu
1               5                   10                  15

Tyr Asn His Leu Lys Ala His
            20


<210> SEQ ID NO 188
<211> LENGTH: 69
<212> TYPE: DNA
<213> ORGANISM: Artificial Sequence
<220> FEATURE:
<223> OTHER INFORMATION: Synthetic polypeptide
```

-continued

<400> SEQUENCE: 188
ttccagtgcg agatctgcgg cgctgctttc agccggtggg aggagctgta caaccacctg 60
aagcggcac 69

<210> SEQ ID NO 189
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 189
ttccagtgcg agatctgcgg cgctcggttc aagcggtggg aggagctgta caaccacctg 60
aagaagcac 69

<210> SEQ ID NO 190
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 190
ttccagtgcg agatgtgcgg cgctgctttc gaccggtggg aggagctgta caaccacaag 60
aacgctcac 69

<210> SEQ ID NO 191
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 191
ttccagtgca gcatctgcgg cgctaccttc agccggtggg aggagctgta caaccacctg 60
ctgaagcac 69

<210> SEQ ID NO 192
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 192
ttccagtgcc aggtgtgcgg cgctcggttc agccggtggg aggagctgta caaccacctg 60
ctgaagcac 69

<210> SEQ ID NO 193
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 193
ttccagtgcg agatctgcgg cgctcggttc ttccggtggg aggagctgta caaccacctg 60
gctaagcac 69

<210> SEQ ID NO 194
<211> LENGTH: 69

<212> TYPE: DNA
<213> ORGANISM: Artificial Sequence
<220> FEATURE:
<223> OTHER INFORMATION: Synthetic polypeptide

<400> SEQUENCE: 194
ttccagtgcg agatctgcgg cgctcggttc agccggtggg aggagctgta caaccacctg 60
aacaagcac 69

<210> SEQ ID NO 195
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 195
ttccagtgcg agatctgcgg cgctaagttc gagaactggg aggacctgta caaccacctg 60
ctgaagcac 69

<210> SEQ ID NO 196
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 196
ttccagtgcg tgcagtgcgg cgctcggttc aaccggtggg aggagctgta cgaccacctg 60
aacaagcac 69

<210> SEQ ID NO 197
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 197
ttccagtgcc aggtgtgcgg cgctcggttc agccggtggg aggagctgta caaccacctg 60
agcaagcac 69

<210> SEQ ID NO 198
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 198
ttccagtgcc agatgtgcgg cgctgctttc gaccggtggg aggagctgta caaccacctg 60
ctggctcac 69

<210> SEQ ID NO 199
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 199
ttccagtgca agtactgcgg cgctgtgttc agccggtggg aggagctgta caaccacctg 60
ctggctcac 69

<210> SEQ ID NO 200
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 200
ttccagtgcg agatctgcgg cgctcggttc agccggtggg aggagctgta caaccacctg 60
ctgaagcac 69

<210> SEQ ID NO 201
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 201
ttccagtgca agcagtgcgg cgctgtgttc aagcggtggg aggagctgta caaccacctg 60
ctggctcac 69

<210> SEQ ID NO 202
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 202
ttccagtgca agcagtgcgg cgctgtgttc agccggtggg aggagctgta caaccacctg 60
aagaaccac 69

<210> SEQ ID NO 203
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 203
ttccagtgca agcagtgcgg cgctgtgttc agccggtggg aggagctgta caaccacctg 60
accaaccac 69

<210> SEQ ID NO 204
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 204
ttccagtgcc agtactgcgg cgctcggttc aaccggtggg aggagctgta cgaccacctg 60
aacaagcac 69

<210> SEQ ID NO 205
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 205
ttccagtgcg agatctgcgg cgctcggttc agccggtggg aggagctgta caaccacctg 60
aagaaccac 69

<210> SEQ ID NO 206
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 206
ttccagtgca accagtgcgg cgctagcttc acccggtggg aggagctgta caaccacctg 60
ctgcggcac 69

<210> SEQ ID NO 207
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 207
ttccagtgcc agtactgcgg cgctgtgttc acccggtggg aggagctgta caaccacctg 60
ctgcggcac 69

<210> SEQ ID NO 208
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 208
ttccagtgca gccagtgcgg cgctgctttc aaccggtggg aggagctgta caaccacctg 60
ctgcggcac 69

<210> SEQ ID NO 209
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 209
ctgcagtgcg agatctgcgg cttcacctgc cggcagaagg gcaacctgct gcggcacatc 60
aagctgcac 69

<210> SEQ ID NO 210
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 210
ttcacctgca ccgcttgcgg cgctaccttc acccgggctg aggagctgaa cacccacctg 60
agcaagcac 69

<210> SEQ ID NO 211

-continued

<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 211
ttccagtgcg agatctgcgg cgctcggttc gagaactggg aggacctgta caaccacctg 60
ctgaagcac 69

<210> SEQ ID NO 212
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 212
ttccagtgcg acaagtgcgg cgctaagttc gaccggtggg aggagctgta caaccacaac 60
aacgctcac 69

<210> SEQ ID NO 213
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 213
taccagtgcg agatctgcgg cgctaccttc agccggtggg aggagctgta caaccacctg 60
aagaagcac 69

<210> SEQ ID NO 214
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 214
ttccagtgcg agatctgcgg cgctcggttc agccggtggg aggagctgta caaccacctg 60
agcaagcac 69

<210> SEQ ID NO 215
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 215
ctgcagtgcg agatctgcgg ctaccagtgc cggcggtggg aggagctgta caaccacctg 60
ctgaagcac 69

<210> SEQ ID NO 216
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 216
ttccagtgcg agatctgcgg cgctgctttc agccggtggg aggagctgta caaccacctg 60
aagaaccac 69

<210> SEQ ID NO 217
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 217
ttccagtgca agcagtgcgg cgctgtgttc acccggtggg aggagctgaa gacccacctg 60
gacgctcac 69

<210> SEQ ID NO 218
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 218
ttccagtgcc agtactgcgg cgctgctttc aaccggtggg aggagctgta caaccacctg 60
ctgaaccac 69

<210> SEQ ID NO 219
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 219
ttcacctgcc agatctgcgg cgctgcttac gagaactggg aggacctgta caaccacctg 60
aagaagcac 69

<210> SEQ ID NO 220
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 220
ttccagtgcg agatctgcgg cgctcggttc agccggtggg aggagctgta caaccacctg 60
gctaagcac 69

<210> SEQ ID NO 221
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 221
ttccagtgca ccaagtgcgg cgctcggttc aaccggtggg aggagctgta caaccacgac 60
ctggctcac 69

<210> SEQ ID NO 222
<211> LENGTH: 69
<212> TYPE: DNA
<213> ORGANISM: Artificial Sequence
<220> FEATURE:

<223> OTHER INFORMATION: Synthetic polypeptide

<400> SEQUENCE: 222
taccagtgcg agatctgcgg cgctcggttc agccggtggg aggagctgta caaccacctg 60
aagaagcac 69

<210> SEQ ID NO 223
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 223
ttccagtgcg agatctgcgg cgctaagttc agccggtggg aggagctgta caaccacctg 60
aacctgcac 69

<210> SEQ ID NO 224
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 224
ttccagtgcc agtactgcgg cgctgtgttc acccggtggg aggagctgta caaccacctg 60
ctgaaccac 69

<210> SEQ ID NO 225
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 225
ctgcagtgcg agatctgcgg cttcacctgc cggcggtggg aggagctgta caaccacctg 60
ctgaaccac 69

<210> SEQ ID NO 226
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 226
ctgcagtgcg aggtgtgcgg cttccagtgc cggcggtggg aggagctgta caaccacctg 60
ctgaagcac 69

<210> SEQ ID NO 227
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 227
ttccagtgcg agatgtgcgg cgctcggttc aaccggtggg aggagctgta caaccacctg 60
cgggctcac 69

<210> SEQ ID NO 228
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 228
ttccagtgcg agatctgcgg cgctgctttc gagaactggg aggacctgta caaccacctg 60
aagaagcac 69

<210> SEQ ID NO 229
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 229
ttccagtgca gcatctgcgg cgctaccttc agccggtggg aggagctgta caaccacctg 60
agcaagcac 69

<210> SEQ ID NO 230
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 230
taccagtgcg agtactgcgg cgctcggttc aaccggtggg aggagctgta caaccacctg 60
ctgaagcac 69

<210> SEQ ID NO 231
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 231
ttccagtgcc agtactgcgg cgctgtgttc gctcggtggg aggagctgta caaccacctg 60
ctgaaccac 69

<210> SEQ ID NO 232
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 232
taccagtgcg agatctgcgg cgctcggttc gaccggtggg aggagctgta caaccacctg 60
aagaaccac 69

<210> SEQ ID NO 233
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 233
ttccagtgcg agatctgcgg cgctcggttc gagtactggg agcagctgta caaccacctg 60
aagaaccac 69

<210> SEQ ID NO 234
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 234
ttccagtgcg agtactgcgg cgctcggttc aaccggtggg aggagctgta caaccacctg 60
ctgaagcac 69

<210> SEQ ID NO 235
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 235
taccagtgcg agatctgcgg cgctcggttc aaccggtggg aggagctgta caaccacctg 60
aagaaccac 69

<210> SEQ ID NO 236
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 236
ttccagtgcg agatctgcgg cgctgctttc agccggtggg aggagctgta caaccacctg 60
ctggctcac 69

<210> SEQ ID NO 237
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 237
ttccagtgca ccatctgcgg cgctaccttc gacaagtggg agaacctgta caaccacctg 60
aacctgcac 69

<210> SEQ ID NO 238
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 238
taccagtgct acatctgcgg cgctgctttc gacaagtggg agctgctgta caaccacctg 60
aagaagcac 69

<210> SEQ ID NO 239
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 239
ttctactgca cccagtgcgg cgctgctttc gaccggtggg aggagctgta caaccacctg 60
ctgaaccac 69

<210> SEQ ID NO 240
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 240
ctgcagtgcg agatctgcgg cttcacctgc cggcgggctg aggagctgaa cacccacctg 60
aacaagcac 69

<210> SEQ ID NO 241
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 241
ttctactgca agcagtgcgg cgctaacttc agccggtggg aggagctgta caaccacctg 60
aaggctcac 69

<210> SEQ ID NO 242
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 242
ttccagtgca agcagtgcgg cgctgtgttc agccgggctg aggagctgaa caagcacctg 60
accgctcac 69

<210> SEQ ID NO 243
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 243
ttccagtgcc ggcagtgcgg cgctgtgttc agccgggctg aggagctgaa caagcacctg 60
aacctgcac 69

<210> SEQ ID NO 244
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 244
ttccagtgcc agtactgcgg cgctgctttc aaccggtggg aggagctgta cgaccacctg 60
aacaagcac 69

```
<210> SEQ ID NO 245
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 245

ttccagtgcc agtactgcgg cgctgtgtgg aagcggtggg aggagctgta caaccacctg     60

ctggctcac                                                             69


<210> SEQ ID NO 246
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 246

ttccagtgcg agatctgcgg cgctgctttc agccggtggg aggagctgta caaccacctg     60

ctgatgcac                                                             69


<210> SEQ ID NO 247
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 247

ttccagtgcc agtactgcgg cgctgctttc aaccggtggg aggagctgta caaccacctg     60

ctggctcac                                                             69


<210> SEQ ID NO 248
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 248

ctgcagtgcg aggtgtgcgg cttccagtgc cggcggtggg aggagctgta caaccacctg     60

accaagcac                                                             69


<210> SEQ ID NO 249
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 249

ttccagtgcg accagtgcgg cgctgtgttc gaccggtggg aggagctgta caaccacctg     60

aaccggcac                                                             69


<210> SEQ ID NO 250
<211> LENGTH: 69
<212> TYPE: DNA
<213> ORGANISM: Artificial Sequence
<220> FEATURE:
<223> OTHER INFORMATION: Synthetic polypedtide

<400> SEQUENCE: 250
```

ttccagtgca accagtgcgg cgctagcttc acccagaagg gcaacctgct gcggcacatc 60
aagctgcac 69

<210> SEQ ID NO 251
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 251
ctgcagtgcg aggtgtgcgg cttccagtgc cggcagcggg ctagcctgaa gtaccacatg 60
accaagcac 69

<210> SEQ ID NO 252
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 252
ctgcagtgcg agatctgcgg cttcacctgc cggcagaagg ctagcctgaa ctggcacatg 60
aagaagcac 69

<210> SEQ ID NO 253
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 253
ttccagtgcc agatctgcgg cgctgctttc aaccggtggg aggagctgta caaccacctg 60
ctgatgcac 69

<210> SEQ ID NO 254
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 254
ttccagtgcg agatgtgcgg cgctcggttc gaccggtggg aggagctgta caaccacctg 60
aacgctcac 69

<210> SEQ ID NO 255
<211> LENGTH: 69
<212> TYPE: DNA
<213> ORGANISM: Artificial Sequence
<220> FEATURE:
<223> OTHER INFORMATION: Synthetic polypeptide

<400> SEQUENCE: 255
ttccagtgcc agtactgcgg cgctgctttc gaccggtggg aggagctgta caaccacctg 60
ctgaaccac 69

<210> SEQ ID NO 256
<211> LENGTH: 69
<212> TYPE: DNA

-continued

```
<213> ORGANISM: Artificial Sequence
<220> FEATURE:
<223> OTHER INFORMATION: Synthetic polypeptide

<400> SEQUENCE: 256

ttccagtgcg agatgtgcgg cgctgctttc gaccggtggg aggagctgta caaccacctg     60

aacgctcac                                                             69


<210> SEQ ID NO 257
<211> LENGTH: 69
<212> TYPE: DNA
<213> ORGANISM: Artificial sequence
<220> FEATURE:
<223> OTHER INFORMATION: Synthetic polypeptide

<400> SEQUENCE: 257

ttccagtgca accagtgcgg cgctagcttc acccggtggg aggagctgta caaccacctg     60

ctgaagcac                                                             69
```